(12) United States Patent
Brai et al.

(10) Patent No.: US 11,000,512 B2
(45) Date of Patent: May 11, 2021

(54) USE OF DDX3 INHIBITORS AS ANTIPROLIFERATIVE AGENTS

(71) Applicant: AZIENDA OSPEDALIERA UNIVERSITARIA SENESE, Siena (IT)

(72) Inventors: Annalaura Brai, Siena (IT); Maurizio Botta, Siena (IT); Cristina Tintori, Siena (IT); Giovanni Maga, Pavia (IT)

(73) Assignee: AZIENDA OSPEDALIERA UNIVERSITARIA SENESE, Siena (IT)

( * ) Notice: Subject to any disclaimer, the term of this patent is extended or adjusted under 35 U.S.C. 154(b) by 0 days.

(21) Appl. No.: 16/086,791

(22) PCT Filed: Mar. 23, 2017

(86) PCT No.: PCT/EP2017/057010
§ 371 (c)(1),
(2) Date: Sep. 20, 2018

(87) PCT Pub. No.: WO2017/162834
PCT Pub. Date: Sep. 28, 2017

(65) Prior Publication Data
US 2019/0099403 A1  Apr. 4, 2019

(30) Foreign Application Priority Data
Mar. 24, 2016 (IT) .................. 102016000031124

(51) Int. Cl.
| | | |
|---|---|---|
| *A61K 31/7056* | (2006.01) | |
| *A61K 31/4192* | (2006.01) | |
| *A61K 31/18* | (2006.01) | |
| *A61K 31/4196* | (2006.01) | |
| *A61K 31/42* | (2006.01) | |
| *A61K 31/4245* | (2006.01) | |
| *A61K 31/433* | (2006.01) | |
| *A61K 31/5377* | (2006.01) | |
| *A61K 31/675* | (2006.01) | |
| *A61K 31/41* | (2006.01) | |
| *A61K 31/497* | (2006.01) | |
| *A61P 35/04* | (2006.01) | |
| *A61K 31/4439* | (2006.01) | |
| *A61K 31/4725* | (2006.01) | |
| *A61K 31/496* | (2006.01) | |
| *A61K 45/06* | (2006.01) | |

(52) U.S. Cl.
CPC .......... *A61K 31/4192* (2013.01); *A61K 31/18* (2013.01); *A61K 31/41* (2013.01); *A61K 31/4196* (2013.01); *A61K 31/42* (2013.01); *A61K 31/4245* (2013.01); *A61K 31/433* (2013.01); *A61K 31/4439* (2013.01); *A61K 31/4725* (2013.01); *A61K 31/496* (2013.01); *A61K 31/497* (2013.01); *A61K 31/5377* (2013.01); *A61K 31/675* (2013.01); *A61K 31/7056* (2013.01); *A61K 45/06* (2013.01); *A61P 35/04* (2018.01)

(58) Field of Classification Search
CPC ............ A61K 31/4192; A61K 31/5377; A61K 31/496; A61K 31/4725; A61K 31/4439; A61K 31/675; A61K 31/42; A61K 31/433; A61K 31/4245; A61K 31/4196; A61K 31/18; A61K 45/06; A61K 31/7056; A61P 35/04
USPC .......................................................... 514/25
See application file for complete search history.

(56) References Cited

U.S. PATENT DOCUMENTS 5,110,738 A * 5/1992 Takano .................. C07K 16/18
435/332

FOREIGN PATENT DOCUMENTS

| KR | 10-2014-0125117 A | | 10/2014 |
|---|---|---|---|
| KR | 2014125117 A | * | 10/2014 |
| KR | 20140125117 A | | 10/2014 |
| WO | 2004022529 A2 | | 3/2004 |
| WO | 2005090297 A1 | | 9/2005 |

(Continued)

OTHER PUBLICATIONS

Min et al.; KR 2014125117 A; Oct. 28, 2014 (English-Machine Translation).*

(Continued)

*Primary Examiner* — Shaojia A Jiang
*Assistant Examiner* — Michael C Henry
(74) *Attorney, Agent, or Firm* — Lucas & Mercanti, LLP

(57) ABSTRACT

The present invention refers to compounds of formula I or II endowed with DDX3 inhibitory activity, relative pharmaceutical compositions and their use as antihyperproliferative agents. (I) or (II).

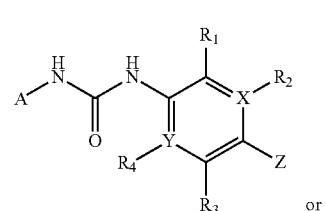

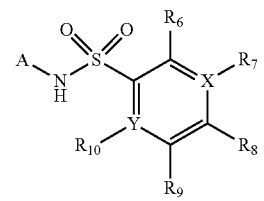

20 Claims, No Drawings

(56) References Cited

FOREIGN PATENT DOCUMENTS

| WO | WO-2006049941 A2 * | 5/2006 |
| WO | 2011161201 A1 | 12/2011 |
| WO | 2014038682 A2 | 3/2014 |
| WO | 2016128541 A1 | 8/2016 |

OTHER PUBLICATIONS

Ross et al.( Ann N Y Acad Sci. Dec. 2001;947:271-92; discussion 292-3).*
Asai et al. (Arteriosclerosis and Thrombosis (1993), 13(6), 892-9) (abstract sent).*
Sarnataro et al. (Mol Pharmacol 70:1298-1306, 2006).*
Bol et al. (Molecular Cancer (2015) 14:188).*
Shadrick et al. (Journal of Biomolecular Screening 18(7) 761-781).*
Wilky et al. (Oncogene (2016) 35, 2574-2583; published online Sep. 14, 2015).*
Hampton (JAMA, Jun. 22/29, 2005—vol. 293, No. 24, 2985-2989).*
Levitt et al. (Antiemetics in the Chemotherapy of Breast Cancer, vol. 328, No. 15, 1081-1084).*
Database WPI, Thomson Scientific, XP002764365, 2014, Week 201501, 4 Pages.
Fazi et al., "Homology Model-Based Virtual Screening for the Identification of Human Heiicase DDX3 Inhibitors", Journal of Chemical Information and Modeling, 2015, vol. 55, No. 11, pp. 2443-2454.
Radi et al., "Discovery of the first small molecule inhibitor of human DDX3 specifically designed to target the RNA binding site: Towards the next generation HIV-1 inhibitors, HIV-1 inhibitors", Bioorganic & Medicinal Chemistry Letters, 2012, vol. 22, No. 5, pp. 2094-2098.
Brai et al., "Human DDX3 protein is a valuable target to develop broad spectrum antiviral agents", PNAS, 2016, vol. 113, No. 19, pp. 5388-5393.
Prachayasittikul et al., "Discovery of novel 1,2,3-triazole derivatives asanticancer agents using QSAR and in silica structural modification", Springerplus, 2015, vol. 4:571, pp. 1-22.
Search Report for Corresponding Italian Application No. ITUA20161994 (9 pages) (Nov. 18, 2016).
International Search Report and Written Opinion for Corresponding International Application No. PCT/EP2017/057010 (16 Pages) (dated May 12, 2017).

* cited by examiner

USE OF DDX3 INHIBITORS AS ANTIPROLIFERATIVE AGENTS

CROSS-REFERENCE TO RELATED APPLICATIONS

This application is a 371 of PCT/EP2017/057010, filed Mar. 23, 2017, which claims the benefit of Italian Patent Application No. 102016000031124, filed Mar. 24, 2016.

FIELD OF THE INVENTION

The present invention refers to compounds with DDX3 inhibitory activity and their use as antihyperproliferative agents.

BACKGROUND ART

The cellular ATPase/RNA helicase X-linked DEAD-box polypeptide 3 (DDX3) is a human protein involved in several biological functions such as RNA metabolism (transcription, splicing, mRNA nuclear-cytoplasmatic export, translation), ribosome biogenesis, cell cycle regulation, apoptosis, Wnt-β-catenin signaling and anti-viral innate immune signaling pathways. On this bases, DDX3 could be an interesting target for the development of new drugs against viruses and neoplastic diseases.

The role of DDX3 in antiviral therapy has been extensively studied in the last years, in particular its implication in anti-HIV and anti-HCV infections. The first small molecule designed to inhibit the ATPase activity of DDX3 (FE15, Ki=5.4 μM) has been identified by Maga et al. in 2008. Interestingly, FE15 inhibited the replication of HIV-1 (IIIB) in MT4-cells with an $EC_{50}$ of 86.7 μm, without showing cytotoxicity ($CC_{50}$>200 μM in MOLT-4 T-lymphocytic). In the same year, Yedavalli et al. identified the ring expanded nucleosides REN as DDX3 ligands by means of a biological screening on a library of known NTPase/helicase inhibitors. REN derivatives were able to inhibit the ATP dependent activity of DDX3 and suppressed HIV-1 replication in T cells and monocyte-derived macrophages. In 2011, a protocol of hit optimization on FE15, led to the identification of a second-generation DDX3 inhibitors endowed with an improved activity profile (as an example FE109 showing a Ki of 0.2 μm). Furthermore, additional inhibitors were identified with a triazine scaffold, with the best one, FE87, which showed a Ki of 0.1 μm on DDX3, an $EC_{50}$ value of 2.0 μm in the inhibition of viral load of peripheral blood mononucleated cells (PBMCs) infected with HIV and a cytotoxicity of 20 μM in HeLa cells (Selectivity Index=10). However, even if some degree of selectivity has been found in in vitro experiments, the major drawbacks of such ATP-mimetics could be represented by a low selectivity in vivo Schutz et al., recently proposed a general mechanism for the opening of the RNA binding site. This observation, coupled with the presence of a conserved residue essential for the helicase activity, suggested that an inhibitor able to target this site could lock the DDX3 helicase in a catalytically inactive conformation. On this basis, the first inhibitors of HIV-1 replication specifically designed to target the DDX3 RNA binding site have been discovered in 2012. Among them, EI01D showed the best activity value being endowed with an $EC_{50}$ of 10 μM in the inhibition of viral load of PBMCs infected with HIV. In 2015 Fazi et al. developed a model of hDDX3 in its closed conformation, which binds the viral RNA. Through a structure-based virtual screening protocol authors identified compound 14, endowed of an $IC_{50}$ of 0.36 μM.

In 2015, Venu and co-workers discovered a new REN analogue named RK-33 as anticancer therapeutic agent (active against prostate cancer, lung cancer and breast cancer). Several RK-33 analogues endowed of multiple anticancer activities have been reported. Simultaneously Botlagunta et al. demonstrated that Ketorolac salt is able to inhibit DDX3 activity and studied this compound in a preclinical oral cancer model.

The DDX3 Family of RNA Helicases

DEAD-box helicases are involved in all aspects of RNA metabolism. Their role is thought to be the unwinding of RNA, i.e. the removal of secondary structure motifs, the unwinding of short RNA-RNA interactions and also the removal of RNA-bound proteins (Yang et al., 2006), DDX3 is an ATPase/RNA helicase containing all nine conserved motifs that characterize the members of the RNA helicase superfamily, including the eponymous Asp-Glu-Ala-Asp (D-E-A-D) motif, within a structurally conserved core element forming two RecA-like domains. The conserved helicase motifs are involved in ATP binding, ATPase activity, RNA substrate binding and unwinding (Linder et al., 2004). The crystal structure of DDX3 shows that these conserved motifs are found in two subdomains connected via a short flexible linker. DDX3 contains a nuclear export signal (NES) at its N-terminus. The amino-terminal domain 1 contains the ATP binding Motifs Q, I (Walker A) and II (Walker B), and the RNA-binding Motifs Ia, Ib and the Motif III. The RNA-binding Motifs IV, V and Motif VI, which may coordinate ATPase and unwinding activities, are found in the carboxyl-terminal domain 2.

Cellular Roles of DDX3

DDX3 is involved in different cellular metabolic pathways. Recent evidence suggests that DDX3 is involved in mRNA nuclear export in association with two other shuttle proteins CRM1 and TAP. The proposed mechanism is that DDX3 binds either mRNAs and TAP in the nucleus and subsequently helps to facilitate mRNPs export to the cytoplasm. The interaction with CRM1 seems to be important only for the export of unspliced or incompletely spliced RNAs of HIV (Kohler A, et al., 2007). DDX3 interacts with translation initiation factors eIF4E, eIF4A, eIF4G, PABP and eIF3. Recently Marsden and coworkers, demonstrated a role for DDX3 in enhancing translation of a specific subset of cellular and viral mRNAs carrying specific structural features within their 5'-UTRs.

These RNA structures must be located immediately adjacent to the cap structure to be unwound by DDX3 in order to prepare the mRNA for ribosome binding.

DDX3 and Transcription Regulation

DDX3 downregulates E-Cadherin (Botlagunta et al., 2008) and stimulates interferon (IFN) and p21 expression by interacting with their respective promoters (Schroder et al., 2008). The DDX3 effect on IFN promoter is independent of its ATPase activity or unwinding function, while the ATPase function is required for p21 promoter stimulation.

Cellular Proliferation

DDX3 possesses multiple cellular activities, it seems to be involved in cell cycle progression, apoptosis, hypoxia. Several publications highlight the potential role of DDX3 as oncogene and onco-suppressor, unfortunately, its exact role is actually unknown.

Knockdown of DDX3, along with overexpression of the oncogene v-Ras, led to premature S-phase entry and enhanced the cellular transformation phenotype of murine fibroblast NIH3T3 cells (Chang et al., 2006). Botlagunta and coworkers found that elevated DDX3 levels are correlated with a more aggressive phenotype of breast cancer cell lines. As investigated by Xie and co-workers, DDX3 is overexpressed in multiple breast cancer cell lines and its expression levels are directly correlated to cellular aggressiveness. In addition Bol et al. found that knockdown of DDX3 by shDDX3 caused cell cycle alterations, and resulted in a G1 phase arrest.

A recent study of Chenn et al. elucidate the role of DDX3 in Wnt-type tumours such as medulloblastoma. In detail they found that small interfering RNA-mediated DDX3 knockdown in various cell lines increased cell-cell adhesion but decreased cell-extracellular matrix adhesion. Moreover, DDX3 depletion suppressed cell motility and impaired directional migration in the wound-healing assay. DDX3 knockdown reduced the levels of both Rac1 and β-catenin proteins, and consequentially downregulated the expression of several β-catenin target genes. In addition Sun and co-workers demonstrated that DDX3 may aid cancer progression by promoting increased levels of the transcription factor Snail that causes the progression of several cancers including Glioblastoma and Prostate cancer.

DDX3 is also involved in the progression of Ewing sarcoma, as demonstrated by Wilky et al. They found high expression of DDX3 in numerous human sarcoma subtypes, and knockdown of DDX3 inhibited oncogenic activity in Ewing sarcoma cells.

The role of DDX3 in lung cancer and colorectal cancer was explored by Bol et al. that analysed DDX3 expression and found that the small molecule RK-33 active in preclinical in vivo studies.

The role of DDX3 in HCC is still under debate. DDX3 expression was found to be downregulated in HCC cells derived from hepatitis B virus (HBV)-infected patients (Chao, et al., 2006). On the contrary, Huang found elevated DDX3 mRNA levels in the majority (64%) of a representative set of HCC samples. Thus, whether DDX3 acts as an oncogene or a tumour suppressor is still debated. RNAi-mediated inhibition of DDX3 expression in HEK293 and PBMC cells, consistently failed to reveal any deleterious effect on cell proliferation or viability. These results suggest that DDX3 functions in cell proliferation are either not essential, or they take place only in the context of altered cell metabolism, such as tumour transformation or viral infections.

Wnt/β Catenin Signaling

Wnt signaling pathways are involved for its role in carcinogenesis and embryonic development. The canonical Wnt pathway is responsible for accumulation of β catenin in the cytoplasm and its consequent translocation into the nucleus where the protein acts as a transcriptional coactivator. In 2013 Cruciat et al. found that DDX3-CK1ε binding stimulates CK1ε phosphorylation with consequent activation of β-catenin. A recent paper (Chen et al. 2014) investigates the role of DDX3 in the regulatory axis Rac1-Wnt/β catenin. Up regulation of Rac-1 mRNA translation by DDX3 increase β-catenin signaling and causes cytoskeleton remodelling.

Hypoxia

Hypoxia is a feature of many different tumours and recovered a central role in cancer progression and in the resistance to the therapy. The angiogenesis represents an adaptive mechanism to the low oxygen concentration and it is induced by the transcription factor HIF-1. In 2011 Botlagunta et al. reported that DDX3 is an hypoxia inducible gene, in facts HIF-1α binds the DDX3 promoter and enhances DDX3 expression. In 2013 Bol and coworkers observed the correlation of DDX3 expression and proteins related to HIF-1α.

Cell Cycle Regulation

DDX3 is involved in the cell cycle progression. Fukumura and coworkers reported that the transition from G1 to S-phase is blocked in DDX3 knockdown cells. This effect is due to the translation of cyclin E1 mRNA translation as previously observed by Lai et al.

Different results were reported by Chao et al. in 2006, in facts DDX3 inhibits cyclin D1 and causes cell cycle arrest. Moreover DDX3 seems to be involved in the p53-p21 regulation, responsible to reduce cell cycle progression (Lee et al.).

Apoptosis

DDX3 is also able to inhibit apoptotic signaling. Sun et al. reported that DDX3 acts as antiapoptotic protein through the formation of a complex with the death receptors GSK3 and cIAP-1. In contrast Chang and coworkers reported that loss of DDX3 enhance cell proliferation and reduced apoptosis, as well as p53 inactivation of DDX3 led to tumour malignancy via MDM2/Slug/E-cadherin pathway (Wu et al. 2014).

SUMMARY OF THE INVENTION

The present invention provides a new class of compounds able to treat hyperproliferative disorders through the inhibition of the enzymatic functions of the cellular protein DDX3 namely DNA/RNA unwinding (helicase).

The compounds presented in this invention (Formula I and II) showed the ability to selectively suppress the enzymatic activity of DDX3 in vitro. They are then particularly suitable for the treatment of cancer, more specifically for the treatment of Breast cancer; Human cervical carcinoma; Human Glioblastoma; Human Prostate Adenocarcinoma; Human Neuroblastoma; Human Hepatoblastoma; Testicular Cancer; Oral Cancer; Lung Cancer; Colorectal Cancer; glioblastoma multiforme, head and neck squamous carcinoma, muscle rhabdomyo sarcoma, osteosarcoma.

The present invention provides a compound of formula:

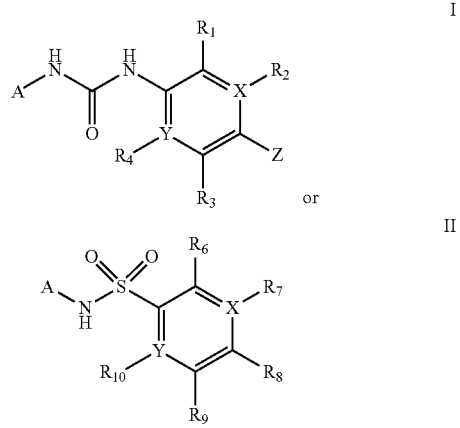

for use in the treatment and/or prevention of a hyperproliferative disorder wherein X and Y are each independently C or N;

A is unsubstituted or substituted aryl or unsubstituted or substituted heteroaryl, wherein the one or more substituents on the aryl or heteroaryl are independently selected from unsubstituted or substituted $C_1$-$C_6$ alkyl, unsubstituted or substituted $C_2$-$C_6$ alkenyl, unsubstituted or substituted $C_2$-$C_6$ alkynyl, haloalkyl, halogen, $OR_A$, $SR_A$, $S(=O)(=O)$—$R_A$, $SO_2NHR_A$, $COOR_B$, $OC(O)R_B$, $C(O)R_B$, $NR_AR_B$, $OP(O)(OR_A)_2$, $NHC(O)R_A$, $COONR_AR_B$, OS or

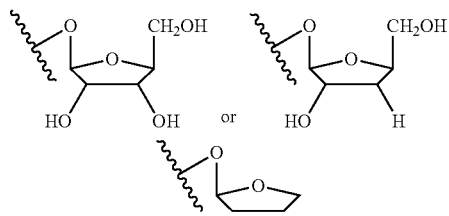

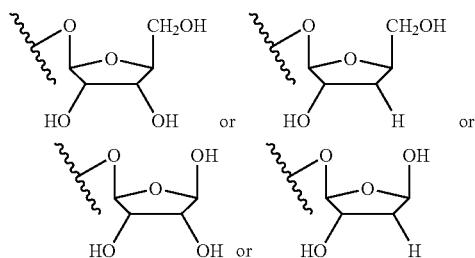

wherein the one or more substituents on the $C_1$-$C_6$ alkyl or on the $C_2$-$C_6$ alkenyl or on the $C_2$-$C_6$ alkynyl are independently selected from $OR_A$, $COOR_B$, $OC(O)R_B$, $C(O)R_B$, $NR_AR_B$, $OP(O)(OR_A)_2$, $NHC(O)R_A$, $NHC(O)OR_A$, $COONR_AR_B$, $SR_A$, $S(=O)(=O)$—$R_A$, $SO_2NHR_A$;

$R_1$, $R_2$, $R_3$, $R_4$, $R_6$, $R_7$ and $R_{10}$ are each independently selected from H, halogen, alkoxy, $C_1$-$C_6$ alkyl, haloalkyl, $OR_A$, $SR_A$, $S(=O)(=O)$—$R_A$, $SO_2NHR_A$, $COOR_B$, $OC(O)R_B$, $NR_AR_B$, $OP(O)(OR_A)_2$, $NHC(O)R_A$, $COONR_AR_B$, $NO_2$, CN;

Z is a heteroaryl group selected from:

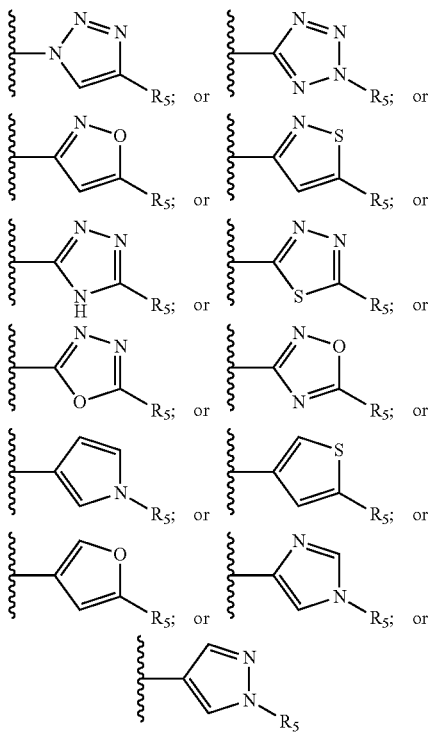

wherein $R_5$ is H, unsubstituted or substituted $C_1$-$C_{10}$ alkyl, unsubstituted or substituted phenyl, wherein the one or more substituents on the $C_1$-$C_{10}$ alkyl are independently selected from halogen, $OR_A$, $COOR_B$, $OC(O)R_B$, $NR_AR_B$, $OP(O)(OR_A)_2$, $OC(O)NR_AR_B$, $C(O)R_B$, $NHC(O)OR_A$, $NHC(O)R_A$, $COONR_AR_B$, $OC(O)CHCHR_C$, $R_A$ and $R_B$ are each independently selected from H, substituted or unsubstituted $C_1$-$C_6$ alkyl, $C_1$-$C_6$ cycloalkyl, unsubstituted or substituted aralkyl, haloalkyl, or $R_A$ and $R_B$ together with the nitrogen to which they are attached, form a 4-7 membered saturated or partially unsaturated ring optionally containing one or more additional heteroatoms independently selected from N, S and O the ring being optionally substituted by one, two or more groups independently selected from halogen, $C_1$-$C_6$ alkyl, haloalkyl, OH, alkoxy;

$R_C$ is substituted or unsubstituted phenyl, 1,3 benzodioxolyl, wherein the one or more substituent(s) on the phenyl are independently selected from halogen, haloalkyl, alkoxy, $C_1$-$C_3$ alkyl, or OH;

wherein the one or more substituents on the phenyl are independently selected from halogen, haloalkyl, alkoxy, $C_1$-$C_3$ alkyl, OH;

$R_8$ and $R_9$ are each independently selected from H, halogen, alkoxy, COOH, nitro and at least one of $R_8$ and $R_9$ is a heteroaryl group selected from:

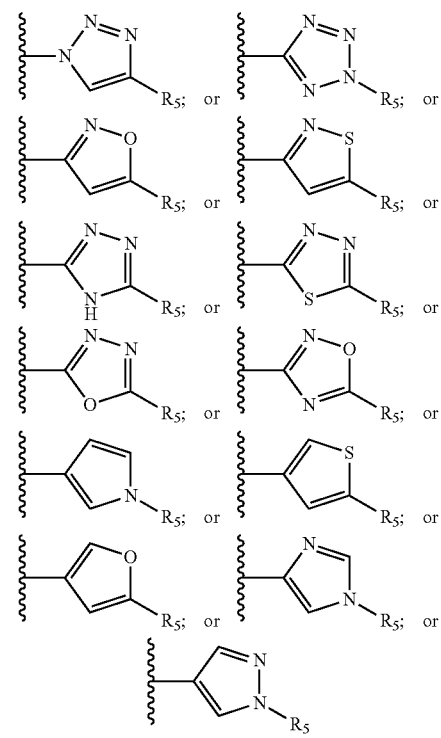

or salt, solvate, stereoisomer thereof, provided that compounds:

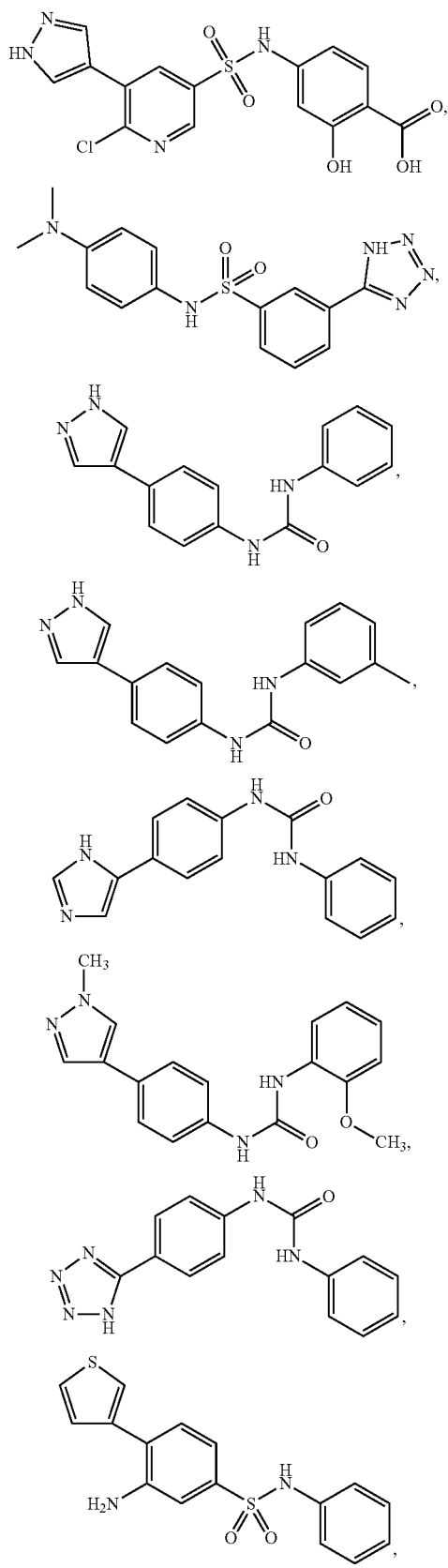

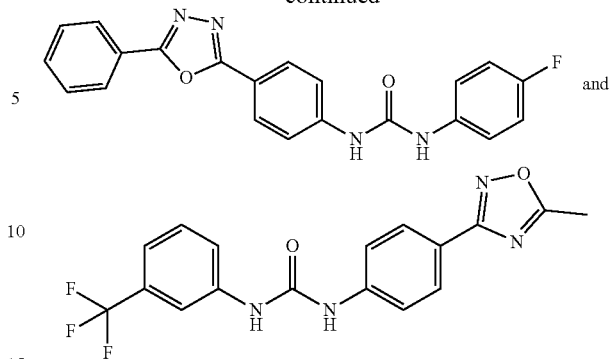

are excluded.

Preferably X and Y are C. Preferably A is substituted aryl. Preferably the substituted aryl is phenyl. Preferably the phenyl is substituted by one, two or more groups independently selected from methyl, isopropyl, $CF_3$, F, Cl, OH, OMe.

Preferably A is unsubstituted or substituted heteroaryl. Preferably the substituted heteroaryl is pyridinyl or isoquinolinyl.

Preferably X and Y are C and A is unsubstituted or substituted heteroaryl, preferably the heteroaryl is pyridinyl or isoquinolinyl, preferably the pyridinyl or isoquinolinyl are substituted by one, two or more groups independently selected from methyl, isopropyl, $CF_3$, F, Cl, OH, OMe.

Preferably $R_A$ and $R_B$ together with the nitrogen to which they are attached, form a 6 membered saturated ring containing one or more additional heteroatoms independently selected from N and O the ring being selected from morpholinyl or piperazinyl optionally substituted by one, two or more groups independently selected from $C_1$-$C_6$ alkyl, haloalkyl, OH, alkoxy.

Still preferably Z is selected from:

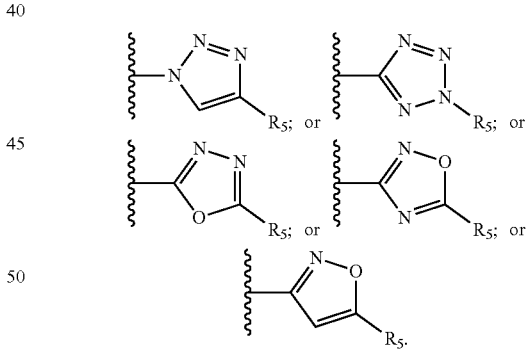

In a preferred embodiment the compound of the invention is of formula I wherein Z is selected from:

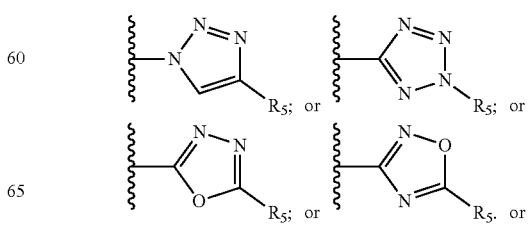

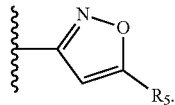

and $R_5$ is butyl, tert-butyl, methyl, ethyl, isopentyl, n-hexanyl, phenyl, $CH_2OH$, $CH_2CH_2OH$, $CH_2CH_2OCH_3$, $CH_2OCH_2CH_3$, $CHOHCH(CH_3)(CH_2CH_2CH_3)$, $CH_2CH_2COOH$, $CH_2CH_2CH_2N(CH_3)_2$, $CH_2NR_AR_B$, $CH_2CH_2NR_AR_B$, $CH_2CH_2CH_2NR_AR_B$, $CH_2CH_2N(CH_3)CH_2C_6H_5$, $CH_2CH_2OP(O)(OCH_3)_2$, $CH_2CH_2OC(O)CHCH$-(benzo[d][1,3]dioxol-5-yl), $CH_2CH_2OC(O)CH_2CH(CH_3)_2$, $C_4F_9$, $CH_2CH_2CH_2F$ or $CHFCH(CH_3)(CH_2CH_2CH_3)$ or

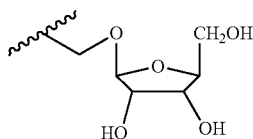 [SMILES: *COC1OC(CO)C(O)C1O]

$R_A$ and $R_B$ together with the nitrogen to which they are attached, form a 6 membered saturated ring selected form:

morpholinyl piperazinyl optionally substituted by one, two or more groups independently selected from $C_1$-$C_6$ alkyl, haloalkyl, OH, alkoxy.

Preferably the compound of the invention is of formula I wherein Z is selected from:

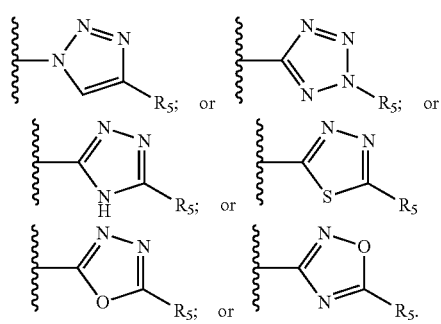

and A is phenyl, pyridinyl or isoquinolinyl, preferably each independently substituted by one, two or more groups independently selected from methyl, isopropyl, $CF_3$, F, Cl, OH or OMe, and $R_5$ is butyl, tert-butyl, methyl, ethyl, isopentyl, n-hexanyl, phenyl, $CH_2OH$, $CH_2CH_2OH$, $CH_2CH_2OCH_3$, $CH_2OCH_2CH_3$, $CHOHCH(CH_3)(CH_2CH_2CH_3)$, $CH_2CH_2COOH$, $CH_2CH_2CH_2N(CH_3)_2$, $CH_2NR_AR_B$, $CH_2CH_2NR_AR_B$, $CH_2CH_2CH_2NR_AR_B$, $CH_2CH_2N(CH_3)CH_2C_6H_5$, $CH_2CH_2OP(O)(OCH_3)_2$, $CH_2CH_2OC(O)CHCH$-(benzo[d][1,3]dioxol-5-yl), $CH_2CH_2OC(O)CH_2CH(CH_3)_2$, $C_4F_9$, $CH_2CH_2CH_2F$, $CHFCH(CH_3)(CH_2CH_2CH_3)$, or

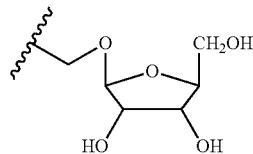 [SMILES: *COC1OC(CO)C(O)C1O]

$R_A$ and $R_B$ together with the nitrogen to which they are attached, form a 6 membered saturated ring selected form:

morpholinyl piperazinyl optionally substituted by one, two or more groups independently selected from $C_1$-$C_6$ alkyl, haloalkyl, OH, alkoxy, and X and Y are C, and $R_1$, $R_3$, $R_4$ are H, and $R_2$ is H, F or OMe.

Preferably the compound of the invention has formula II wherein one of $R_8$ or $R_9$ is selected from:

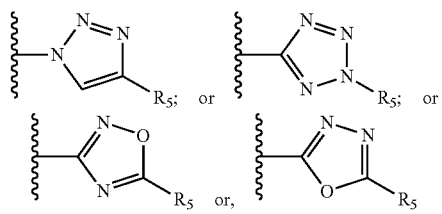

and the other one of $R_8$ or $R_9$ is H.

Preferably the compound of the invention has formula II wherein one of $R_8$ or $R_9$ is selected from:

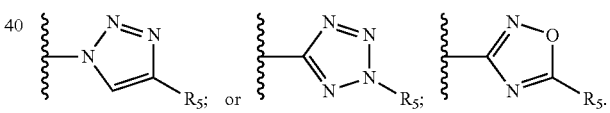

and the other one of $R_8$ or $R_9$ is H, and A is phenyl, preferably substituted by methyl, isopropyl, $CF_3$, F, Cl, OH or OMe.

Preferably the compound of the invention has formula II wherein one of $R_8$ or $R_9$ is selected from:

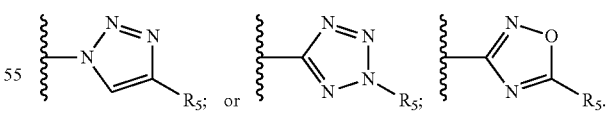

and the other one of $R_8$ or $R_9$ is H, and A is phenyl, preferably substituted by methyl, isopropyl, $CF_3$, F, Cl, OH, or OMe, and $R_5$ is H, butyl, isopentyl or $CH_2OCH_2CH_3$, and X and Y are C, and $R_6$, $R_7$ and $R_{10}$ are H.

Preferably the compound of the invention has formula II wherein one of $R_8$ or $R_9$ is selected from:

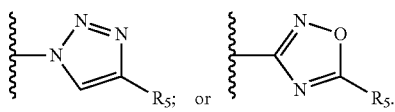

and the other one of $R_8$ or $R_9$ is H,
and A is phenyl, preferably substituted by methyl, isopropyl, $CF_3$, F, Cl, OH or OMe,
and $R_5$ is H, butyl, isopentyl or $CH_2OCH_2CH_3$,
and X and Y are C,
and $R_6$, $R_7$ and $R_{10}$ are H.

Preferably the compound of the invention has formula II wherein one of $R_8$ or $R_9$ is selected from:

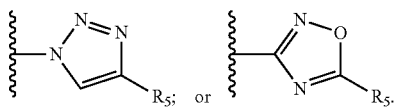

and the other one of $R_8$ or $R_9$ is H,
and A is isoquinolinyl
and $R_5$ is H, butyl, isopentyl or $CH_2OCH_2CH_3$,
and X and Y are C,
and $R_6$, $R_7$ and $R_{10}$ are H.

Preferably the compound of the invention has formula II wherein one of $R_8$ or $R_9$ is selected from:

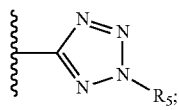

and the other one of $R_8$ or $R_9$ is H,
and A is phenyl, preferably substituted by methyl, isopropyl, $CF_3$, F, Cl, OH or OMe,
and $R_5$ is H,
and X and Y are C,
and $R_6$, $R_7$ and $R_{10}$ are H.

In a preferred embodiment the compound of the invention for medical use has formula II wherein $R_8$ and $R_9$ are each independently selected from H, halogen, alkoxy, COOH, and at least one of $R_8$ or $R_9$ is nitro or heteroaryl group selected from:

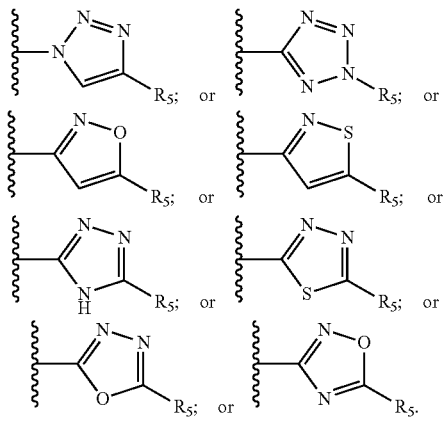

Preferably the compound of the invention for medical use has formula II wherein one of $R_8$ or $R_9$ is nitro.

Preferably the compound of the invention for medical use has formula II wherein $R_8$ is nitro and $R_9$ is H or $R_8$ is H and $R_9$ is nitro and A is phenyl, preferably substituted by methyl, isopropyl, $CF_3$, F, Cl, OH, or OMe.

Preferably the compound of the invention for medical use has formula II wherein $R_8$ is nitro and $R_9$ is H or $R_8$ is H and $R_9$ is nitro and A is phenyl, preferably substituted by methyl, isopropyl, $CF_3$, F, Cl, OH, or OMe,
and X and Y are C,
and $R_6$, $R_7$ and $R_{10}$ are H.

Preferably the compound is selected from:

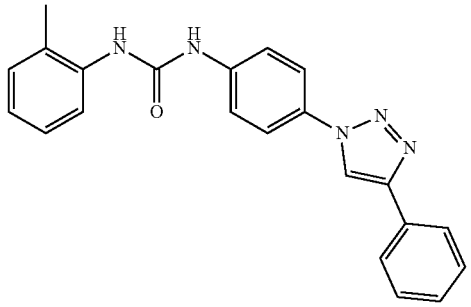

8a

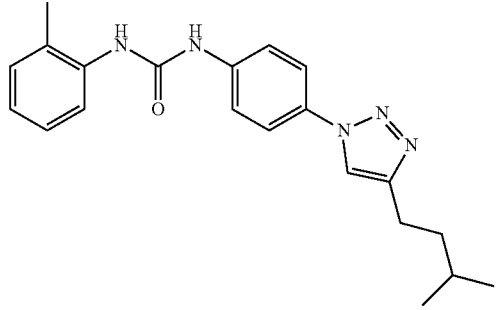

20b

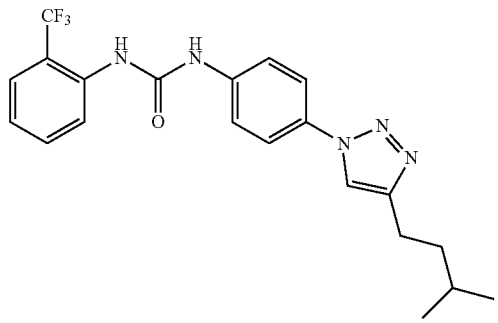

22b

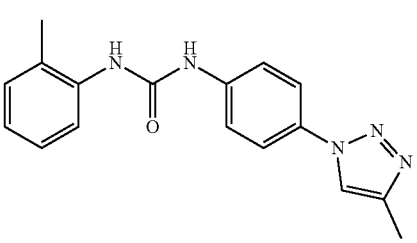

8f

-continued

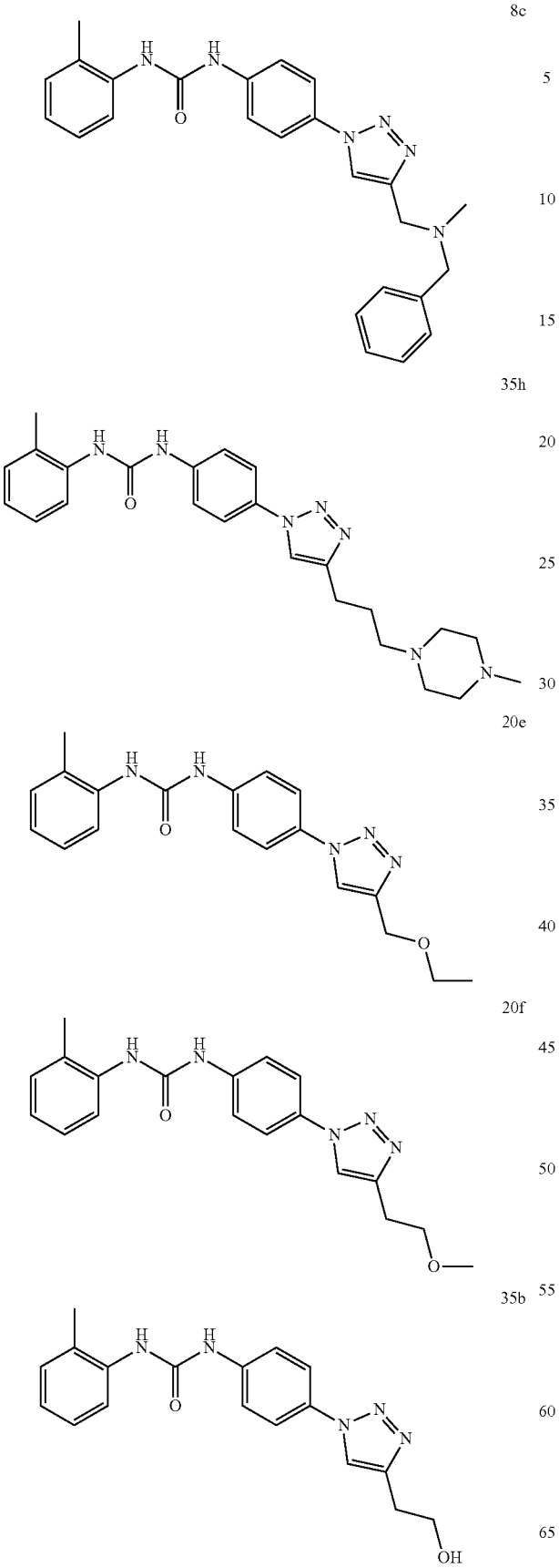
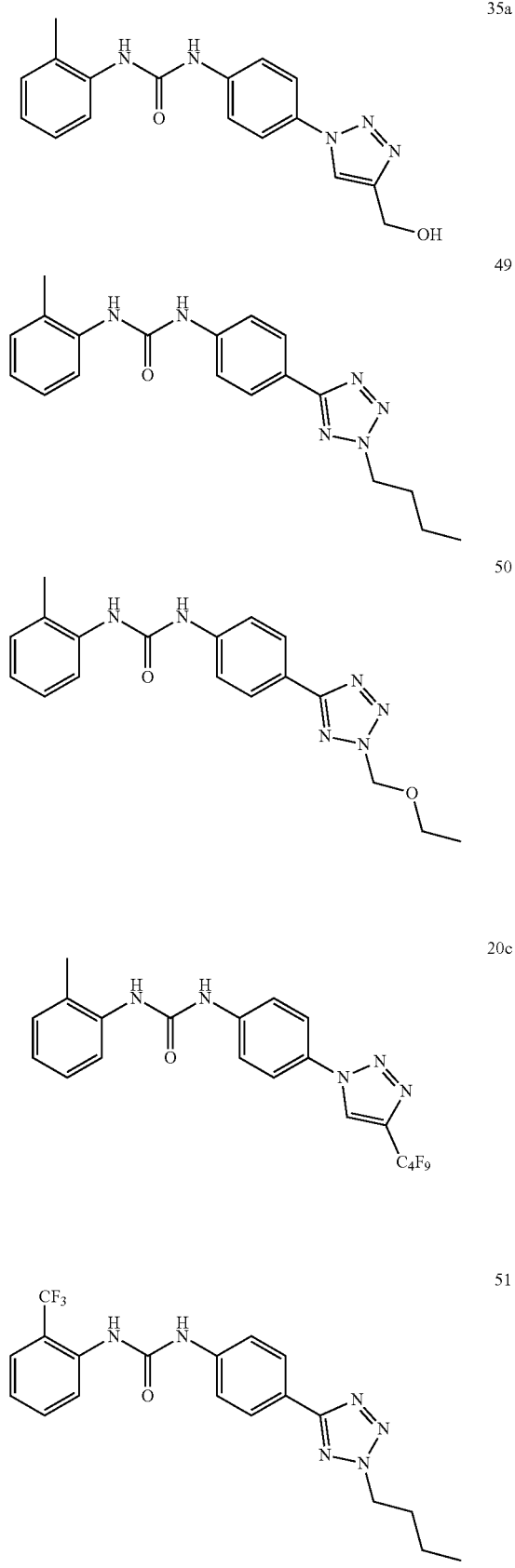

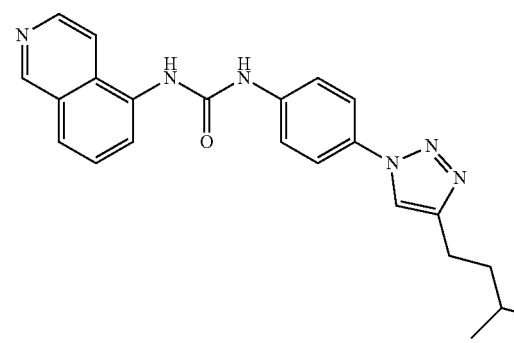
55f
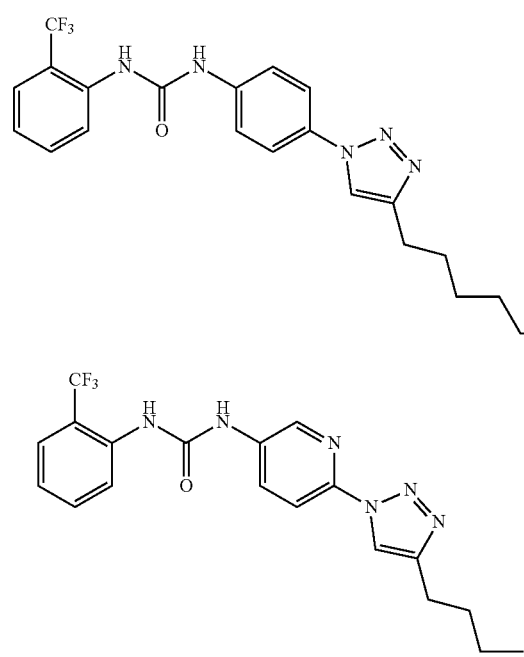
8d
86
42b
81
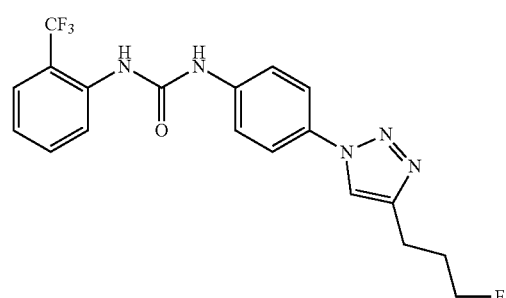
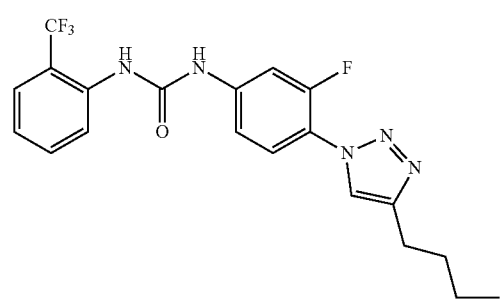
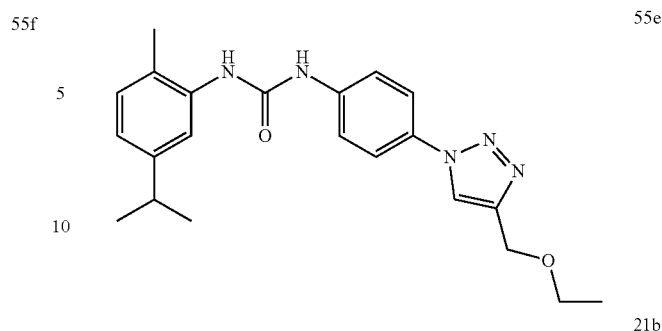
55e
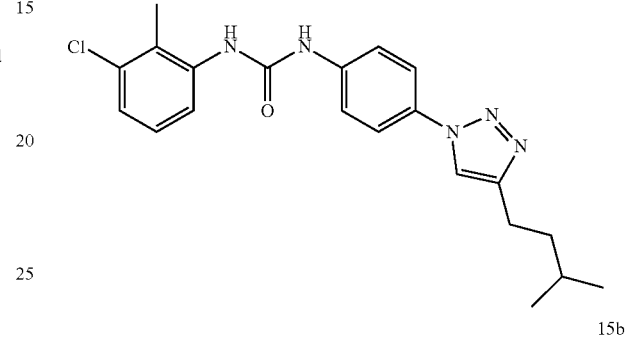
21b
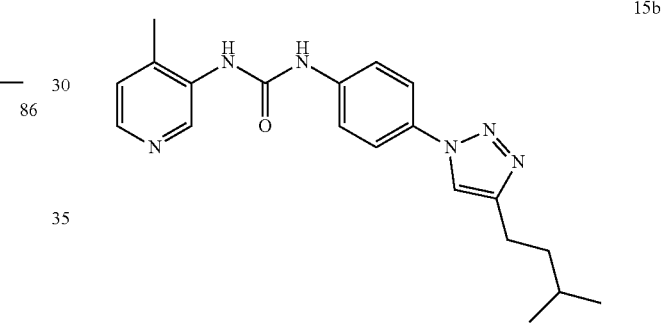
15b
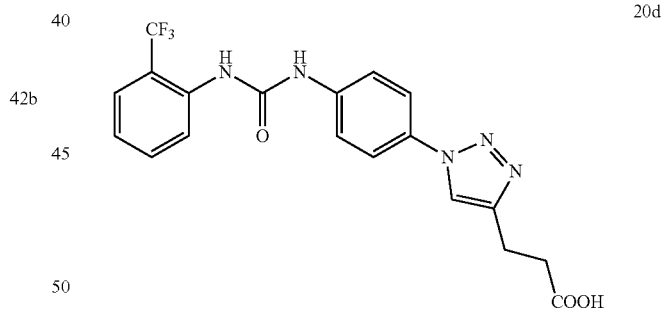
20d
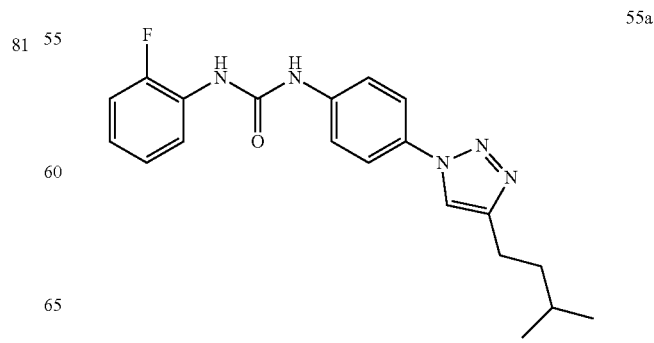
55a

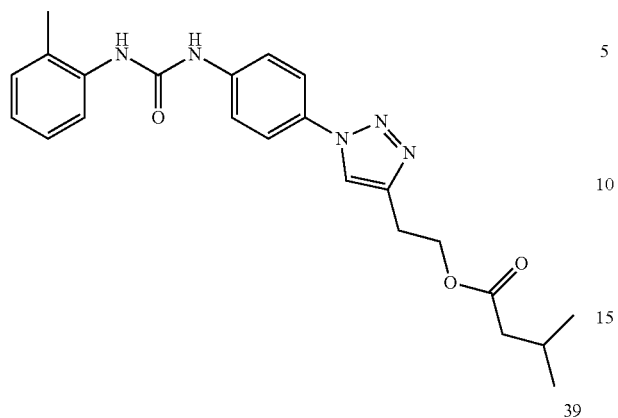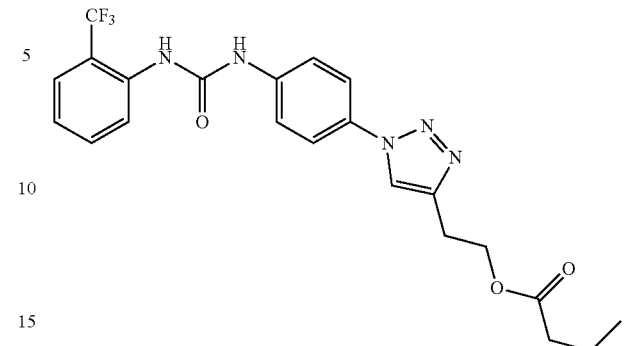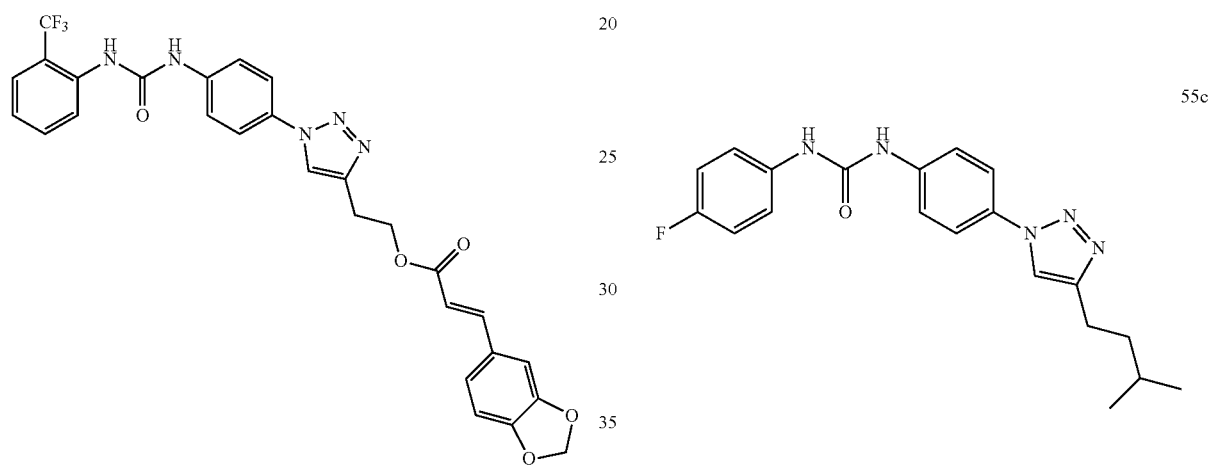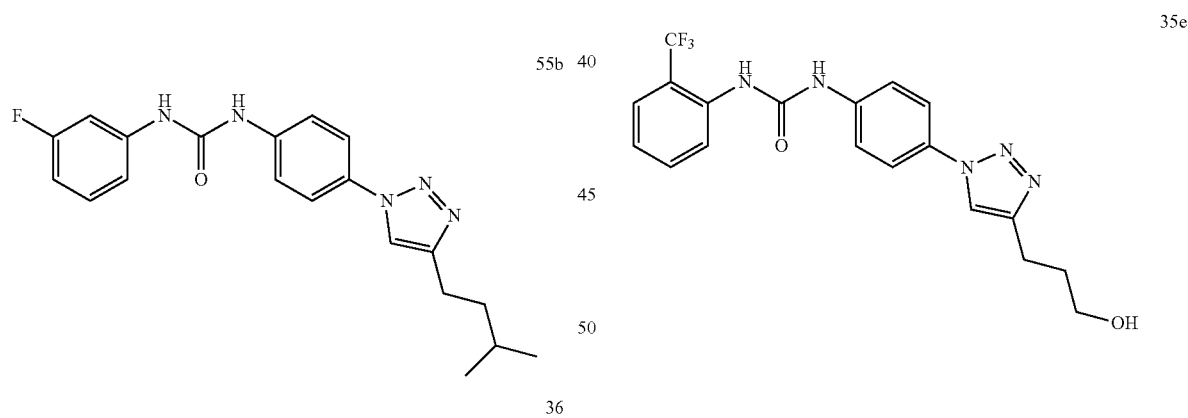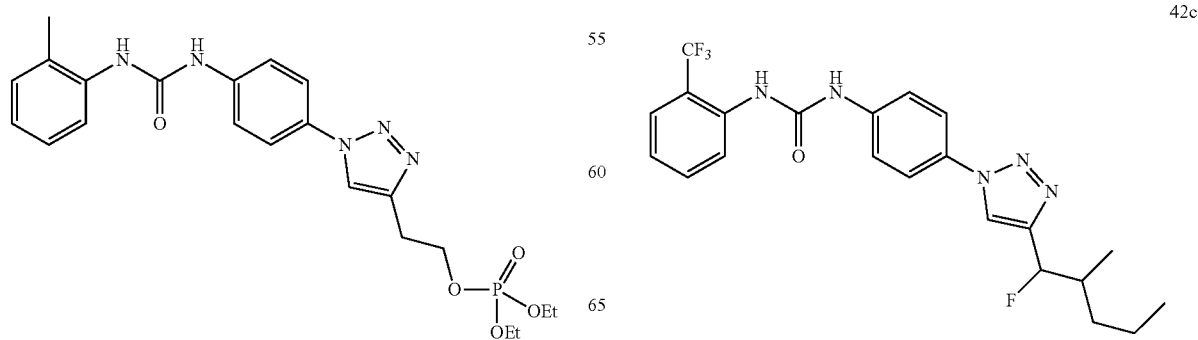

-continued
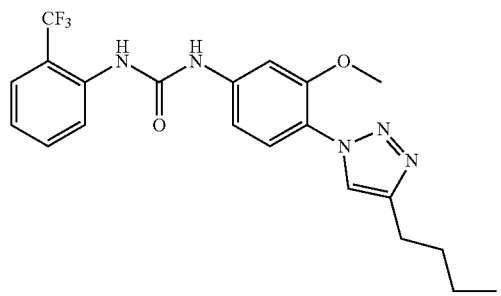
78
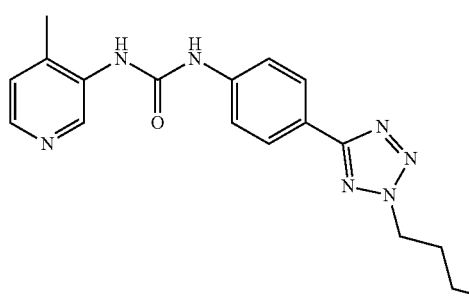
52
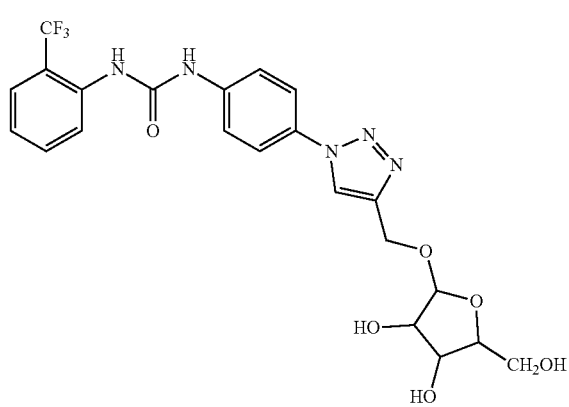
22g
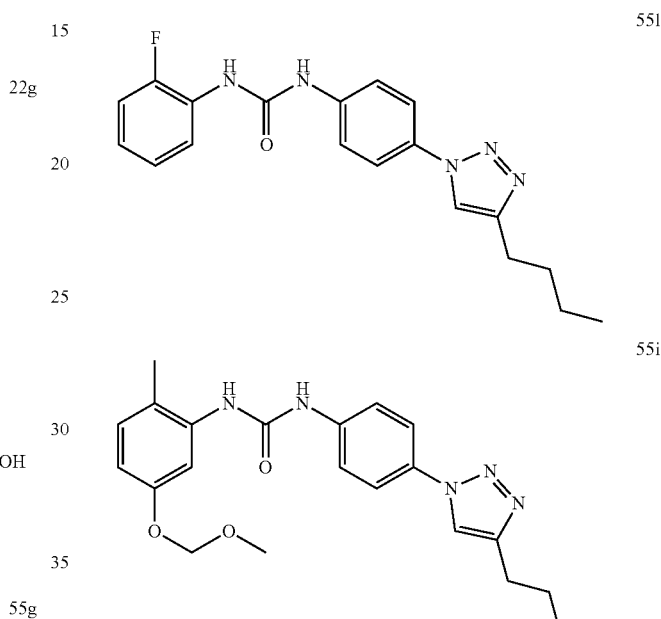
55l
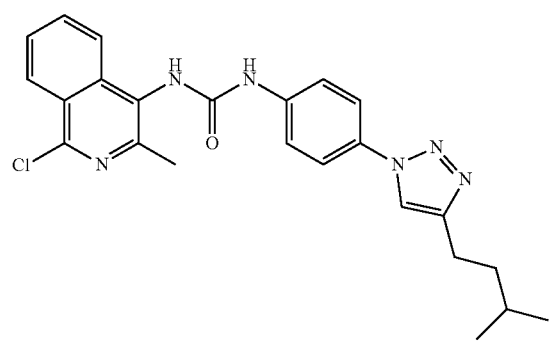
55g
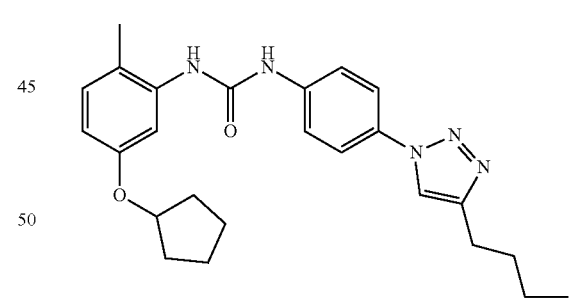
55i
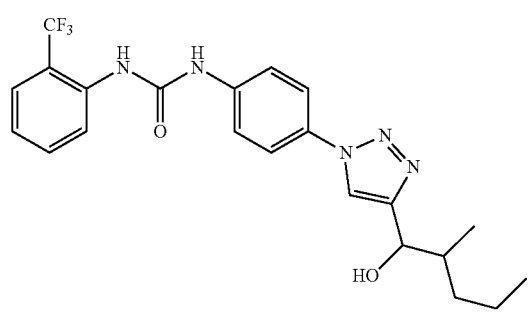
35d
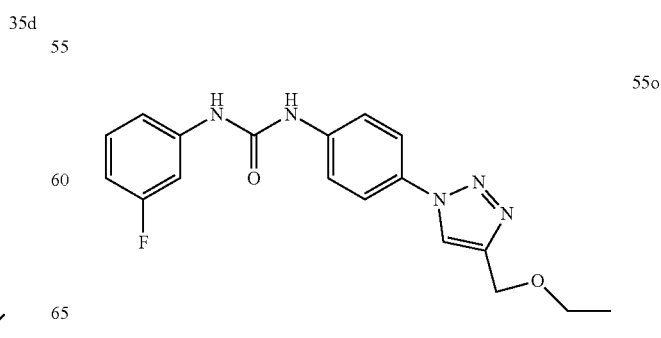
55h
55o

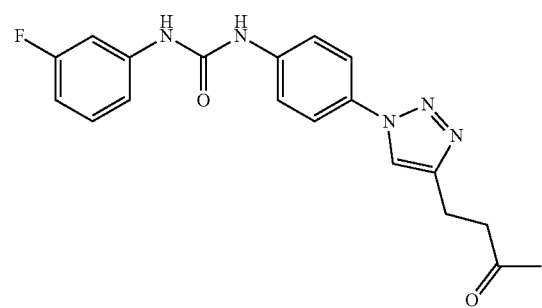
55n
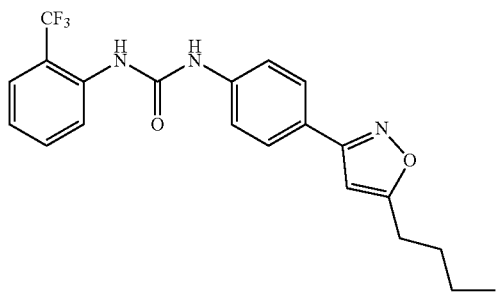
102
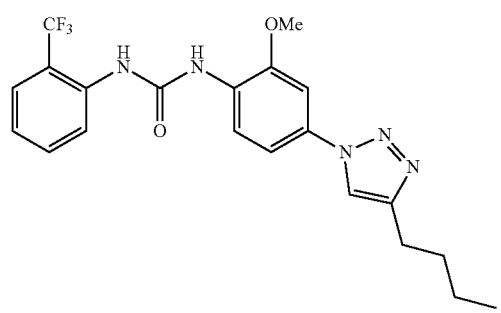
55m
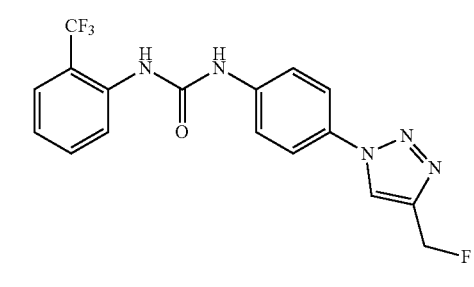
42a
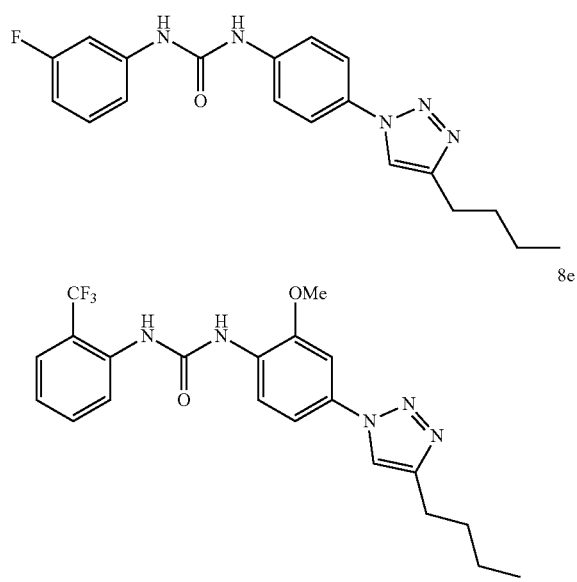
8e
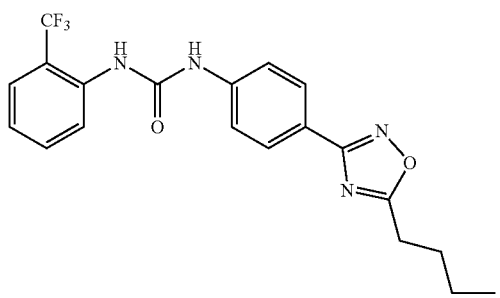
106
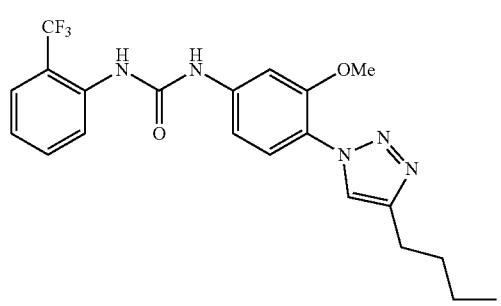
81
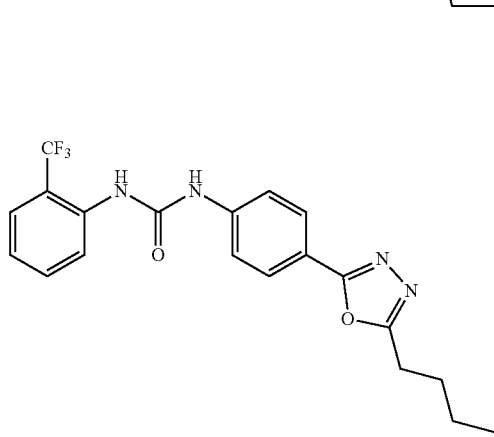
112
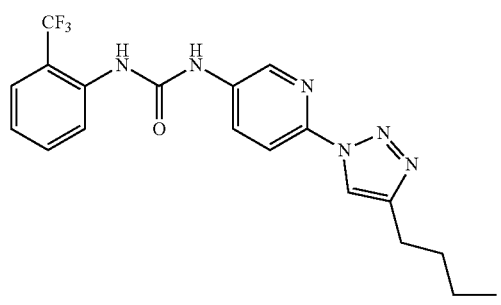
51
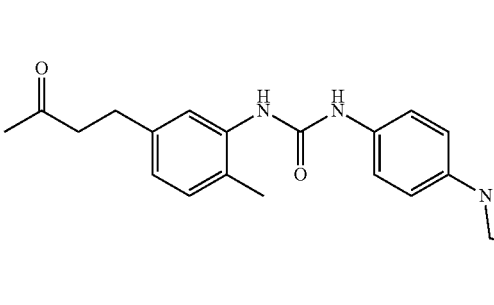
55p

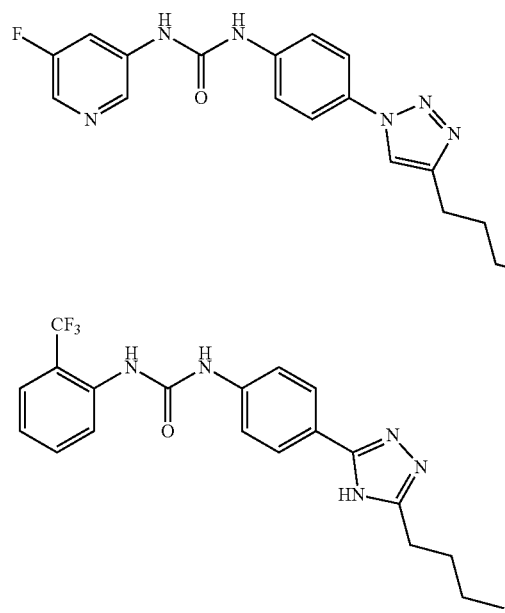
55q
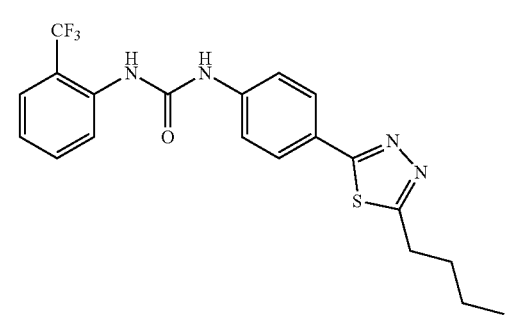
119
124
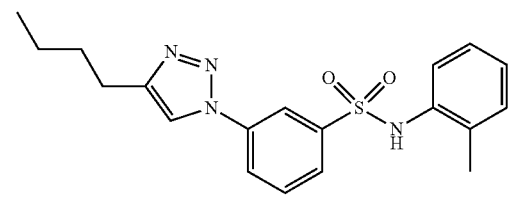
64a
64c
64d
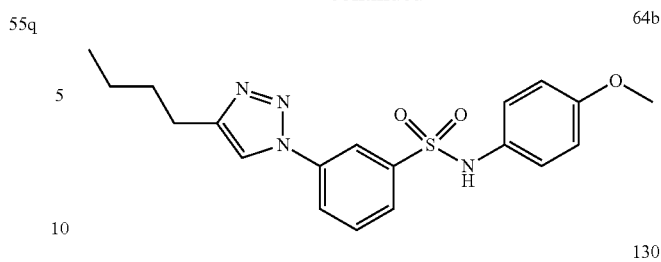
64b
130
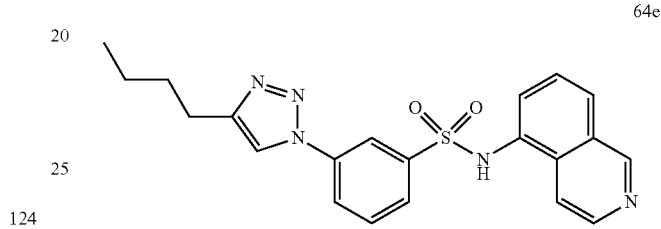
64e
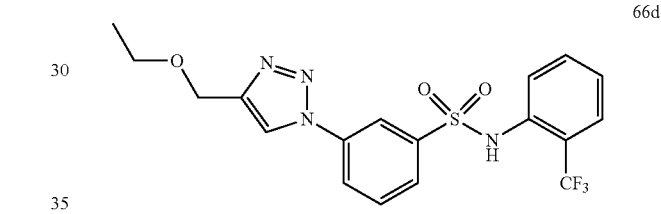
66d
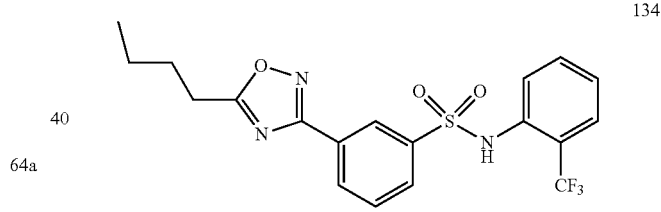
134
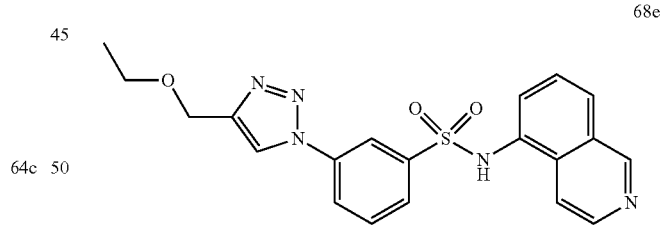
68e
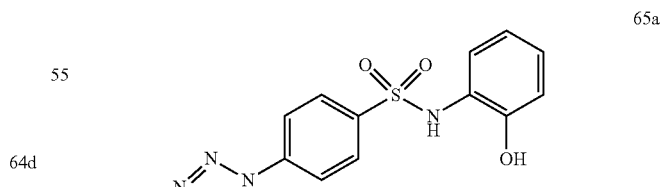
65a

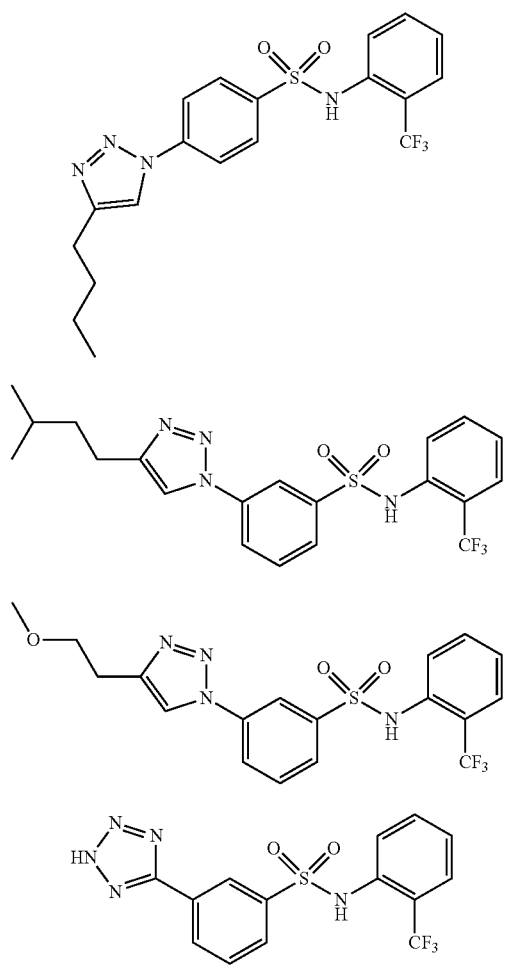
or salt, solvate, stereoisomer thereof.
Still preferably the compound is selected from:
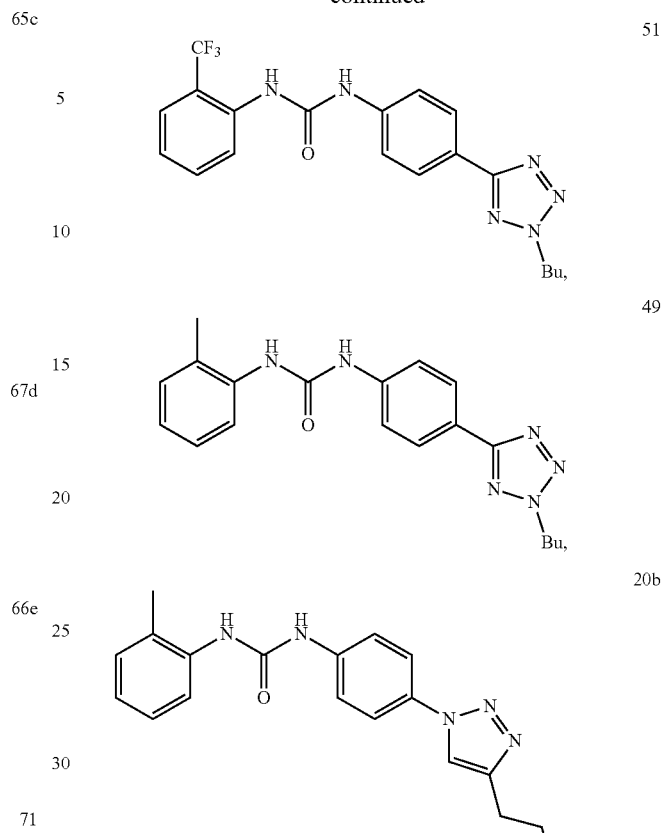
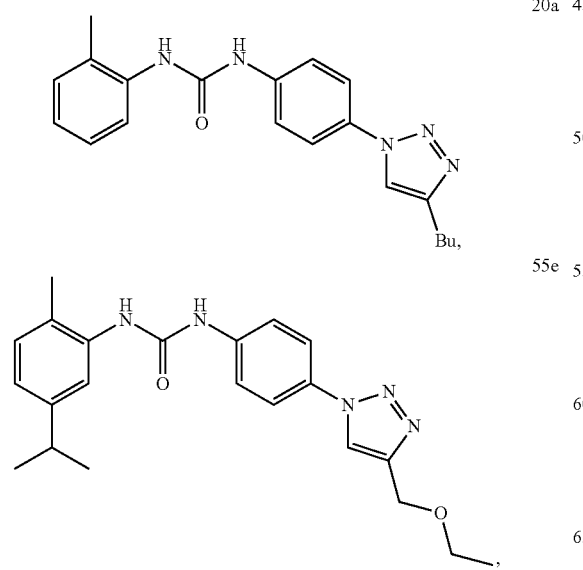
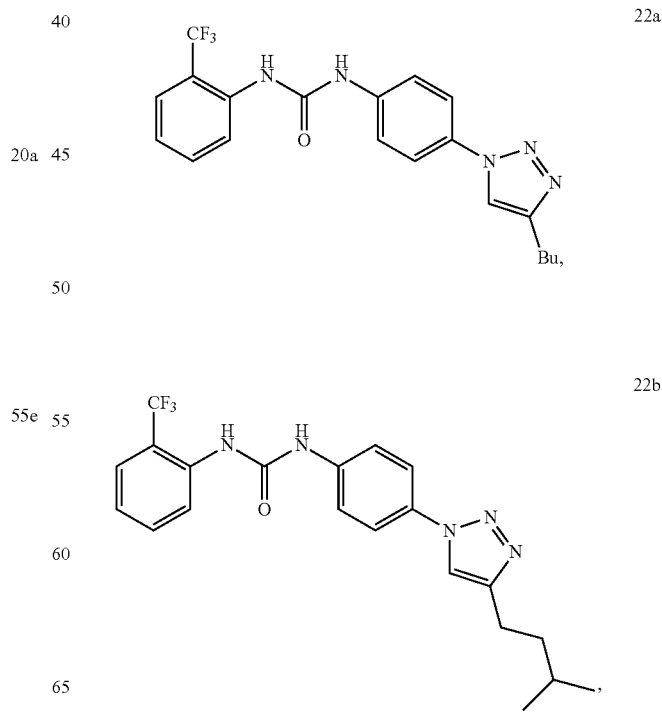

20e
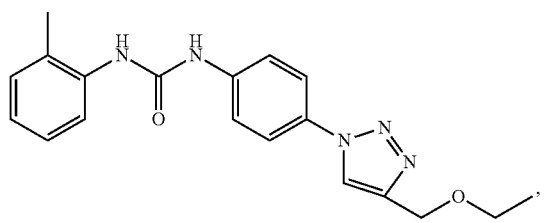
81
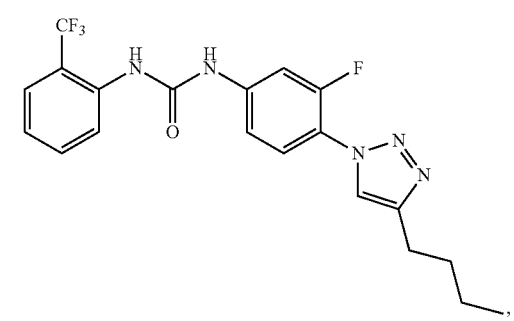
55f
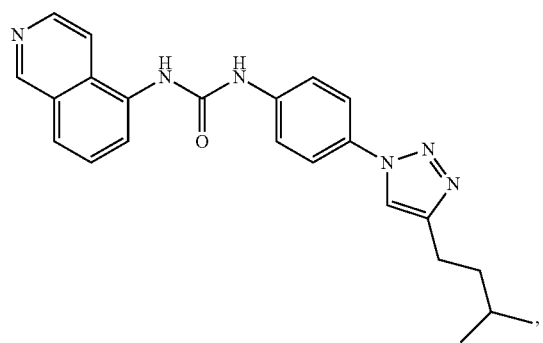
38
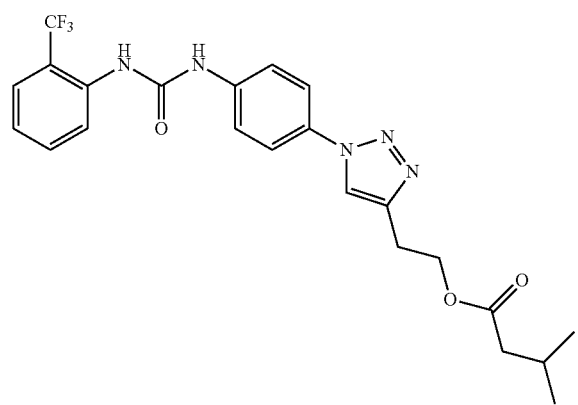
42c
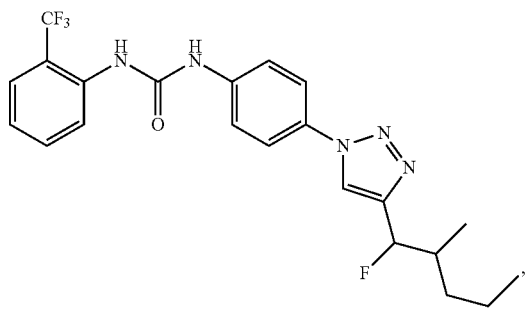
55a
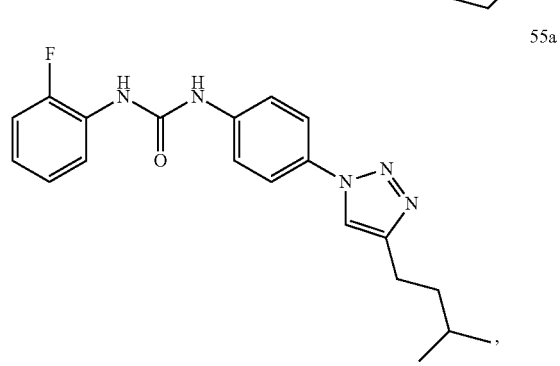
55b
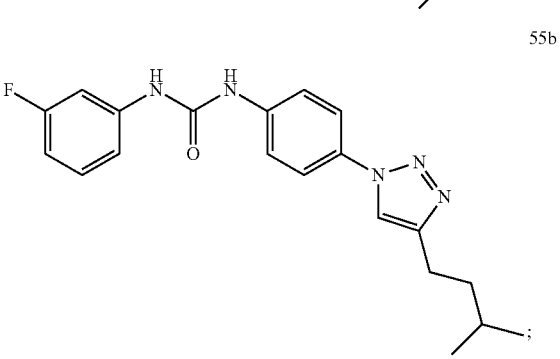
64d
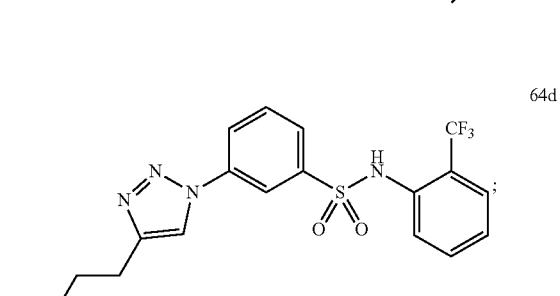
66d
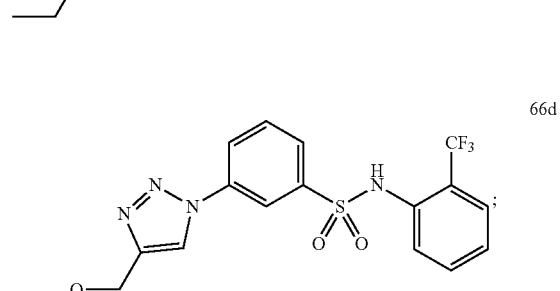

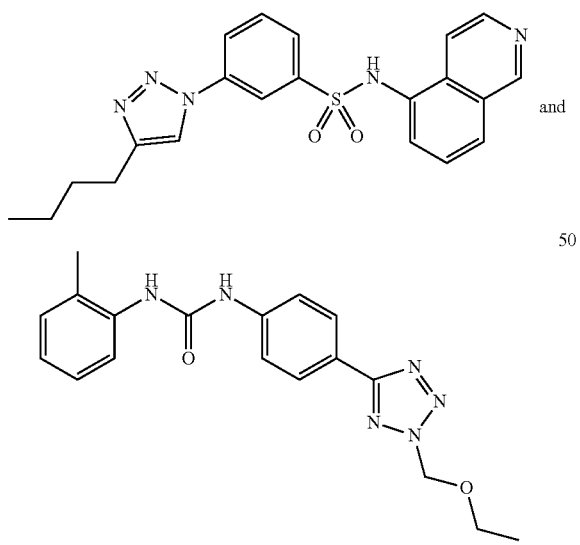

or salt, solvate, stereoisomer thereof.

The invention also provides a compound of formula:

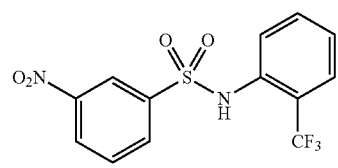
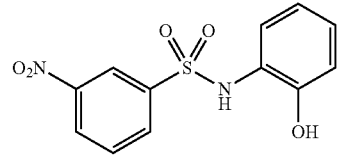
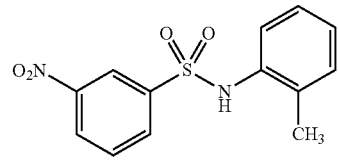
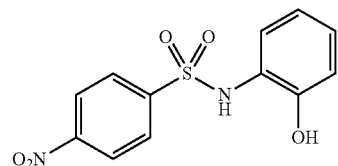
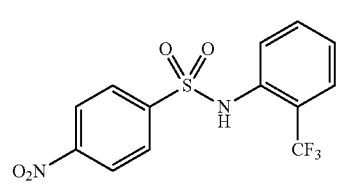

salt, solvate, stereoisomer thereof, for use in the treatment and/or prevention of a hyperproliferative disorder.

Preferably the hyperproliferative disorder is cancer. More preferably the cancer is selected from the group consisting of: breast cancer, prostate cancer, lung cancer, glioblastoma, glioblastoma multiforme, kidney cancer, oral cancer, colorectal cancer, neuroblastoma, medulloblastoma, head and neck squamous carcinoma, muscle rhabdomyosarcoma, osteosarcoma, Ewing sarcoma, cervical carcinoma, pontine tumours, hepatocarcinoma, retinoblastoma, hepatoblastoma, gallbladder cancer, melanoma, sarcomas and leukemia.

Still preferably the cancer is a primary cancer or a metastasis.

The term leukemia encompass any form of leukemia, —acute lymphoblastic leukemia (ALL), acute myeloid leukemia (AML), chronic lymphocytic leukemia (CLL) and chronic myeloid leukemia (CML). Preferably the cancer is a primary cancer or a metastasis. Preferably the cancer is resistant to known anti-tumoral agents.

Preferably the compound is used together with a further anti-hyperproliferative treatment and/or therapeutic agent.

Preferably the further anti-hyperproliferative treatment is selected from the group consisting of: radiotherapy and chemotherapy.

Preferably the chemotherapy is selected from the group consisting of: a pro-apoptotic agent, a monoclonal antibody, an interleukin or interferon.

Preferably the further therapeutic agent is selected from the group of: anti-pain agent, anti-emetic agent (such as aprepitant, fosaprepitant, Dolasetron, granisetron, ondansetron, palonosetron, tropisetron, or ramosetron, Dexamethasone).

The present invention also provides a pharmaceutical composition comprising the compound as defined above and pharmaceutically acceptable excipient for use in the treatment and/or prevention of a hyperproliferative disorder.

Preferably the pharmaceutical composition further comprises a therapeutic agent, for instance as defined above. Further, the pharmaceutical composition may be combined with an anti-hyperproliferative treatment such as radiotherapy.

Preferably the hyperproliferative disorder is modulated by DDX3.

The term "hyperproliferative disorder" or "hyperproliferative disease" refers to or describes a cellular disorder characterized by uncontrolled or disregulated cell proliferation, inappropriate ability to invade surrounding tissue, and/or ability to establish new growth at ectopic sites and include cancer and other diseases such as neoplasias and hyperplasias.

Cancer and tumours are particular examples of hyperproliferative disorders. The term "cancer" includes, but is not limited to, solid tumors and bloodborne tumors. Examples of cancer include, but are not limited to, epithelial cell cancer, breast cancer, prostate cancer, ovarian cancer, lung cancer, brain cancer (for example pontine tumours, glioblastoma, neuroblastoma), blood cancer, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, liver cancer, bladder cancer, hepatoma, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

The term "tumour" as used herein refers to any mass of tissue that results from excessive cell growth or proliferation, either benign (noncancerous) or malignant (cancerous). Preferably the hyperproliferative disorder is a cancer.

Preferably the cancer or the hyperproliferative disorder is selected from the group consisting of: breast cancer, prostate cancer, lung cancer, glioblastoma, kidney cancer, oral cancer, colorectal cancer, neuroblastoma, medulloblastoma, glio-blastoma, Ewing sarcoma, cervical carcinoma, pontine tumours, hepatocarcinoma, retinoblastoma, hepatoblastoma, gallbladder cancer, melanoma, sarcomas and leukemias.

In the present invention:

The term "substituted" means that the specified group or moiety has any hydrogen atom, on independently at least one carbon atom, nitrogen atom or other atom, which may be independently replaced by a substituent.

The term "halogen" or "halo" refers to fluoro, chloro, bromo, or iodo.

The term "alkyl" refers to a linear or branched hydrocarbon chain radical, consisting solely of carbon and hydrogen atoms. Suitable examples of said alkyl include but are not limited to methyl, ethyl, n-propyl, isopropyl, butyl, sec-butyl, tert-butyl, pentyl, isopentyl, tert-pentyl, hexyl, heptyl, octyl, nonyl, decanyl, hexadecanyl, eicosanyl, etc.

The term "$C_1$-$C_{10}$ alkyl" refers to a linear or branched hydrocarbon chain radical, consisting solely of carbon and hydrogen atoms, having from one to ten carbon atoms. Suitable examples of $C_{1-10}$ alkyl include but are not limited to methyl, ethyl, n-propyl, isopropyl, butyl, sec-butyl, tert-butyl, pentyl, isopentyl, tert-pentyl, hexyl, heptyl, octyl, nonyl, decanyl.

The term "$C_1$-$C_6$ alkyl" refers to a linear or branched hydrocarbon chain radical, consisting solely of carbon and hydrogen atoms, having from one to six carbon atoms. Suitable examples of $C_1$-$C_6$ alkyl include but are not limited to methyl, ethyl, n-propyl, isopropyl, butyl, sec-butyl, tert-butyl, pentyl, isopentyl, tert-pentyl, hexyl.

The term "$C_1$-$C_3$ alkyl" refers to a linear or branched hydrocarbon chain radical, consisting solely of carbon and hydrogen atoms, having from one to three carbon atoms. Suitable examples of $C_1$-$C_3$ alkyl are methyl, ethyl, n-propyl.

The term "$C_2$-$C_6$ alkenyl" refers to a linear or branched unsaturated hydrocarbon chain radical, containing at least one carbon-carbon double bond, consisting solely of carbon and hydrogen atoms, having from two to six carbon atoms. Suitable examples of $C_2$-$C_6$ alkenyl but are not limited to ethenyl, propenyl, allyl, isobuthenyl, pentenyl, prenyl, esenyl, etc.

The term "$C_2$-$C_6$ alkynyl" refers to a linear or branched unsaturated hydrocarbon chain radical, containing at least one carbon-carbon triple bond, consisting solely of carbon and hydrogen atoms, having from two to six carbon atoms. Suitable examples of $C_2$-$C_6$ alkynyl but are not limited to acetylenyl, ethynyl, propynyl, etc.

The term "haloalkyl" group is a linear or branched alkyl group wherein at least one hydrogen atom on the carbon atom is replaced by halogen and alkyl is as defined herein above. The "haloalkyl" group may optionally be substituted. Preferably, the one or more substituents on the haloalkyl are independently selected from unsubstituted or unsubstituted $C_1$-$C_6$ alkyl, $OR_A$, $COOR_B$, $OC(O)R_B$, $C(O)R_B$, $NR_AR_B$, $OP(O)(OR_A)_2$, $NHC(O)R_A$, $NHC(O)OR_A$, $COONR_AR_B$, $SR_A$, $S(=O)(=O)$—$R_A$, $SO_2NHR_A$, CN, $NO_2$. Most preferably, the one or more is methyl. "Haloalkyl" preferably is a linear or branched $C_1$-$C_{10}$ haloalkyl group, more preferably $C_1$-$C_8$ haloalkyl group, more preferably linear or branched $C_1$-$C_6$ haloalkyl group, also preferably is a linear or branched $C_1$-$C_4$ haloalkyl group, or a $C_1$-$C_2$ haloalkyl group, being in particular, $CHFCH(CH_3)(CH_2CH_2CH_3)$, $CH_2CH_2CH_2F$, $C_4F_9$, $CF_3$, $CHF_2$, $CH_2F$.

The term "$C_1$-$C_{10}$ haloalkyl" refers to linear or branched alkyl group having from one to ten carbon atoms wherein at least one hydrogen on a carbon atom is replaced by halogen and alkyl is as defined herein above. Analogous definition is for $C_1$-$C_8$ haloalkyl, $C_1$-$C_6$ haloalkyl, $C_1$-$C_4$ haloalkyl and $C_1$-$C_4$ haloalkyl having from one to eight, one to six and one to four or one to two carbon atoms respectively.

The term "alkoxy" denotes an organic unit having the general formula —OR, wherein R is an aliphatic. An alkoxy group can be, for example, methoxy and ethoxy. Suitable examples of alkoxy groups include, but are not limited to propoxy, isopropoxy, isobutoxy, and tert-butoxy.

The term "aryl" represents a mono or bicyclic aromatic ring system of, respectively, 6, 9 or 10 atoms, suitable examples of such an aryl are phenyl, indenyl, indanyl and naphthyl.

The term "aralkyl" represents any univalent radical derived from an alkyl radical by replacing one or more hydrogen atoms by aryl groups, wherein the aryl is as defined herein above.

Suitable examples of such an aralkyl are benzyl.

"Aralkyl substituted group" means that any hydrogen atom on independently each carbon atom may be independently replaced by a substituent, suitable examples of substituents include but are not limited to F, Cl, Br, $CF_3$, O—$C_1$-$C_6$ alkyl, $C_1$-$C_6$ alkyl, OH, $COC_1$-$C_6$ alkyl, $COOC_1$-$C_6$ alkyl.

The term "heteroaryl" means a monocyclic- or polycyclic 5-12 membered aromatic ring comprising carbon atoms, hydrogen atoms, and one or more heteroatoms, preferably, 1 to 3 heteroatoms, independently selected from nitrogen, oxygen, and sulfur. Illustrative examples of heteroaryl groups include, but are not limited to pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, tetrazolyl, furyl, thienyl, isoxazolyl, thiazolyl, isoxazolyl, oxazolyl, indazolyl, indolyl, benzoimidazolyl, quinolyl, isoquinolinyl and the like.

Salts of the compounds of the present invention are also encompassed within the scope of the invention. Because of their potential use in medicine, the salts of the compounds of formula I and II are preferably pharmaceutically acceptable. Suitable pharmaceutically acceptable salts comprise conventional non-toxic salts obtained by salification of a compound of formula I and II with inorganic acids (e.g. hydrochloric, hydrobromic, sulphuric, or phosphoric acids), or with organic acids (e.g. acetic, propionic, succinic, benzoic, sulfanilic, 2-acetoxy-benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see (32).

In addition pharmaceutically acceptable base addition salts can be formed with a suitable inorganic or organic base such as triethylamine, ethanolamine, triethanolamine, dicyclohexylamine, ammonium hydroxide, pyridine. The term "inorganic base," as used herein, has its ordinary meaning as understood by one of ordinary skill in the art and broadly refers to an inorganic compound that can act as a proton acceptor. The term "organic base," as used herein, also has its ordinary meaning as understood by one of ordinary skill in the art and broadly refers to an organic compound that can act as a proton acceptor.

Other suitable pharmaceutically acceptable salts include pharmaceutically acceptable alkali-metal or alkaline-earth-metal salts such as sodium, potassium, calcium or magnesium salts; in particular pharmaceutically acceptable salts of one or more carboxylic acid moieties that may be present in the compound of formula I and II.

Other salts, which are not pharmaceutically acceptable, for example the trifluoroacetate salt, may be useful in the preparation of compounds of this invention and these form a further aspect of the invention. The invention includes within its scope all possible stoichiometric and nonstoichiometric forms of the salts of the compounds of formula I and II.

In addition, the compounds of formula I and II may exist in unsolvated as well as in solvated forms with pharmaceutically acceptable solvents such as water, EtOH and the like.

Certain compounds of formula I and II may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula I and II as mixtures with isomers thereof in which one or more chiral centers are inverted. Racemic mixtures may be separated to give their individual enantiomer using preparative HPLC using a column with chiral stationary phase or resolved to yield individual enantiomers utilizing methods known to those skilled in the art. In addition, chiral intermediate compounds may be resolved and used to prepare individual enantiomers.

The compounds of the invention or solvates/hydrates of the compounds of formula I and II or salts, may exist in one or more polymorphic forms. The invention extends to all such forms whether in a pure polymorphic form or when admixed with any other material, such as another polymorphic form.

The compounds of formula I and II may exist in zwitterionic form. Likewise it is understood that compounds of formula I and II may exist in tautomeric forms other than that shown in the formula and these are also included within the scope of the present invention.

It will be appreciated by those skilled in the art that certain protected derivatives of the compounds of the invention, which may be made prior to a final deprotection stage, may not possess pharmacological activity as such, but may, in certain instances, be administered orally or parenterally and thereafter metabolized in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drug of Today, Volume 19, Nuber 9, 1983, pp 499-538 and in Topics in Chemistry, Chapter 31, pp 306-316 and in "Design of Prodrugs" by H. Bundgaard, Elsevier, 1985, Chapter 1 (the disclosure in which document is incorporated herein by reference). It will be further appreciated by those skilled in the art that certain moieties, known to those skilled in the art as "pro-moieties", for described by H. Bundgaard, in "Design of Prodrugs" (the disclosure in which document is incorporated herein by reference) may be placed on appropriate functionalities when such functionalities are present within the compound defined in the first aspect.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^3H$ or $^{14}C$ is incorporated, are useful in drug and/or substrate tissue distribution studies. Further, substitution with isotopes such as deuterium $^2H$, may afford certain therapeutic advantages resulting from greater metabolic stability. Isotopic variations of the compounds of the invention can generally be prepared by conventional procedures such as by the illustrative methods or by the preparations described in the examples hereafter using appropriate isotopic variations of suitable reagents.

The pharmaceutical composition of the invention may comprise a combination of at least two of the compounds of the invention or a pharmaceutically acceptable salt thereof, and suitable excipients and/or diluents and may be also administered in combination with pharmaceutical compositions of approved drugs for the treatment of cancers as part of combinatorial multidrug cancer therapy.

In the present invention the compounds of the invention or their salts may be administered as pure or as pharmaceutical formulations. i.e. suitable for parenteral, oral, or rectal administrations. Each of said formulations may contain excipients and/or tillers and/or additives and/or binders, coatings and/or suspending agents and/or emulsifying agents, preserving and/or control release agents. suitable for the selected pharmaceutical form. It is a further object of the invention a method for inhibiting the human DEAD-box RNA helicases DDX3 comprising contacting the compound of the invention or the composition as defined above with human DDX3, thereby inhibiting the activity of DDX3.

It is a further object of the invention a method for treating a hyperproliferative disorder, preferably cancer in a cell, comprising contacting the cell with the compound or the composition of the invention.

The invention also provides pharmaceutical compositions comprising at least one compound of this invention or a pharmaceutical acceptable salt or solvate thereof and one or more pharmaceutically acceptable carriers, excipients and/or diluents.

The pharmaceutical compositions can be chosen based on the treatment requirements. Such compositions are prepared by blending and are suitably adapted to oral or parenteral administration, and as such can be administered in the form of tablets, capsules, oral preparations, powders, granules, pills, injectable, or infusible liquid solutions, suspensions, suppositories, preparation for inhalation. Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional. Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Topical transdermal formulations comprise conventional aqueous and non-aqueous vectors, such as creams, oils, lotions or pastes or can be in the form of membranes or medicated patches.

To allow access of the active ingredients of the composition to deeper-lying skin cells, vehicles which improve penetration through outer layers of the skin, e.g., the stratum corneum, are useful. Vehicle constituents for this purpose include, but are not limited to, ethanol, isopropanol, diethylene glycol ethers such as diethylene glycol monoethyl ether, azone (1-dodecylazacycloheptan-2-one), oleic acid, linoleic acid, propylene glycol, hypertonic concentrations of glycerol, lactic acid, glycolic acid, citric acid, and malic acid. In one embodiment, propylene glycol is used as a delivery vehicle. In a preferred embodiment, a mixture of propylene glycol:ethanol:isopropyl myristate (1:2.7:1) containing 3% benzylsulfonic acid and 5% oleyl alcohol is used.

In another embodiment, a liposome preparation can be used. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used. The compositions of the invention intended to target skin conditions can be administered before, during, or after exposure of the skin of the mammal to UV or agents causing oxidative damage. Other suitable formulations can employ niosomes. Niosomes are lipid vesicles similar to liposomes, with membranes consisting largely of non-ionic lipids, some forms of which are effective for transporting compounds across the stratum corneum.

In order to increase bioavailability the compounds can be pharmaceutically formulated in nanoparticles. Acceptable nanoparticles include albumin nanoparticles and gold nanoparticles. Other suitable delivery methods intended primarily for skin include use of a hydrogel formulation, comprising an aqueous or aqueous-alcoholic medium and a gelling agent in addition to the oligonucleotide(s). Suitable gelling agents include methylcellulose, carboxymethylcellulose, hydroxypropylmethylcellulose, carbomer (carbopol), hypan, polyacrylate, and glycerol polyacrylate. A reference for the formulations is the book by Remington (33).

The compounds of the present invention may be employed for use in the treatment and/or prevention of the above mentioned conditions alone as a sole therapy or in combination with other therapeutic agents either by separate administrations, or by including the two or more active principles in the same pharmaceutical formulation. The compounds may be administered simultaneously or sequentially.

Still further aspects include combining the compounds of the invention described herein with other anticancer therapies for synergistic or additive benefit.

The other therapeutic agents may be any approved drugs for the treatment of hyperproliferative disorder, in particular cancer. Non-exhaustive examples of suitable additional agents include in particular drugs belonging to the group of: a pro-apoptotic agent, a monoclonal antibody, interleukins or interferons. In particular the compounds of the invention may be used together with Abitrexate (Methotrexate Injection), Abraxane (Paclitaxel Injection), Adcetris (Brentuximab Vedotin Injection), Adriamycin (Doxorubicin), Adrucil Injection (5-FU (fluorouracil)), Afinitor (Everolimus), Afinitor Disperz (Everolimus), Alimta (PEMETREXED), Alkeran Injection (Melphalan Injection), Alkeran Tablets (Melphalan), Aredia (Pamidronate), Arimidex (Anastrozole), Aromasin (Exemestane), Arranon (Nelarabine), Arzerra (Ofatumumab Injection), Avastin (Bevacizumab), Bexxar (Tositumomab), BiCNU (Carmustine), Blenoxane (Bleomycin), Bosulif (Bosutinib), Busulfex Injection (Busulfan Injection), Campath (Alemtuzumab), Camptosar (Irinotecan), Caprelsa (Vandetanib), Casodex (Bicalutamide), CeeNU (Lomustine), CeeNU Dose Pack (Lomustine), Cerubidine (Daunorubicin), Clolar (Clofarabine Injection), Cometriq (Cabozantinib), Cosmegen (Dactinomycin), CytosarU (Cytarabine), Cytoxan (Cytoxan), Cytoxan Injection (Cyclophosphamide Injection), Dacogen (Decitabine), DaunoXome (Daunorubicin Lipid Complex Injection), Decadron (Dexamethasone), DepoCyt (Cytarabine Lipid Complex Injection), Dexamethasone Intensol (Dexamethasone), Dexpak Taperpak (Dexamethasone), Docefrez (Docetaxel), Doxil (Doxorubicin Lipid Complex Injection), Droxia (Hydroxyurea), DTIC (Decarbazine), Eligard (Leuprolide), Ellence (Ellence (epirubicin)), Eloxatin (Eloxatin (oxaliplatin)), Elspar (Asparaginase), Emcyt (Estramustine), Erbitux (Cetuximab), Erivedge (Vismodegib), Erwinaze (Asparaginase Erwinia chrysanthemi), Ethyol (Amifostine), Etopophos (Etoposide Injection), Eulexin (Flutamide), Fareston (Toremifene), Faslodex (Fulvestrant), Femara (Letrozole), Firmagon (Degarelix Injection), Fludara (Fludarabine), Folex (Methotrexate Injection), Folotyn (Pralatrexate Injection), FUDR (FUDR (floxuridine)), Gemzar (Gemcitabine), Gilotrif (Afatinib), Gleevec (Imatinib Mesylate), Gliadel Wafer (Carmustine wafer), Halaven (Eribulin Injection), Herceptin (Trastuzumab), Hexalen (Altretamine), Hycamtin (Topotecan), Hycamtin (Topotecan), Hydrea (Hydroxyurea), Iclusig (Ponatinib), Idamycin PFS (Idarubicin), Ifex (Ifosfamide), Inlyta (Axitinib), Intron A alfab (Interferon alfa-2a), Iressa (Gefitinib), Istodax (Romidepsin Injection), Ixempra (Ixabepilone Injection), Jakafi (Ruxolitinib), Jevtana (Cabazitaxel Injection), Kadcyla (Ado-trastuzumab Emtansine), Kyprolis (Carfilzomib), Leukeran (Chlorambucil), Leukine (Sargramostim), Leustatin (Cladribine), Lupron (Leuprolide), Lupron Depot (Leuprolide), Lupron DepotPED (Leuprolide), Lysodren (Mitotane), Margibo Kit (Vincristine Lipid Complex Injection), Matulane (Procarbazine), Megace (Megestrol), Mekinist (Trametinib), Mesnex (Mesna), Mesnex (Mesna Injection), Metastron (Strontium-89 Chloride), Mexate (Methotrexate Injection), Mustargen (Mechlorethamine), Mutamycin (Mitomycin), Myleran (Busulfan), Mylotarg (Gemtuzumab Ozogamicin), Navelbine (Vinorelbine), Neosar Injection (Cyclophosphamide Injection), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Oncaspar (Pegaspargase), Oncovin (Vincristine), Ontak (Denileukin Diftitox), Onxol (Paclitaxel Injection), Panretin (Alitretinoin), Paraplatin (Carboplatin), Perjeta (Pertuzumab Injection), Platinol (Cisplatin), Platinol (Cisplatin Injection), PlatinolAQ (Cisplatin), PlatinolAQ (Cisplatin Injection), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), Rituxan (Rituximab), RoferonA alfaa (Interferon alfa-2a), Rubex (Doxorubicin), Sandostatin (Octreotide), Sandostatin LAR Depot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b Injection (Sylatron)), Synribo (Omacetaxine Injection), Tabloid (Thioguanine), Taflinar (Dabrafenib), Tarceva (Erlotinib), Targretin Capsules (Bexarotene), Tasigna (Decarbazine), Taxol (Paclitaxel Injection), Taxotere (Docetaxel), Temodar (Temozolomide), Temodar (Temozolomide Injection), Tepadina (Thiotepa), Thalomid (Thalidomide), TheraCys BCG (BCG), Thioplex (Thiotepa), TICE BCG (BCG), Toposar (Etoposide Injection), Torisel (Temsirolimus), Treanda (Bendamustine hydrochloride), Trelstar (Triptorelin Injection), Trexall (Methotrexate), Trisenox (Arsenic trioxide), Tykerb (lapatinib), Valstar (Valrubicin Intravesical), Vantas (Histrelin Implant), Vectibix (Panitumumab), Velban (Vinblastine), Velcade (Bortezomib), Vepesid (Etoposide), Vepesid (Etoposide Injection), Vesanoid (Tretinoin), Vidaza (Azacitidine), Vincasar PFS (Vincristine), Vincrex (Vincristine), Votrient (Pazopanib), Vumon (Teniposide), Wellcovorin IV (Leucovorin Injection), Xalkori (Crizotinib), Xeloda (Capecitabine), Xtandi (Enzalutamide), Yervoy (Ipilimumab Injection), Zaltrap (Ziv-aflibercept Injection), Zanosar (Streptozocin), Zelboraf (Vemurafenib), Zevalin (Ibritumomab Tiuxetan), Zoladex (Goserelin), Zolinza (Vorinostat), Zometa (Zoledronic acid), Zortress (Everolimus), Zytiga (Abiraterone), Nimotuzumab and immune checkpoint inhibitors such as nivolumab, pembrolizumab/MK-3475, pidilizumab and AMP-224 targeting PD-1; and BMS-935559, MEDI4736, MPDL3280A and MSB0010718C targeting PD-L1 and those targeting CTLA-4 such as ipilimumab, mitomycin C, cisplatin, etoposide, vincristine, doxorubicin, isotretinoin and cyclophosphamide.

The combination can be administered as separate compositions (simultaneous, sequential) of the individual components of the treatment or as a single dosage form containing all agents. When the compounds of this invention are in combination with others active ingredients, the active ingredients may be separately formulated into single-ingredient preparations of one of the above-described forms and then provided as combined preparations, which are given at the same time or different times, or may be formulated together into a two- or more ingredients preparation.

Radiotherapy means the use of radiation, usually X-rays, to treat illness. X-rays were discovered in 1895 and since then radiation has been used in medicine for diagnosis and investigation (X-rays) and treatment (radiotherapy). Radiotherapy may be from outside the body as external radiotherapy, using X-rays, cobalt irradiation, electrons, and more rarely other particles such as protons. It may also be from within the body as internal radiotherapy, which uses radioactive metals or liquids (isotopes) to treat cancer.

Compounds of general formula I and II may be administered to a patient in a total daily dose of, for example, from 0.001 to 1000 mg/kg body weight daily. Dosage unit compositions may contain such amounts of submultiples thereof to make up the daily dose. The compound may also be administered weekly or any other day. The determination of optimum dosages for a particular patient is well known to one skilled in the art. As is common practice, the compositions are normally accompanied by written or printed instructions for use in the treatment in question.

Compounds of the invention may be prepared in a variety of ways. These processes form further aspects of the invention.

The present invention is illustrated by means of non limiting examples.

DETAILED DESCRIPTION OF THE INVENTION

Material and Methods
Synthesis
General

Reagents were obtained from commercial suppliers (for example Sigma-Aldrich). All commercially available chemicals were used as purchased without further purification. $CH_3CN$ was dried over calcium hydride, $CH_2Cl_2$ was dried over calcium hydride and THF was dried over Na/benzophenone prior to use while DMF was bought already anhydrous. Anhydrous reactions were run under a positive pressure of dry $N_2$ or argon. TLC was carried out using Merck TLC plates silica gel 60 F254. Chromatographic purifications were performed on columns packed with Merk 60 silica gel, 23-400 mesh, for flash technique. $^1$H-NMR and $^{13}$C-NMR spectra were recorded at 400 MHz on a Brucker Avance DPX400 spectrometer. Chemical shifts are reported relative to tetramethylsilane at 0.00 ppm. $^1$H patterns are described using the following abbreviations: s=singlet, d=doublet, t=triplet, q=quartet, quint=quintet, sx=sextet, sept=septet, m=multiplet, br=broad signal, br s=broad singlet.

Mass spectra (MS) data were obtained using an Agilent 1100 LC/MSD VL system (G1946C) with a 0.4 mL/min flow rate using a binary solvent system 25 of 95:5 methyl alcohol/water. UV detection was monitored at 254 nm. Mass spectra were acquired in positive and negative mode scanning over the mass range.

Microwave Irradiation Experiments

Microwave irradiation experiments were conducted using CEM Discover Synthesis Unit (CEM Corp., Matthews, N.C.). The machine consists of a continuous focused microwave power delivery system with operator selectable power output from 0 to 300 W. The temperature of the contents vessels was monitored using calibrate infrared temperature control mounted under the reaction vessel. All the experiments were performed using a stirring option whereby the contents of the vessels are stirred by means of rotating magnetic plate located below the floor of the microwave cavity and a Teflon-coated magnetic stir bar in the vessel.

In the present invention the following abbreviations are used:

| | |
|---|---|
| NMR (Nuclear Magnetic Resonance) | $^1$H (proton) |
| MHz (Megahertz) | $^{13}$C (carbon) |
| $^{19}$F (fluorine) | LC-MS (Liquid Chromatography Mass Spectrum) |
| Hz (Hertz) | HPLC (High Performance Liquid Chromatography) |
| s (seconds) | min (minutes) |
| h (hour(s)) | mg (milligrams) |
| g (grams) | μL (microlitres) |
| mL (millilitres) | mmol (millimoles) |
| nm (nanometers) | μM (micromolar) |
| M (molarity) | SI selectity index |
| DMEM (Dulbecco's Modified Eagle's Medium) | o.n. (overnight) |
| BOC or boc (tert-butyloxycarbonyl) | DMF (dimethylformamide) |
| DCM (dichloromethane) | ACN (acetonitrile) |
| Pyr Pyridine | RT or rt or r.t. (room temperature) |
| DMF (dimethylformamide) | DMSO (dimethyl sulfoxide) |
| DMSO d-$_6$ (deuterated dimethyl sulfoxide) | MeOH (methanol) |
| MeOD-d$_4$ (deuterated methanol) | CDCl$_3$-d (deuterated chloroform) |
| Et$_2$O (diethyl ether) | EtOAc or EA (ethyl acetate) |
| EtOH (ethanol) | AcOH (acetic acid) |
| iPrOH (isopropanol) | D$_2$O (deuterated water) |
| TEA (triethylamine) | THF (tetrahydrofuran) |
| TMSN$_3$ (Trimethylsilyl Azide) | t-BuONO (tert-Butyl nitrite) |
| PE (petroleum ether) | t-Bu (tert-butyl) |
| t$_R$ (retention time) | Cmpd. (compound) |
| wt wild type | MTBE (methyl tert-butyl ether) |

Except where indicated otherwise, all temperatures are expressed in ° C. (degrees centigrade) or K (Kelvin).

The yields were calculated assuming that products were 100% pure if not stated otherwise.

EXAMPLES

Example 1

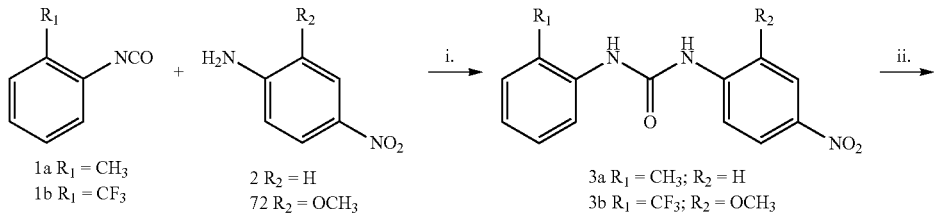

1a R$_1$ = CH$_3$
1b R$_1$ = CF$_3$

2 R$_2$ = H
72 R$_2$ = OCH$_3$

3a R$_1$ = CH$_3$; R$_2$ = H
3b R$_1$ = CF$_3$; R$_2$ = OCH$_3$

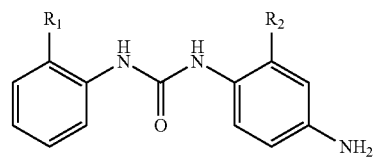

4a R$_1$ = CH$_3$; R$_2$ = H
4b R$_1$ = CF$_3$; R$_2$ = OCH$_3$

↓ iii.

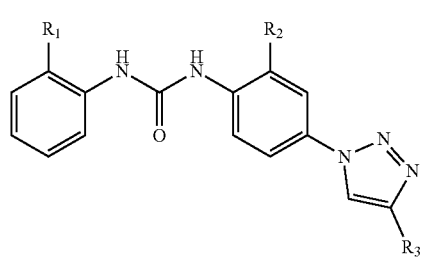
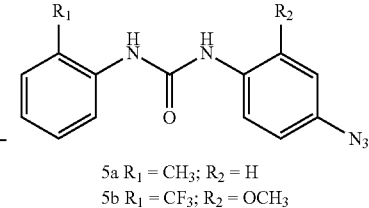
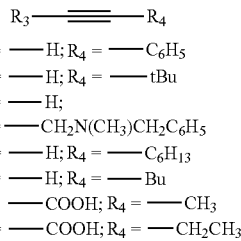

8a: R₁ = CH₃; R₂ = H; R₃ = ——C₆H₅
8b: R₁ = CH₃; R₂ = H; R₃ = ——tBu
8c: R₁ = CH₃; R₂ = H; R₃ = ——CH₂N(CH₃)CH₂C₆H₅
8d: R₁ = CF₃; R₂ = H; R₃ = ——C₆H₁₃
8e: R₁ = CF₃; R₂ = OCH₃; R₃ = ——Bu

5a R₁ = CH₃; R₂ = H
5b R₁ = CF₃; R₂ = OCH₃

6a: R₃ = ——H; R₄ = ——C₆H₅
6b: R₃ = ——H; R₄ = ——tBu
6c: R₃ = ——H;
R₄ = ——CH₂N(CH₃)CH₂C₆H₅
6d: R₃ = ——H; R₄ = ——C₆H₁₃
6e: R₃ = ——H; R₄ = ——Bu
7f: R₃ = ——COOH; R₄ = ——CH₃
7g: R₃ = ——COOH; R₄ = ——CH₂CH₃

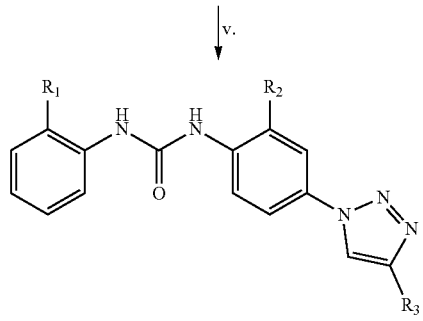

8f: R₁ = CH₃; R₂ = H; R₃ = ——CH₃
8g: R₁ = CH₃; R₂ = H; R₃ = ——CH₂CH₃

Reagents and conditions: i.o-tolyl-isocyanate CH₂Cl₂, 5 h reflux, ii. H₂, Pd/C, MeOH, 1 h; iii. a) t-BuONO,CH₃CN, 20 min. 0° C.; b) TMSN₃, CH₃CN, 2 h r.t.; iv. Alkyne 6a-c, CuSO₄.5 H₂O, sodium ascorbate, H₂O tBuOH (1:1), MW 120° C., 10 min; v. alkynoic acid 7 d-e, CuCl, L-Proline, K₂CO₃, DMSO (dry) MW 65° C., 20 min.

General Procedure for the Synthesis of Compounds 3a and 3b:

The opportuene aniline 2 or 72 (3.62 mmol) was added to a solution of the opportune isocyanate 1 or 1a (5.43 mmol) in anhydrous CH₂Cl₂ (10 mL) in one portion. The solution was stirred for 4 hours at 60° C. under a nitrogen atmosphere. The yellow precipitate was filtered, washed with cool DCM and petroleum ether and dried under high vacuum to afford the desired product as a white solid.

1-(4-nitrophenyl)-3-o-tolylurea (3a). Yield=63%; $^1$H NMR (400 MHz, DMSO d-₆): δ 9.7 (s, 1H, NH), 8.19-8.16 (d, J=9.2 Hz, 2H), 8.13 (s, 1H), 7.78-7.76 (d, J=8.0 Hz, 1H), 7.69-7.66 (d, J=12.0 Hz, 2H), 7.19-7.13 (m, 2H), 7.00-6.97 (t, 1H, J=12.0 Hz), 2.24 (s, 3H) ppm. MS (ESI) m/z 270 [M−H]⁻, 306 [M+Cl]⁻.

1-(2-methoxy-4-nitrophenyl)-3-(2-(trifluoromethyl)phenyl)urea (3b): Yield=56%; $^1$H NMR (400 MHz, MeOD): δ8.40-8.38 (d, J=8.8 Hz, 1H), 7.95-7.91 (m, 2H), 7.74-7.73 (d, J=2.0 Hz, 1H), 7.66-7.64 (d, J=8.0 Hz, 1H), 7.61-7.57 (t, J=7.8 Hz, 1H), 7.45 (s, 1H), 3.97 (s, 3H) ppm. MS (ESI) m/z 354 [M−H]⁻.

General Procedure for the Synthesis of 4a and 4b:

The opportune Urea 3a or 3b (1.10 mmol) was solubilized in 30 mL of anhydrous MeOH, and Palladium on charcoal (50 mg) was added. The reaction mixture was stirred under Hydrogen atmosphere for 1 h, then the mixture was filtered off on a celite pad, the solvent evaporated at reduced pressure and the residue crystallized from acetonitrile.

1-(4-aminophenyl)-3-o-tolylurea (4a). Yield=70%; white solid. $^1$H NMR (400 MHz, DMSO d-₆): δ 8.48 (s, 1H), 7.83-7.81 (d, J=8.0 Hz, 2H), 7.67 (s, 1H), 7.15-7.05 (m, 4H), 6.89-6.87 (d, J=8.0 Hz, 1H), 6.50-6.48 (d, J=8.0 Hz, 2H), 4.72 (s, 2H), 2.20 (s, 3H) ppm. MS (ESI) m/z 242.0 [M+H]+, 264 [M+Na]⁺, 505 [2M+Na]⁺.

1-(4-amino-2-methoxyphenyl)-3-(2-(trifluoromethyl)phenyl)urea (4b): Yield=70%; white solid. $^1$H NMR (400 MHz, MeOD): δ 8.04-8.02 (d, J=8.0 Hz, 1H), 7.49-7.44 (m, 2H), 7.38-7.36 (d, J=8.0 Hz, 1H), 7.10-7.06 (t, J=7.6 Hz, 1H), 6.27-6.26 (d, J=6.0 Hz, 2H), 3.74 (s, 3H) ppm. MS (ESI) m/z 326 [M+H]⁺.

General Procedure for the Synthesis of 5a and 5b:

The opportune Aniline 4a or 4b (0.41 mmol) was dissolved in CH₃CN and cooled to 0° C. in an ice-salt bath. To this stirred solution, was added tBuONO (0.61 mmol), and the mixture was stirred for 10 min, after this time, TMSN₃ (654, 0.49 mmol) was added dropwise, during 10 minutes, and the resulting brown solution was stirred at r.t. One hour later the solvent was removed at reduced pressure and the residue was purified by flash chromatography on silica gel 1-(4-azidophenyl)-3-o-tolylurea (5a). (Purification Eluent: DCM-MeOH 9:1). Yield 67%. $^1$H NMR (400 MHz, CDCl₃-d) δ 9.10 (s, 1H), 7.91 (s, 1H), 7.80-7.78 (d, J=8.0 Hz, 1H), 7.50-7.48 (d, J=8.0 Hz, 2H), 7.16-7.19 (m, 2H), 7.04-7.02 (d, J=8.0 Hz, 2H), 7.95-7.91 (t, J=8.0 Hz, 1H), 2.22 (s, 3H) ppm. MS (ESI) m/z 267 [M+Na]⁺, 557 [2M+Na]⁺.

1-(4-azido-2-methoxyphenyl)-3-(2-(trifluoromethyl)phenyl)urea (5b): (Purification Eluent: PE-EA=5:3). Yield=98%; yellow solid. $^1$H NMR (400 MHz, MeOD-d₄): δ 8.41 (s, 1H), 8.23-8.18 (t, J=9.0 Hz, 1H), 8.06-8.00 (m, 2H), 7.62-7.55 (m, 2H), 7.24-7.20 (t, J=7.6 Hz, 1H), 3.84 (s, 3H) ppm.

General Procedure for the Preparation of Compounds 8a-e

The appropriate alkyne (0.10 mmol) and azide 5 (25 mg, 0.09 mmol) were suspended in a 1:1 mixture of water and t-BuOH (1.5 mL each) in a 10 mL glass vial equipped with a small magnetic stirring bar. To this, was added sodium ascorbate (0.1 equiv) and copper(II) sulfate pentahydrate (0.10 mmol). The mixture was then heated for 10 min. at 125° C. under microwave irradiation, using an irradiation power of 300 W. After this time the precipitate was filtered-off and purified on silica, to give final products 8a, 8b, 8c, 8d or 8e.

1-(4-(4-phenyl-1H-1,2,3-triazol-1-yl)phenyl)-3-o-tolylurea (8a). The residue was purified by flash chromatography on silica gel (DCM/MeOH 98:2). Yield 97%, white solid. $^1$H NMR (400 MHz, DMSO d-$_6$): δ 9.42 (s, 1H), 9.18 (s, 1H), 8.08 (s, 1H), 7.93-7.91 (d, J=8.0 Hz, 2H), 7-85-7-80 (m, 3H), 7.70-7.68 (d, J=8.0 Hz, 2H), 7.50-7.46 (m, 3H), 7.38-7.34 (t, J=8.0 Hz, 1H), 7.18-7.14 (m, 2H), 6.97-6.94 (t, J=12.0 Hz, 1H), 2.25 (s, 3H) ppm. $^{13}$C-NMR (100 MHz, DMSO d-$_6$): δ 153.09, 148.24, 140.57, 137.65, 131.33, 130.87, 130.71, 129.45, 128.63, 126.66, 125.79, 123.48, 121.83, 121.35, 119.88, 119.12 ppm. MS (ESI) m/z 368 [M−H]$^−$, 404 [M+Cl]$^−$.

1-(4-(4-tert-butyl-1H-1,2,3-triazol-1-yl)phenyl)-3-o-tolylurea (8b). The residue was purified by flash chromatography on silica gel (DCM/MeOH 98:2). Yield 91%, white solid. $^1$H NMR (400 MHz, DMSO d-$_6$): δ 9.23 (s, 1H), 8.45 (s, 1H), 7.96 (s, 1H), 7.80-7.75 (m, 3H, Ph), 7.63-7.61 (d, J=8.0 Hz, 2H), 7.17-7.11 (m, 2H), 6.96-6.93 (t, J=12.0 Hz, 1H), 2.23 (s, 3H), 1.32 (s, 9H) ppm. $^{13}$C-NMR (100 MHz, DMSO d-$_6$): δ 158.38, 155.30, 139.59, 135.73, 131.87, 131.75, 130.66, 126.64, 125.48, 124.84, 121.22, 120.18, 117, 50, 30.33, 17.83 ppm. MS (ESI) m/z 348 [M−H]$^−$, 384 [M+Cl]$^−$.

1-(4-(4-methanamine,N-[(phenyl)methyl]-N-methyl-1H-1,2,3-triazol-1yl)phenyl)-3-o-tolylurea (8c). The residue was purified by flash chromatography on silica gel (DCM/MeOH 98:2). Yield 90%, white solid. $^1$H NMR (400 MHz CDCl$_3$-d): δ 8.43 (s, 1H), 7.80 (s, 1H), 7.57 (s, 1H), 7.51-7.43 (m, 6H), 7.31-7.23 (m, 4H), 7.12-7.07 (m, 2H), 7.00-6.99 (t, J=12.0 Hz 1H), 3.75 (s, 2H), 3.58 (s, 2H), 2.25 (s, 3H), 2.14 (s, 1H) ppm. $^{13}$C-NMR (100 MHz CDCl$_3$-d): δ 154.31, 145.73, 139.98, 137.90, 135.90, 131.48, 130.60, 129.15, 128.39, 127.36, 126.58, 125.26, 124.61, 121.13, 120.08, 61.58, 51.88, 42.11, 17.89 ppm. MS (ESI) m/z 425.0 [M−H]$^−$, 461.1 [M+Cl]$^−$.

1-(4-(4-hexyl-1H-1,2,3-triazol-1-yl)phenyl)-3-(2-(trifluoromethyl)phenyl)urea) (8d). The residue was purified by flash chromatography on silica gel (DCM/MeOH 98:2). Yield 83%, white solid. $^1$H NMR (400 MHz, MeOD): δ 8.16 (s, 1H), 7.93-7.91 (d, J=8.0 Hz, 1H), 7.71-7.69 (dd, J=8.0 Hz 2H), 7.63-7.61 (dd, J=8.0 Hz, 2H), 7.59-7.55 (m, 4H), 7.27-7.23 (t, J=8.0 Hz, 1H), 2.74-2.70 (t, J=8.0 Hz 2H), 1.70-1.65 (m, 2H), 1.37-1.31 (m, 6H), 0.87 (s, 3H) ppm.

$^{13}$C-NMR (100 MHz, MeOD): δ 153.58, 148.75, 139.86, 135.97, 132.58, 131.99, 125.99, 125.66, 124.06, 122.64, 120.74, 119.77, 119.30, 31.30, 29.08, 28.57, 24.92, 22.21, 12.98 ppm. MS (ESI) m/z 432 [M+H]$^+$, 454 [M+Na]$^+$.

1-(4-(4-butyl-1H-1,2,3-triazol-1-yl)-2-methoxyphenyl)-3-(2-(trifluoromethyl)phenyl)urea (8e): The residue was purified by flash chromatography on silica gel (PE/EA 7:3). Yield 60%, white solid. $^1$H NMR (400 MHz, CDCl$_3$): δ 8.21-8.19 (d, J=8.8 Hz, 1H), 7.91-7.89 (d, J=8.4 Hz, 2H), 7.63 (s, 1H), 7.50-7.46 (t, J=7.8 Hz, 1H), 7.20-7.15 (m, 2H), 7.04-7.03 (d, J=1.6 Hz, 1H), 3.79 (s, 3H), 2.75-2.71 (t, J=7.6 Hz, 2H), 1.62-1.53 (m, 3H), 0.90-0.88 (d, J=6.0 Hz, 2H) ppm. $^{13}$C-NMR (100 MHz, CDCl$_3$): δ 154.00, 149.16, 135.94, 133.03, 128.55, 125.87, 124.30, 120.04, 118.70, 112.20, 103.47, 56.21, 38.30, 28.00, 23.74, 22.40 ppm. MS (ESI) m/z 448 [M+H]$^+$.

General Procedure for the Preparation of Compounds 8f and g

L-Proline (1.9 mg, 0.01 mmol), CuCl (8.2 mg, 0.08 mmol), K$_2$CO$_3$, (13.7 mg, azide (20 mg, 0.08 mmol), the appropriate alkynoic acid (0.08 mmol), were sequentially added to a 10 mL glass vial equipped with a magnetic stirrer. The vial was closed with a septum and irradiated at 65° C. After 15 min., the mixture was partitioned between water 20 mL and AcOEt (40 mL), the organic layer was separated, dried (Na$_2$SO$_4$), and solvent removed in vacuo to furnish a brown residue, that was purified by flash chromatography on silica gel (DCM-MeOH 98:2) to give the desired triazole compounds 8e or 8f.

1-(4-(4-methyl-1H-1,2,3-triazol-1-yl)phenyl)-3-o-tolylurea (80. The residue was purified by flash chromatography on silica gel (DCM/MeOH 98:2). Yield 77%, white solid. Yield $^1$H NMR (400 MHz, MeOD-d$_4$): δ 8.15 (s, 1H), 7.72-7.69 (d, J=8.0 Hz, 2H), 7.64-7.62 (m, 3H), 7.21-7.15 (m, 2H), 7.05-7.02 (t, J=8.0 Hz, 1H), 2.38 (s, 1H), 2.30 (s, 3H) ppm. $^{13}$C-NMR (100 MHz, MeOD-d$_4$): δ 153.20, 151.00, 141.20, 138.2, 133.01, 131.8, 126.08, 124.23, 123.13, 120.77, 120.28, 119.23, 16.60, 9.06 ppm. MS (ESI) m/z 306 [M−H]$^−$, 342 [M+Cl]$^−$.

1-(4-(4-ethyl-1H-1,2,3-triazol-1-yl)phenyl)-3-o-tolylurea (8g). The residue was purified by flash chromatography on silica gel (DCM/MeOH 98:2). Yield 82%, white solid. $^1$H NMR (400 MHz, MeOD-d$_4$): δ 8.21 (s, 1H), 7.73-7.71 (d, J=8.0 Hz, 2H), 7.65-7.63 (m, 3H), 7.21-7.15 (m, 2H), 7.05-7.02 (t, J=8.0 Hz, 1H), 2.82-2.76 (q, J=6.0 Hz, 2H), 2.30 (s, 3H), 1.35-1.31 (t, J=8.0 Hz, 3H), ppm. $^{13}$C-NMR (100 MHz, MeOD-d$_4$): δ 152.60, 149.76, 140.30, 137.38, 131.86, 130.21, 128.32, 126.25, 123.33, 121.92, 120.59, 118.95, 118.77, 18.75, 17.20, 13.17 ppm. MS (ESI) m/z 320 [M−H]$^−$, 356 [M+Cl]$^−$.

Example 2

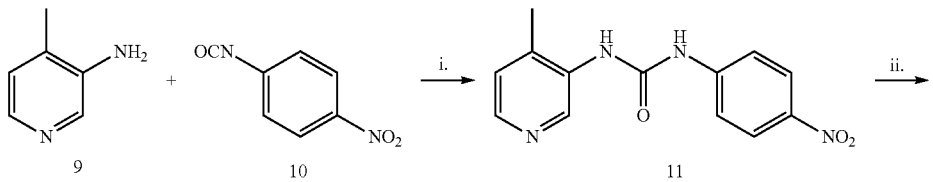

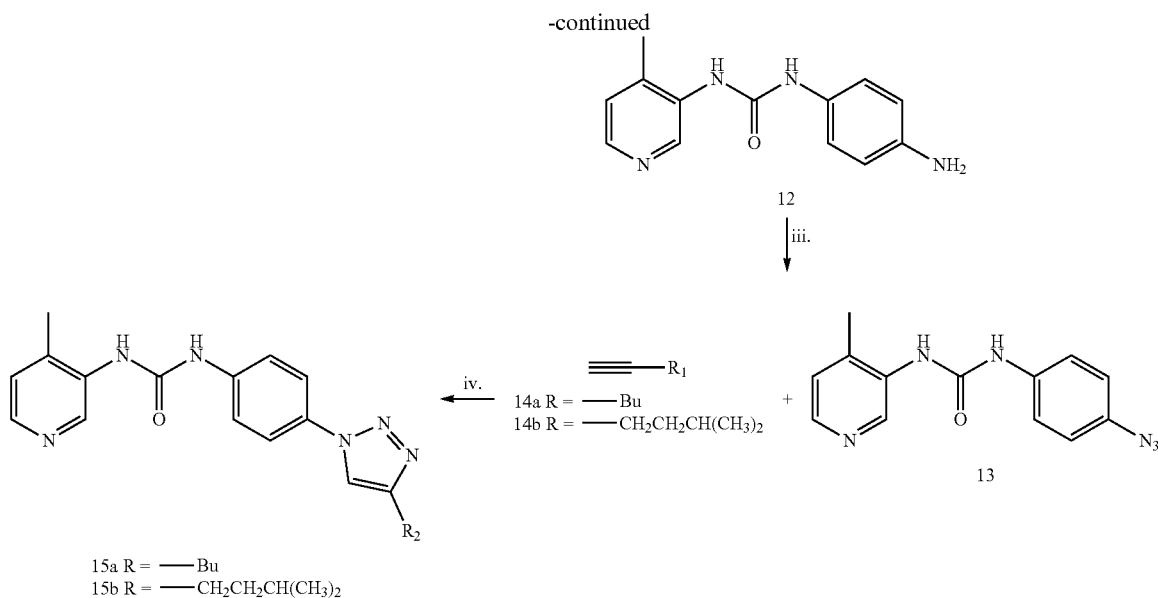

Reagents and conditions: i. CH$_2$Cl$_2$, 6 h reflux ii. H$_2$, Pd/C, MeOH; iii. NaNO$_2$, H$_2$SO$_4$ 25%, 20 min. 0° C.; iv. NaN$_3$ 2 h r.t.; v. alkyne, CuSO$_4$.5H$_2$O, sodium ascorbate, H$_2$O tBuOH (1:1), MW 80° C., 5 min.

1-(4-methylpyridin-3-yl)-3-(4-nitrophenyl)urea (11). 9 (500 mg, 3.62 mmol) was added to a solution of o-tolyl-isocyanate 10 (673 µL, 5.43 mmol) in anhydrous CH$_2$Cl$_2$ (10 mL) in one portion. The solution was stirred for 6 hours at r.t under a nitrogen atmosphere. The yellow precipitate was filtered, washed with cool DCM and petroleum ether and dried under high vacuum to afford the desired product 11 as a white solid. Yield=93%; $^1$H NMR (400 MHz, DMSO d-$_6$): δ 9.7 (s, 1H, NH), 8.19-8.16 (d, J=9.2 Hz, 2H), 8.13 (s, 1H), 7.78-7.76 (d, J=8.0 Hz, 1H), 7.69-7.66 (d, J=12.0 Hz, 2H), 7.19-7.13 (m, 2H), 7.00-6.97 (t, 1H, J=12.0 Hz), 2.24 (s, 3H) ppm. MS (ESI) m/z 272 [M+H]$^+$, 306 [M+Cl]$^-$.

1-(4-methylpyridin-3-yl)-3-(4-nitrophenyl)urea (12). Urea 11 (500 mg, 1.8 mmol) was solubilized in 30 mL of anhydrous MeOH, and 10% Palladium on charcoal (50 mg) was added. The reaction mixture was stirred under Hydrogen atmosphere for 2 hr, then the mixture was filtered off on a celite pad, and purified by flash chromatography on silica gel (DCM-MeOH 98:2). Yield=80%; white solid. $^1$H NMR (400 MHz, DMSO d-$_6$): δ 8.48 (s, 1H), 7.83-7.81 (d, J=8.0 Hz, 2H), 7.67 (s, 1H), 7.15-7.05 (m, 4H), 6.89-6.87 (d, J=8.0 Hz, 1H), 6.50-6.48 (d, J=8.0 Hz, 2H), 4.72 (s, 2H), 2.20 (s, 3H) ppm. MS (ESI) m/z 242.0 [M+H]+, 264 [M+Na]$^+$, 505 [2M+Na]$^+$.

1-(4-azidophenyl)-3-(4-methylpyridin-3-yl)urea (13). To a stirred suspension of amine 12 (400 mg, 1.6 mmol) in a 25% aq. solution of H$_2$SO$_4$, at 0° C., was added NaNO$_2$ (227.9 mg, 3.3 mmol) in water, dropwise during 20 min. After this time a solution of NaN$_3$ (208 mg, 3.2 mmol) in water (3 mL) was added dropwise during 20 min at 0° C., then the reaction mixture was stirred at r.t. Four hours later a solution of aq. NaOH was added and the pH basified until 10. The reaction mixture was then extracted with EtOAc (3×40 mL), washed with brine, and dried over anhydrous Na$_2$SO$_4$. The solvent was removed at reduced pressure and the residue was purified by flash chromatography on silica gel (DCM-MeOH 9:1). Yield 67%. $^1$H NMR (400 MHz, CDCl$_3$-d) δ 9.10 (s, 1H), 7.91 (s, 1H), 7.80-7.78 (d, J=8.0 Hz, 1H), 7.50-7.48 (d, J=8.0 Hz, 2H), 7.16-7.19 (m, 2H), 7.04-7.02 (d, J=8.0 Hz, 2H), 7.95-7.91 (t, J=8.0 Hz, 1H), 2.22 (s, 3H) ppm. MS (ESI) m/z 267 [M+Na]$^+$, 557 [2M+Na]$^+$.

General Procedure for the Preparation of Compounds 15a-b

The appropriate alkyne (0.10 mmol) and azide 13 (25 mg, 0.09 mmol) were suspended in a 1:1 mixture of water and t-BuOH (1.5 mL each) in a 10 mL glass vial equipped with a small magnetic stirring bar. To this, sodium ascorbate (0.1 equiv) and copper(II) sulfate pentahydrate (0.10 mmol) were added. The mixture was then heated for 5 min. at 80° C. under microwave irradiation, using an irradiation power of 300 W. After this time the precipitate was filtered-off and purified on silica, to give final products 15a or 15b.

1-(4-(4-butyl-1H-1,2,3-triazol-1-yl)phenyl)-3-(4-methylpyridin-3-yl)urea (15a). The residue was purified by flash chromatography on silica gel (DCM/MeOH 98:2). Yield 68%, white solid.

$^1$H NMR (400 MHz, MeOD-d$_4$): δ8.87 (s, 1H), 8.20 (s, 1H), 8.15-8.14 (d, J=4 Hz, 1H), 7.74-7.71 (d, J=8.0 Hz, 2H), 7.65-7.63 (J=8.0 Hz, 2H), 7.30-7.29 (d, J=4 Hz, 1H), 4.70-4.67 (t, J=7.0 Hz, 2H), 2.36 (s, 3H), 2.06-1.99 (quint, J=7.0 Hz, 2H), 1.41-1.36 (q, J=6.0 Hz, 2H), 1.00-0.96 (q, J=8.0 Hz, 2H) ppm. $^{13}$C-NMR (100 MHz, MeOD-d$_4$): δ 164.69, 153.67, 143.82, 143.19, 141.39, 140.12, 134.50, 127.09, 125.50, 121.37, 118.72, 50.61, 30.06, 18.51, 14.20, 11.30 ppm. MS (ESI) m/z 320 [M−H]$^-$, 356 [M+Cl]$^-$.

1-(4-(4-isopentyl-1H-1,2,3-triazol-1-yl)phenyl)-3-(4-methylpyridin-3-yl)urea (15b). The residue was purified by flash chromatography on silica gel (DCM/MeOH 98:2). Yield 74%, white solid. $^1$H NMR (400 MHz, MeOD-d$_4$): δ 8.80 (s, 1H), 8.20 (s, 1H), 8.15-8.14 (d, J=4 Hz, 1H), 7.84-7.81 (d, J=8.0 Hz, 2H), 7.67-7.65 (J=8.0 Hz, 2H), 7.34-7.31 (d, J=4 Hz, 1H), 2.78-2.74 (t, J=8.0 Hz, 2H), 2.35 (s, 3H), 1.63-1.60 (m, 3H), 0.97-0.95 (d, J=8.0 Hz, 2H) ppm. $^{13}$C-NMR (100 MHz, MeOD-d$_4$): δ 164.69, 153.67, 143.82, 143.19, 141.39, 140.12, 134.50, 127.09, 125.50, 121.37, 118.72, 38.28, 27.38, 22.87, 21.32, 16.59 ppm. MS (ESI) m/z 363 [M−H]$^-$, 399 [M+Cl].

Example 3
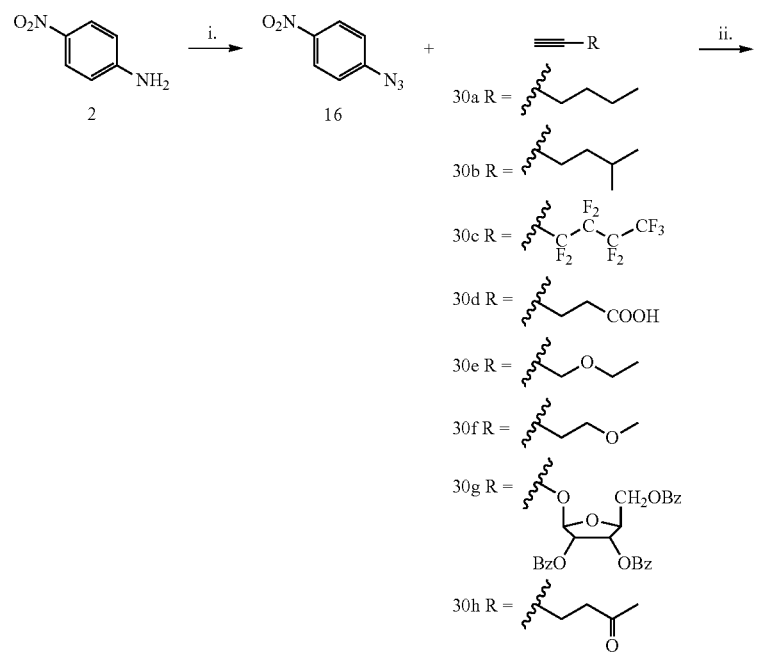
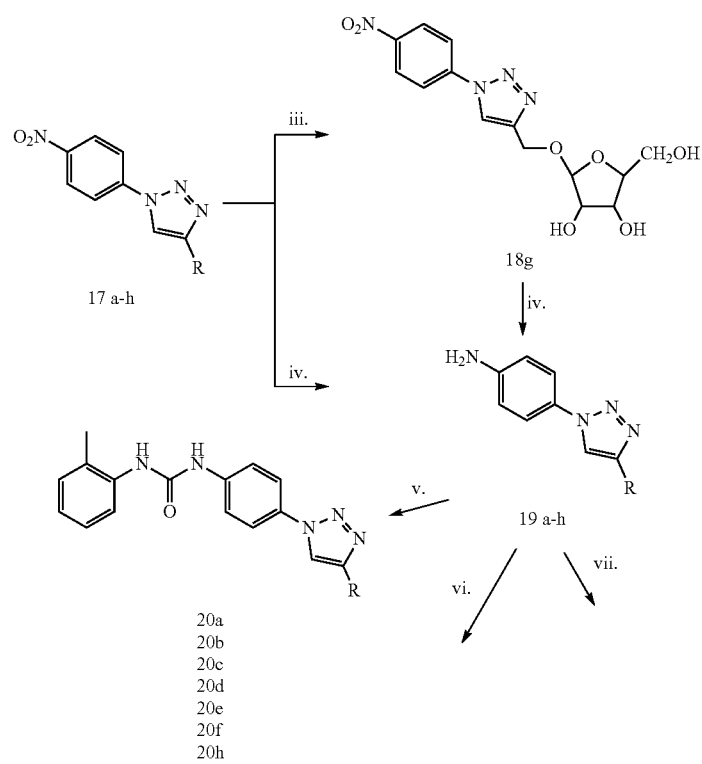

-continued

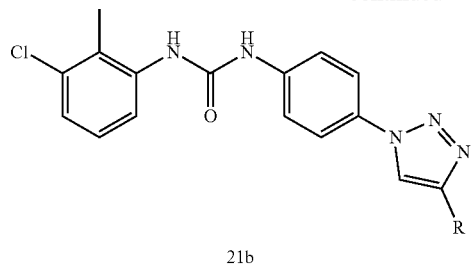

21b

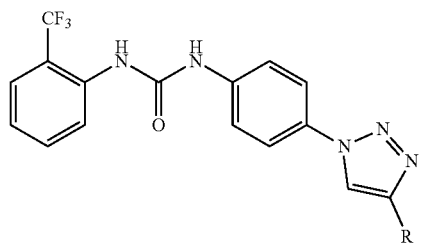

22a
22b
22g

Reagents and conditions: i. a) t-BuONO, CH₃CN, 20 min. 0° C.; b) TMSN₃, CH₃CN, 2 h r.t.; ii. Alkyne 30a-g, CuSO₄.5 H₂O, sodium ascorbate, H₂O tBuOH (1:1), MW 120° C., 10 min; iii. MeOH/NH₄OH 3:1, r.t., 24 h.; iv. H₂, Pd/C, MeOH, 1 h, v. o-tolyl-isocyanate, CH₂Cl₂, 12 h, r.t.; vi. 2-(Trifluoromethyl)phenyl isocyanate, CH₂Cl₂, CH₂Cl₂ 12 h, vii. 5-Chloro-2-methylphenyl isocyanate, CH₂Cl₂, 12 h, r.t.

1-azido-4-nitrobenzene (16). 4-nitroaniline 2 (1000 mg, 7.24 mmol) was dissolved in CH₃CN and cooled to 0° C. in an ice-salt bath. To this stirred solution, was added tBuONO (1033 µL, 8.69 mmol), and the mixture was stirred for 10 min, after this time, TMSN₃ (1441 µL, 10.86 mmol) was added dropwise, during 10 minutes, and the resulting brown solution was stirred at r.t. One hour later the solvent was removed at reduced pressure and the residue was purified by flash chromatography on silica gel (EP-EtOAc 9:1). Yield 99%. ¹H NMR (400 MHz, CDCl₃-d) δ 9.10 (s, 1H), 7.91 (s, 1H), 7.80-7.78 (d, J=8.0 Hz, 1H), 7.50-7.48 (d, J=8.0 Hz, 2H), 7.16-7.19 (m, 2H), 7.04-7.02 (d, J=8.0 Hz, 2H), 7.95-7.91 (t, J=8.0 Hz, 1H), 2.22 (s, 3H) ppm. MS (ESI) m/z 165 [M+H]⁺, 188 [M+Na]⁺.

General Procedure for the Preparation of Compounds 17a-h

The appropriate alkyne 30a-h (4.34 mmol) and azide 16 (594.11 mg, 3.62 mmol) were suspended in a 1:1 mixture of water and t-BuOH (1.5 mL each) in a 10 mL glass vial equipped with a small magnetic stirring bar. To this, was added sodium ascorbate (1.81 mmol) and copper(II) sulfate pentahydrate (1.81 mmol). The mixture was then heated for 10 min. at 120° C. under microwave irradiation, using an irradiation power of 300 W. After this time the precipitate was filtered-off and purified on silica, to give the desired triazole compounds 17a, 17b, 17c, 17d, 17e, 17f, 17g or 17h.

4-butyl-1-(4-nitrophenyl)-1H-1,2,3-triazole (17a). (Purification eluent: DCM/MeOH 98:2). Yield 80%, yellow solid. Yield ¹H NMR (400 MHz, MeOD-d₄): δ 8.48 (s, 1H), 8.42-8.44 (d, J=8.0 Hz, 2H), 8.12-8.10 (d, J=8.0 Hz, 2H), 2.80-2.77 (t, J=7.6 Hz, 2H), 1.74-1.78 (q, J=7.3 Hz, 2H), 1.46-1.40 (q, J=7.3 Hz, 2H), 0.99-0.952 (t, J=7.2 Hz, 3H) ppm. MS (ESI) m/z 245 [M−H]⁻, 281 [M+Cl]⁻.

4-isopentyl-1-(4-nitrophenyl)-1H-1,2,3-triazole (17b). (Purification eluent: PE/EtOAc 9:1). Yield 86%, yellow solid. ¹H NMR (400 MHz, MeOD-d₄): δ 8.45-8.39 (m, 3H), 8.11-8.09 (dd, J=8.0 Hz, 2H), 2.81-2.77 (t, 7.6 Hz, 2H), 1.64-1.61 (m, 3H), 0.98-0.96 (d, J=7.4 Hz, 2H) ppm. MS (ESI) m/z 260.9 [M+H]⁺.

1-(4-nitrophenyl)-4-(perfluorobutyl)-1H-1,2,3-triazole (17c). (Purification eluent: PE/EA 95:5). Yield 73%, white solid. ¹H NMR (400 MHz, CDCl₃-d): δ 8.48-8.46 (dd, J=8.1 Hz, 2H), 8.42 (s, 1H), 8.05-8.03 (dd, J=8.1 Hz, 2H) ppm. MS (ESI) m/z 442.9 [M+Cl]⁻.

3-(1-(4-nitrophenyl)-1H-1,2,3-triazol-4-yl)propanoic acid (17d). (Purification eluent: DCM/MeOH 98:2). Yield 70%, yellow solid. ¹H NMR (400 MHz, Acetone-d₆): δ 8.52 (s, 1H), 8.43-8.41 (dd, J=8.0 Hz, 2H), 8.18-8.16 (dd, J=8.0 Hz, 2H), 3.06-3.03 (t, J=12.0 Hz, 2H), 2.78-2.74 (t, J=8.0 Hz, 2H) ppm. MS (ESI) m/z 261 [M−H]⁻.

4-(2-ethoxymethyl)-1-(4-nitrophenyl)-1H-1,2,3-triazole (17e). (Purification eluent: DCM/MeOH 98:2). Yield 80%, light yellow solid. ¹H NMR (400 MHz CDCl₃-d): δ 8.34-8.31 (d, J=8.8 Hz, 2H), 8.14 (s, 1H), 7.95-7.93 (d, J=8.8 Hz, 2H), 4.65 (s, 2H), 3.61-3.56 (q, J=6.9 Hz, 2H), 1.20-1.16 (t, J=7 Hz, 3H) ppm. MS (ESI) m/z 283.2 [M+Cl]⁻.

4-(2-methoxyethyl)-1-(4-nitrophenyl)-1H-1,2,3-triazole (17f). (Purification eluent: DCM/MeOH 98:2). Yield 78%, pale yellow solid. ¹H NMR (400 MHz, CDCl₃-d): δ 8.40-8.38 (d, J=8.0 Hz, 2H), 7.97-7.95 (d, J=8.4 Hz, 2H), 3.74-3.71 (t, J=6.0 Hz, 2H), 3.38 (s, 3H), 3.10-3.07 (t, J=6.0, 2H) ppm. MS (ESI) m/z 283.2 [M+Cl]⁻.

2-((benzoyloxy)methyl)-5-((1-(4-nitrophenyl)-1H-1,2,3-triazol-4-yl)methoxy)tetrahydrofuran-3,4-diyl dibenzoate (17g). (Purification eluent: DCM/MeOH 98:2). Yield 86%, foam. ¹H NMR (400 MHz, CDCl₃-d): δ 8.31-8.29 (d, J=8.0 Hz, 2H), 8.12 (s, 1H), 7.99-7.95 (m, 4H), 7.92-7.89 (d, J=8.1 Hz, 2H), 7.85-7.83 (d, J=8.0 Hz, 2H), 7.54-7.29 (m, 5H), 7.29-7.25 (m, 4H), 5.87-5.86 (m, 1H), 5.73-5.72 (m, 1H), 5.43 (s, 1H), 4.99-4.96 (d, J=12 Hz, 1H), 4.84-4.74 (m, 3H), 4.58-4.54 (m, 1H) ppm. MS: m/z 270.9 [M+Na]⁺

4-(1-(4-nitrophenyl)-1H-1,2,3-triazol-4-yl)butan-2-one (17h). (Purification eluent: DCM/MeOH 98:2). Yield 74%, pale yellow solid. ¹H NMR (400 MHz, CDCl₃) δ 8.32 (d, J=9.0 Hz, 1H), 7.91-7.88 (m, 2H), 3.32-2.77 (m, 4H), 2.12 (s, 3H). MS (ESI) m/z 259.1 [M−H]⁻.

2-(hydroxymethyl)-5-((1-(4-nitrophenyl)-1H-1,2,3-triazol-4-yl)methoxy)tetrahydrofuran-3,4-diol (18g). Compound 17g (155 mg, 0.23 mmol) was dissolved in 4:1 methanol/concentrated ammonium hydroxide (15 mL) and stirred at room temperature for 24 h. The reaction mixture was concentrated in vacuo and azeotroped 3 times with ethanol. The crude product was dissolved in water (5 mL), extracted with methylene chloride (3×50 mL) and the aqueous layer concentrated in vacuo. Yield 99%. ¹H NMR (400 MHz, MeOD-d₄): δ 8.64 (s, 1H), 8.43-8.41 (dd, J=8.0 Hz, 2H), 8.14-8.12 (dd, J=8.0 Hz, 2H), 5.46 (s, 1H), 5.13-5.11 (d, J=8.0 Hz, 1H), 4.70-4.67 (d, J=12 Hz, 1H), 4.13-4.11 (m, 1H), 3.98-3.91 (m, 2H), 3.78-3.66 (m, 1H), 3.60-3.56 (m, 1H) ppm. MS: m/z 375 [M+Na]⁺

General Procedure for the Preparation of Compounds 19a-h

The opportune triazole compound 17a-f, or 18g (400 mg, 1.60 mmol) was solubilized in 30 mL of anhydrous MeOH, and 10% Palladium on charcoal (25 mg) was added. The reaction mixture was stirred under Hydrogen atmosphere for 1 h, then the mixture was filtered off on a celite pad, the solvent evaporated at reduced pressure and the residue purified by flash chromatography on silica gel with the opportune eluent.

4-butyl-1-(4-aminophenyl)-1H-1,2,3-triazole (19a). (Purification eluent: DCM/MeOH 95:5). Yield 80%, white solid. $^1$H NMR (400 MHz, MeOD-$d_4$): δ 7.98 (s, 1H), 7.43-7.41 (d, J=8.0 Hz, 2H), 6.78-6.76 (d, J=8.0 Hz, 2H), 2.72-2.68 (t, –J=7.6 Hz, 2H), 1.70-1.64 (q, J=7.5 Hz, 2H), 1.40-1.35 (q, J=6.7 Hz, 2H), 0.95-0.90 (t, J=7.1 Hz, 3H) ppm. MS (ESI) m/z 217 [M+H]$^+$, 240 [M+Na]$^+$.

4-isopentyl-1-(4-aminophenyl)-1H-1,2,3-triazole (19b). (Purification eluent: DCM/MeOH 98:2). Yield 86%, yellow solid. Yield $^1$H NMR (400 MHz, CDCl$_3$-d): δ 7.99 (s, 1H), 7.43-7.41 (dd, J=7.8 Hz, 2H), 6.78-6.76 (dd, J=7.8 Hz, 2H), 4.84 (s, 2H), 2.74-2.70 (t, J=7.6 Hz, 2H), 1.59-1.56 (m, 3H), 0.94-0.92 (d, J=7.4 Hz, 2H) ppm. MS (ESI) m/z 245 [M–H]$^-$, 281 [M+Cl]$^-$.

4-(4-(perfluorobutyl)-1H-1,2,3-triazol-1-yl)aniline (19c). The product was obtained as a pure compound. Yield 99%, white solid. $^1$H NMR (400 MHz, Acetone-$d_6$): δ 8.94 (s, 1H), 7.61-7.59 (dd, J=8.0 Hz, 2H), 6.86-6.84 (dd, J=8.0 Hz, 2H), 5.13 (s, 2H) ppm. $^{13}$C NMR (100 MHz Acetone-$d_6$): δ 150.01, 136.84, 126.31, 123.92, 123.21, 118.89, 114.42, 113.29 ppm. MS (ESI) m/z 377 [M–H]$^-$, 413 [M+Cl]$^-$.

3-(1-(4-aminophenyl)-1H-1,2,3-triazol-4-yl)propanoic acid. (19d) The product was obtained as a pure compound. Yield 99%, white solid. $^1$H NMR (400 MHz, MeOD): δ 8.02 (s, 1H), 7.40-7.39 (dd, J=4.0 Hz, 2H), 6.75-6.74 (dd, J=4.0 Hz, 2H), 3.03-3.00 (t, J=12.0 Hz, 2H), 2.64-2.60 (t, J=8.0 Hz, 2H) ppm. MS (ESI) m/z 233 [M+H]$^+$, 255 [M+Na]$^+$.

4-(2-ethoxymethyl)-1-(4-aminophenyl)-1H-1,2,3-triazole (19e). The product was obtained as a pure compound. Yield 99% white solid. $^1$H NMR (400 MHz, CDCl$_3$-d): δ 7.77 (s, 1H), 7.29-7.28 (d, J=8.4 Hz, 2H), 6.61-6.59 (d, J=8.4 Hz, 2H), 4.57 (s, 2H), 4.06 (s, 2H), 3.55-3.50 (q, J=6.9 Hz, 2H), 1.16-1.12 (t, J=7.0 Hz, 3H) ppm. MS (ESI): m/z 219 [M+H]$^+$.

4-(2-methoxyethyl)-1-(4-aminophenyl)-1H-1,2,3-triazole (19f). The product was obtained as a pure compound. Yield 99% white solid. $^1$H NMR (400 MHz, CDCl$_3$-d): δ 7.66 (s, 1H), 7.40-7.38 (d, J=8.0 Hz, 2H), 6.69-6.67 (d, J=8 Hz, 2H), 3.82 (s, 2H), 3.69-3.66 (t, J=6.4 Hz, 2H) 3.34 (s, 3H), 3.03-3.00 (t, J=6 Hz, 2H) ppm. MS (ESI) m/z 219 [M+H]$^+$.

2-(hydroxymethyl)-5-((1-(4-aminophenyl)-1H-1,2,3-triazol-4-yl)methoxy)tetrahydrofuran-3,4-diol (19g). The product was obtained as a pure compound. Yield 99% Foam. $^1$H NMR (400 MHz, CDCl$_3$-d): δ 8.20 (s, 1H), 7.41-7.39 (dd, J=8.0 Hz, 2H), 6.76-6.74 (dd, J=8.0 Hz, 2H), 5.01 (s, 1H), 4.66-4.63 (d, J=12 Hz, 1H), 4.15, 4.12 (m, 1H), 4.01-3.98 (m, 1H), 3.96-3.95 (m, 1H), 3.79-3.75 (m, 1H), 3.62-3.57 (m, 1H) ppm. MS (ESI): m/z 345 [M+H]$^+$.

4-(1-(4-aminophenyl)-1H-1,2,3-triazol-4-yl)butan-2-one (19h): The product was obtained as a pure compound. Yield 99% white solid. $^1$H NMR (400 MHz, CDCl$_3$-d) δ 7.60 (s, 1H), 7.39 (d, J=8.6 Hz, 2H), 6.71 (d, J=8.6 Hz, 2H), 3.80 (s, 2H), 3.00 (t, J=6.7 Hz, 2H), 2.91 (t, J=6.7 Hz, 2H), 2.14 (s, 3H). ppm. MS (ESI) m/z 231.1 [M+H]$^+$.

General Procedure for the Preparation of Compounds 20-22a-h

The opportune aniline 19a-h (100 mg, 0.46 mmol) was added to a solution of the appropriate isocyanate (85 μL, 0.65 mmol) in anhydrous CH$_2$Cl$_2$ (10 mL) in one portion. The solution was stirred for 4 hours at r.t. under a nitrogen atmosphere. The solvent was removed, at reduced pressure and the residue purified by flash chromatography using the opportune eluent.

1-(4-(4-butyl-1H-1,2,3-triazol-1-yl)phenyl)-3-o-tolylurea (20a). (Purification eluent: DCM/MeOH 98:2). Yield 85%, white solid. $^1$H NMR (400 MHz, DMSO-$d_6$): δ 9.23 (s, 1H), 8.43 (s, 1H), 7.97 (s, 1H), 7.81-7.79 (d, J=7.9, 1H), 7.76-7.74 (d, J=8.9 Hz, 2H), 7.63-7.61 (d, J=8.9 Hz, 2H), 7.17-7.11 (m, 2H), 6.96-6.93 (t, J=7.1 Hz, 1H), 2.69-2.65 (t, J=7.5 Hz, 2H), 2.23 (s, 3H), 1.66-1.59 (m, 2H), 1.40-1.31 (m, 2H), 0.92-0.88 (t, J=7.3, 3H) ppm. $^{13}$C-NMR (100 MHz, MeOD-$d_4$): δ 153.09, 140.57, 137.65, 131.33, 130.69, 128.42, 126.62, 123.44, 121.86, 121.09, 120.49, 119.08, 31.41, 25.18, 22.17, 18.34, 14.15 ppm. MS (ESI) m/z 348 [M–H]$^-$, 384 [M+Cl]$^-$.

1-(4-(4-isopentyl-1H-1,2,3-triazol-1-yl)phenyl)-3-o-tolylurea (20b). (Purification eluent: DCM/MeOH 98:2). Yield 89%, white solid. $^1$H NMR (400 MHz, MeOD-$d_4$): δ8.18 (s, 1H), 7.71-7.69 (d, J=8.0 Hz, 2H), 7.64-7.61 (m, 3H), 7.2-7.1 (m, 2H), 7.04-7.01 (t, J=8.0 Hz, 1H), 2.78-2.74 (t, J=8.0 Hz, 2H), 2.29 (s, 3H), 1.63-1.60 (m, 3H), 0.97 (s, 6H), ppm. $^{13}$C-NMR (100 MHz, MeOD-$d_4$): δ 155.0, 150.71, 144.20, 140.26, 132.41, 130.09, 128.32, 126.08, 124.22, 123.12, 120.79, 119.76, 119.23, 38.28, 27.38, 22.87, 21.32, 16.59 ppm. MS (ESI) m/z 362 [M–H]$^-$, 398 [M+Cl]$^-$.

1-(4-(4-(perfluorobutyl)-1H-1,2,3-triazol-1-yl)phenyl)-3-(o-tolyl)urea (20c). (Purification eluent: DCM/MeOH 98:2). Yield 70%, white solid. $^1$HNMR (400 MHz, MeOD-$d_4$): δ 9.13 (s, 2H), 7.82-7.79 (dd, J=8.1 Hz, 2H), 7.70-7.68 (dd, J=8.1 Hz, 2H), 7.21-7.15 (m, 3H), 7.06, 7.02 (t, J=8.2 Hz, 1H), 2.30 (s, 3H) ppm. $^{13}$CNMR (100 MHz, MeOD-$d_4$): δ 154.16, 141.22, 136.08, 130.84, 130.07, 126.15, 124.43, 123.43, 121.48, 119.03, 115.86, 112.69, 110.20, 107.28, 16.93 ppm. $^{19}$FNMR (280 MHz, MeOD-$d_4$): δ 83.03, 110.64, 124.80, 127.30 ppm MS (ESI) m/z 510 [M–H]$^-$, 545.9 [M+Cl]$^-$.

3-(1-(4-(3-(2-(trifluoromethyl)phenyl)ureido)phenyl)-1H-1,2,3-triazol-4-yl)propanoic acid (20d). The residue was purified by flash chromatography on silica gel (DCM/MeOH 95:5). Yield 65%, white solid. $^1$H NMR (400 MHz, MeOD-$d_4$): δ 8.20 (s, 1H), 7.92-7.90 (d, J=8.0 Hz, 1H), 7.72-7.62 (m, 5H), 7.60-7.57 (t, J=12.0 Hz, 1H), 7.30-7.26 (t, J=8.0 Hz, 1H), 3.05-3.02 (t, J=12.0 Hz, 2H), 2.72-2.69 (t, 2H) ppm. MS (ESI) m/z 418 [M–H]$^-$.

1-(4-(4-(ethoxymethyl)-1H-1,2,3-triazol-1-yl)phenyl)-3-(o-tolyl)urea (20e). (Purification eluent: DCM/MeOH 95:5). Yield 83%, white solid. $^1$HNMR (400 MHz, MeOD-$d_4$): δ 8.41 (s, 1H), 7.73-7.64 (m, 5H), 4.59 (s, 2H), 3.64-3.59 (q, J=6.9 Hz, 2H), 2.30 (s, 3H), 1.23-1.20 (t, J=6.7 Hz, 3H)ppm. $^{13}$C NMR (100 MHz, MeOD-$d_4$) δ 153.69, 144.40, 140.44, 134.71, 132.83, 131.00, 129.85, 129.41, 125.84, 121.65, 120.1, 115.08, 65.65, 63.12, 16.45, 14.27 ppm. MS (ESI): m/z 351.9[M+H]$^+$ 1-(4-(4-(2-methoxyethyl)-1H-1,2,3-triazol-1-yl)phenyl)-3-o-tolylurea (20l). (Purification eluent: DCM/MeOH 95:5). Yield 78%, white solid. $^1$HNMR (400 MHz, CDCl$_3$-d): δ 8.22 (s, 1H), 7.73-7.67 (d, J=8.0 Hz, 2H), 7.65-7.62 (m, 3H), 7.21-7.15 (d, J=8.0 Hz, 2H), 7.05-7.01 (t, J=8.0 Hz, 1H), 3.72-3.69 (t, J=6.0 Hz, 2H), 3.03-3.0 (t, J=6.0 Hz, 2H), 2.30 (s, 3H), $^{13}$C NMR (100 MHz, CDCl$_3$-d): δ 145.76, 140.09, 130.10, 126.08, 124.24, 123.14, 120.84, 120.68, 119.24, 70.97, 57.42, 25.61, 16.60 ppm. MS (ESI): m/z 351.9 [M+H]$^+$ 1-(4-(4-(3-oxobutyl)-1H-1,2,3-triazol-1-yl)phenyl)-3-(o-tolyl)urea (20h): (Purification eluent: DCM/MeOH 95:5). Yield 81%, white solid. $^1$H NMR (400 MHz, CDCl$_3$-d) δ 8.08 (s, 1H), 7.85-7.67 (m, 2H), 7.20-7.02 (m, 3H), 6.91 (s, 1H), 6.88-6.69 (m, 2H), 6.38 (d, J=6.8 Hz, 2H), 3.09-2.98 (m, 2H), 2.96-2.85 (m, 2H), 2.22-2.14 (m, 6H)ppm. $^{13}$C NMR (100 MHz, CDCl$_3$-d) δ 206.98, 153.62, 137.21, 136.75, 131.73, 129.47, 127.74, 124.73, 123.07, 123.07, 122.19, 122.17, 121.34, 41.35, 28.57, 20.36, 17.35 ppm. MS (ESI): m/z 362.5 [M−H]$^−$ 1-(3-chloro-2-methylphenyl)-3-(4-(4-isopentyl-1H-1,2,3-triazol-1-yl)phenyl)urea (21b). (Purification eluent: DCM/MeOH 98:2). Yield 80%, white solid. $^1$HNMR (400 MHz, MeOD-d$_4$): δ 7.89 (s, 1H), 7.64-7.57 (m, 4H), 7.08-7.06 (d, J=8.0 Hz, 1H), 6.95-6.93 (d, J=8.0 Hz, 1H), 2.77-2.73 (t, J=7.2 Hz, 2H), 2.23 (s, 3H), 1.60-1.56 (m, 3H), 0.94-0.93 (d, J=6.0 Hz, 6H) ppm. $^{13}$C NMR (100 MHz, CDCl$_3$-d): δ 153.48, 149.08, 139.85, 137.69, 131.73, 131.14, 126.60, 123.47, 121.61, 121.16, 119.74 ppm. MS (ESI): m/z 396 [M−H]$^−$ 1-(4-(4-butyl-1H-1,2,3-triazol-1-yl)phenyl)-3-(2-(trifluoromethyl)phenyl)urea (22a). (Purification eluent: DCM/MeOH 98:2). Yield 78%, white solid. $^1$HNMR (400 MHz, MeOD-d$_4$): δ 8.16 (s, 1H), 7.93-7.92 (d, J=8.0 Hz, 2H), 7.71-7.68 (m, 2H), 7.64-7.61 (m, 3H), 7.59-7.55 (t, J=7.8 Hz, 1H), 7.27-7.23 (t, J=8.0 Hz), 2.75-2.71 (t, J=7.6 Hz), 1.72-1.64 (quint J=7.5 Hz, 2H), 1.42-1.34 (sx J=7.6 Hz, 2H), 0.96-0.92 (t, J=7.6 Hz, 3H) ppm $^{13}$C NMR (100 MHz, CDCl$_3$-d): δ 153.67, 148.70, 139.78, 135.85, 132.39, 131.91, 125.96, 125.62, 124.03, 120.85, 119.82, 119.40, 31.30, 24.60, 21.97, 12.99 ppm. MS (ESI): m/z 402 [M−H]$^−$.

1-(4-(4-isopentyl-1H-1,2,3-triazol-1-yl)phenyl)-3-(2-(trifluoromethyl)phenyl)urea (22b). (Purification eluent: DCM/MeOH 98:2). Yield 72%, white solid. $^1$HNMR (400 MHz, CDCl$_3$-d): δ 9.11 (s, 1H), 7.83-7.81 (m, 2H), 7.654 (s, 1H), 7.48-7.46 (m, 4H), 7.41-7.37 (t, J=8.0 Hz, 1H), 7.10-7.06 (t, J=8.0 Hz, 1H), 2.76-2.72 (t, J=7.2 Hz, 2H), 1.60-1.54 (m, 3H), 0.88-0.87 (d, J=6.0 Hz). $^{13}$C NMR (100 MHz, CDCl$_3$-d): δ 153.78, 149.36, 139.65, 135.58, 132.44, 131.92, 127.93, 126.53, 126.05, 125.22, 124.45, 122.48, 122.16, 121.09, 120.11, 119.37, 38.38, 27.62, 23.43, 22.27 ppm. MS (ESI): m/z 416.2 [M+H]$^+$.

1-(4-(4-(((3,4-dihydroxy-5-(hydroxymethyl)tetrahydrofuran-2-yl)oxy)methyl)-1H-1,2,3-triazol-1-yl)phenyl)-3-(2-(trifluoromethyl)phenyl)urea (22g). (Purification eluent: DCM/MeOH 98:2). Yield 86%, white solid. $^1$HNMR (400 MHz, Acetone-d$_6$): δ 9.05 (s, 1H), 8.43 (s, 1H), 8.13-8.11 (d, J=8.0 Hz, 2H), 7.79-7.72 (m, 5H), 7.67-7.61 (m, 2H), 7.29-7.26 (t, J=7.6 Hz, 1H), 5.03 (s, 1H), 4.85-4.82 (d, J=12 Hz, 1H), 4.69-4.66 (d, J=12 Hz, 1H), 4.23 (s, 2H), 4.08-4.06 (d, J=8.0 Hz, 1H), 3.98-3.94 (m, 2H), 3.81-3.79 (m, 1H), 3.62-3.56 (m, 1H) ppm. $^{13}$C NMR (100 MHz, Acetone d-$_6$): δ 152.41, 145.37, 140.16, 136.73, 1332.82, 131.91, 125.92, 125.47, 123.78, 121.56, 121.30, 120.99, 119.27, 114.23, 106.76, 84.67, 75.10, 70.93, 63.07, 60.13 ppm. MS (ESI): m/z 508 [M−H]$^−$, 543 [M+Cl]$^−$.

Compounds 30a and 30b were purchased from Sigma Aldrich and used without further purification.

Example 4

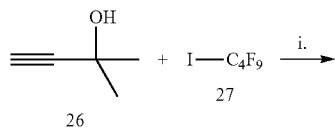

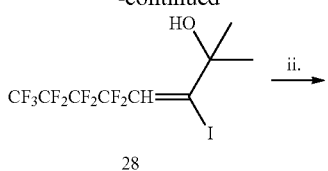

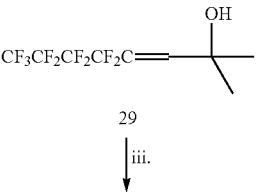

Reagents and conditions: i. Zn hu, CF$_3$COOH, CH$_2$Cl$_2$, 1 h, rt; ii. KOH, H$_2$O, 2h r.t; iii. NaOH, H$_2$O, 2 h reflux 5,5,6,6,7,7,8,8,8-nonafluoro-3-iodo-2-methyloct-3-en-2-ol (28). Compound 27 (2.04 mL 11.8 mmol) and 3 mL of CH$_2$Cl$_2$ were added to a stirred suspension of Zinc dust (777 mg, 11.8 mmol) in 26 (1.15 mL, 11.8 mmol). To this were added 2 drops of CF$_3$COOH, and the mixture was stirred at r.t under hv irradiation for 1 h. After that time, the reaction mixture was filtered off on a celite pad and the solvent removed at reduced pressure to give a colourless oil. Yield 92%. $^1$HNMR (400 MHz, CDCl$_3$-d): δ 6.85-6.78 (t, J=12 Hz, 1H), 2.85 (s, 1H), 1.52-1.51 (s, 6H) ppm. $^{13}$C NMR (100 MHz, CDCl$_3$-d): δ 126.49, 120.64, 118.77, 115.92, 113.40, 87.36, 71.79, 29.35 ppm. MS (ESI): m/z 429 [M−H]$^−$ 5,5,6,6,7,7,8,8,8-nonafluoro-2-methyloct-3-yn-2-ol (29). To a stirring solution of KOH (434 mg, 7.7 mmol) in a mixture of EtOH (20 mL) and water (5 mL) 28 (3330 mg, 7.7 mmol) was added dropwise. The reaction mixture was stirred at r.t for 2 h, after then HCl was added, and the pH adjusted to 7. Et$_2$O was added and the reaction mixture extracted several times and dried over anhydrous Na$_2$SO$_4$. Yield 90%, yellow oil. $^1$HNMR (400 MHz, CDCl$_3$-d): δ 1.49 (s, 6H) ppm. $^{13}$C NMR (100 MHz, CDCl$_3$-d): δ 120.49, 118.68, 115.88, 113.38, 111.10, 82.10, 76.49, 64.83, 29.10 ppm. MS (ESI): m/z 431 [M−H]$^−$ 3,3,4,4,5,5,6,6,6-nonafluorohex-1-yne (30c). Compound 29 (2114 mg, 7 mmol) was added to a solution of 280 mg of NaOH in water. The mixture was heated and immediately distilled (b.p. 40° C.). Yield 78%. Colourless oil. $^1$HNMR (400 MHz, CDCl$_3$-d): δ 2.16, (s, 1H)ppm. $^{13}$C NMR (100 MHz, CDCl$_3$-d): δ 117.0, 108.12, 107.50, 80.32, 71.63 ppm. MS (ESI): m/z 243 [M−H]$^−$

Example 5

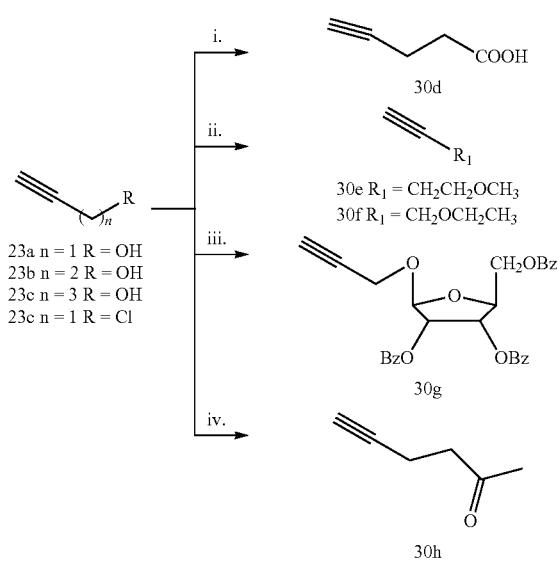

Reagents and conditions: i. Jones reagent, r.t, acetone, 1 h; ii. a) opportune alcohol, NaOH (6M) 20 min. r.t; b) dimethylsulfate or diethylsulfate, 50-55° C.; iii. a) β-D-ribofuranose 1-acetate 2,3-5 tribenzoate, BF$_3$ Et$_2$O 0° C., CH$_2$Cl$_2$, 15 min; b) K$_2$CO$_3$ 15 min; iv. K$_2$CO$_3$, acetylacetone, EtOH, 90° C., 12 h.

pent-4-ynoic acid (30d). 23d (1 mL, 10.7 mmol) was dissolved in Acetone and cooled to 0° C. Jones reagent was added dropwise to the solution, under vigorous stirring, until the reaction mixture remained orange. The mixture was allowed to reach r.t., and more Jones reagent was added to maintain the orange colour. The reaction mixture was stirred at r.t. for 1 h, then water was added, and was extracted with Et$_2$O several times, washed with Brine and dried over anhydrous Na$_2$SO$_4$. The solvent was removed at reduced pressure and the resulting oil purified by flash chromatography on silica gel (Hexane/Et$_2$O 8:2). Yield 82%, colourless oil. $^1$HNMR (400 MHz CDCl$_3$-d): δ 2.61-2.59 (m, 2H), 2.52-2.48 (m, 2H), 1.98-1.95 (m, 1H) ppm.

General Procedure for the Preparation of Compounds 30e and 30f

To a stirring solution of 200 g of NaOH in 300 mL of water (0.3 mol, 16.8 g) was added the opportune alcohol (2.5 mL, 33.02 mmol). To this, was slowly added the corresponding sulfate (15 mmol, 2082 mg) in 2 h dropwise and the mixture was heated at 50° C. The final product was distilled off, the distillation was stopped at 95° C., then the content of the receiver was washed with cold NH$_4$Cl aq solution and separated.

3-ethoxyprop-1-yne (30e). Yield 68% colourless oil. $^1$H NMR (400 MHz, CDCl$_3$-d): δ 4.13-4.13 (d, J=2.4 Hz, 2H), 3.60-3.55 (q, 2H), 2.41-2.40 (t, J=4.8 Hz, 1H), 1.24-1.22 (t, J=4 Hz, 3H) ppm 4-methoxybut-1-yne (30f). Yield 52% colourless oil. $^1$H NMR (400 MHz, CDCl$_3$-d): δ 3.52-3.49 (m, 2H), 3.33 (s, 3H), 2.47-2.43 (m, 2H), 1.99-1.97 (m, 1H) ppm.

1-propynyl-2,3,4-tri-O-benzoyl-ribofuranose (30g): To a solution of β-D-ribofuranose 1-acetate 2,3-5 tribenzoate (937 mg, 1.8 mmol) in dichloromethane (8 mL) was added propargyl alcohol (129 μL, 2.23 mmol) and BF$_3$.Et$_2$O (344 μL, 2.79 mmol) at 0° C. and the reaction mixture was stirred at room temperature for 2 h. After this time, K$_2$CO$_3$ (450 mg) was added and stirring was continued for further 15 min. Then the reaction mixture was filtered and washed with dichloromethane. The filtrate was washed with water, the aqueous phase was separated and extracted with dichloromethane (3×20 mL) and the combined organic phases were dried (Na$_2$SO$_4$) and concentrated to yield the desired compound 30g as a crystalline solid. Yield 85%. $^1$H NMR (400 MHz CDCl$_3$-d): δ 8.07-7.00 (m, 4H), 7.87-7.85 (d, J=8.1 Hz, 2H), 7.55-7.43 (m, 3H), 7.41-7.34 (m, 4H), 7.29-7.25 (m, 2H), 5.93-5.90 (m, 1H), 5.77-5.76 (d, J=4.2 Hz, 1H), 5.50 (s, 1H), 4.70-4.65 (m, 2H), 4.50-4.46 (m, 1H), 4.20 (s, 2H), 2.45 (s, 1H) ppm.

$^{13}$C NMR (100 MHz, CDCl$_3$-d): δ 166.10, 165.26, 165.07, 133.44, 133.33, 133.10, 129.75, 129.67, 129.11, 128.84, 128.43, 128.34, 128.29, 103.30, 79.30, 78.25, 75.48, 75.24, 72.07, 64.42, 54.49 ppm. MS (ESI) m/z: 523 [M+Na]$^+$.

hex-5-yn-2-one (30h): A mixture of propargyl chloride (485 μL, 6.71 mmol), acetylacetone (758 μL, 7.38 mmol) and K$_2$CO$_3$ (1112 mg, 8.0 mmol) was stirred in EtOH (10 mL), at 80° C., for 12 h. After this time, EtOH was partially removed under reduced pressure, water (15 mL) was added, the aqueous phase was separated and extracted with MTBE (3×20 mL). The combined organic phases were dried (Na$_2$SO$_4$). 30h was finally purified by distillation bp=71° C. $^1$H NMR (400 MHz, CDCl$_3$) δ 2.66 (t, J=7.1 Hz, 1H), 2.41 (t, J=5.9 Hz, 1H), 2.14 (s, 1H), 1.92 (s, 1H)ppm.

Example 6

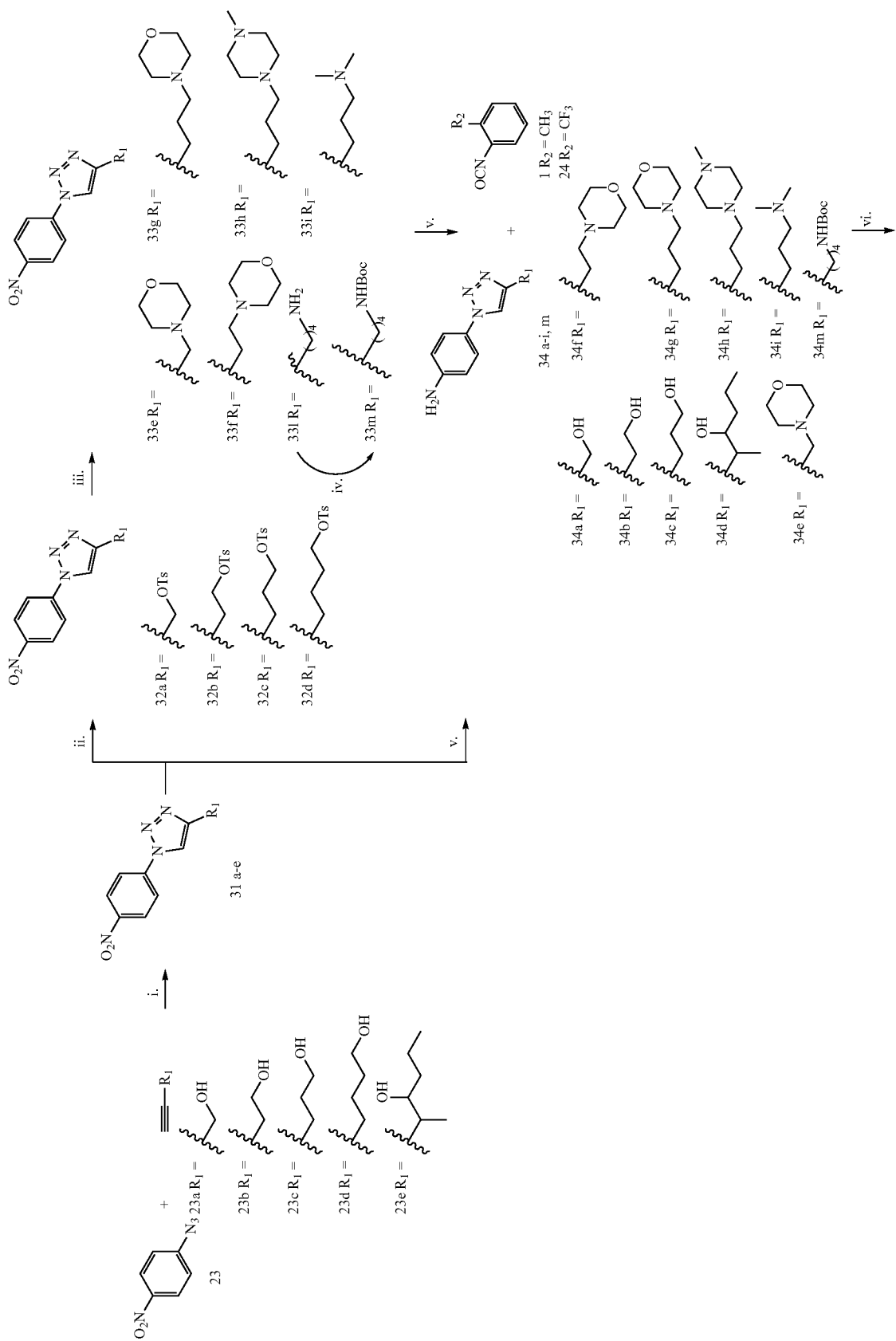

-continued
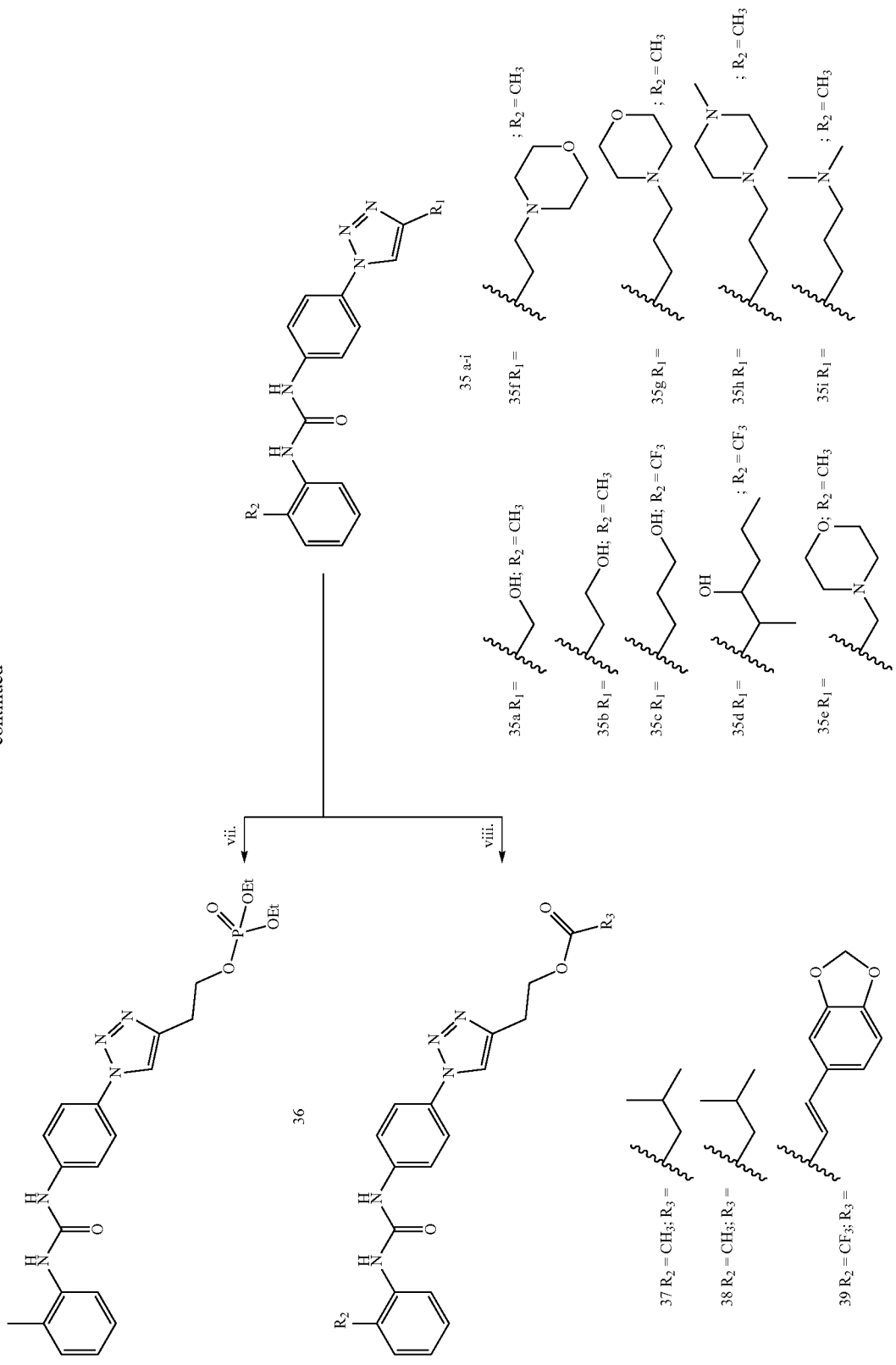

Reagents and conditions: i. alkyne, CuSO$_4$.5 H$_2$O, sodium ascorbate, H$_2$O tBuOH (1:1), MW 10 min, 120° C.; ii. KOH, TsCl, THF (dry) 24 h; iii. opportune amine, DCM, 9 h, 80° C.; iv 5%. NaOH(aq), di tert-butyl dicarbonate, THF, rt 12 h V. H$_2$, Pd/C, MeOH, 1 h, vi. opportune isocyanate CH$_2$Cl$_2$, 5 h reflux; vii. titanium isopropoxyde; diethyl phosphonate, TEA, CH$_2$Cl$_2$ o.n. r.t.; viii. opportune acid, DCC, DMAP, CH$_2$Cl$_2$, DMF 9 h, r.t.

General Procedure for the Preparation of Compounds 31a-e

The appropriate alkyne (6.08 mmol) and azide 16 (831 mg, 5.07 mmol) were suspended in a 1:1 mixture of water and t-BuOH (1.5 mL each) in a 10 mL glass vial equipped with a small magnetic stirring bar. To this, was added sodium ascorbate (2.5 mmol) and copper(II) sulfate pentahydrate (2.50 mmol). The mixture was then heated for 10 min. at 125° C. under microwave irradiation, using an irradiation power of 300 W. After that time the solvent was removed at reduced pressure water was added and the mixture was extracted with EtOAc (3×20 mL). The organic layers were collected, washed with Brine and dried over Na$_2$SO$_4$. The crude was purified by flash chromatography on silica gel using the opportune eluent to give the desired triazole compounds 31a, 31b, 31c, 31d or 31e.

(1-(4-nitrophenyl)-1H-1,2,3-triazol-4-yl)methanol (31a). (Purification eluent: DCM/MeOH 98:2). Yield 90%, yellow solid. $^1$H NMR (400 MHz, MeOD-d$_4$): δ 8.47 (s, 1H), 8.42, 8.40 (d, J=8.0 Hz, 2H), 8.12, 8.09 (d, J=8.0 Hz, 2H), 2.34 (s, 2H) ppm. MS (ESI) m/z 221 [M+H]$^+$, 243 [M+Na]$^+$.

(1-(4-nitrophenyl)-1H-1,2,3-triazol-4-yl)ethanol (31b). (Purification eluent: DCM/MeOH 98:2). Yield 84%, yellow solid. $^1$H NMR (400 MHz, MeOD-d$_4$): δ 8.50 (1H, NCH), δ 8.44-8.42 (d, J=8.0 Hz, 2H), 8.14-8.12 (d, J=8.0 Hz, 2H), 3.90-3.87 (t, J=6.0 Hz, 2H), 3.02-2.99 (t, J=6.0 Hz, 2H) ppm. MS (ESI) m/z 235 [M+H]$^+$, 257 [M+Na]$^+$.

(1-(4-nitrophenyl)-1H-1,2,3-triazol-4-yl)propanol (31c). (Purification eluent: DCM/MeOH 98:2). Yield 88%, yellow solid $^1$H NMR (400 MHz, MeOD-d$_4$): δ8.47 (s, 1H), 8.42, 8.40 (d, J=8.0 Hz, 2H), 8.12, 8.09 (d, J=8.0 Hz, 2H), 3.66-3.63 (t, J=6.0 Hz, 2H), 2.89-2.85 (t, J=8.0 Hz, 2H), 1.98-1.92 (t, J=8.0 Hz, 2H). MS (ESI) m/z 227 [M+H]$^+$, 271 [M+Na]$^+$.

4-(1-(4-nitrophenyl)-1H-1,2,3-triazol-4-yl)butan-1-((1 (31d). (Purification eluent: DCM/MeOH 98:2). Yield 85%, yellow solid $^1$H NMR (400 MHz, MeOD-d$_4$) δ 8.43 (s, 1H), 8.35 (d, J=9.0 Hz, 2H), 8.08 (m, Hz, 2H), 3.59 (t, J=6.4 Hz, 2H), 2.79 (t, J=7.6 Hz, 2H), 1.78 (q, J=15.2 Hz, 2H), 1.61 (dt, J=13.1, 6.4 Hz, 2H)ppm. MS (ESI) m/z 361[M−H]$^−$.

2-methyl-1-(1-(4-nitrophenyl)-1H-1,2,3-triazol-4-yl)pentan-1-ol (31e). (Purification eluent: DCM/MeOH 98:2). Yield 88%, yellow solid $^1$H NMR (400 MHz, CDCl$_3$-d): δ 8.39-8.37 (d, J=8.0 Hz, 2H), 8.05 (s, 1H), 7.98-7.96 (d, J=8.0 Hz, 2H), 4.91-4.84 (m, 1H), 2.82 (s, 1H), 2.06-2.03 (m, 1H), 1.51-1.12 (m, 4H), 0.93-0.86 (m, 6H)ppm. $^{13}$C NMR (100 MHz, CDCl$_3$-d): δ 152.24, 147.33, 141.61, 125.52, 124.92, 120.36, 119.28, 71.60, 70.98, 38.88, 38.63, 35.06, 33.80, 20.31, 20.13, 15.25, 14.24, 13.80 ppm. MS (ESI) m/z 325.0 [M+Cl]$^−$.

General Procedure for the Preparation of Compounds 32a-d

Tosyl Chloride, (1.88 mmol, 359.00 mg), KOH (4.28 mmol, 240.39 mg), and the opportune alcohol, were stirred in 15 mL of anhydrous THF in an ice-salt bath, at 0° C. under nitrogen atmosphere. After 30 min. the reaction mixture was stirred at r.t. Twelve hours later the solvent was removed at reduced pressure, water was added and the reaction mixture was extracted with DCM (100 mL×3). The combined organic layers were washed with brine, dried (Na$_2$SO$_4$), and concentrated. The residue was purified by flash chromatography on silica gel (PE/EtOAc 5:3).

3-(1-(4-nitrophenyl)-1H-1,2,3-triazol-4-yl)methyl 4-methylbenzenesulfonate (32 a). Yield 72%. White solid. $^1$H NMR (400 MHz, CDCl$_3$-d): δ 8.44-8.41 (d, J=9.2 Hz, 2H), 8.17 (s, 1H), 7.96-7.93 (d, J=9.2 Hz, 2H), 7.84-7.82 (d, J=8.4 Hz, 2H), 7.37-7.35 (d, J=8 Hz, 2H), 5.29 (s, 2H), δ 2.45 (s, 3H) ppm. MS (ESI): m/z 397 [M+Na]$^+$ 3-(1-(4-nitrophenyl)-1H-1,2,3-triazol-4-yl)ethyl 4-methylbenzenesulfonate (32 b). Yield 78%. White solid. $^1$H NMR (400 MHz, CDCl$_3$-d): δ 8.42-8.39 (d, J=9.2 Hz, 2H), 7.98 (s, 1H), 7.95-7.93 (d, J=8.8 Hz, 2H), 7.75-7.73 (d, J=8.4 Hz, 2H), 7.32-7.30 (d, J=8 Hz, 2H), 4.37-4.34 (t, J=6.4 Hz, 2H), 3.21-3.18 (t, J=6.4 Hz, 2H), 2.40 (s, 3H) ppm. MS (ESI): m/z 410.8 [M+Na]$^+$ 3-(1-(4-nitrophenyl)-1H-1,2,3-triazol-4-yl)propyl 4-methylbenzenesulfonate (32 c). Yield 83%. White solid. $^1$H NMR (400 MHz, CDCl$_3$-d): δ 8.35-8.33 (d, J=8.8 Hz, 2H), 7.94-7.92 (m, 3H), 7.74-7.72 (d, J=8.0 Hz, 2H), 7.75-7.73 (d, J=8.4 Hz, 2H), 7.31-7.29 (d, J=8 Hz, 2H), 4.09-4.06 (t, J=6.0 Hz, 2H), 2.88-2.84 (t, J=8.0 Hz, 2H), 2.38 (s, 3H), 2.12-2.07 (quint, J=6.0 Hz, 2H ppm. MS (ESI): m/z 402.8 [M+H]$^+$, 424.8 [M+Na]$^+$ 4-(1-(4-nitrophenyl)-1H-1,2,3-triazol-4-yl)butyl 4-methylbenzenesulfonate (32d). Yield 90%. White solid. $^1$H NMR (400 MHz, CDCl$_3$-d): δ 8.38 (d, J=9.0 Hz, 1H), 7.94 (d, J=8.9 Hz, 1H), 7.86 (s, 1H), 7.75 (d, J=8.3 Hz, 1H), 7.32 (d, J=8.0 Hz, 1H), 4.06 (t, J=5.8 Hz, 1H), 2.80 (t, J=7.1 Hz, 1H), 2.42 (s, 2H), 1.89-1.64 (m, 3H). MS (ESI): m/z 417.1 [M+H]$^+$ General Procedure for the Preparation of Compounds 33e-i.

To a solution of the opportune tosylate, was added the corresponding amine, at 0° C. The reaction mixture was stirred at 80° C. in a sealed tube. After 24 h the solvent was removed at reduced pressure and the residue purified by flash chromatography on silica gel.

4-(3-(1-(4-nitrophenyl)-1H-1,2,3-triazol-4-yl)methyl) morpholine (33e). (Purification eluent: DCM-methanol 98:2). Yield 95%. White solid. $^1$H NMR (400 MHz, MeOD-d$_4$): δ 8.6 (s, 1H), 8.46-8.44 (d, J=8 Hz, 2H), 8.17-8.14 (d, J=8.0 Hz, 2H), 3.76 (s, 2H), 3.71-3.69 (m, 4H), 2.57-2.55 (m, 4H) ppm. MS(ESI): m/z 412.9 [M+Na]$^+$, 289.9 [M+H]$^+$.

4-(3-(1-(4-nitrophenyl)-1H-1,2,3-triazol-4-yl)ethyl)morpholine (33f). (Purification eluent: DCM-methanol 98:2). Yield 92%. White solid. $^1$H NMR (400 MHz, MeOD-d$_4$): δ 8.51 (s, 1H), 8.43-8.40 (d, J=8 Hz, 2H), 8.13-8.10 (d, J=8 Hz, 2H), 3.72-3.69 (m, 4H), 3.01-2.99 (t, J=2 Hz, 2H) 2.77-2.73 (t, J=8 Hz, 2H), δ 2.57-2.55 (m, 4H). MS (ESI): m/z 303.9 [M+H]$^+$.

4-(3-(1-(4-nitrophenyl)-1H-1,2,3-triazol-4-yl)propyl) morpholine (33g). (Purification eluent: DCM-methanol 98:2). Yield 90%. White solid. $^1$H NMR (400 MHz, Acetone): δ 8.51 (s, 1H), 8.43-8.41 (d, J=8.9 Hz, 2H), 8.19-8.16 (d, J=8.9 Hz, 2H), 3.59-3.57 (m, 4H), 2.83-2.80 (t, J=7.6 Hz, 2H) 2.40-2.36 (m, 4H), δ 2.57-1.93-1.86 (t, J=7.6 Hz, 2H). MS (ESI): m/z 303.9 [M+H]$^+$.

1-methyl-4-(3-(1-(4-nitrophenyl)-1H-1,2,3-triazol-4-yl)propyl)piperazine (33h).

(Purification eluent: DCM-methanol 98:2). Yield 69% white solid. $^1$H NMR (400 MHz, CDCl$_3$-d): δ 8.22-8.20 (d, J=8.0 Hz, 2H), 7.85-7.82 (m, 3H), 2.69-2.66 (t, J=6.0 Hz, 2H), 2.31-2.26 (m, 10H), 2.10 (s, 3H), 1.82-1.74 (quint, J=5.9 Hz, 2H) ppm. MS (ESI): m/z 330.9 [M+H]$^+$, 353 [M+Na]$^+$.

4-(3-(1-(4-nitrophenyl)-1H-1,2,3-triazol-4-yl)propyl)dimethylamine (33i). (Purification eluent: DCM-methanol 95:5). Yield 69% white solid. $^1$H NMR (400 MHz, CDCl$_3$-d): δ 8.63 (s, 1H), 8.43-8.41 (d, J=8.8 Hz, 2H), 8.16-8.14 (d, J=8.8 Hz, 2H), 3.14-3.10 (t, J=6.0 Hz, 2H), 2.93-2.90 (t, J=6.0 Hz, 2H), 2.81 (s, 6H), 2.21-2.13 (quint, J=8.0 Hz, 2H) ppm. MS (ESI): m/z 317.9 [M+H]$^+$, 339.9 [M+Na]$^+$.

4-(1-(4-nitrophenyl)-1H-1,2,3-triazol-4-yl)butan-1-amine (33l). 32d (500 mg, 1.2 mmol) was solubilized in anhydrous DCM (2 mL), in a vial. The rxn mixture was cooled to −78° C., and ammonia was bubbled in the solution. The tube was sealed and the resulting mixture was stirred at rt for 12 hrs. After this time the solvent was removed at reduced pressure. HCl 3N was added and the resulting yellow pp was filtered-off and recrystallized from ACN. Yield 80%, white solid $^1$H NMR (400 MHz, MeOD) δ 8.42 (s, 1H), 8.33 (d, J=8.6 Hz, 3H), 8.04 (d, J=8.5 Hz, 3H), 2.77-2.74 (m, 4H), 1.80-1.66 (m, 2H), 1.57-1.55 (m, 2H), 0.81 (m, 2H)ppm. MS (ESI): m/z 262 [M+H]$^+$, 284 [M+Na]$^+$.

tert-butyl (4-(1-(4-nitrophenyl)-1H-1,2,3-triazol-4-yl)butyl)carbamate (33m): 33l (110 mg, 0.42 mmol) and Boc$_2$O (139 mg, 0.63 mmol), were stirred in a mixture of 5% NaOH(aq) 10 mL, and THF (10 mL) at rt for 8 hrs. After this time the solvent was removed at reduced pressure and the pH adjusted to 6 by addition of 1N HCl. The reaction mixture was extracted with EtOAc (100 mL×3). The combined organic layers were washed with brine, dried (Na$_2$SO$_4$), and concentrated. The residue was purified by flash chromatography on silica gel (DCM/MeOH 98:2). Yield 93% white solid. $^1$H NMR (400 MHz, CDCl$_3$) δ 8.35 (d, J=7.5 Hz, 1H), 7.95-7.92 (m 2H), 4.61 (s, 1H), 3.13-3.10 (m 2H), 2.78 (m, 2H), 1.75-1.70 (m, 2H), 1.49-1.43 (m, 2H), 1.39 (s, 9H) ppm.

General Procedure for the Preparation of Compounds 34a-i and m.

The opportune triazole compound 31a-d, or 33e-i (400 mg, 1.60 mmol) was solubilized in 30 mL of anhydrous MeOH, and 10% Palladium on charcoal (25 mg) was added. The reaction mixture was stirred under Hydrogen atmosphere for 1 h, then the mixture was filtered off on a celite pad, the solvent evaporated at reduced pressure.

(1-(4-aminophenyl)-1H-1,2,3-triazol-4-yl)methanol (34a). Yield 99%, white solid. $^1$H NMR (400 MHz, MeOD-d$_4$): δ 8.09 (s, 1H), 7.46-7.41 (d, J=8.0 Hz, 2H), 6.81-6.75 (d, J=8.0 Hz 2H), 2.29 (s, 2H) ppm. MS (ESI) m/z 191 [M+H]$^+$, 213 [M+Na]$^+$.

(1-(4-aminophenyl)-1H-1,2,3-triazol-4-yl)ethanol (34b). Yield 99%, white solid. $^1$H NMR (400 MHz, MeOD-d$_4$): δ 8.09 (s, 1H), 7.46-7.41 (d, J=8.0 Hz, 2H), 6.81-6.75 (d, J=8.0 Hz 2H), 3.86-3.83 (t, J=6 Hz, 2H) 2.95-2.93 (t, J=6 Hz 2H) ppm. MS (ESI) m/z 205 [M+H]$^+$, 227 [M+Na]$^+$.

1-(1-(4-aminophenyl)-1H-1,2,3-triazol-4-yl)-2-methylpentan-1-ol (34d). Yield 99%, white solid. $^1$H NMR (400 MHz, MeOD-d$_4$): δ 8.12 (s, 1H), 7.45-7.43 (d, J=8.4 Hz, 2H), 6.79-6.77 (d, J=8.4 Hz, 2H), 4.76-4.62 (m, 1H), 1.98-1.90 (m, 1H), 1.54-1.12 (m, 4H), 0.94-0.88 (m, 6H)ppm. MS (ESI): m/z 261.3 [M+H]$^+$, 282.9 [M+Na]$^+$.

4-(4-(3-morpholinomethyl)-1H-1,2,3-triazol-1-yl)benzenamine (34e). Yield 99%, white solid. $^1$H NMR (MeOD-d$_4$): δ 8.25 (s, 1H), 7.47-7.43 (d, J=8 Hz, 2H), 6.80-6.76 (d, J=8 Hz, 2H), 3.84 (s, 2H) 3.72-3.71 (m, 4H), 2.68-2.67 (m, 4H) ppm. MS (ESI): m/z 259.9 [M+H]$^+$, 281.9 [M+Na]$^+$.

4-(4-(3-morpholinoethyl)-1H-1,2,3-triazol-1-yl)benzenamine (34f). Yield 99%, white solid. $^1$H NMR (400 MHz, MeOD-d$_4$): δ 8.09 (s, 1H), 7.44-7.40 (d, J=8 Hz, 2H), 6.79-6.75 (d, J=8 Hz, 2H), 3.71-3.68 (m, 4H), 2.97-2.93 (t, J=8 Hz, 2H) 2.73-2.69 (t, J=8 Hz, 2H), 2.54-2.53 (m, 4H) ppm. MS: m/z 273.9 [M+H]$^+$.

4-(4-(3-dimethylaminopropyl)-1H-1,2,3-triazol-1-yl)benzenamine (34g). Yield 99%, white solid. $^1$H NMR (400 MHz, MeOD-d$_4$): δ 8.21 (s, 1H), 7.47-7.45 (d, J=8.0 Hz, 2H), 6.82-6.80 (d, J=8.0 Hz, 2H), 3.25-3.21 (t, J=6.0 Hz, 2H), 2.90-2.85 (m, 8H), 2.15-2.18 (quint, J=8.0 Hz, 2H) ppm. MS (ESI): m/z 246.0 [M+H]$^+$.

4-(4-(3-morpholinopropyl)-1H-1,2,3-triazol-1-yl)benzenamine (34h). Yield 99%, white solid. $^1$H NMR (400 MHz, MeOD-d$_4$): δ 8.04 (s, 1H), 7.44-7.42 (d, J=8.0 Hz, 2H), 6.78-6.76 (d, J=8 Hz, 2H), 3.67-3.64 (m, 4H), 2.74-2.72 (t, J=7.6 Hz, 2H), 2.43-2.38 (m, 6H), 1.91-1.84 (quint, J=8.0 Hz, 2H) ppm. MS (ESI): m/z 287.9 [M+H]$^+$, 309.9 [M+Na]$^+$, 4-(4-(3-methylpiperazinopropyl)-1H-1,2,3-triazol-1-yl)benzenamine (34l). Yield 99%, white solid. $^1$H NMR (400 MHz, MeOD-d$_4$): δ 7.56 (s, 1H) 7.37-7.26 (d, J=8.2 Hz, 2H), 6.69-6.67 (d, J=8 Hz, 2H), 2.75-2.72 (t, J=7.6 Hz, 2H), 2.48-2.40 (m, 9H), 2.26 (s, 1H), 1.90-1.86 (quint, J=7.4 Hz, 2H) ppm. MS (ESI): m/z 301.1 [M+H]$^+$, 323.2 [M+Na]$^+$ tert-butyl (4-(1-(4-aminophenyl)-1H-1,2,3-triazol-4-yl)butyl)carbamate (34m): Yield 99%, white solid. $^1$H NMR (400 MHz, CDCl$_3$) δ 7.57 (s, 1H), 7.39 (d, J=8.6 Hz, 2H), 6.70 (d, J=8.7 Hz, 2H), 4.62 (s, 1H), 3.12 (s, 2H), 2.74 (t, J=7.5 Hz, 2H), 1.79-1.61 (m, 2H), 1.61-1.43 (m, 2H), 1.39 (s, 9H). ppm. MS (ESI): m/z 332.4 [M+H]$^+$, 354.1 [M+Na]$^+$ General Procedure for the Preparation of Compounds 35a-i.

The opportune aniline 34a-i (0.10 mmol) was added to a solution of the appropriate isocyanate 1 or 24 (0.15 mmol) in anhydrous MeOH (10 mL) in one portion. The solution was stirred for 9 hours at r.t. under a nitrogen atmosphere. The solvent was removed at reduced pressure and the residue purified on silica to afford the final product 35a, 35b or 35g as white solid. Alternatively the residue was crystallized from MeOH to afford compound 35e or 35f.

1-(4-(4-(hydroxymethyl)-1H-1,2,3-triazol-1-yl)phenyl)-3-o-tolylurea (35a). (Purification eluent: DCM-methanol 95:5). Yield 79% white solid. $^1$H NMR (400 MHz, DMSO d$_6$): δ 9.23 (s, 1H), 8.54 (s, 1H), 7.97 (s, 1H), 7.80-7.76 (d, J=8 Hz, 2H), 7.80-7.76 (m, 3H), 7.64-7.62 (d, J=8.0 Hz, 2H), 7.17-7.12 (m, 2H), 6.96-6.93 (t, J=6.0 Hz, 1H), 4.58 (s, 2H), 2.24 (s, 3H)ppm.

$^{13}$C-NMR (100 MHz, DMSO d$_6$): δ 153.09, 140.57, 137.78, 131.50, 131.09, 128.46, 127.04, 123.60, 122.38, 121.27, 120.49, 118.84, 55.44, 18.36 ppm. MS (ESI) m/z 322.1 [M−H]$^-$, 358 [M+Cl]$^-$.

1-(4-(4-(hydroxyethyl)-1H-1,2,3-triazol-1-yl)phenyl)-3-o-tolylurea (35b). (Purification eluent: DCM-methanol 95:5). Yield 75% white solid. $^1$H NMR (400 MHz, DMSO d$_6$): δ 9.23 (s, 1H), 8.54 (s, 1H), 8.04 (1H, s), 7.80-7.76 (d, J=8.0 Hz, 2H), 7.75-7.73 (1H, d, J=8.4 Hz), 7.64-7.62 (d, J=8.0 Hz, 2H), 7.17-7.11 (2H, m), 6.96-6.93 (t, J=6.0 Hz, 1H), 3.71-3.67 (t, J=6.4 Hz, 2H), 2.84-2.81 (t, J=6.8 Hz, 2H) 2.24 (s, 3H) ppm. $^{13}$C NMR (100 MHz, DMSO d$_6$): δ 145.80, 140.71, 137.74, 131.44, 130.79, 128.38, 126.71, 123.47, 121.89, 121.15, 119.11, 66.75, 29.68, 18.37 ppm. MS(ESI): m/z 360 [M+Na]$^+$ 1-(4-(4-(3-hydroxypropyl)-1H-1,2,3-triazol-1-yl)phenyl)-3-(2-(trifluoromethyl)phenyl)urea (35c). (Purification eluent: DCM/MeOH 98:2). Yield 80%, white solid $^1$H NMR (400 MHz, MeOD-d$_4$): 7.79-7.77 (d, 1H), 7.70 (s, 1H), 7.49-7.47 (m, 3H), 7.43-7.40 (m, 3H), 7.12-7.10 (t, 1H), 3.66-3.63 (t, J=6.0 Hz, 2H), 2.89-2.85 (t, J=8.0 Hz, 2H), 1.98-1.92 (t, J=8.0 Hz, 2H). MS (ESI) m/z 407 [M+H]$^+$, 429 [M+Na]$^+$.

1-(4-(4-(3-hydroxyhexan-2-yl)-1H-1,2,3-triazol-1-yl) phenyl)-3-(2-(trifluoromethyl)phenyl) urea (35d). (Purification eluent: DCM/MeOH 98:2). Yield 77%. $^1$H NMR (400 MHz, MeOD-d$_4$): δ 7.81-7.79 (d, 1H), 7.68 (s, 1H), 7.51-7.49 (m, 3H), 7.42-7.38 (m, 3H), 7.11-7.08 (m, 1H), 4.76-4.62 (m, 1H), 1.98-1.90 (m, 1H), 1.54-1.12 (m, 4H), 0.94-0.88 (m, 6H) ppm. MS (ESI): m/z 446 [M−H]$^-$.

1-(4-(4-(morpholinomethyl)-1H-1,2,3-triazol-1-yl)phenyl)-3-o-tolylurea (35e). The residue was crystallized from MeOH. Yield 69% white crystals. $^1$H NMR (MeOD-d$_4$): δ 8.37 (s, 1H), 7.75-7.73 (d, J=9.2 Hz, 2H), 7.66-7.606 (m, 3H), 7.21-7.17 (m, 2H), 7.06-7.02 t, J=7.6 Hz, 1H), 3.73 (s, 2H)), 3.71-3.69 (m, 4H) 2.565-2.54 (m, 4H), 2.30 (s, 3H) ppm. $^{13}$C NMR (MeOD-d$_4$): δ 144.47, 143.79, 140.39, 131.54, 130.09, 126.08, 124.23, 123.11, 122.06, 120.89, 119.23, 66.20, 52.92, 16.85 ppm. MS: m/z 392.9 [M+H]$^+$ 1-(4-(4-(morpholinoethyl)-1H-1,2,3-triazol-1-yl)phenyl)-3-o-tolylurea (35l). The residue was crystallized from MeOH. Yield 75% White solid. $^1$H NMR (400 MHz, DMSO d$_6$): δ 9.24 (s, 1H), 8.44 (s, 1H), 7.97 (s, 1H), 7.80-7.78 (d, J=8 Hz, 2H), 7.75-7.72 (d, J=9.2 Hz, 2H), 7.63-7.61 (d, J=8.8 Hz, 2H), 7.17-7.11 (m, 3H), 6.96-6.92 (t, J=7.2 Hz, 1H), 3.57-3.55 (m, 4H) 2.87-2.83 (t, J=7.6 Hz, 3H), 2.62-2.58 (t, J=8 Hz, 2H), 2.41-2.40 (m, 4H) 2.23 (s, 3H) ppm. $^{13}$C NMR (100 MHz, DMSO d$_6$): δ 145.59, 140.51, 137.64, 131.36, 130.69, 128.36, 126.64, 123.44, 121.81, 121.12, 120.72, 119.09, 66.66, 58.12, 53.62, 23.20, 18.33 ppm. MS (ESI): m/z 421.2 [M+H]$^+$, 443 [M+Na]$^+$.

1-(4-(4-(morpholinopropyl)-1H-1,2,3-triazol-1-yl)phenyl)-3-o-tolylurea (35g). (Purification eluent: DCM-methanol 98:2). Yield 70% white solid. $^1$H NMR (400 MHz, MeOD-d$_4$): δ 8.23 (s, 1H), 7.73-7.71 (d, J=8.0 Hz, 2H), 7.65-7.63 (d, J=7.6 Hz, 2H), 7.21-7.15 (m, 2H), 7.05-7.02 (t, J=7.4 Hz, 1H), 3.70-3.67 (m, 4H), 2.82-2.78 (t, J=8 Hz, 2H), 2.48-2.43 (m, 6H), 2.29 (s, 1H), 1.98-1.90 (quin. J=8.0 Hz, 2H) ppm. $^{13}$C NMR (100 MHz, MeOD-d$_4$) δ 145.61, 140.53, 137.67, 131.38, 130.71, 128.37, 126.66, 123.48, 121.87, 121.21, 120.77, 119.21, 66.21, 58.22, 53.47, 25.78, 22.99, 18.11 ppm. MS (ESI): m/z 406.9 [M+H]$^+$, 428.9 [M+Na]$^+$.

4-(4-(3-(4-methylpiperazin-1-yl)propyl)-1H-1,2,3-triazol-1-yl)benzenamine (35h). (Purification eluent: DCM-methanol 99:1). Yield 69% white solid. $^1$H NMR (400 MHz, MeOD-d$_4$): δ 8.24 (s, 1H), 7.72-7.63 (m, 4H), 7.19-7.14 (m, 2H), 7.04-7.00 (t, J=8 Hz, 1H), 2.81-2.78 (t, J=7.6 Hz, 2H), 2.63-2.60 (m, 8H), 2.52-2.48 (t, J=8 Hz, 2H), 2.36 (s, 1H), 2.30 (s, 1H), 1.98-1.91 (quint, J=7.6 Hz, 2H) ppm. $^{13}$C NMR (100 MHz, MeOD-d$_4$) δ 154.19, 147.95, 140.27, 136.32, 131.61, 130.03, 126.13, 124.15, 123.14, 120.73, 120.14, 120.01, 119.28, 57.08, 53.97, 51.82, 44.18, 25.78, 22.72, 16.78 ppm. MS (ESI): m/z 434 [M+H]$^+$, 457.2[M+Na]$^+$.

1-(4-(4-(dimethylaminopropyl)-1H-1,2,3-triazol-1-yl) phenyl)-3-o-tolylurea (35i). (Purification eluent: DCM-methanol 95:5). Yield 67% white solid. $^1$H NMR (400 MHz, MeOD-d$_4$): δ 8.30 (s, 1H), 7.74-7.72 (d, J=8.0 Hz, 2H), 7.67-7.62 (m, 3H), 7.21-7.15 (m, 2H), 7.06-7.02 (t, J=8.0 Hz, 1H), 3.08-3.04 (t, J=8 Hz, 2H), 2.89-2.85 (t, J=7.4 Hz, 2H), 2.62-2.58 (t, J=8.0 Hz, 2H), 2.77 (s, 6H), 2.3 (s, 3H), 2.15-2.08 (quint, J=7.6 Hz, 2H), ppm. $^{13}$C NMR (100 MHz, MeOD-d$_4$): δ 154.17, 146.69, 140.35, 136.28, 131.54, 130.10, 126.06, 124.2, 123.10, 120.76, 120.34, 119.2, 57.27, 42.5, 29.28, 24.43, 21.97, 16.69 ppm. MS (ESI): m/z 376.9 [M−H]$^-$, 412.9 [M+Cl]$^-$ diethyl (2-(1-(4-(3-(o-tolyl)ureido)phenyl)-1H-1,2,3-triazol-4-yl)ethyl) phosphate (36). 35b (35 mg, 0.10 mmol), was solubilized in 6 mL of anhydrous CH$_2$Cl$_2$, then (Et$_2$O)$_2$POCl (17 μL, 0.12 mmol), TEA (42 μL, 0.30 mmol), and Ti(tBuO)$_4$ were added sequentially via syringe. The reaction mixture was stirred at r.t for 11 h, then the solvent was removed at reduced pressure and the residue purified by flash chromatography on silica gel. (PE-EtOAc 2:1). Yield 75% yellow oil. $^1$H NMR (400 MHz, CDCl$_3$-d): δ 8.37 (s, 1H), 7.70-7.68 (m, 2H), 7.48-7.38 (m, 5H), 7.20-7.12 (m, 2H), 7.02-6.98 (t, J=8.0 Hz, 1H), 4.40-4.36 (t J=8.0 Hz, 2H), 4.13-4.07 (q, J=7.6 Hz, 4H), 3.18-3.15 (t, J=6.2 Hz, 2H), 2.23 (s, 3H), 1.32-1.29 (t, J=7.0 Hz, 3H)ppm. $^{13}$C NMR (100 MHz, CDCl$_3$-d): δ 153.60, 143.78, 140.09, 136.29, 131.37, 130.69, 130.42, 129.97, 126.87, 126.62, 124.50, 123.44, 120.95, 120.12, 119.53, 66.42, 66.25, 27.06, 17.90, 16.03 ppm. MS (ESI): m/z 472 [M−H]$^-$, 508 [M+Cl]$^-$ General Procedure for the Preparation of Compounds 37-39.

The opportune alcohol 35b-c, (25 mg, 0.07 mmol), acid (104, 0.07 mmol), N,N'-dicyclohexylcarbodiimide (22 mg, 0.11 mmol), and DMAP (3 mg, 0.01 mmol), were stirred at 0° C. for 30 min. in a mixture of CH$_2$Cl$_2$ 10 mL and DMF 2 mL. After that time, the reaction mixture was allowed to reach r.t. and stirred for 12 h. The solvent was then removed at reduced pressure, EtOAc was added and the mixture was washed with 5% LiCl aq. Solution, dried over anhydrous Na$_2$SO$_4$, and concentrated in vacuo. The residue was purified by flash chromatography on silica gel with the opportune eluent.

2-(1-(4-(3-(o-tolyl)ureido)phenyl)-1H-1,2,3-triazol-4-yl) ethyl 3-methylbutanoate (37). (Purification eluent: DCM-methanol 98:2). Yield 74% white solid. $^1$H NMR (400 MHz, CDCl$_3$-d): δ 7.72 (s, 1H), 7.56-7.48 (m, 5H), 7.25-7.23 (m, 3H), 7.17-7.14 (m, 2H), 6.61 (s, 1H), 4.41-4.38 (t, J=6.6 Hz, 2H), 3.14-3.11 (t, J=6.6 Hz, 2H), 2.28 (s, 3H), 2.18-2.16 (d, J=7.6 Hz, 2H), 0.92-0.89 (d, J=6.8 Hz, 6H) ppm. $^{13}$C NMR (100 MHz, CDCl$_3$): δ 173.05, 153.62, 144.95, 139.21, 136.93, 135.65, 136.19, 132.73, 132.18, 131.54, 131.00, 127.53, 126.98, 126.62, 125.34, 121.28, 120.30, 119.94, 62.75, 43.32, 25.57, 22.45, 17.88 ppm. MS (ESI): m/z 420 [M−H]$^-$, 456 [M+Cl]$^-$ 2-(1-(4-(3-(2-(trifluoromethyl)phenyl)ureido)phenyl)-1H-1,2,3-triazol-4-yl)ethyl 3-methylbutanoate (38). (Purification eluent: DCM-methanol 98:2). Yield 68% white solid. $^1$H NMR (400 MHz, CDCl$_3$-d): δ 8.19 (s, 1H), 7.98-7.96 (d, J=8 Hz, 1H), 7.76 (s, 1H), 7.58-7.50 (m, 5H), 7.38 (s, 1H), 7.21-7.17 (t, J=7.6 Hz, 1H), 4.43-4.39 (t, J=6.6 Hz, 2H), 3.16-3.13 (t, J=6.6 Hz, 2H), 2.19-2.17 (d, J=7.2 Hz, 2H), 2.15-2.08 (m, 1H), 0.92-0.90 (d, J=8 Hz, 2H) ppm.

$^{13}$C NMR (100 MHz, CDCl$_3$-d): δ 172.0, 150.9, 139.4, 132.9, 130.1, 129.3, 125.7, 124.7, 124.2, 121.2, 120.7, 118.0, 116.0, 65.7, 46.4, 26.0, 25.0, 20.6 ppm. MS (ESI): m/z 474 [M−H]$^-$, 510 [M+Cl]$^-$ 2-(1-(4-(3-(2-(trifluoromethyl)phenyl)ureido)phenyl)-1H-1,2,3-triazol-4-yl)ethyl 3-(benzo[d][1,3]dioxol-5-yl) acrylate (39). (Purification eluent: DCM-methanol 98:2). Yield 68% white solid. $^1$H NMR (400 MHz, CDCl$_3$-d): δ 8.12 (s, 1H), 8.02-8.00 (d, J=8 Hz, 1H), 7.60 (s, 1H), 7.58-7.52 (m, 7H), 7.34 (s, 1H), 7.22-7.18 (t, J=8 Hz, 1H), 7.00-6.97 (m, 2H), 6.80-6.78 (d, J=8 Hz), 6.28-6.24 (d, J=12 Hz, 1H), 5.99 (s, 2H), 4.55-4.52 (t, J=12.4 Hz, 2H), 3.22-3.25 (t, J=12.0 Hz, 2H) ppm. $^{13}$C NMR (100 MHz, CDCl$_3$-d): δ 167.7, 152.9, 118.6, 117.9, 145.8, 138.4, 133.4, 131.6, 129.7, 126.4, 124.9, 121.3, 118.7, 116.2, 115.9, 108.4, 106.7, 103.1, 69.0, 24.2 ppm. MS (ESI): m/z 564.5 [M−H]$^-$, 600.3 [M+Cl]$^-$

Example 7

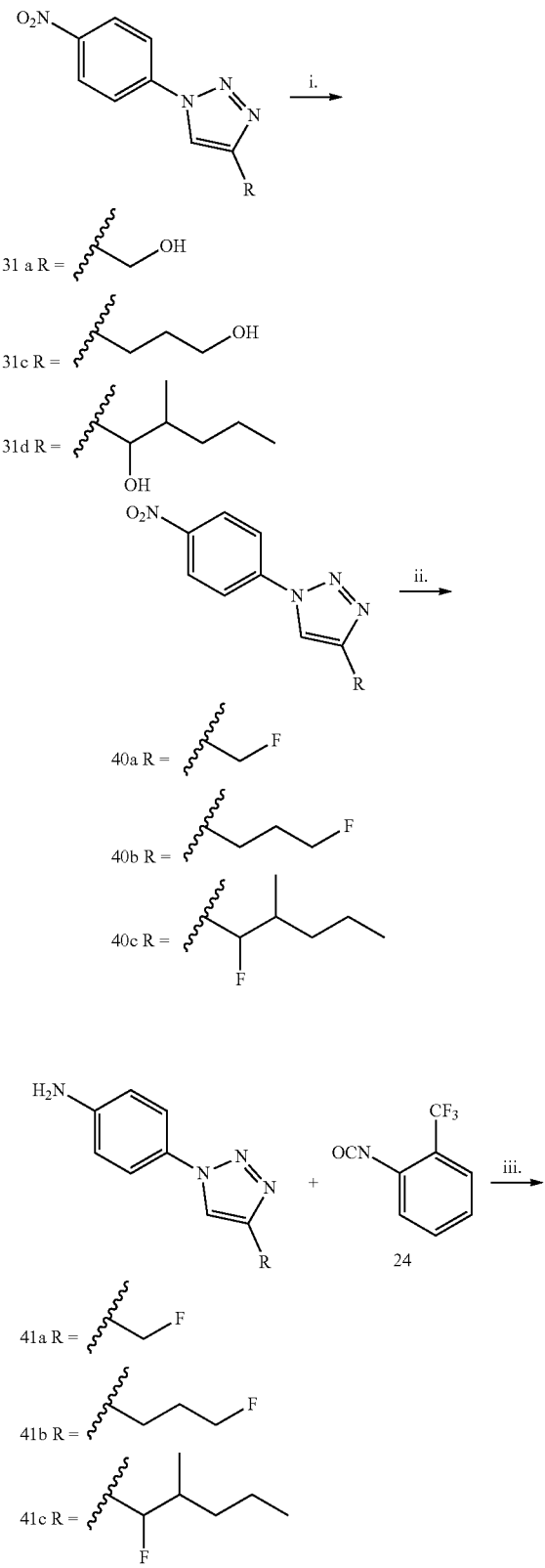

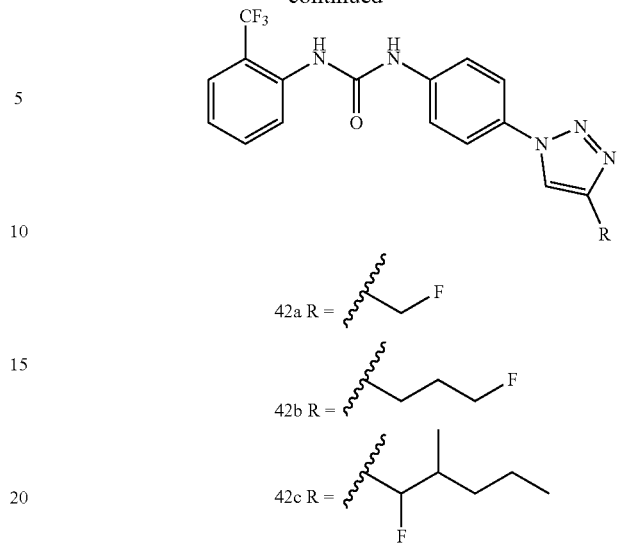

Reagents and conditions: i. Deoxo-Fluor®, anhydrous $CH_2Cl_2$, 12 hr.t; ii. $H_2$, Pd/C, MeOH, 1 h, iii. 2-(Trifluoromethyl)phenyl isocyanate $CH_2Cl_2$, 5 hr.t;

General Procedure for the Preparation of Fluorinated Compounds 40a-c:

The opportune alcohol 31a, 31c, or 31d (400 mg, 1.38 mmol) was dissolved in 15 mL of $CH_2Cl_2$, and Deoxo-Fluor® (533 µL, 2.48 mmol), was added at −40° C. After stirring for 2 h at −40° C. the reaction mixture was warmed up to r.t. and stirred overnight. The solvent was removed at reduced pressure and the residue purified by flash chromatography on silica gel.

4-(fluoromethyl)-1-(4-nitrophenyl)-1H-1,2,3-triazole (40a): (Purification Eluent: DCM/MeOH 98:2) Yield: 67%, white solid $^1$H NMR (400 MHz, ACETONE-$d_6$): δ 8.94 (s, 1H), 8.49-8.46 (dd, J=8.8 Hz, 2H), 8.25-8.23 (dd, J=8.8 Hz, 2H), 5.64 (s, 1H), 5.52 (s, 1H) ppm. $^{13}$C-NMR (100 MHz, ACETONE-$d_6$): δ 147.50, 144.31, 141.34, 125.43, 123.38, 120.89, 76.00-74.39 ($J_{CF}$=161.0 Hz) ppm.

4-(3-fluoropropyl)-1-(4-nitrophenyl)-1H-1,2,3-triazole (40b): (Purification eluent: DCM-methanol 98:2). Yield 57% white solid. $^1$H NMR (400 MHz, $CDCl_3$-d): δ 8.40-8.38 (d, J=9.2 Hz, 2H), 7.97-7.95 (d, J=9.2 Hz, 2H), 7.90 (s, 1H), 4.61-4.59 (t, J=5.7 Hz, 1H), 4.49-4.46 (t, J=5.7 Hz, 1H), 2.98-2.94 (t, J=7.6 Hz, 2H), 2.23-2.10 (m, 2H)ppm. $^{13}$C NMR (100 MHz $CDCl_3$-d): δ 184.54, 147.08, 141.29, 125.53, 120.27, 119.09, 83.73-82.09 ($J_{CF}$=164 Hz), 29.86-29.66 ($J_{CF}$=20 Hz), 21.41 ppm.

4-(1-fluoro-2-methylpentyl)-1-(4-nitrophenyl)-1H-1,2,3-triazole (40c): (Purification eluent: DCM-methanol 98:2). Yield 67% white solid. $^1$H NMR (400 MHz, $CDCl_3$-d): δ 8.38-8.35 (d, J=8.8 Hz, 2H), 5.63-5.45 (m, 1H), 2.22-2.16 (m, 1H), 1.56-1.38 (m, 4H), 0.84-0.92 (m, 3H), 0.79-0.75 (t, J=7.2 Hz, 3H) ppm. MS (ESI) m/z 291 [M−H]$^-$, 327 [M+Cl]$^-$.

General Procedure for the Preparation of Compounds 41a-c

The opportune triazole compound 40a 40b or 40c (100 mg, 0.34 mmol) was solubilized in 10 mL of anhydrous MeOH, and 10% Palladium on charcoal (30 mg) was added. The reaction mixture was stirred under Hydrogen atmosphere for 1 h, then the mixture was filtered off on a celite pad, the solvent evaporated at reduced pressure.

4-(4-(fluoromethyl)-1H-1,2,3-triazol-1-yl)aniline (41a): Yield 99% white solid. $^1$H NMR (400 MHz, ACETONE-$d_6$): δ 7.94 (s, 1H), 7.46-7.44 (dd, J=8.8 Hz, 2H), 6.77-6.75 (dd, J=8.4 Hz, 2H), 5.62 (s, 1H), 5.50 (s, 1H) ppm. MS (ESI) m/z 193 [M+H]$^+$, 215 [M+Na]$^+$.

4-(4-(3-fluoropropyl)-1H-1,2,3-triazol-1-yl)aniline (41b): Yield 99% white solid. $^1$H NMR (400 MHz CDCl$_3$-d): δ 8.51 (s, 1H), 7.84-7.82 (d, J=8.7 Hz, 2H), 7.36-7.34 (d, J=8.6 Hz, 2H), 7.90 (s, 1H), 5.91-4.89 (t, J=5.7 Hz, 1H), 4.99-4.96 (t, J=5.7 Hz, 1H), 2.98-2.94 (t, J=7.6 Hz, 2H), 2.23-2.10 (m, 2H) ppm. MS (ESI) m/z 221 [M+H]$^+$, 243 [M+Na]$^+$.

4-(4-(1-fluoro-2-methylpentyl)-1H-1,2,3-triazol-1-yl)aniline (41c): Yield 99% white solid.

$^1$H NMR (400 MHz CDCl$_3$-d): δ 7.83 (s, 1H), 7.42-7.40 (d, J=8.4 Hz, 2H), 6.71-6.69 (d, J=8.4 Hz, 2H), 5.60-5.41 (m, 1H), 4.08 (s, 2H), 2.22-2.18 (m, 1H), 1.60-1.20 (m, 4H), 0.94-0.82 (m, 3H), 0.89-0.85 (t, J=7.2 Hz, 3H) ppm. MS (ESI) m/z 263 [M+H]$^+$, 285 [M+Na]$^+$.

General Procedure for the Preparation of Compounds 42a 42b and 42c

The opportune aniline compound 41a-c (100 mg, 0.46 mmol) was added to a solution of the 0-(Trifluoromethyl) phenyl isocyanate 24 (85 μL, 0.65 mmol) in anhydrous CH$_2$Cl$_2$ (10 mL) in one portion. The solution was stirred for 4 hours at r.t. under a nitrogen atmosphere. The solvent was removed, at reduced pressure and the residue purified by flash chromatography using the opportune eluent.

1-(4-(4-(fluoromethyl)-1H-1,2,3-triazol-1-yl)phenyl)-3-(2-(trifluoromethyl)phenyl)urea (42a). (Purification Eluent: DCM/EA 95:5). Yield 79% $^1$H NMR (400 MHz, ACETONE-$d_6$): δ 9.09 (s, 1H), 8.64-8.63 (d, J=2.8 Hz, 1H), 8.15-8.13 (d, J=8.0 Hz, 1H), 7.82-7.64 (m, 5H), 7.31-7.27 (t, J=7.2 Hz, 1H), 5.60 (s, 1H), 5.44 (s, 1H) ppm $^{13}$C-NMR (100 MHz, ACETONE-$d_6$): δ 152.2, 140.56, 140.57, 132.95, 131.72, 125.90, 125.48, 123.78, 122.80, 121.13, 119.28, 76.16-74.53 (J$_{CF}$=163.0 Hz) ppm MS (ESI) m/z 378 [M−H]$^−$, 414 [M+Cl]$^−$.

1-(4-(4-(3-fluoropropyl)-1H-1,2,3-triazol-1-yl)phenyl)-3-(2 (trifluoromethyl) phenyl) urea. (42b). Yield 87% white solid. $^1$H NMR (400 MHz, CDCl$_3$-d): δ 8.80 s (1H), 7.93 (s, 1H), 7.75-7.73 (d, 1H), 7.71 (s, 1H), 7.51-7.49 (m, 3H), 7.42-7.39 (m, 3H), 7.11-7.09 (t, 1H), 5.91-4.89 (m, J=5.7 Hz, 1H), 4.99-4.96 (m, J=5.7 Hz, 1H), 2.98-2.94 (t, J=7.6 Hz, 2H), 2.23-2.10 (m, 2H) ppm. MS (ESI) m/z 408 [M+H]$^+$, 430 [M+Na]$^+$. $^{13}$C NMR (100 MHz CDCl$_3$-d): δ 152.91, 139.44, 132.83, 129.62, 126.77, 121.88, 120.43, 119.13, 115.88, 83.73-82.09 (J$_{CF}$=164 Hz), 32.71-32.51 (J$_{C-F}$=20 Hz), 27.31 ppm.

1-(4-(4-(1-fluoro-2-methylpentyl)-1H-1,2,3-triazol-1-yl) phenyl)-3-(2-(trifluoromethyl) phenyl) urea (42c): Yield 99% white solid. $^1$H NMR (400 MHz CDCl$_3$-d): δ 8.83 s (1H), 7.90 (s, 1H), 7.79-7.77 (d, 1H), 7.70 (s, 1H), 7.49-7.47 (m, 3H), 7.43-7.40 (m, 3H), 7.12-7.10 (t, 1H), 5.61-5.42 (m, 1H), 2.32-2.10 (m, 1H), 1.42-1.40 (m, 2H), 1.29-1.21 (m, 2H), 0-98-0.86 (m, 6H)ppm. $^{13}$C NMR (100 MHz CDCl$_3$-d): δ 153.85, 147.65, 139.63, 135.31, 132.49, 131.75, 127.90, 126.82, 126.14, 125.17, 124.81, 122.84, 122.54, 121.20, 120.34, 92.81-91.18 (J$_{C-F}$=164 Hz), 90.72-90.49 (J$_{C-F}$=23 Hz), 37.64-37.44 (J$_{C-F}$=20 Hz); 34.45, 33.55, 19.98, 14.07, 13.80 ppm. MS (ESI) m/z 450.1 [M+H]$^+$, 472.1[M+Na]$^+$.

Example 8

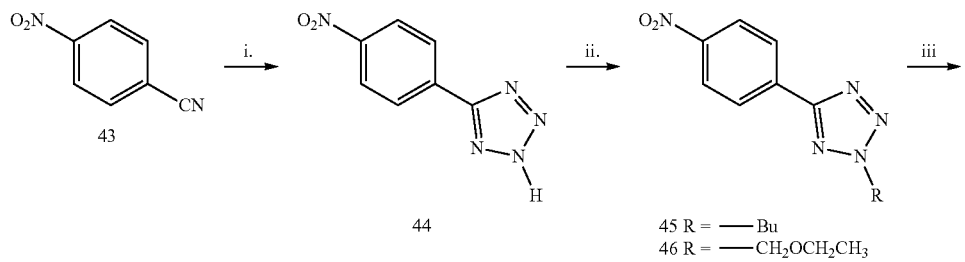

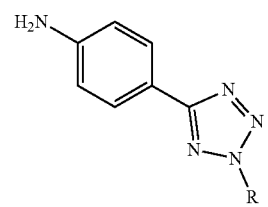

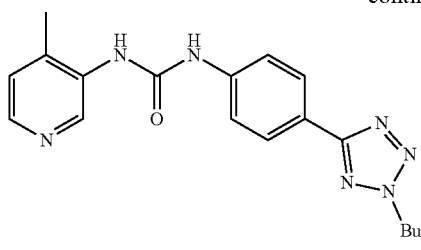
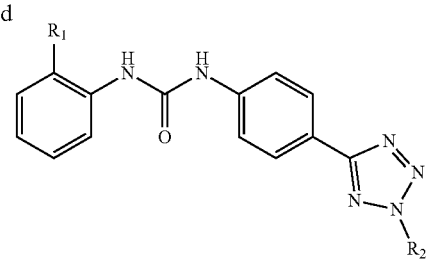

52

49 R₁ = —CH₃  R₂ = —Bu
50 R₁ = —CH₃  R₂ = —CH₂OCH₂CH₃
51 R₁ = —CF₃  R₂ = —Bu

Reagents and conditions: i. NaN₃, NH₄Cl, DMF, 12 h, reflux; ii. K₂CO₃, 1-iodobutane or 1-chloromethylethyether, CH₃CN, 12 h, r.t; iii. H₂, Pd/C, MeOH 30 min.; iv. Opportune isocyanate CH₂Cl₂, 9 h r.t; v. a) 3-amino,4-methylpyridine, triphosgene, DMAP, CH₂Cl₂, 0° C., b). opportune aniline 9 h r.t CH₂Cl₂, 9 h r.t;

5-(4-nitrophenyl)-2H-tetrazole (44). A mixture of 4-nitrobenzonitrile (600 mg, 4.05 mmol) sodium azide (790 mg, 12.15 mmol) ammonium chloride (867 mg, 16.20 mmol) and DMF (5 mL) was heated at 120° C. for 12 hr. Then the reaction was allowed to cool to r.t., water was added with continuous stirring. The mixture was then acidified to pH 2 with HCl 6N. The reaction mixture was extracted with EtOAc (3×20 mL) and dried over Na₂SO₄, and the solvent was removed under reduced pressure, to give a yellow residue that was crystallized from Ethanol Yield 80% white solid ¹H NMR (MeOD-d₄): δ 8.40-8.38 (d, 2H, J=7.2 Hz), 8.28-8.28 (d, 2H, J=8 Hz) ppm. ¹³C NMR (MeOD-d₄): δ 156.72, 149.46, 131.32, 128.18, 124.07 ppm. MS: m/z 189.9 [M−H]⁻

2-butyl-5-(4-nitrophenyl)-2H-tetrazole (45). A suspension of 44 (200 mg, 1.05 mmol), K₂CO₃ (174 mg, 1.26 mmol) and n-butyliodide (144 μL, 1.26 mmol), in Acetonitrile was refluxed for 4 h. After that time, the reaction mixture was concentrated in vacuo, water was added and the residue was extracted with AcOEt (3×25 mL), washed with brine, and dried over Na₂SO₄. The resulting residue was purified by flash chromatography on silica gel (PE-DCM 1:8). Yield 82%, yellow solid. ¹H NMR (400 MHz CDCl₃-d): δ 8.26 (m, 4H), 4.67-4.63 (t, J=7.6 Hz, 2H), 2.03-1.98 (quint, J=6.8 Hz, 2H), 1.40-1.34 (sx. J=7.2 Hz, 2H) 0.95-0.92 (t, J=7.2 Hz, 3H) ppm. ¹³C NMR (100 MHz CDCl₃-d): δ 163.05, 148.74, 133.42, 127.53, 124.10, 53.20, 31.22, 19.57, 13.30 ppm. MS: m/z 220 [M+H]+

2-(ethoxymethyl)-5-(4-nitrophenyl)-2H-tetrazole (46). A suspension of 44 (50 mg, 0.26 mmol), K₂CO₃ (43 mg, 0.31 mmol) and chloromethylethylether (284, 0.31 mmol), in Acetonitrile was refluxed for 12 h. After that time, the reaction mixture was concentrated in vacuo, water was added and the residue was extracted with AcOEt (3×25 mL), washed with brine, and dried over Na₂SO₄. The resulting residue was purified by flash chromatography on silica gel (PE-DCM 1:7). Yield 66%, yellow solid. A suspension of ¹H NMR (Acetone d-₆): δ 8.42-8.34 (m, 4H), 6.05 (s, 2H), 3.79-3.69 (m, 2H), 1.19-1.09 (m, 3H) ppm; ¹³C NMR (Acetone d-₆): δ 163.80, 149.22, 133.18, 127.83, 123.94, 81.90, 66.35, 14.34 ppm.

4-(2-butyl-2H-tetrazol-5-yl)aniline (47). Compound 45 (100 mg, 0.40 mmol) was solubilized in 30 mL of anhydrous MeOH, and 10% Palladium on charcoal (5 mg) was added. The reaction mixture was stirred under Hydrogen atmosphere for 1 h, then the mixture was filtered off on a celite pad, the solvent evaporated at reduced pressure. Yield 99% ¹H NMR (400 MHz CDCl₃-d): δ 7.90-7.88 (d, J=8.0 Hz, 2H), 6.71-6.69 (d, J=8.0 Hz, 2H), 4.57-4.53 (t, J=7.6 Hz, 2H), 4.03 (s, 2H), 2.00-1.92, (quint, J=8.1 Hz, 2H), 1.38-1.23 (sx, J=8.0 Hz, 2H), 0.93-0.89 (t, J=8.0 Hz, 3H) ppm. ¹³C NMR (100 MHz, CDCl₃-d): δ 165.62, 148.77, 128.04, 117.56, 114.87, 113.12, 52.69, 31.38, 19.56, 12.17 ppm MS (ESI): m/z 218 [M+H]+, 239.9 [M+Na]⁺.

4-(2-(ethoxymethyl)-2H-tetrazol-5-yl)aniline (48). Compound 46 (150 mg, 0.60 mmol) was solubilized in 30 mL of anhydrous MeOH, and 10% Palladium on charcoal (5 mg) was added. The reaction mixture was stirred under Hydrogen atmosphere for 1 h, then the mixture was filtered off on a celite pad, the solvent evaporated at reduced pressure. Yield 99% ¹H NMR (400 MHz CDCl₃-d): δ 7.97-7.95 (d, 2H, J=7.2 Hz), 6.75-6.73 (d, 2H, J=7.2 Hz), 5.870 (s, 2H), 3.69-68 (m, 2H), 1.241 (s, 3H) ppm. MS: m/z 220 [M+H]+

1-(4-(2-butyl-2H-tetrazol-5-yl)phenyl)-3-(o-tolyl)urea (49). Compound 47 (0.10 mmol) was added to a solution of o-tolyl isocyanate (0.15 mmol) in anhydrous MeOH (10 mL) in one portion. The solution was stirred for 9 hours at r.t. under a nitrogen atmosphere. The solvent was removed at reduced pressure and the residue purified on silica to furnish the final product as white solid. (DCM-MeOH 98:2). Yield 73% ¹H NMR (Acetone d-₆): δ 8.60 (s, 1H), 8.03-8.01 (d, J=8 Hz, 2H), 7.92-7.90 (d, J=8.0 Hz, 2H), 7.55 (s, 1H), 7.18-7.14 (m, 2H), 6.99-6.95 (t, J=7.6 Hz, 1H), 4.71-4.67 (t, J=, 2H), 2.27 (s, 1H), 2.03-1.98 (m, 2H), 1.43-1.34 (sx, J=7.6 Hz, 2H), 0.97-0.94 (t, J=7.4 Hz, 3H) ppm. ¹³C NMR (Acetone): δ 164.91, 152.54, 142.16, 137.33, 130.35, 128.48, 127.64, 126.40, 123.44, 122.20, 121.37, 118.75, 52.47, 31.09, 19.34, 17.17, 12.73 ppm. MS: m/z 351 [M+H]+

1-(4-(2-(ethoxymethyl)-2H-tetrazol-5-yl)phenyl)-3-(o-tolyl)urea (50). Compound 48 (0.10 mmol) was added to a solution of o-tolyl isocyanate (0.15 mmol) in anhydrous MeOH (10 mL) in one portion. The solution was stirred for 9 hours at r.t. under a nitrogen atmosphere. The solvent was removed at reduced pressure and the residue purified on silica to furnish the final product as white solid. (DCM-MeOH 98:2). Yield 62% ¹H NMR (400 MHz CDCl₃-d): δ 8.06-8.04 (d, 2H, J=8 Hz), 7.65-7.62 (m, 3H), 7.21-7.15 (m, 2H), 7.05-7.01 (t, 1H, J=7.6 Hz), 5.95 (s, 2H), 3.74-3.69 (q, 2H), 2.30 (s, 3H), 1.20-1.17 (t, 3H, J=6.8 Hz) ppm. ¹³C NMR (100 MHz CDCl₃-d): δ 142.06, 136.14, 130.47, 127.51, 126.33, 124.73, 123.05, 120.95, 118.61, 80.93, 66.18, 16.61, 13.32 ppm. MS: m/z 375 [M+Na]+

1-(4-(2-butyl-2H-tetrazol-5-yl)phenyl)-3-(2-(trifluoromethyl)phenyl)urea (51). Compound 47 (0.10 mmol) was added to a solution of o-tolyl isocyanate (0.15 mmol) in anhydrous MeOH (10 mL) in one portion. The solution was stirred for 9 hours at r.t. under a nitrogen atmosphere. The solvent was removed at reduced pressure and the residue purified on silica to furnish the final product as white solid. (DCM-MeOH 98:2). Yield 70%, white solid. $^1$H NMR (400 MHz CDCl$_3$-d): δ 7.93-7.91 (d, J=8 Hz, 2H), 7.82-7.80 (d, J=8.0 Hz, 1H), 7.48-7.39 (m, 2H), 7.36-7.34 (d, J=7.2 Hz, 2H), 7.09-7.05 (t, J=7.2 Hz, 1H), 4.60-4.57 (t, J=6.8 Hz, 2H), 2.01-1.97 (m, 2H), 1.39-1.33 (m, 2H), 0.95-0.91 (t, J=7.2 Hz, 3H) ppm. $^{13}$C NMR (100 MHz, CDCl$_3$-d): δ 153.54, 140.20, 135.38, 132.54, 127.60, 126.29, 126.11, 125.23, 124.54, 122.43, 122.01, 120.07, 52.96, 31.27, 19.60, 13.34 ppm MS (ESI) m/z 405 [M+H]$^+$, 428 [M+Na]$^+$.

1-(4-(2-butyl-2H-tetrazol-5-yl)phenyl)-3-(4-methylpyridin-3-yl)urea (52): A solution of 4-methylpyridin-3-amine (41 mg, 0.3835 mmol) and DMAP (19 mg, 0.1534 mmol) in 5 mL of CH$_2$Cl$_2$ was added dropwise to an ice cold solution of triphosgene in CH$_2$Cl$_2$, during 30 min., then aniline 47 was added in one portion, and the reaction mixture was stirred at rt for 12 h. After this time, 2M HCl was added and the mixture was extracted with CH$_2$Cl$_2$ (3×20 mL). The organic layers were collected, washed with Brine and dried over Na$_2$SO$_4$. The crude was purified by flash chromatography on silica gel (CH$_2$Cl$_2$-MeOH 98:2). Yield 70%. $^1$H NMR (400 MHz, MeOD-d$_4$): δ 8.87 (s, 1H), 8.15 (d, 1H), 8.03-8.61 (d, J=8.0 Hz, 2H), 7.63-7.61 (d, J=8.0 Hz, 2H), 7.30-7.29 (d, J=4 Hz, 1H), 4.71-4.67 (t, J=7.8 Hz, 2H), 2.35 (s, 3H), 2.06-1.99 (q, J=9.3 Hz, 2H), 1.42-1.36, (q, 2H), 1.00-0.97 (t, J=8.0 Hz, 3H)ppm. $^{13}$C NMR (MeOD-d$_4$): δ 164.69, 153.57, 143.82, 143.19, 141.39, 140.12, 134.50, 127.09, 125.50, 121.37, 118.72, 52.64, 31.03, 19.38, 16.20, 12.29 ppm. MS (ESI) m/z 353.2 [M+H]$^+$, 375.2 [M+Na]$^+$.

Example 9

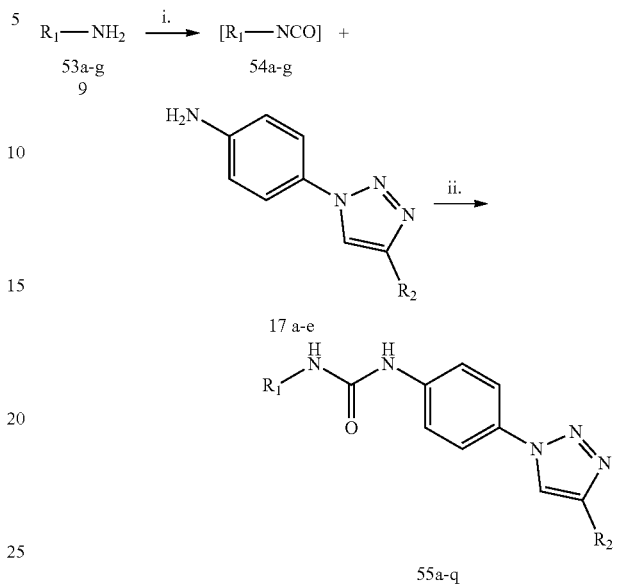

Reagents and conditions: i. triphosgene, opportune aromatic amine, DMAP, CH$_2$Cl$_2$ 0° C. 20 min., ii. opportune aniline r.t CH$_2$Cl$_2$, 9 h r.t;

Urea derivatives 55a-q are reported in Table 1

TABLE 1

List of urea derivatives 55a-q

| Entry | Aromatic amine | R$_1$ | Isocyanate | Amine | R$_2$ |
|---|---|---|---|---|---|
| 1 | 53a | 2-F-phenyl | 54a | 17b | isobutyl chain |
| 2 | 53b | 3-F-phenyl | 54b | 17b | isobutyl chain |
| 3 | 53c | 4-F-phenyl | 54c | 17b | isobutyl chain |

TABLE 1-continued

List of urea derivatives 55a-q

| # | R1 ID | R1 | R2 ID | R2 ref | R2 |
|---|---|---|---|---|---|
| 4 | 53d | 3-chloro-2-methylphenyl | 54d | 17b | 4-methylpentyl |
| 5 | 53e | 4-methyl-3-isopropylphenyl (approx.) | 54e | 17b | ethoxymethyl |
| 6 | 53f | isoquinolin-5-yl | 54f | 17b | 4-methylpentyl |
| 7 | 53g | 1-chloro-3-methylisoquinolin-4-yl | 54g | 17b | 4-methylpentyl |
| 8 | 53h | 3-cyclopentyloxy-4-methylphenyl | 54h | 19a | pentyl |
| 9 | 53i | 3-(methoxymethoxy)-4-methylphenyl | 54i | 19a | pentyl |
| 10 | 53a | 2-fluorophenyl | 54a | 19a | pentyl |
| 11 | 53b | 3-fluorophenyl | 54b | 19a | pentyl |

TABLE 1-continued
List of urea derivatives 55a-q
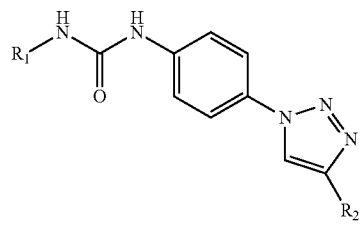
| | | R1 | | R2 |
|---|---|---|---|---|
| 12 | 53b | 3-F-phenyl | 55n | butanone chain |
| 13 | 53b | 3-F-phenyl | 19e | ethoxymethyl |
| 14 | 53l | 3-(3-oxobutyl)-4-methylphenyl | 19a | butyl |
| 15 | 53l | 5-F-pyridin-3-yl | 19a | butyl |
| Entry | Compound | |
|---|---|---|
| 1 | (structure) | 55a |
| 2 | (structure) | 55 b |

TABLE 1-continued
List of urea derivatives 55a-q
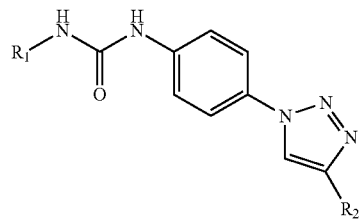
| 3 | 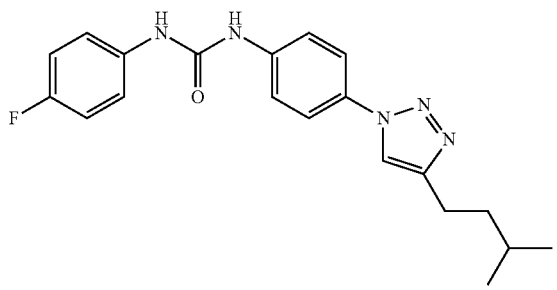 [SMILES: CC(C)CCc1cn(-c2ccc(NC(=O)Nc3ccc(F)cc3)cc2)nn1] | 55c |
| 4 | 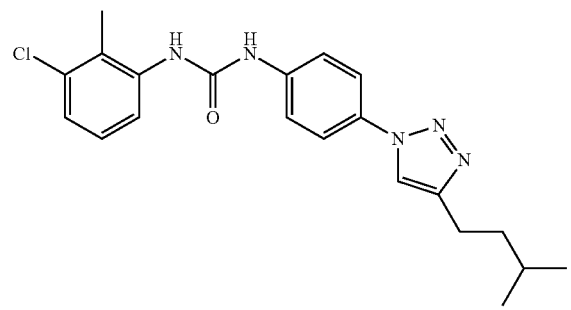 [SMILES: Cc1c(Cl)cccc1NC(=O)Nc1ccc(-n2cc(CCC(C)C)nn2)cc1] | 55d |
| 5 | 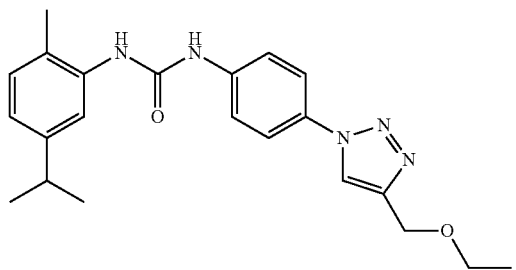 [SMILES: CCOCc1cn(-c2ccc(NC(=O)Nc3cc(C(C)C)ccc3C)cc2)nn1] | 55e |
| 6 | 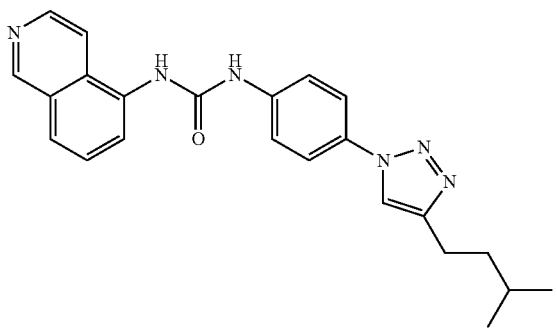 [SMILES: CC(C)CCc1cn(-c2ccc(NC(=O)Nc3cccc4cnccc34)cc2)nn1] | 55f |

TABLE 1-continued
List of urea derivatives 55a-q
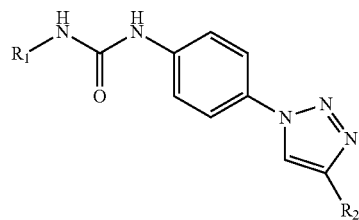
| 7 | 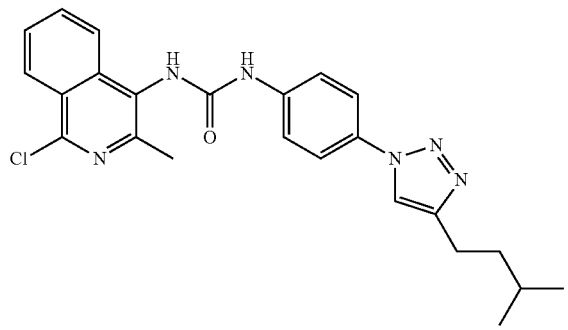 [SMILES: Cc1nc(Cl)c2ccccc2c1NC(=O)Nc1ccc(-n2cc(CCC(C)C)nn2)cc1] | 55g |
| --- | --- | --- |
| 8 | 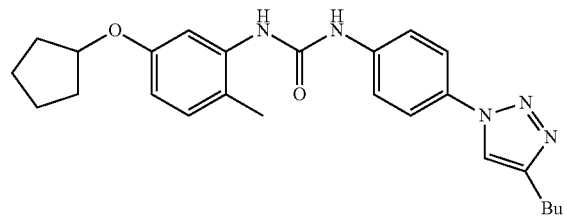 | 55h |
| 9 | 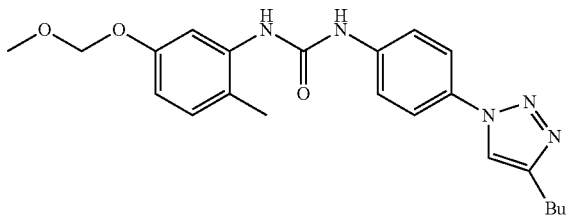 | 55i |
| 10 | 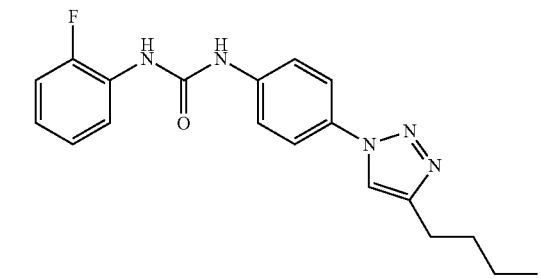 [SMILES: CCCCc1cn(-c2ccc(NC(=O)Nc3ccccc3F)cc2)nn1] | 55l |
| 11 | 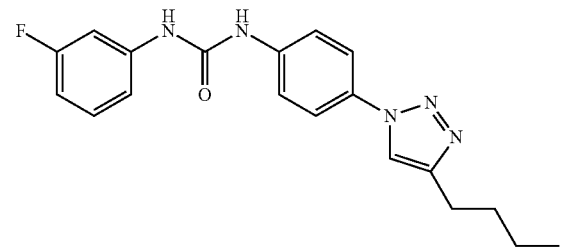 | 55m |

TABLE 1-continued

List of urea derivatives 55a-q

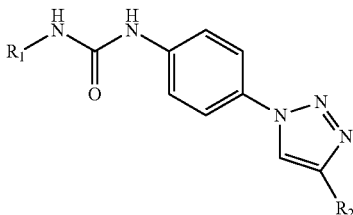

| | | |
|---|---|---|
| 12 | 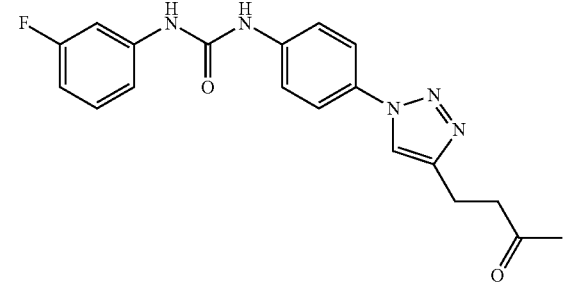 | 55n |
| 13 | 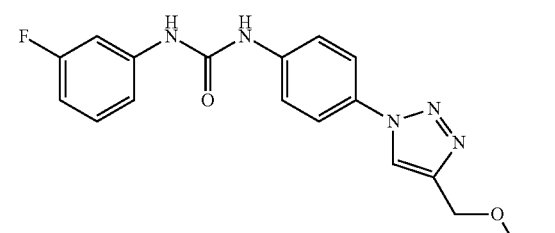 | 55o |
| 14 | 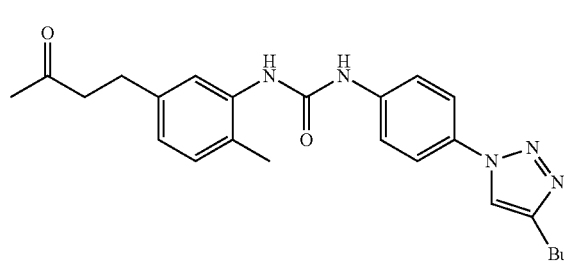 | 55p |
| 15 | 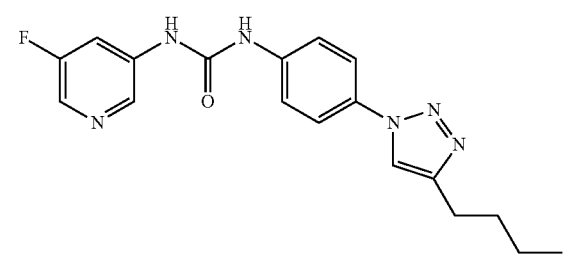 [SMILES: CCCCc1cn(-c2ccc(NC(=O)Nc3cccc(F)c3)cc2)nn1] | 55q |

General Procedure for the Preparation of 55a-q:

A solution of the opportune aromatic amine (41 mg, 0.3835 mmol) and DMAP (19 mg, 0.1534 mmol) in 5 mL of $CH_2Cl_2$ was added dropwise to an ice cold solution of triphosgene in $CH_2Cl_2$, during 30 min., then the opportune aniline 17a-c was added in one portion, and the reaction mixture was stirred at r.t. for 12 h. After this time, 2M HCl was added and the mixture was extracted with $CH_2Cl_2$ (3×20 mL). The organic layers were collected, washed with Brine and dried over $Na_2SO_4$. The crude was purified by flash chromatography on silica gel using the opportune eluent.

1-(2-fluorophenyl)-3-(4-(4-isopentyl-1H-1,2,3-triazol-1-yl)phenyl)urea (55a): (Purification eluent: DCM/MeOH 98:2). Yield 68%, white solid. $^1$HNMR (400 MHz, MeOD-$d_4$): δ 8.07-8.03 (t, J=8.0 Hz, 1H), 7.64 (s, 1H), 7.56-7.50 (m, 4H), 7.08-6.75 (m, 3H) 2.76-2.72 (t, J=8.0 Hz, 2H), 1.64-1.54 (m, 3H), 0.92-0.90 (d, 6H) ppm. $^{13}$CNMR (MeOD-$d_4$): δ 154.32, 152.91, 139.45, 132.87, 129.94, 129.06, 123.88, 121.63, 119.11, 115.72, 38.37, 27.62, 23.41, 22.29 ppm. MS (ESI) m/z 366 [M–H]$^-$, 402 [M+Cl]$^-$.

1-(3-fluorophenyl)-3-(4-(4-isopentyl-1H-1,2,3-triazol-1-yl)phenyl)urea (55b): (Purification eluent: DCM/MeOH 98:2). Yield 70%, white solid. $^1$HNMR (400 MHz, MeOD-d$_4$): δ 7.74-7.73 (m, 1H), 7.54-7.53 (m, 4H), 7.34-7.32 (m, 1H), 7.25-7.24 (m, 1H), 7.18-7.16 (m 1H), 7.07-7.06 (m, 1H), 6.68-6.65 (t, J=8.0 Hz, 1H), 2.75-2.73 (t, J=8.0 Hz, 2H), 1.62-1.58 (m, 3H), 0.92-0.90 (d, 6H)ppm. $^{13}$CNMR (MeOD-d$_4$): δ 164.10, 153.91, 139.83, 137.51, 133.81, 133.49, 131.51, 129.82, 121.61, 119.17, 117.24, 116.51, 42.71, 29.12, 27.21, 23.27 ppm. MS (ESI) m/z 366 [M−H]$^−$, 402 [M+Cl]$^−$.

1-(4-fluorophenyl)-3-(4-(4-isopentyl-1H-1,2,3-triazol-1-yl)phenyl)urea (55c): (Purification eluent: PE/EA 7:3). Yield 63%, white solid. $^1$H NMR (400 MHz, Acetone-d$_6$): δ 8.48 (s, 1H), 8.34 (s, 1H), 8.15 (s, 1H), 7.71-7.66 (m, 4H), 7.53-7.49 (m, 2H), 7.02-6.97 (m, 2H), 2.72-2.68 (m, 2H), 1.60-1.53 (m, 3H), 0.90-0.88 (d, J=8.0 Hz, 6H) ppm. $^{13}$C-NMR (100 MHz, Acetone-d$_6$): δ 159.71, 152.58, 140.25, 136.40, 131.97, 130.07, 124.70, 120.60, 119.06, 118.60, 115.20, 38.53, 27.36, 23.31, 21.58 ppm. MS (ESI) m/z 366 [M−H]$^−$, 402 [M+Cl]$^−$.

1-(3-chloro-2-methylphenyl)-3-(4-(4-isopentyl-1H-1,2,3-triazol-1-yl)phenyl) urea (55d): (Purification eluent: DCM/MeOH 98:2). Yield 80%, white solid. $^1$HNMR (MeOD-d$_4$): δ 7.89 (s, 1H), 7.64-7.57 (m, 4H), 7.08-7.06 (d, J=8.0 Hz, 1H), 6.95-6.93 (d, J=8.0 Hz, 1H), 2.77-2.73 (t, J=7.2 Hz, 2H), 2.23 (s, 3H), 1.60-1.56 (m, 3H), 0.94-0.93 (d, J=6.0 Hz, 6H) ppm. $^{13}$C NMR (100 MHz CDCl$_3$-d): δ 153.48, 149.08, 139.85, 137.69, 131.73, 131.14, 126.60, 123.47, 121.61, 121.16, 119.74 ppm. MS (ESI): m/z 396 [M−H]$^−$ 1-(4-(4-(ethoxymethyl)-1H-1,2,3-triazol-1-yl)phenyl)-3-(5-isopropyl-2-methyl phenyl) urea (55e): (Purification eluent: DCM/MeOH 98:2). Yield 70%, white solid. $^1$HNMR (400 MHz CDCl$_3$-d): δ 8.39 (s, 1H), 7.85 (s, 1H), 7.46-7.37 (m, 4H), 7.02-7.00 (d, J=8.0 Hz, 1H), 6.89-6.87 (d, J=8.0 Hz, 1H), 4.66 (s, 2H), 3.63-3.58 (q, J=7.8 Hz, 2H), 2.81, 2.75 (m, 1H), 2.10 (s, 1H), 1.23-1.20 (t, J=6.8 Hz, 3H), 1.16-1.14 (d, J=8.0 Hz, 6H)ppm. $^{13}$CNMR (100 MHz CDCl$_3$-d): δ 154.22, 147.65, 145.95, 139.97, 135.57, 131.52, 131.52, 130.54, 128.69, 123.47, 122.80, 121.22, 120.96, 120.01, 66.40, 63.90, 33.66, 23.92, 17.42, 15.09 ppm. MS (ESI) m/z 394.1 [M+H]$^+$, 416.1 [M+Na]$^+$.

1-(4-(4-isopentyl-1H-1,2,3-triazol-1-yl)phenyl)-3-(isoquinolin-5-yl)urea (55f): (Purification eluent: DCM/MeOH 98:2). Yield 63%, white solid. $^1$HNMR (400 MHz CDCl$_3$-d): δ 9.22 (s, 1H), 8.46 (m, 1H), 8.22-8.20 (m, 2H), 7.96 (s, 1H), 7.89-7.87 (d, J=8.0 Hz, 1H), 7.73-7.67 (m, 5H), 2.78-2.74 (t, J=7.2 Hz, 2H), 1.61-1.57 (m, 3H), 0.93-0.92 (d, J=6.0 Hz, 6H) ppm. $^{13}$CNMR (100 MHz CDCl$_3$-d): δ 152.81, 142.11, 140.21, 139.45, 132.84, 129.87, 129.01, 124.88, 121.62, 119.11, 115.75, 114.81, 112.42, 42.66, 30.11, 27.76, 23.21 ppm. MS (ESI) m/z 399.1 [M−H]$^−$, 435.1 [M+Cl]$^−$ 1-(1-chloro-3-methylisoquinolin-4-yl)-3-(4-(4-isopentyl-1H-1,2,3-triazol-1-yl)phenyl)urea (55g): (Purification eluent: DCM/MeOH 98:2). Yield 60%, white solid. $^1$HNMR (400 MHz, MeOD-d$_4$): δ 8.34-8.32 (d, J=8.0 Hz, 1H), 8.21 (s, 1H), 8.08-8.06 (d, J=8.0 Hz, 1H), 7.89-7.84 (t, J=8.0 Hz, 1H), 7.74, 7.20 (m, 3H), 7.67-7.65 (d, J=8.0 Hz, 2H), 2.79-2.75 (t, J=7.2 Hz, 2H), 2.62 (s, 3H), 1.64-1.61 (m, 3H), 0.93-0.92 (d, J=6.0 Hz, 6H) ppm. $^{13}$CNMR (100 MHz CDCl$_3$-d): δ 151.88, 148.47, 139.86, 137.05, 134.65, 132.12, 131.84, 128.04, 126.23, 122.63, 121.02, 119.62, 119.1, 114.81, 112.41, 38.27, 29.45, 27.45, 22.84, 21.44, 19.03 ppm. MS (ESI) m/z 447.1 [M−H]$^−$, 483.1 [M+Cl]$^−$.

1-(4-(4-butyl-1H-1,2,3-triazol-1-yl)phenyl)-3-(5-(cyclopentyloxy)-2-methylphenyl)urea (55h)): (Purification eluent: DCM/MeOH 98:2). Yield 76%, white solid. $^1$HNMR (400 MHz, Acetone-d$_6$): δ 8.64 (s, 1H), 8.17 (s, 1H), 7.74-7.65 (m, 5H), 7.48 (s, 1H), 7.01-7.99 (d, J=3.9 Hz, 1H), 6.51-6.48 (dd, J=5.6 Hz, J=5.6 Hz, 0.2 Hz, 1H), 4.75-4.74 (m, 1H), 2.75-2.70 (t, J=7.8 Hz, 2H), 2.16 (s, 3H), 1.91-1.88 (m, 2H), 1.77-1.63 (m, 8H), 1.42-1.38 (m, 2H), 1.01-1.98 (t, J=8 Hz, 3H). $^{13}$CNMR (100 MHz Acetone-d$_6$): δ 154.56, 153.62, 136.75, 136.64, 135.76, 128.05, 125.09, 123.49, 123.07, 123.07, 122.17, 122.17, 109.66, 106.38, 82.15, 33.39, 33.39, 29.99, 27.92, 24.10, 24.10, 22.18, 17.35, 14.02.

1-(4-(4-butyl-1H-1,2,3-triazol-1-yl)phenyl)-3-(5-(methoxymethoxy)-2-methylphenyl)urea (55i): (Purification eluent: DCM/MeOH 98:2). Yield 70%, white solid. $^1$HNMR (400 MHz, Acetone-d$_6$): δ=8.63 (s, 1H), 8.16 (s, 1H), 7.76-7.60 (m, 5H), 7.51 (s, 1H), 7.03 (d, J=8.3 Hz, 2H), 6.64 (dd, J=8.3, 2.6 Hz, 2H), 5.12 (s, 2H), 3.39 (s, 3H), 2.71 (t, J=7.6, 2H), 2.17 (s, 3H), 1.66 (m, 2H), 1.43-1.34 (m, 2H), 0.93-0.89 (t, J=7.8 Hz, 3H)ppm. $^{13}$CNMR (100 MHz Acetone-d$_6$): δ 156.07, 152.45, 148.35, 140.15, 138.13, 131.93, 131.11, 129.97, 120.57, 119.10, 118.18, 111.30, 109.96, 109.81, 94.35 55.45, 29.99, 27.92, 22.18, 17.35, 14.02 ppm. MS (ESI) m/z 408.1 [M−H]$^−$, 444.1 [M+Cl]$^−$.

1-(4-(4-butyl-1H-1,2,3-triazol-1-yl)phenyl)-3-(3-fluorophenyl)urea (55l): (Purification eluent: DCM/MeOH 98:2). Yield 80%, white solid. $^1$H NMR (400 MHz, CDCl$_3$-d) δ 7.34 (s, 2H), 7.11-6.93 (m, 4H), 6.66 (s, 2H), 6.48 (s, 2H), 6.25 (d, J=7.5 Hz, 4H), 6.14-6.03 (m, 4H), 5.94 (s, 2H), 5.73 (s, 2H), 2.03-1.98 (m, 4H), 1.00-0.95 (m, 3H), 0.69-0.64 (m, 3H), 0.28-0.22 (m, 6H). $^{13}$C NMR (100 MHz, CDCl$_3$-d) δ: 160.36, 154.56, 154.07, 140.81, 136.75, 135.76, 129.04, 125.09, 123.07, 123.07, 122.17, 122.17, 117.53, 111.81, 110.08, 29.99, 27.92, 22.18, 14.02. ppm. MS (ESI) m/z 352 [M−H]$^−$, 388 [M+Cl]$^−$.

1-(4-(4-butyl-1H-1,2,3-triazol-1-yl)phenyl)-3-(3-fluorophenyl)urea (55m): (Purification eluent: DCM/MeOH 98:2). Yield 80%, white solid. $^1$H NMR (400 MHz, CDCl$_3$-d) δ: 7.78 (s, 1H), 7.59 (m, 4H), 7.37 (d, J=10.6, 1H), 7.22 (dd, J=15.4, 7.2, 1H), 7.08 (d, J=8.0, 1H), 6.71 (t, J=8.2, 1H), 2.77 (t, J=7.6, 2H), 1.77-1.54 (m, 2H), 1.47-1.17 (m, 2H), 0.96-0.93 (t, J=7 Hz, 3H)ppm. $^{13}$C NMR (100 MHz, CDCl$_3$-d) δ 160.36, 154.56, 154.07, 140.81, 136.75, 135.76, 129.04, 125.09, 123.07, 123.07, 122.17, 122.17, 117.53, 111.81, 110.08, 29.99, 27.92, 22.18, 14.02 ppm. MS (ESI) m/z 352 [M−H]$^−$, 388 [M+Cl]$^−$.

1-(3-fluorophenyl)-3-(4-(4-(3-oxobutyl)-1H-1,2,3-triazol-1-yl)phenyl)urea (55n): (Purification eluent: DCM/MeOH 98:2). Yield 75%, white solid. $^1$H NMR (400 MHz, Acetone-d6) δ 8.54-8.51 (m, 2H), 8.15 (s, 1H), 7.81-7.56 (m, 4H), 7.58-7.55 (d, J=12 Hz, 1H), 7.22 (m, 1H), 7.28-7.26 (d, J=8 Hz, 1H), 6.73-6.69 (t, J=7.3 Hz, 1H), 2.95-2.88 (m, 4H), 2.12 (s, 3H), ppm. $^{13}$C NMR (100 MHz, Acetone-d$_6$) δ 206.98, 160.36, 154.07, 153.06, 140.81, 136.75, 135.76, 129.04, 123.07, 123.07, 122.17, 122.17, 121.34, 117.53, 111.81, 110.08, 41.35, 28.57, 20.36. ppm. MS (ESI) m/z 366 [M−H]$^−$, 402 [M+Cl]$^−$.

1-(4-(4-(ethoxymethyl)-1H-1,2,3-triazol-1-yl)phenyl)-3-(3-fluorophenyl)urea (55o): (Purification eluent: DCM/MeOH 98:2). Yield 72%, white solid. $^1$H NMR (400 MHz, Acetone-d6) δ: 8.46-8.38 (m, 3H), 7.76-7.70 (m, 4H), 7.58-7.55 (d, J=11 Hz, 1H), 7.27-7.24 (t, J=δ6 Hz, 1H), 7.17-7.15 (d, J=7 Hz, 1H), 6.74-6.71 (t, J=7 Hz, 1H), 4.59 (s, 1H), 3.57-3.52 (q, J=6.7 Hz, 2H), 1.16-1.13 (t, J=6.6 Hz, 3H)ppm. $^{13}$C NMR (100 MHz, Acetone d6) δ 164.26, 161.86, 152.22, 145.85, 140.05, 131.95, 130.14, 121.06, 120.89, 119.35, 114.13, 108.63, 108.42, 105.64, 105.38, 65.30, 63.54, 14.55, −43.88. ppm. MS (ESI) m/z 354 [M−H]$^−$, 390 [M+Cl]$^−$.

1-(4-(4-butyl-1H-1,2,3-triazol-1-yl)phenyl)-3-(2-methyl-5-(3-oxobutyl)phenyl)urea (55p): (Purification eluent:

DCM/MeOH 98:2). Yield 72%, white solid. $^1$H NMR (400 MHz, MeOD-d$_4$) δ 8.18 (s, 1H), 7.70 (d, J=9.0 Hz, 2H), 7.62 (d, J=8.9 Hz, 2H), 7.49 (s, 1H), 7.08 (d, J=7.7 Hz, 1H), 6.87 (d, J=6.7 Hz, 1H), 2.79-2.73 (m, 4H), 2.23 (s, 3H), 2.11 (s, 3H), 1.68 (m, 2H), 1.47-1.36 (m, 2H), 0.95 (t, J=7.3 Hz, 3H)ppm. $^{13}$C NMR (100 MHz MeOD-d4) δ 208.15, 154.56, 139.69, 138.44, 136.75, 135.76, 130.90, 128.16, 125.90, 125.09, 123.54, 123.07, 123.07, 122.17, 122.17, 40.44, 31.99, 29.99, 28.57, 27.92, 22.18, 17.35, 14.02 ppm. MS (ESI) m/z 417.9 [M−H]$^-$, 453.8 [M+Cl]$^-$.

1-(4-(4-butyl-1H-1,2,3-triazol-1-yl)phenyl)-3-(5-fluoropyridin-3-yl)urea (55q): (Purification eluent: DCM/MeOH 99:2). Yield 67%, white solid. $^1$H NMR (400 MHz, MeOD-d$_4$) δ 9.30 (d, J=1.4 Hz, 1H), 8.10-7.99 (m, 2H), 7.92 (d, J=7.4 Hz, 2H), 7.66-7.57 (m, 3H), 6.52 (d, J=4.8 Hz, 2H), 2.74 (t, J=8.0 Hz, 2H), 1.71 (p, J=7.9 Hz, 2H), 1.48-1.34 (m, 2H), 1.00 (t, J=6.6 Hz, 3H). ppm. $^{13}$C NMR (100 MHz MeOD-d$_4$) δ 159.43, 154.56, 154.07, 139.94, 136.75, 135.76, 134.14, 133.93, 125.09, 123.07, 123.07, 122.17, 115.14, 29.99, 27.92, 22.18, 14.02 ppm. MS (ESI) m/z 353 [M−H]$^-$.

Example 10

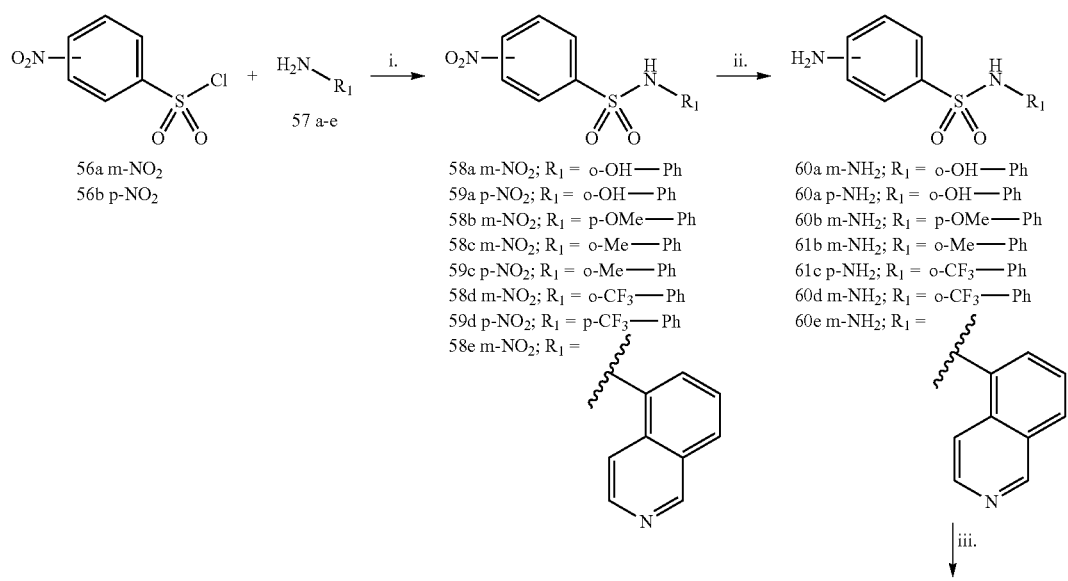

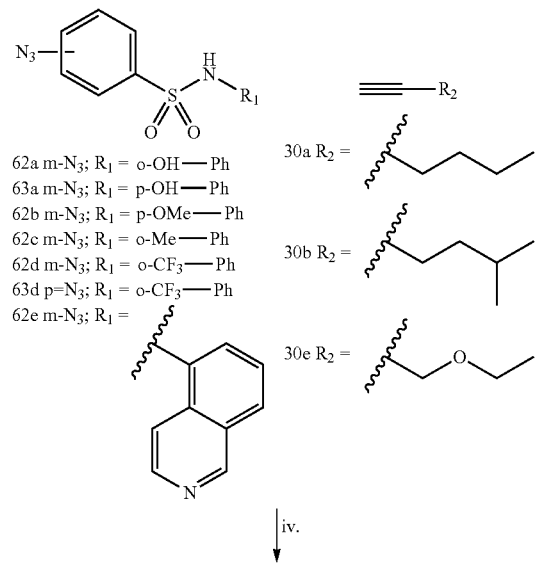

-continued

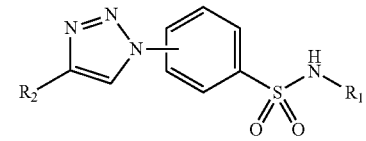

64a m-triazolyl; R₁ = o-OH—Ph; R₂ = butyl;
65a p-triazolyl; R₁ = o-OH—Ph; R₂ = butyl;
64b m-triazolyl: R₁ = p-OMe—Ph; R₂ = butyl;
64c m-triazolyl; R₁ = o-Me—Ph; R₂ = butyl;
64d m-triazolyl; R₁ = o-CF₃—Ph; R₂ = butyl;
66d m-triazolyl; R₁ = o-CF₃—Ph; R₂ =

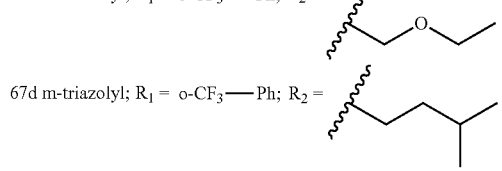

67d m-triazolyl; R₁ = o-CF₃—Ph; R₂ =

64e m-triazolyl; R₁ =

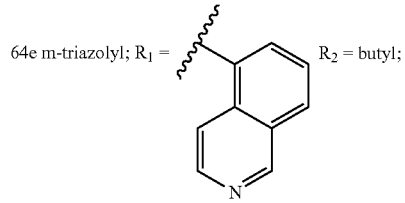

R₂ = butyl;

68e m-triazolyl; R₁ =

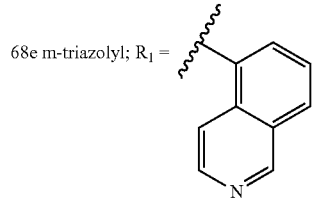

R₂ = butyl;

Reagents and conditions: i. Pyr, 5 h r.t. ii. H₂, Pd/C, MeOH; iii a) t-BuONO, CH₃CN, 20 min. 0° C.; b) TMSN₃, CH₃CN, 2 h r.t.; iii (for 58e) a) NaNO₂, H₂SO₄ 25%, 20 min. 0° C.; b) NaN₃ 2 h r.t.; v. alkyne, CuSO₄·5 H₂O, sodium ascorbate, H₂O tBuOH (1:1), MW 10 min, 120° C.;

The list of synthesized sulfonamide derivatives is reported in Table 2.

TABLE 2

List of synthesized sulfonamide derivatives

| Entry | Chloryde | Aromatic amine | R₁ | Nitro Cmpd. | Amino-Cmpd. | Azide | Alkyne |
|---|---|---|---|---|---|---|---|
| 1 | 56a | 57a | o-OH—Phe | 58a | 60a | 62a | 30a |
| 2 | 56b | 57a | o-OH—Phe | 59a | 61a | 63a | 30a |
| 3 | 56a | 57b | p-MeO—Phe | 58b | 60b | 62b | 30a |
| 4 | 56a | 57c | p-Me—Phe | 58c | 60c | 62c | 30a |
| 5 | 56a | 57d | o-CF₃—Phe | 58d | 60d | 62d | 30a |
| 6 | 56a | 57d | o-CF₃—Phe | 58d | 60d | 62d | 30f |

TABLE 2-continued

List of synthesized sulfonamide derivatives

| 7 | 56a | 57d | o-CF$_3$—Phe | 58d | 60d | 62d | 30b |
| 8 | 56b | 57c | o-CF$_3$—Phe | 59c | 61c | 63c | 30a |
| 9 | 56a | 57e | (5-isoquinolinyl) | 58e | 60e | 62e | 30a |
| 10 | 56a | 57e | (5-isoquinolinyl) | 58e | 60e | 62e | 30f |

| Entry | R$_2$ | Compound | |
|---|---|---|---|
| 1 | —Butyl | [3-(4-butyl-1H-1,2,3-triazol-1-yl)-N-(2-hydroxyphenyl)benzenesulfonamide] | 64a |
| 2 | —Butyl | [4-(4-butyl-1H-1,2,3-triazol-1-yl)-N-(2-hydroxyphenyl)benzenesulfonamide] | 65a |
| 3 | —Butyl | [3-(4-butyl-1H-1,2,3-triazol-1-yl)-N-(4-methoxyphenyl)benzenesulfonamide] | 64b |
| 4 | —Butyl | [3-(4-butyl-1H-1,2,3-triazol-1-yl)-N-(2-methylphenyl)benzenesulfonamide] | 64c |

TABLE 2-continued

List of synthesized sulfonamide derivatives

| # | R | Structure | ID |
|---|---|---|---|
| 5 | —Butyl | | 64d |
| 6 | —CH$_2$OCH$_2$CH$_3$ | | 66d |
| 7 | —Isopentyl | | 67d |
| 8 | —Butyl | | 65 c |
| 9 | —Butyl | | 64e |
| 10 | —CH$_2$OCH$_2$CH$_3$ | | 68e |

General Procedure for the Preparation of Sulfonamides 58-59a-e

To a stirred solution of the opportune aromatic amine (1 eq.) in 5 mL of anhydrous pyridine, was added the corresponding sulphonyl chloride (1.1 eq) at 0° C. The corresponding solution was stirred at r.t. under nitrogen atmosphere, for 5 h. After completion of the reaction the mixture was acidified with 20 mL of 2N HCl, the aqueous phase was extracted with several times and the combined organic phases were dried (Na$_2$SO$_4$) and concentrated.

N-(2-hydroxy)-3-nitro-phenylbenzenesulfonamide (58a). The residue was purified by flash chromatography on silica gel (Hexane-AcOEt 3:1). Yield 84%. $^1$H NMR (Acetone): δ 8.70 (s, 1H), 8.59, (s, 1H), 8.45-8.42 (d, J=12 Hz, 1H), 8.13-8.12 (d, J=4.3 Hz, 1H), 7.83-7.79 (t, J=8.1 Hz, 1H), 7.36-7.34 (d, J=8.2 Hz, 1H), 7.02-6.98 (t, J=8 Hz, 1H), 6.83-6.76 (m, 2H). MS (ESI): m/z 292.8 [M–H]$^-$.

N-(2-hydroxy)-4-nitro-phenylbenzenesulfonamide (59a). $^1$H NMR (MeOD-d$_4$): δ 8.25-8.22 (dd, 2H, J=8.4 Hz), δ 7.93-7.91 (dd, 2H, J=8.4 Hz), 7.33-7.31 (d, 1H), 6.97-6.94 (t, J=7.6 Hz, 1H), 6.76-6.73 (t, J=7.6 Hz, H), 6.66-6.64 (d, J=8 Hz, 1H) ppm. $^{13}$C NMR (MeOD-d$_4$): δ 150.36, 150.06, 128.56, 127.06, 125.55, 123.55, 119.29, 115.53 ppm. MS: m/z 292.8 [M–H]$^-$ N-(4-methoxy)-3-nitro-phenylbenzenesulfonamide (58b). The residue was purified by flash chromatography on silica gel (Hexane-AcOEt 3:1). Yield 84%. $^1$H NMR (400 MHz CDCl$_3$-d): δ 8.57 (s, 1H), 8.39-8.37 (d, J=8 Hz, 1H), 7.97-7.95 (d, J=8.0 Hz, 1H), 7.65-7.61 (t, J=7.7 Hz, 1H), 6.99-6.97 (dd, J=8.1 Hz, 2H), 6.78-6.76 (dd, J=8.1 Hz, 2H), 6.69 (s, 1H), 3.75 (s, 3H) ppm. MS (ESI): m/z 309 [M+H]$^+$.

N-(2-trifluoromethyl)-3-nitro-phenylbenzenesulfonamide (58c). The residue was purified by flash chromatography on silica gel (Hexane-AcOEt 3:1). Yield 84%. $^1$H NMR (400 MHz CDCl$_3$-d): δ 8.56 (s, 1H), 8.40-8.38 (d, J=8.4 Hz, 1H), 8.06-8.04 (d, J=8 Hz, 1H), 7.86-7.84 (d, J=8 Hz, 1H), 7.69-7.64 (t, J=8 Hz, 1H), 7.61-7.57 (t, J=7.8 Hz, 1H), 7.52-7.50 (d, J=8.0 Hz, 1H), 7.31-7.27 (t, J=8.1 Hz, 1H), 6.86 (s, 1H). $^{13}$C NMR (100 MHz CDCl$_3$-d): δ 148.16, 140.78, 133.53, 133.17, 132.66, 130.53, 127.79, 126.83, 126.78, 126.31, 124.91, 122.51, 122.02 MS (ESI): m/z 286.8 [M+Na]$^+$.

N-(2-trifluoromethyl)-4-nitro-phenylbenzenesulfonamide (59c) The residue was purified by flash chromatography on silica gel (Hexane-AcOEt 3:1). Yield 84%. $^1$H NMR (400 MHz CDCl$_3$-d): δ 8.27-8.25 (d, J=8.0 Hz, 1H), 7.91-7.89 (d, J=8.0 Hz, 1H), 7.87-7.85 (d, J=8.0 Hz, 2H), 7.61-7.57 (t, J=8.0 Hz, 1H), 7.53-7.51 (d, J=8.0 Hz, 1H), 7.32-7.25 (t, J=8 Hz, 1H), 6.91 (s, 1H) ppm. $^{13}$C NMR (100 MHz CDCl$_3$-d): δ 150.80, 144.33, 139.34, 133.61, 128.99, 127.14, 126.03, 124.00 ppm.

N-(2-methyl)-3-nitro-phenylenzenesulfonamide (58d) The residue was purified by flash chromatography on silica gel (Hexane-AcOEt 3:1). Yield 84%. $^1$H NMR (Acetone): δ 8.49-8.47 (m, 2H), 8.09-8.07 (d, J=8 Hz, 1H), 7.87-7.83 (t, J=8 Hz, 1H), 7.17-7.10 (m, 4H) ppm.

N-(isoquinolin-6-yl)-3-nitrobenzenesulfonamide (58e) (Purification eluent: PE-AcOEt: 4-1) Yield 67%. $^1$H NMR (DMSO d$_6$): δ 9.56 (s, 1H), 8.52-8.50 (d, J=6.4 Hz, 1H), 8.44-8.41 (m, 2H), 8.21-8.19 (d, J=8.0 Hz, 1H), 8.07-8.05 (d, J=6.4 Hz, 1H), 8.01-7.99 (d, J=7.6 Hz, 1H), 7.79-7.70 (m, 2H), 7.55-7.53 (d, J=7.7 Hz, 1H) ppm.

N-(2-methyl)-4-nitro-phenylenzenesulfonamide (59d) The residue was purified by flash chromatography on silica gel (Hexane-AcOEt 3:1). Yield 84%. $^1$H NMR (400 MHz CDCl$_3$-d): δ 8.28-8.251 (m, 2H), 7.91-7.88 (m, 2H), 7.27-7.25 (d, J=6.4 Hz, 2H), 7.18-7.12 (m, 2H), 2.02 (s, 3H) ppm. $^{13}$C NMR (100 MHz CDCl$_3$-d): δ 150.17, 145.28, 133.35, 131.20, 128.45, 127.27, 125.19, 124.30, 17.61 ppm. MS: m/z 314.8 [M+Na]$^+$ General Procedure for the Preparation of Sulfonamides 60a-e and 61 a-d The opportune sulfonamide (400 mg, 1.35 mmol) was solubilized in 20 mL of anhydrous EtOH, and Palladium on charcoal (60 mg) was added. The reaction mixture was stirred under Hydrogen atmosphere for 1 h. Then the mixture was filtered-off on a celite pad, was concentrated in vacuo and the crude product was purified by flash chromatography on silica gel with the appropriate eluent.

3-amino-N-(2-hydroxyphenyl)benzenesulfonamide (60a) (Purification eluent: Hexane-AcOEt 3:1). Yield 92%. $^1$H NMR (Acetone): δ 8.29 (s, 1H), 7.27-7.24 (d, J=12 Hz, 1H), 7.14-7.09 (m, 2H), 6.99-6.97 (d, J=8 Hz, 1H), 6.95-6.92 (t, J=8 Hz, 1H), 6.82-6.75 (m, 2H), 6.74-6.72 (t, J=4 Hz, 1H), MS (ESI): m/z 286.8 [M+Na]$^+$.

4-amino-N-(2-hydroxyphenyl)benzenesulfonamide (61a) $^1$H NMR (MeOD-d$_4$): δ 7.55-7.53 (dd, J=8.8 Hz, 2H), 7.42-7.40 (dd, J=8.8 Hz, 2H), 7.22-7.18 (m, 1H), 6.90-6.84 (m, 2H), 6.70-6.66 (m, 2H), 6.55-6.53 (d, J=8.8 Hz, 1H) ppm. MS: m/z 286.8 [M+H]+.

3-amino-N-(4-methoxyphenyl)benzenesulfonamide (60b) (Purification eluent: Hexane-AcOEt 3:1). Yield 92%. $^1$H NMR (Acetone): δ 7.3 (s, 1H), 7.26 (s, 1H), 7.17-7.14 (m, 2H), 6.96-6.94 (dd, J=8 Hz, 2H), 6.72-6.70 (dd, J=8.0 Hz, 2H), 3.72 (s, 3H)ppm. MS: m/z 300.8 [M+Na]$^+$.

3-amino-N-(2-(trifluoromethyl)phenyl)benzenesulfonamide (60c) (Purification eluent: Hexane-AcOEt 3:1). Yield 84%. $^1$H NMR (Acetone): δ 7.63-7.61 (d, J=8 Hz, 1H), 7.51-7.58 (m, 2H), 7.24-7.20 (t, J=8 Hz, 1H), 7.19-7.17 (m, 2H), 7.07-7.05 (d, J=8 Hz, 1H), 6.90-6.88 (d, J=8 Hz, 1H), 5.10 (s, 1H). MS (ESI): m/z 338.8 [M+Na]$^+$.

4-amino-N-(2-(trifluoromethyl)phenyl)benzenesulfonamide (61c) (Purification eluent: Hexane-AcOEt 3:1). Yield 84%. $^1$H NMR (Acetone): δ 7.53-7.51 (d, J=8 Hz, 1H), 7.49-7.46 (m, 2H), 7.45-7.43 (d, J=8 Hz, 2H), 7.30-7.28 (t, J=8 Hz, 1H), 6.62-6.60 (d, J=7.4 Hz, 1H), 5.10 (s, 1H). MS (ESI): m/z 338.8 [M+Na]$^+$.

3-amino-N-(o-tolyl)benzenesulfonamide (60d) $^1$H NMR (Acetone): δ 8.14 (s, 1H), 7.2-6.92 (m, 6H), 6.92-6.86 (d, J=8 Hz, 1H), 6.85-6.84 (d, J=8 Hz, 1H), 2.11 (s, 3H) ppm. MS (ESI): m/z 262.9 [M+H]$^+$, 284.8 [M+Na]$^+$.

3-amino-N-(isoquinolin-6-yl)benzenesulfonamide (60e): Compound 59e (400 mg, 1.35 mmol) was solubilized in 20 mL of anhydrous EtOH, and Palladium on charcoal (60 mg) was added. The reaction mixture was stirred under Hydrogen atmosphere for 1 h. Then the mixture was filtered-off on a celite pad, concentrated in vacuo and the crude product was purified by flash chromatography on silica gel (PE-AcOEt: 4-1) Yield 67%. $^1$H NMR (DMSO d$_6$): δ 10.23 (s, 1H), 9.25 (s, 1H), 9.41-9.40 (d, J=6.4 Hz, 1H), 7.95-7.84 (m, 2H), 7.59-7.56 (t, J=8 Hz, 1H), 7.43-7.41 (d, J=8.0 Hz, 1H), 7.09-7.06 (t, J=8.0 Hz, 1H), 6.80-6.78 (d, J=8.0 Hz, 1H), 6.66-6.64 (d, J=8.0 Hz), 5.50 (s, 2H) ppm. MS (ESI): m/z 299.8 [M+H]$^+$, 321.8 [M+Na]$^+$.

General Procedure for the Preparation of Azides 62a-c and 63 a-d

Amine (100 mg, 0.41 mmol) was dissolved in CH$_3$CN and cooled to 0° C. in an ice-salt bath. To this stirred solution, was added tBuONO, and the mixture was stirred for 10 min, after this time, TMSN$_3$ was added dropwise, during 10 minutes, and the resulting brown solution was stirred at r.t. One hour later the solvent was removed at reduced pressure and the residue was purified by flash chromatography on silica gel with the appropriate eluent.

3-azido-N-(2-hydroxyphenyl)benzenesulfonamide (62a). (Purification eluent: Hexane-AcOEt 3:1). $^1$H NMR (Acetone): δ 8.42 (s, 1H), 7.58-7.56 (d, J=8 Hz, 1H), 7.53-7.49 (t, J=8.0 Hz, 1H), 7.44 (s, J=8 Hz, 1H), 7.34-7.32 (d, J=8.0 Hz, 1H), 7.28-7.27 (d, J=4.0 Hz, 1H), 7.00-6.96 (t, J=8.0 Hz, 1H) 6.81-6.77 (m, 2H). MS (ESI): m/z 288.8 [M–H]$^-$.

4-azido-N-(2-hydroxyphenyl)benzenesulfonamide (63a). (Purification eluent: Hexane-AcOEt 3:1). $^1$H NMR (MeOD-d$_4$): δ 7.73-7.72 (dd, J=2.4 Hz, 2H), 7.36-7.35 (d, J=6.4 Hz, 1H), 7.09-7.07 (dd, J=8.8 Hz, 2H), 6.94-6.90 (m, H), 6.73-6.66 (m, 2H) ppm. MS: m/z 312.8 [M+Na]$^+$ 3-azido-N-(2-methoxyphenyl) benzenesulfonamide (62b). (Purification eluent: Hexane-AcOEt 3:1). Yield 92%. $^1$H NMR (Acetone): δ 7.5 (s, 1H), 7.26 (s, 1H), 7.27-7.24 (m, 2H), 7.06-7.04 (dd, J=8 Hz, 2H), 6.74-6.72 (dd, J=8.0 Hz, 2H), 3.73 (s, 3H)ppm. MS: m/z 300.8 [M+Na]$^+$.

3-azido-N-(o-tolyl)benzenesulfonamide (62c). (Purification eluent: Hexane-AcOEt 4:1). $^1$H NMR (400 MHz CDCl$_3$-d): δ 7.51-7.49 (d, J=8 Hz, 1H), 7.43-7.39 (t, J=8 Hz, 1H), 7.36 (s, 1H), 7.30-7.28 (d, J=8 Hz, 1H), 7.15-7.09 (m, 4H), 6.75 (s, 1H), 2.02 (s, 3H) ppm. MS (ESI): m/z 310.8 [M+Na]$^+$.

3-azido-N-(2-(trifluoromethyl)phenyl)benzenesulfonamide (62d). (Purification eluent: Hexane-AcOEt 4:1). $^1$H NMR (400 MHz CDCl$_3$-d): δ 7.84-7.81 (d, J=8.4 Hz, 1H), 7.56-7.50 (m, 3H), 7.43-7.37 (m, 2H), 7.27-7.23 (t, J=7.6 Hz, 1H), 7.18-7.16 (d, J=8 Hz, 1H), 6.87 (s, 1H) ppm. MS (ESI): m/z 364.8 [M+Na]$^+$.

4-azido-N-(2-(trifluoromethyl)phenyl)benzenesulfonamide (63c). (Purification eluent: Hexane-AcOEt 4:1). $^1$H NMR (400 MHz CDCl$_3$-d): δ 7.81-7.79 (d, J=7.6 Hz, 1H), 7.74-7.71 (d, J=7.4 Hz, 1H), 7.52-7.46 (m, 2H), 7.22-7.18 (t, J=8 Hz, 1H), 7.02-6.98 (m, 3H) ppm. m/z 364.7 [M+Na]$^+$.

3-azido-N-(isoquinolin-6-yl)benzenesulfonamide (62e): The opportune amine (100 mg, 0.41 mmol) was dissolved in CH$_3$CN and cooled to 0° C. in an ice-salt bath. To this stirred solution, was added tBuONO, and the mixture was stirred for 10 min, after this time, TMSN$_3$ was added dropwise, during 10 minutes, and the resulting brown solution was stirred at r.t. One hour later the solvent was removed at reduced pressure and the residue was purified by flash chromatography on silica gel (PE-AcOEt: 4-1) Yield 67%. $^1$H NMR (DMSO d-$_6$): δ $^1$H NMR (DMSO d-$_6$): δ 9.03 (s, 1H), 8.62 (s, 1H), 8.26 (s, 1H), 7.74-7.33 (m, 6H), 7.09-7.07 (d, J=8.0 Hz, 1H) ppm. MS (ESI): m/z 325.8 [M+H]$^+$, 347.7 [M+Na]$^+$.

General Procedure for the Preparation of Compounds 64a, 64b, 64c, 64d, 64e, 64f, 65a, 65c, 66d, 67d and 68.

The appropriate alkyne (6.08 mmol) and the opportune azide (5.07 mmol) were suspended in a 1:1 mixture of water and t-BuOH (1.5 mL each) in a 10 mL glass vial equipped with a small magnetic stirring bar. To this, was added sodium ascorbate (2.5 mmol) and copper(II) sulfate pentahydrate (2.50 mmol). The mixture was then heated for 10 min. at 125° C. under microwave irradiation, using an irradiation power of 300 W. After that time the solvent was removed at reduced pressure water was added and the mixture was extracted with EtOAc (3×20 mL). The organic layers were collected, washed with Brine and dried over Na$_2$SO$_4$. The crude was purified by flash chromatography on silica gel using the opportune eluent to give the desired triazole compounds 64a, 64b, 64c, 64d, 64e, 64f, 65a, 65c, 66d, 67d and 68.

3-(4-butyl-1H-1,2,3-triazol-1-yl)-N-(2-hydroxyphenyl)benzenesulfonamide (64a). (Purification eluent: Hexane-AcOEt 3:1). Yield 82%. $^1$H NMR (400 MHz, Acetone): δ 8.48 (s, 1H), 8.34-8.31 (m, 2H), 8.11-8.09 (d, J=8 Hz, 1H), 7.81-7.79 (d, J=8 Hz, 1H), 7.71-7.67 (t, J=8 Hz, 1H), 7.37-7.35 (d, J=8 Hz, 1H), 6.99-6.95, (t, J=8 Hz, 1H), 6.81-6.77 (m, 2H). $^{13}$C NMR (100 MHz, Acetone): δ 149.88, 142.46, 137.68, 130.44, 137.68, 130.44, 126.66, 126.50, 124.40, 124.19, 123.58, 119.90, 119.47, 118.32, 115.59, 31.30, 24.94, 21.95, 13.19. MS (ESI): m/z 370.7 [M–H]$^-$.

4-(4-butyl-1H-1,2,3-triazol-1-yl)-N-(2-hydroxyphenyl)benzenesulfonamide (65a). (Purification eluent: Hexane-AcOEt 4:1). Yield 80 $^1$H NMR (400 MHz, MeOD-d$_4$): δ 8.34 (s, H), 7.93-7.87 (m, 4H), 7.33-7.31 (d, J=6.8 Hz, 1H), 6.96-6.92 (m, 1H), 6.765-7.727 (t, J=7.6 Hz, 1H), 6.67-6.65 (d, J=8 Hz, 1H), 2.78-2.74 (t, J=7.6 Hz, 2H) 1.74-1.66 (quint, 2H), 1.45-1.36 (sx, 2H), 1.27-1.22 (t, J=7.2 Hz, 3H) ppm. $^{13}$C NMR (100 MHz, MeOD-d$_4$): δ 150.64, 149.22, 140.03, 129.07, 126.59, 125.18, 124.12, 119.86, 115.45, 31.12, 24.93, 22.10, 12.91 ppm. MS: m/z 372.8 [M+H]+, 394.8 [M+Na]$^+$ 3-(4-butyl-1H-1,2,3-triazol-1-yl)-N-(4-methoxyphenyl)benzenesulfonamide (64b). (Purification Eluent: Hexane-AcOEt 3:1). Yield 79%. $^1$H NMR (400 MHz, CDCl$_3$-d): δ 8.10 (s, 1H), 7.95-7.93 (d, J=7.6 Hz, 1H), 7.71 (s, 1H), 7.68-7.66 (d, J=7.7 Hz, 1H), 7.61 (s, 1H), 7.56-7.52 (t, J=7.9 Hz, 1H), 7.07-7.04 (dd, J=8.2 Hz, 2H), 6.77-6.75 (dd, J=8.2 Hz, 2H), 3.73 (s, 3H), 2.78-2.75 (t, J=7.7 Hz, 2H), 1.71-1.64 (quin. J=7.4 Hz, 2H), 1.43-1.36 (sx, J=7.6 Hz, 2H), 0.95-0.91 (t J=7.6 Hz, 3H)ppm. $^{13}$C NMR (100 MHz, MeOD-d$_4$): δ 158.45, 149.70, 141.20, 137.55, 130.75, 127.59, 125.89, 124.43, 119.27, 118.84, 114.46, 55.90, 31.84, 25.52, 21.87, 13.85 ppm. MS: m/z 372.8 [M+H]+, 394.8 [M+Na]$^+$ 3-(4-butyl-1H-1,2,3-triazol-1-yl)-N-(o-tolyl)benzenesulfonamide (64c). (Purification eluent: Hexane-AcOEt 3:1). Yield 90%. $^1$H NMR (400 MHz, Acetone): δ 8.56 (s, 1H), 8.35. 8.33 (d, J=8 Hz, 1H), 8.25-8.23 (d, J=8.0 Hz, 1H), 8.14-8.11 (t, J=7.2 Hz, 1H), 7.74-7.72 (m, 2H), 7.17-7.10 (m 4H), 2.77-2.73 (t, J=7.4 Hz, 2H), 1.73-1.65 (q, J=8.0 Hz, 2H), 1.43-1.37 (quint, J=8.0 Hz, 2H), 0.95-0.91 (t, J=8 Hz, 1H) ppm. $^{13}$C NMR (100 MHz, Acetone): 149.06, 142.56, 137.76, 134.78, 134.16, 130.91, 130.72, 126.78, 126.51, 126.37, 126.28, 123.51, 119.46, 118.11 31.22, 24.95, 21.95, 17.18, 13.18 ppm. MS (ESI): m/z 371.7 [M+H]$^+$.

3-(4-butyl-1H-1,2,3-triazol-1-yl)-N-(2-(trifluoromethyl) phenyl)benzenesulfonamide (64d) (Purification eluent: Hexane-AcOEt 3:1). Yield 90%. $^1$H NMR (Acetone): δ 8.78 (s, 1H), 8.41-8.37 (m, 3H), 8.18-8.16 (d, J=8.2 Hz, 1H), 7.89-7.87 (d, J=7.6 Hz, 1H), 7.82-7.78 (t, J=7.8 Hz, 1H), 7.69-7.61 (m 2H), 7.54-7.52 (d, J=8 Hz, 1H), 7.45-7.44 (t, J=7.4 Hz, 1H), 2.77-2.73 (t, J=7.4 Hz, 2H), 1.71-1.67 (q, J=8.0 Hz, 2H), 1.45-1.35 (quint, J=8.0 Hz, 2H), 0.94-0.89 (t, J=8.0 Hz, 1H) ppm. $^{13}$C NMR (Acetone): 149.1, 142.66, 137.89, 134.15, 133.28, 130.93, 127.40, 126.90, 126.28, 124.80, 123.85, 122.29, 119.54, 118.03, 31.22, 24.95, 21.95, 13.18 ppm. MS (ESI): m/z 425 [M+H]$^+$.

4-(4-butyl-1H-1,2,3-triazol-1-yl)-N-(2-(trifluoromethyl) phenyl)benzenesulfonamide (65c). (Purification eluent: Hexane-AcOEt 3:1). Yield 93%. $^1$H NMR (400 MHz, CDCl$_3$-d): δ 8.79-7.81 (m, 4H) 7.75 (s, 1H), 7.57-7.53 (t, J=8 Hz, 1H), 7.51-7.49 (d, J=8 Hz, 1H), 8.41-8.37 (m, 3H), 8.18-8.16 (d, J=8.2 Hz, 1H), 7.89-7.87 (d, J=7.6 Hz, 1H), 7.82-7.78 (t, J=7.8 Hz, 1H), 7.69-7.61 (m 2H), 7.54-7.52 (d, J=8 Hz, 1H), 6.94 (s, 1H), 2.79-2.75 (t, J=7.4 Hz, 2H), 1.73-1.65 (quint, J=8.0 Hz, 2H), 1.43-1.36 (sx, J=8.0 Hz, 2H), 0.95-0.91 (t, J=8.0 Hz, 1H) ppm. $^{13}$C NMR (100 MHz, CDCl$_3$-d): 149.9, 140.8, 137.99, 133.88, 133.56, 129.53, 126.71, 125.70, 124.94, 124.09, 122.27, 120.88, 118.45, 31.32, 25.24, 22.24, 13.76 ppm. MS (ESI): m/z 425 [M+H]$^+$.

3-(4-butyl-1H-1,2,3-triazol-1-yl)-N-(isoquinolin-6-yl) benzenesulfonamide (64e). (Purification eluent: Hexane-AcOEt 3:1). Yield 77%. $^1$H NMR (400 MHz, CDCl$_3$-d): δ 9.23 (s, 1H), 8.42 (s, 1H), 8.26 (s, 1H), 7.89-7.83 (m, 3H), 7.66-7.62 (m, 3H), 7.55-7.46 (m, 2H), 2.74-2.71 (t, J=7.8 Hz, 2H), 1.66-1.59 (quint, J=8.0 Hz, 2H), 1.39-1.25 (sx, J=8.0 Hz, 2H), 0.90-0.86 (t, J=8.0 Hz, 1H) ppm. $^{13}$C NMR (100 MHz, CDCl$_3$-d): 152.43, 149.84, 142.93, 141.34, 137.68, 132.70, 131.10, 130.51, 129.38, 128.51, 127.38, 126.85, 124.13, 118.81, 115.75, 31.36, 25.25, 22.26, 13.62 ppm. MS (ESI): m/z 408.8 [M+H]$^+$.

3-(4-(ethoxymethyl)-1H-1,2,3-triazol-1-yl)-N-(2-(trifluoromethyl)phenyl) benzenesulfonamide (66d): (Purification eluent: PE/EtOAc 7:2) Yield 85% white solid $^1$H NMR (400 MHz, CDCl$_3$-d): δ 8.09 (1H, s), 7.99-7.97 (d, J=6.8 Hz, 1H), 7.79-7.75 (t, 8.8 Hz, 1H), 7.60-7.47 (m, 3H), 7.26-7.22 (t, J=7.2 Hz, 1H), 4.66 (s, 2H), 3.63-3.58 (q, 2H), 1.24-1.20 (t, J=6.8 Hz, 3H) ppm. $^{13}$C NMR (100 MHz, CDCl$_3$-d): 146.95, 140.78, 137.44, 133.39, 130.80, 126.99, 126.07, 125.84, 124.87, 124.69, 122.09, 120.58, 118.71, 66.39, 63.99, 15.07 ppm. MS (ESI): m/z 427 [M+H]$^+$.

3-(4-isopentyl-1H-1,2,3-triazol-1-yl)-N-(2 (trifluoromethyl)phenyl) benzene sulfonamide (67d): (Purification eluent: PE/EtOAc 7:2), Yield 78%, yellow solid. $^1$H NMR (CDCl$_3$): δ 8.06 (s, 1H), 8.01-8.00 (d, J=7.6 Hz, 1H), 7.84-7.82 (d, J=8.0 Hz, 1H), 7.76-7.74 (d, J=7.6 Hz, 1H), 7.69 (1H, s), 7.60-7.56 (t, J=8.4 Hz, 1H), 7.53-7.49 (t, J=7.6 Hz, 2H), 7.27-7.25 (d, J=8.0 Hz, 1H), 2.80-2.78 (m, 2H), 1.62 (m, 3H), 0.99-0.94 (m, 6H)ppm. $^{13}$C NMR (CDCl$_3$): δ 149.95, 145.96, 143.95, 137.71, 133.39, 160.71, 126.68, 125.29, 124.91, 124.15, 118.51, 38.27, 27.62, 23.51, 22.36 ppm. MS: m/z 438.8 [M+H]$^+$ 3-(4-(ethoxymethyl)-1H-1,2,3-triazol-1-yl)-N-(isoquinolin-6-yl)benzenesulfonamide (68e): (Purification eluent: Hexane-AcOEt 3:1). Yield 74%. $^1$H NMR (400 MHz, CDCl$_3$-d): δ 8.22 (s, 1H), 7.93 (s, 1H), 7.90-7.17 (m, 3H), 7.70-7.67 (d, J=8.0 Hz, 1H), 7.63. 7.61 (d, J=8.0 Hz, 1H), 7.56-7.48 (m, 2H), 4.66 (s, 2H), 3.62-3.57 (q, J=7.4 Hz, 2H), 1.22-1.18 (t, J=7.8 Hz, 3H) ppm. $^{13}$C NMR (100 MHz, CDCl$_3$-d): 152.57, 146.93, 143.22, 141.49, 137.46, 132.52, 130.90, 128.22, 127.44, 124.33, 120.66, 119.97, 66.51, 63.97, 15.11 ppm. MS (ESI): m/z 425 [M+H]$^+$.

Example 11

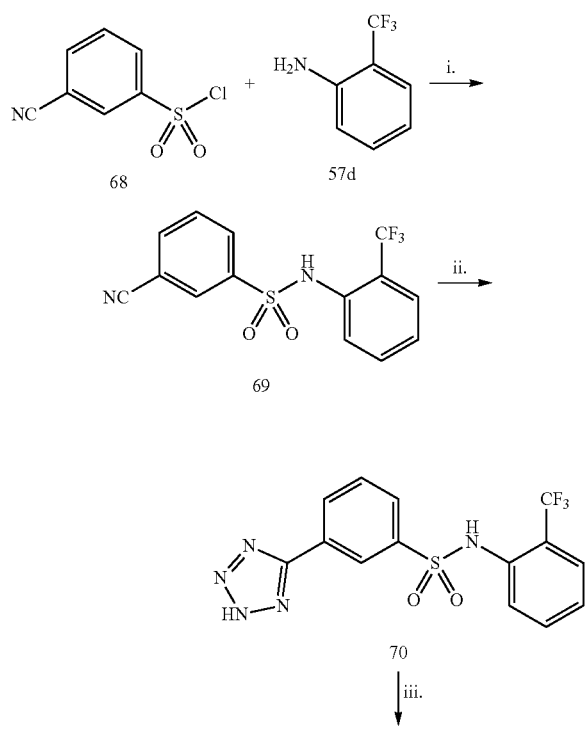

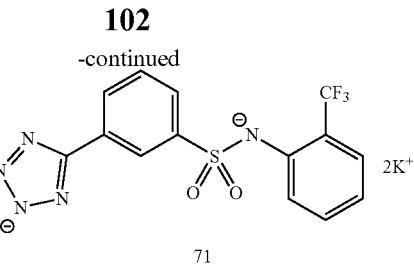

Reagents and conditions: i. Pyr, 5 h r.t.; ii. NaN$_3$, NH$_4$Cl, DMF, 12 h, reflux; iii. K$_2$CO$_3$, H$_2$O, 15 min. reflux.

3-cyano-N-(2-(trifluoromethyl)phenyl)benzenesulfonamide (69) To a stirred solution of 68 (1 eq.) in 5 mL of anhydrous pyridine, was added sulphonyl chloride 57 d (1.1 eq) at 0° C. The corresponding solution was stirred at r.t. under nitrogen atmosphere, for 5 h. After completion of the reaction the mixture was acidified with 1N HCl, the aqueous phase was extracted with several times and the combined organic phases were dried (Na$_2$SO$_4$) and concentrated. (PE-AcOEt 7:3). Yield 75%, white solid. $^1$H NMR (400 MHz, CDCl$_3$-d): δ 7.99-7.94 (m, 2H), 7.82-7.80 (m, 2H), 7.60-7.51 (m, 3H), 7.30-7.26 (t, J=8 Hz, 1H), 6.97 (s, 1H) ppm. MS (ESI): m/z 425 [M+H]$^+$.

3-(2H-tetrazol-5-yl)-N-(2-(trifluoromethyl)phenyl)benzenesulfonamide (70) A mixture of 69 (500 mg, 1.53 mmol), NaN$_3$ (299 mg, 4.60 mmol), NH$_4$Cl (328 mg, 6.12 mmol) in DMF (5 mL), was heated at 130° C. for 6 h. After that time the rxn was allowed to r.t. water was added with continuous stirring. The mixture was then acidified to pH 2. The mixture was extracted with DCM (3×25 mL) and washed with aq 5% solution of LiCl, then dried over anhydrous Na$_2$SO$_4$. The solvent was removed at reduced pressure and the residue purified by flash chromatography on silica gel (DCM-MeOH 94:6). Yield 95%, white solid. mp 138.40° C.

$^1$HNMR (400 MHz, CDCl$_3$-d): δ 8.47 (s, 1H), 8.20-8.18 (d, J=7.6 Hz, 1H), 7.88 (s, 1H), 7.75-7.73 (d, J=8.0 Hz, 1H), 7.48-7.40 (m, 2H), 7.31-7.28 (m, 2H), 7.07-7.03 (t, J=7.6 Hz, 1H) ppm. $^{13}$CNMR (100 MHz, CDCl$_3$-d): δ 163.42, 140.86, 133.70, 133.01, 131.54, 130.13, 130.00, 129.15, 127.37, 126.62, 126.10, 125.85, 124.65, 123.08, 119.22 ppm MS 3-(2H-tetrazol-5-yl)-N-(2-(trifluoromethyl)phenyl)benzenesulfonamide benzenesulfonamide potassium salt (71). 70 (50 mg, 0.13 mmol) and K$_2$CO$_3$ (37.42 mg, 0.26 mmol) were dissolved in 1.5 mL of water. After the evolution of CO$_2$ ceased, the solution was refluxed for 15 minutes and afterwards evaporated to dryness. The resulting solid was recrystallized from ACN. Mp 224-226 Yield 82% white solid $^1$HNMR (400 MHz, CDCl$_3$-d): δ 8.02 (s, 1H), 7.81-7.79 (d, J=7.6 Hz, 1H), 7.56-7.54 (d, J=8.0 Hz, 1H), 7.44-7.40 (t, J=7.6 Hz, 1H), 6.44-6.40 (t, J=7.9 Hz, 1H) ppm.

Example 12

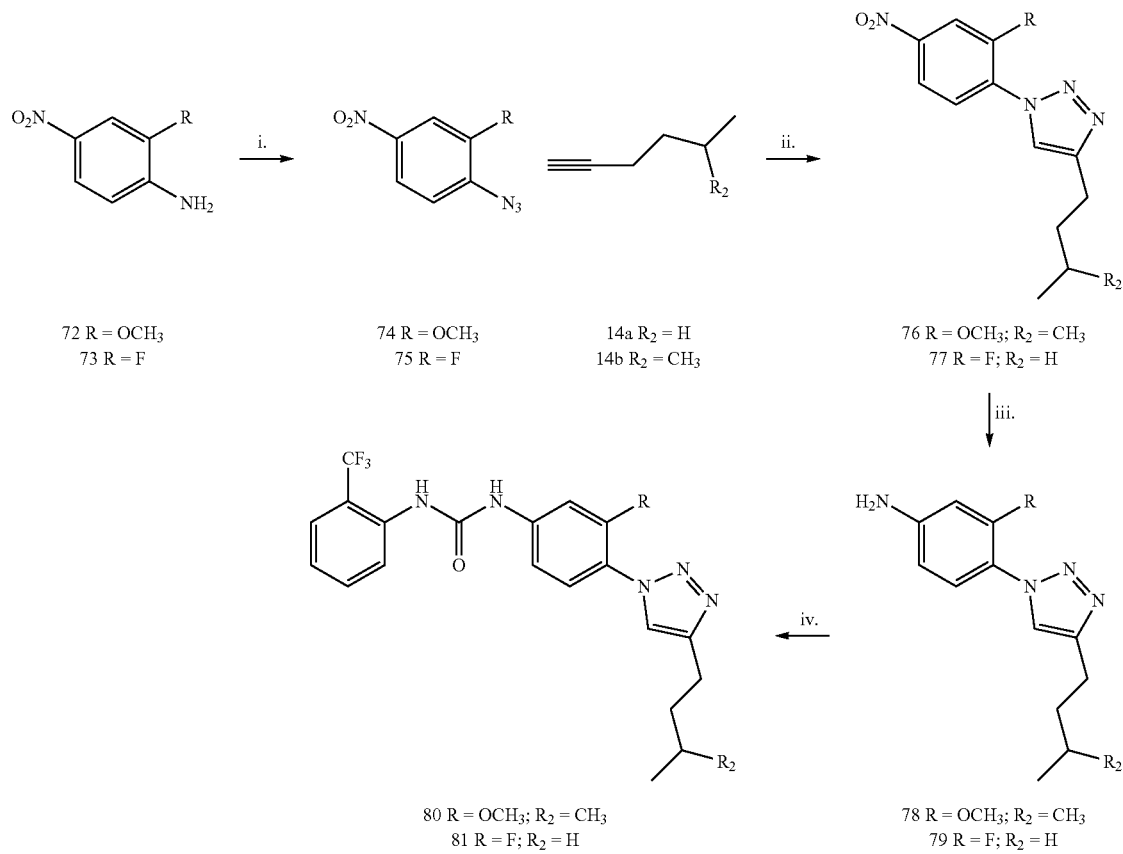

Reagents and conditions: i. a) t-BuONO, CH₃CN, 20 min. 0° C.; b) TMSN₃, CH₃CN, 2 h r.t.; ii. CuSO₄.5 H₂O, sodium ascorbate, H₂O tBuOH (1:1), MW 120° C., 10 min, iii. H₂, Pd/C, MeOH, 1 h, iv. 2-(Trifluoromethyl)phenyl isocyanate, CH₂Cl₂, 5 h r.t.

General Procedure for the Preparation of Compounds 74 and 75.

Opportune 4-nitroaniline (7.24 mmol) was dissolved in CH₃CN and cooled to 0° C. in an ice-salt bath. To this stirred solution, was added tBuONO (8.69 mmol), and the mixture was stirred for 10 min, after this time, TMSN₃ (10.86 mmol) was added dropwise, during 10 minutes, and the resulting brown solution was stirred at r.t. One hour later the solvent was removed at reduced pressure and the residue was purified by flash chromatography on silica gel 1-azido-2-methoxy-4-nitrobenzene (74): (Purification eluent: PE/AcOEt 7:3). Yield 88%, white solid. $^1$HNMR (400 MHz, CDCl₃-d): δ 7.74-7.72 (d, J=8.0 Hz, 2H), 7.65 (s, 1H), 6.96-6.94 (d, J=8.0 Hz, 2H), 3.91 (s, 3H)ppm. $^{13}$CNMR (100 MHz, CDCl₃-d): δ 152.03, 144.93, 153.31, 120.03, 117.03, 106.97, 56.42 ppm. MS (ESI) m/z 195.1 [M+H]⁺, 218.1 [M+Cl]⁻.

1-azido-2-fluoro-4-nitrobenzene (75): (Purification eluent: PE/EA 9:1). Yield 60%, yellow solid. $^1$H NMR (400 MHz, CDCl₃): δ 8.02-7.92 (m, 2H), 7.19-7.15 (t, J=16 Hz, 1H) ppm.

General Procedure for the Preparation of Compounds 76 and 77.

The appropriate alkyne 14a or 14b (0.10 mmol) and the opportune azide (0.09 mmol) were suspended in a 1:1 mixture of water and t-BuOH (1.5 mL each) in a 10 mL glass vial equipped with a small magnetic stirring bar. To this, was added sodium ascorbate (0.1 equiv) and copper(II) sulfate pentahydrate (0.10 mmol). The mixture was then heated for 10 min. at 125° C. under microwave irradiation, using an irradiation power of 300 W. After this time the precipitate was filtered-off and purified on silica, to give final products 76 or 77.

4-isopentyl-1-(2-methoxy-4-nitrophenyl)-1H-1,2,3-triazole (76): (Purification eluent: PE/EA 8:3). Yield 94%, white solid. $^1$H NMR (400 MHz, CDCl₃): δ 8.24 (s, 1H), 8.00-7.98 (d, J=8.0 Hz, 1H), 7.84-7.80 (m, 2H), 2.76-2.72 (t, J=7.2 Hz, 2H), 1.60-1.54 (m, 3H), 0.88-0.87 (d, J=6.0 Hz)ppm. MS (ESI) m/z 291.32 [M+H]⁺

4-butyl-1-(2-fluoro-4-nitrophenyl)-1H-1,2,3-triazole (77). (Purification eluent: PE/EA 7:3). Yield 63%, yellow solid. $^1$H NMR (400 MHz, CDCl₃-d): δ 8.24-8.20 (t, J=8.0 Hz, 1H), 8.12-8.10 (m, 2H), 7.91-7.90 (d, J=4.0 Hz, 1H), 2.72-2.69 (t, J=12.0 Hz, 2H), 1.65-1.58 (m, 2H), 1.36-1.27 (m, 2H), 0.86-0.82 (m, 3H) ppm.

General Procedure for the Preparation of Compounds 78 and 79

The opportune triazole compound 76, or 78 (1.60 mmol) was solubilized in 30 mL of MeOH, and 10% Palladium on charcoal (25 mg) was added. The reaction mixture was stirred under Hydrogen atmosphere for 1 h, then the mixture was filtered off on a celite pad, the solvent evaporated at reduced pressure to obtain 78 or 79 as pure compounds.

4-(4-isopentyl-1H-1,2,3-triazol-1-yl)-3-methoxyaniline (78): The product was obtained as a pure compound. Yield 99%, yellow solid. Yield $^1$H NMR (400 MHz, CDCl$_3$-d): δ 7.58 (s, 1H), 7.27-7.25 (dd, J=8.0 Hz, 2H), 6.28 (s, 1H), 6.22-6.20 (dd, J=8.0 Hz, 2H), 4.14 (s, 2H), 3.64 (s, 3H), 2.73-2.69 (t, J=7.6 Hz, 2H), 1.57-1.54 (m, 3H), 0.89-0.88 (d, J=5.6 Hz, 6H)ppm.

4-(4-butyl-1H-1,2,3-triazol-1-yl)-3-fluoroaniline (79). The product was obtained as a pure compound. Yield 99%, white solid. $^1$H NMR (400 MHz, CDCl$_3$-d): δ 7.57 (s, 1H), 7.41-7.39 (d, J=8.0 Hz 1H), 6.44-6.42 (d, J=8.0 Hz, 2H), 4.25 (s, 2H), 1.65-1.62 (d, J=6.0 Hz, 2H), 1.65-1.62 (m, 2H), 1.35-1.32 (m, 2H), 0.89-0.85 (m, 3H) ppm. MS (ESI) m/z 235 [M+H]$^+$.

General Procedure for the Preparation of Compounds 80 and 81.

The opportune aniline 78 or 79 (0.10 mmol) was added to a solution of 2-(Trifluoromethyl)phenyl isocyanate (0.15 mmol) in anhydrous DCM (15 mL) in one portion. The solution was stirred for 9 hours at r.t. under a nitrogen atmosphere. The solvent was removed at reduced pressure and the residue purified on silica to afford the final product 80 or 81.

1-(4-(4-isopentyl-1H-1,2,3-triazol-1-yl)-3-methoxyphenyl)-3-(2-(trifluoromethyl) phenyl)urea (80): (Purification eluent: DCM/MeOH 98:2). Yield 78%, white solid. $^1$H NMR (400 MHz, CDCl$_3$-d): δ 8.12-8.06 (m, 2H), 7.92 (s, 1H), 7.61-7.54 (m, 3H), 7.26-7.21 (m, 2H), 7.18 (s, 1H), 3.97 (s, 3H), 2.83-2.80 (t, J=7.8 Hz, 2H), 1.71-1.63 (m, 3H), 0.98-0.97 (d, J=7.8 Hz, 6H)ppm. $^{13}$C NMR (100 MHz, CDCl$_3$): δ 153.05, 152.05, 148.40, 136.61, 134.63, 132.90, 127.92, 126.70, 126.17, 124.85, 124.78, 122.62, 122.53, 121.46, 121.08, 114.12, 56.43, 38.52, 27.77, 23.66, 22.52 ppm. MS (ESI) m/z 448.3 [M+H]$^+$ 1-(4-(4-butyl-1H-1,2,3-triazol-1-yl)-3-fluorophenyl)-3-(2-(trifluoromethyl) phenyl)urea (81). (Purification eluent: DCM/MeOH 98:2). Yield 70%, yellow solid. $^1$H NMR (400 MHz, CDCl$_3$-d): δ 7.99-7.97 (d, J=12.0 Hz, 1H), 7.91-7.89 (d, J=8.0, 1H), 7.86-7.79 (m, 2H), 7.75 (s, 1H), 7.72-7.68 (t, J=8.0, 1H), 7.60-7.53 (m, 2H), 7.27-7.20 (m, 2H), 2.79-2.75 (t, J=8.0 Hz, 2H), 1.71-1.67 (t, 16.0 Hz, 2H), 1.42-1.37 (m, 2H), 0.94-0.90 (t, 16.0 Hz, 3H) ppm. MS (ESI) m/z 420 [M−H]$^−$.

Example 13

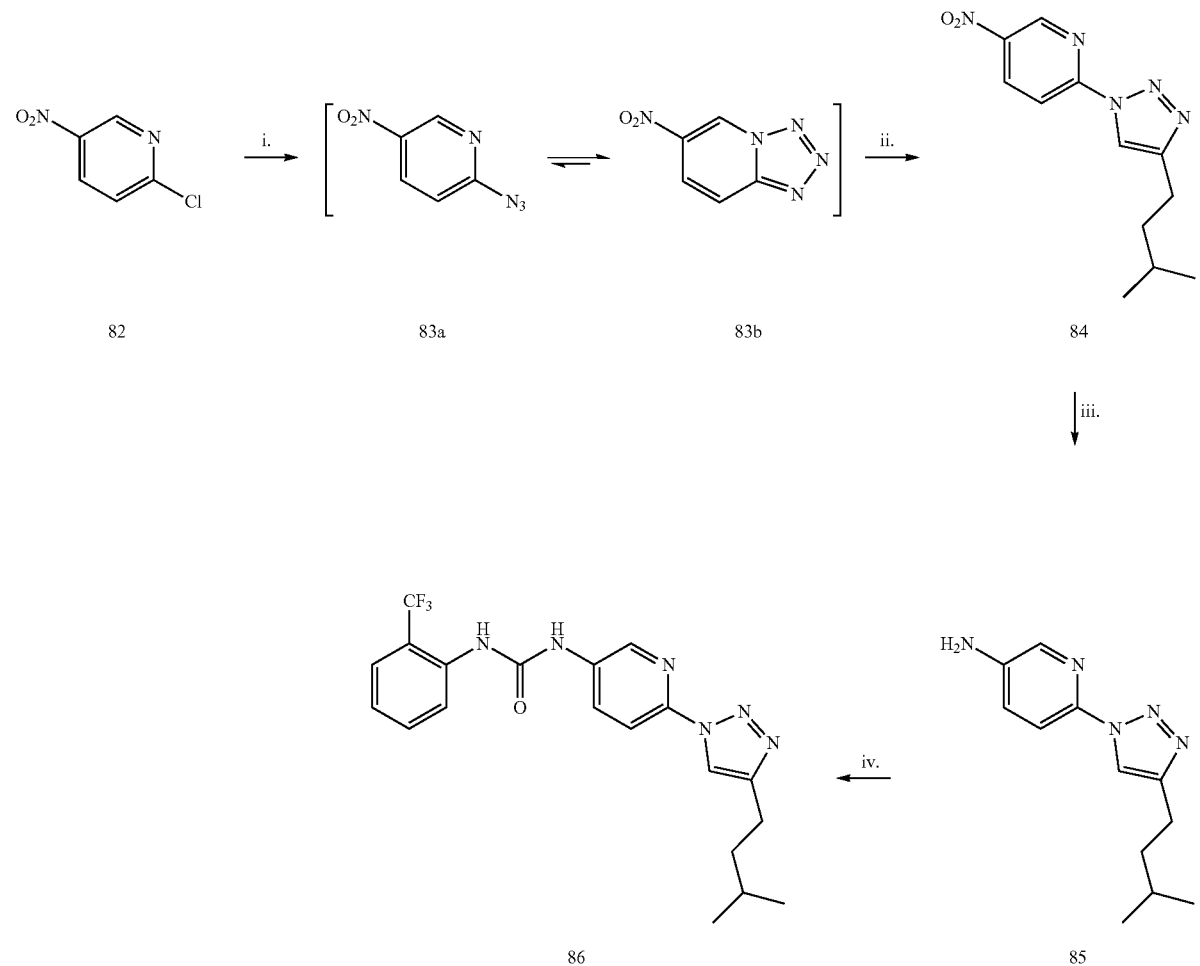

Reagents and conditions: i. NaN₃, HCl, EtOH: H₂O, reflux, 12 h; ii. CuSO₄.5H₂O, sodium ascorbate, H₂O-THF (1:1), rt, 5 h, iii. H₂, Pd/C, MeOH, 1 h, iv. 2-(Trifluoromethyl) phenyl isocyanate CH₂Cl₂, 5 h r.t.

2-(4-isopentyl-1H-1,2,3-triazol-1-yl)-5-nitropyridine (84). A solution of 2-chloro-5-nitropyridine 82 (100 mg, 0.63 mmol) in a mixture of ethanol (8 mL) and water (3 mL) was carefully treated with NaN₃ (81 mg, 1.26 mmol). Concentrated HCl (0.8 mL) was added dropwise at rt. The reaction was stirred at reflux on, then cooled to rt. After that time saturated NaHCO₃ was added and the pH adJusted to 7. DCM (15 mL) was added and the rxn was washed with water. The organic layers were dried over Na₂SO₄ and concentrated to afford a yellow residue. The residue and the appropriate alkyne (90 µL, 0.75 mmol) were suspended in a 1:1 mixture of water and THF (1.5 mL each). To this, was added sodium ascorbate (1.0 equiv) and copper(II) sulfate pentahydrate (1.0 mmol). The mixture was stirred at r.t. for 5 h. After that time the reaction was partitioned between sat. aq. solution of NH₄Cl and AcOEt, and stirred for 15 min. The organic layer was separated, dried over Na₂SO₄ and the solvent removed in vacuo. The residue was purified by flash chromatography on silica gel (DCM/MeOH 98:2). Yield 75%, yellow solid. ¹H NMR (400 MHz, CDCl₃): δ 9.28 (s, 1H), 8.67-8.64 (m, 1H), 8.36-8.32 (m, 2H), 2.80-2.76 (t, J=7.8 Hz, 2H), 1.67-1.58 (m, 3H), 0.84-0.82 (d, J=8.0 Hz, 6H) ppm. ¹³C NMR (100 MHz, CDCl₃-d): δ 152.24, 150.03, 144.99, 143.23, 134.59, 118.55, 114.44, 113.60, 38.08, 27.56, 23.48, 22.32 ppm. MS (ESI) m/z 260.3 [M−H]⁻

6-(4-isopentyl-1H-1,2,3-triazol-1-yl)pyridin-3-amine (85): 84 (1.60 mmol) was solubilized in 30 mL of anhydrous MeOH, and 10% Palladium on charcoal (25 mg) was added. The reaction mixture was stirred under Hydrogen atmosphere for 1 h, then the mixture was filtered off on a celite pad, the solvent evaporated at reduced pressure. The product was obtained as a pure compound. Yield 99%, yellow solid. Yield ¹H NMR (400 MHz, CDCl₃-d): δ 8.14 (s, 1H), 7.92-7.90 (m, 2H), 7.17-7.14 (m, 1H), 3.89 (s, 2H), 2.80-2.76 (t, J=7.8 Hz, 2H), 1.74-1.58 (m, 3H), 0.95-0.93 (d, J=8.0 Hz, 6H)ppm. MS (ESI) m/z 232.3 [M+H]⁺.

1-(6-(4-isopentyl-1H-1,2,3-triazol-1-yl)pyridin-3-yl)-3-(2-(trifluoromethyl) phenyl)urea (86). Aniline 85 (0.10 mmol) was added to a solution of 2-(Trifluoromethyl)phenyl isocyanate (0.15 mmol) in anhydrous CH₂Cl₂ (15 mL) in one portion. The solution was stirred for 9 hours at r.t. under a nitrogen atmosphere. The solvent was removed at reduced pressure and the residue purified on silica to furnish the final product as white solid. (Purification eluent: DCM-MeOH 98:2). Yield 61%, white solid. ¹H NMR (400 MHz, Acetone-d₆): δ 9.14 (s, 1H), 8.66 (s, 1H), 8.37 (s, 1H), 8.28-8.24 (d, J=8.0 Hz, 1H), 8.14-8.12 (d, J=8.0 Hz, 1H), 8.06-8.04 (d, J=8.0 Hz, 1H), 7.81 (s, 1H), 7.70-7.64 (m, 2H), 7.33-7.30 (t, J=8.0 Hz, 1H), 2.80-2.75 (t, J=7.7 Hz, 2H), 1.64-1.61 (m, 3H), 0.96-0.94 (d, J=8.0 Hz, 6H) ppm. ¹³C NMR (100 MHz, Acetone-d₆): δ 152.31, 148.41, 144.17, 138.61, 138.26, 136.46, 132.84, 128.80, 125.95, 125.65, 123.96, 117.98, 117.71, 113.35, 38.34, 27.33, 23.23, 21.91, 21.64 ppm. MS (ESI) m/z 419.3 [M+H]⁺.

Example 14

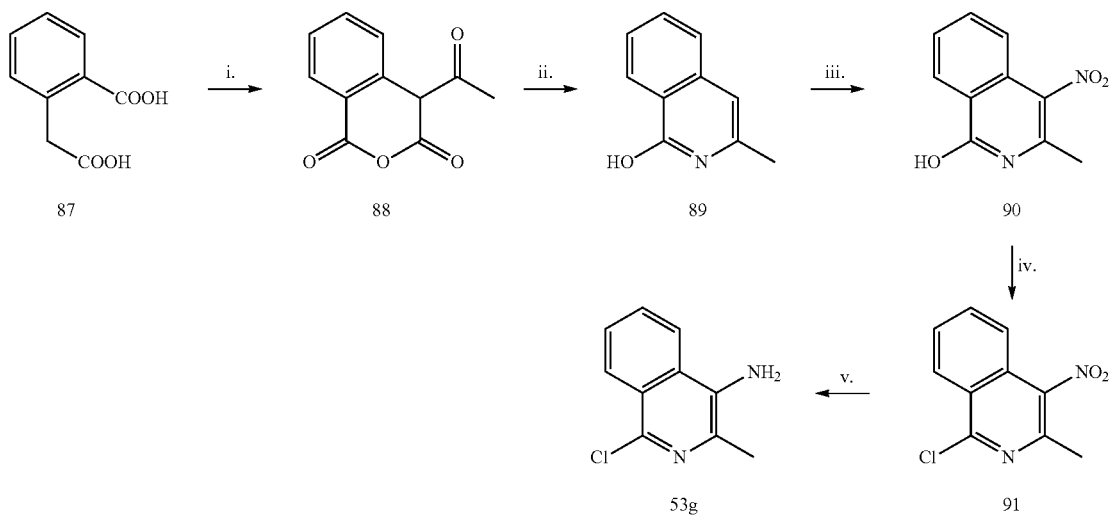

Reagents and conditions: i. Ac₂O, pyr, 0° C. to rt; ii. NH₄OH, 95° C., 5 h; iii. HNO₃, CH₃COOH, 0° C. to rt, 3 h; iv. POCl₃, 110° C., 1 h; v. H₂, Pd/C, MeOH, 1h; vi. SnCl₂.2H₂O, HCl rt, 18 h.

4-acetylisochroman-1,3-dione (88): Pyridine (2 mL) was slowly added to a slurry of homophtalic acid (1000 mg, 5.55 mmol) in acetic anhydride at 0° C. with stirring. The resulting solution was stirred at room temperature for 5 h. After that time Et₂O was added and the resulting white solid was collected by filtration and rinsed twice with ether. Yield 75% white solid. ¹H NMR (400 MHz, CDCl₃ d): δ 8.25-8.23 (d, J=8.0 Hz, 1H), 7.70-7.68 (d, J=8.0 Hz, 1H), 7.60-7.58 (d, J=8.0 Hz, 1H), 7.39-7.37 (d, J=8.0 Hz, 1H), 2.64 (s, 3H), 2.62 (s, 1H), 3-methylisoquinolin-1-ol (89): To 4-acetyl isochroman-1,3-dione (1000 mg, 4.90 mmol) was added slowly sat aq. NH₄OH (9 mL). The resulting bright yellow suspension was heated in a sealed tube at 95° C. for 5 h. Then the reaction mixture was cooled to r.t and diluted with water. The resulting white solid was collected by filtration at reduced pressure and dried. Yield 99%. White solid. ¹H NMR (400 MHz, CDCl₃ d): δ 11.61 (br s, 1H), 8.39-8.37 (d, J=8.0 Hz, 1H), 7.62-7.58 (t, J=8.0 Hz, 1H), 7.46-7.39 (m, 2H), 6.30 (s, 1H), 2.40 (s, 3H)ppm.

3-methyl-4-nitroisoquinolin-1-ol (90): To a solution of 89 (800 mg, 5.02 mmol), in acetic acid (7 mL), was slowly added 90% nitric acid (fuming) (2 mL), at 0° C. with stirring. The reaction mixture is allowed to warm to rt and stirred for 3 h. Water was added and the resulting solid was collected by filtration and dried. Yield 90% yellow solid $^1$H NMR (400 MHz, CDCl$_3$ d): δ 12.03 (br s, 1H), 8.21-8.19 (d, J=8.0 Hz, 1H), 7.82-7.78 (t, J=8.0 Hz, 1H), 7.73-7.17 (d, 1H), 7.58-7.54 (t, J=8.0 Hz, 1H), 2.42 (s, 3H)ppm.

1-chloro-3-methyl-4-nitroisoquinoline (91): A mixture of 90 (100 mg, 0.49 mmol), and POCl$_3$ (5 mL) was heated with stirring at 110° C. for 1 h. POCl$_3$ was removed by distillation, and the resulting residue was neutralized with aq NaHCO$_3$ and extracted with AcOEt (3×25 mL). The organic layers were collected and washed with brine, dried over anhydrous Na$_2$SO$_4$ filtered and evaporated under reduced pressure to obtain pure compound. Yield 99% $^1$H NMR (400 MHz, CDCl$_3$ d): δ 8.31-8.29 (d, J=8.0 Hz, 1H), 7.84-7.80 (t, J=8.0 Hz, 1H), 7.71-7.68 (m, 1H), 2.65 (s, 3H)ppm.

1-chloro-3-methylisoquinolin-4-amine (53 g). To a solution of 91 (800 mg, 3.59 mmol) in concentrated HCl (15 mL), was added SnCl$_2$ 2H$_2$O. The reaction mixture was stirred for 18 h at rt. After that time was poured into ice-water and the pH adjusted to 8 by addition of 1N NaOH. The rxn mixture was extracted with AcOEt (3×25 mL) and the combined organic layers were dried over Na$_2$SO$_4$ to obtain a residue that was crystallized from Ethanol to obtain pure compound. Yield 84% $^1$H NMR (400 MHz, CDCl$_3$ d): δ 8.23-8.20 (d, J=8.0 Hz, 1H), 7.75-7.73 (d, J=8.0 Hz, 1H), 7.73-7.64 (t, 1H), 7.59-7.55 (t, J=8.0 Hz, 1H), 3.95 (s, 2H), 2.53 (s, 3H)ppm. MS (ESI) m/z 193.0 [M+H]$^+$.

Example 15

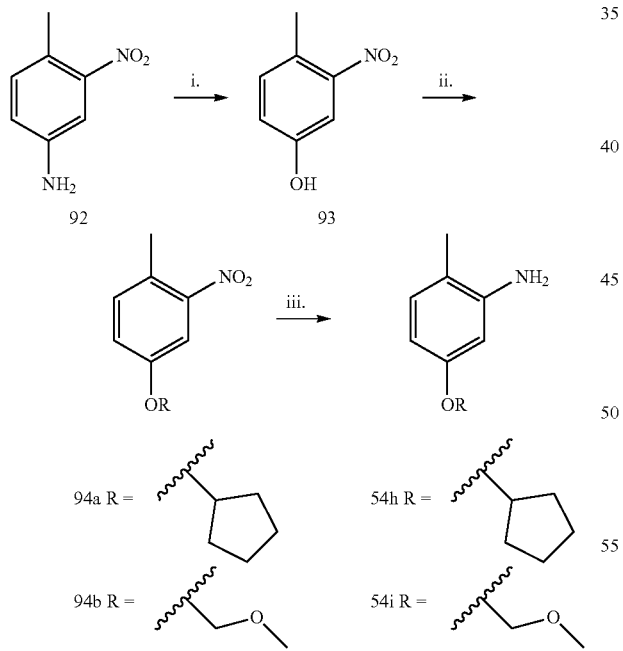

Reagents and conditions: i. a) H$_2$SO$_4$—H$_2$O (3:1), 100° C., 30 min.; b) NaNO$_2$ 0° C. to rt; ii. a) NaH, DMF 0° C. to rt b) cyclopentyl iodide (for 94a) or MOM-Cl (for 94b) 65° C., 1 h; iii. H$_2$, Pd/C, MeOH, 1 h.

4-methyl-3-nitrophenol (93): 92 (200 mg, 1.31 mmol) was dissolved in a 3:1 mixture of H$_2$SO$_4$—H$_2$O. The resulting mixture was heated to 100° C. for 30 minutes. After that time, rxn was cooled to 0° C. and a solution of NaNO$_2$ was added dropwise. After 1 hr the mixture was heated to reflux. After completion of the reaction the mixture was extracted with EtOAc several times and the combined organic phases were dried (Na$_2$SO$_4$) and concentrated. The resulting mixture was purified by flash chromatography (Purification eluent: PE-AcOEt 9:1). Yellow solid, Yield 70%. $^1$H NMR (400 MHz, CDCl$_3$) δ 7.48 (s, 1H), 7.17 (d, J=8.4 Hz, 1H), 7.01 (dd, J=8.4, 2.4 Hz, 1H), 5.84 (s, 1H), 2.48 (s, 3H)ppm.

General Procedure for the Synthesis of 94a and 94b:

93 (500 mg, 3.26 mmol) was dissolved in anhydrous DMF (3 mL) under nitrogen atmosphere. To this, NaH (86 mg, 3.58 mmol) was added at 0° C. in one portion. After 20 minutes, a solution of the opportune halogen derivative (3.9 mmol) in DMF (1 mL) (cyclopentyl iodide for 94a or chloromethyl methyl ether for 94b) was added via cannula. The resulting solution was stirred at rt for 2 hrs. After completion of the reaction a water was added, and the mixture was extracted with EtOAc several times, washed with 5% LiCl (aq), and the combined organic phases were dried (Na$_2$SO$_4$) and concentrated.

4-(cyclopentyloxy)-1-methyl-2-nitrobenzene (94a): (Purification eluent: PE-AcOEt 95:5). Yield 70% yellow liquid, $^1$H NMR (400 MHz, CDCl$_3$) δ 7.44-7.43 (m, 1H), 7.16 (d, J=8.4 Hz, 1H), 6.98 (dd, J=8.4, 2.5 Hz, 1H), 4.81-4.68 (m, 1H), 2.48 (s, 3H), 1.98-1.69 (m, 6H), 1.67-1.52 (m, 2H)ppm. MS (ESI) m/z 222.0 [M+H]$^+$.

4-(methoxymethoxy)-1-methyl-2-nitrobenzene (94b): 94b was obtained as a pure compound. Yield 99% yellow liquid, $^1$H NMR (400 MHz, CDCl$_3$) δ 7.62 (s, 1H), 7.34-6.90 (m, 2H), 5.16 (s, 2H), 3.45 (s, 3H), 2.49 (s, 3H). ppm. MS (ESI) m/z 198.2 [M+H]$^+$.

General Procedure for the Synthesis of 54a and 54b:

The opportune nitro compound 94a or 94b (0.40 mmol) was solubilized in 30 mL of MeOH, and 10% Palladium on charcoal (5 mg) was added. The reaction mixture was stirred under Hydrogen atmosphere for 1 h, then the mixture was filtered-off on a celite pad and the solvent was evaporated at reduced pressure to furnish 54a or 54b as a pure compound.

5-(cyclopentyloxy)-2-methylaniline (Ma): yellow solid, Yield 99%. $^1$H NMR (400 MHz, CDCl$_3$) δ 6.92 (d, J=8.0 Hz, 1H), 6.31-6.24 (m, 2H), 4.93-4.49 (m, 1H), 3.57 (s, 2H), 2.10 (s, 3H), 1.86-1.78 (m, 6H), 1.61 (s, 2H) ppm. MS (ESI) m/z 192.3[M+H]$^+$.

5-(methoxymethoxy)-2-methylaniline (54b): yellow solid, Yield 99%. $^1$H NMR (400 MHz, CDCl$_3$-d) δ 6.93 (d, J=8.8 Hz, 1H), 6.40 (m, 2H), 5.11 (s, 2H), 3.59 (s, 2H), 3.47 (s, 3H), 2.09 (s, 3H). MS (ESI) m/z 168.1 [M+H]$^+$.

Example 16

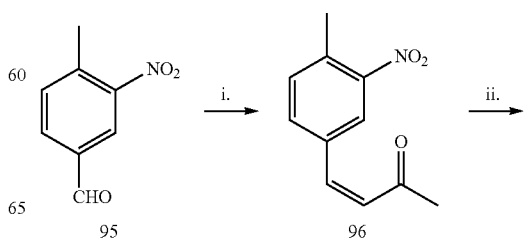

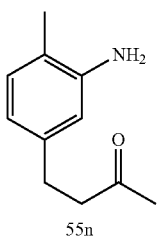

55n

Reagents and conditions: i. NaOH, H₂O 40° C., 20 min.; ii. H₂, Pd/C, MeOH, 12 h.

4-(4-methyl-3-nitrophenyl)but-3-en-2-one (96): To a mixture of 3-nitro-4-methylbenzaldehyde (300 mg, 1.8 mmol), acetone (20 mL) and water (10 mL) 5% aqueous NaOH (1 mL) was slowly added at 40° C. After 20 minutes, acetone was removed under reduced pressure. The residue was extracted with ethyl acetate. The organic layer was separated, washed with brine, dried (Na₂SO₄) and concentrated under reduced pressure. (yield 76%) yellow oil. ¹H NMR (400 MHz, CDCl₃) δ 7.93 (s, 1H), 7.51 (s, 1H), 7.33 (d, J=16.0 Hz, 1H), 6.60 (d, J=15.9 Hz, 1H), 2.42 (s, 4H), 2.24 (s, 3H)ppm.

4-(3-amino-4-methylphenyl)butan-2-one (55n): Compound 95 (0.40 mmol) was solubilized in 30 mL of MeOH, and 10% Palladium on charcoal (5 mg) was added. The reaction mixture was stirred under Hydrogen atmosphere for 12 h, then the mixture was filtered off on a celite pad and the solvent was evaporated at reduced pressure. Yield 99% ¹H NMR (400 MHz, CDCl₃) δ 7.02-6.86 (m, 1H), 6.55-6.40 (m, 1H), 3.93 (s, 2H), 3.38 (s, 1H), 2.73 (d, J=6.8 Hz, 1H), 2.65 (dd, J=21.6, 14.4 Hz, 1H), 2.10 (s, 1H), 2.08 (s, 1H). MS (ESI) m/z 178.0 [M+H]⁺.

benzaldehyde oxime (98): Hydroxylamine hydrochloride (1103 mg, 15.8 mmol) was dissolved in water (10 mL) and neutralized with a 10% NaOHaq solution. A solution of 97 (2000 mg, 13.2 mmol) in ethanol was added slowly to this mixture with stirring at rt for 1 hr. After this time ethanol was evaporated at reduced pressure. Water was added and the rxn mixture was extracted with dichloromethane (3×40 mL). The combined organic phase was washed with brine and dried with anhydrous sodium sulfate. 98 was used for further reactions without additional purification. ¹HNMR (400 MHz, CDCl₃-d): δ 8.25-8.23 (d, J=7.2 Hz, 2H), 8.23 (s, 1H), 7.75 (s, 1H), 7.73-7.72 (t, J=7.2 Hz, 2H) ppm. MS (ESI) m/z 164.9 [M−H]⁻

N-hydroxy-4-nitrobenzimidoyl chloride (99): 98 (100 mg, 0.60 mmol) was dissolved in dry DMF (2 mL) under nitrogen atmosphere. To this stirring solution, N-chlorosuccinimide was added (96.5 mg, 0.72 mmol). Initiation of the reaction was accelerated by use of UV light for 20 min. After 3 hrs the mixture was poured onto crushed ice, and extracted three times with Et₂O. The organic layers were collected, dried over anhydrous Na₂SO₄ and the solvent was evaporated. 99 was used for further reactions without additional purification.

5-butyl-3-(4-nitrophenyl)isoxazole (100): 1-hexyne (28 μL, 0.25 mmol), 99 (50 mg, 0.25 mmol), KHCO₃ (119 mg, 1.08 mmol) were suspended in a 1:1 mixture of water and t-BuOH (1.5 mL each) in a 10 mL glass vial equipped with a small magnetic stirring bar. To this, was added sodium ascorbate (2 mg, 0.02 mmol) and copper(II) sulfate pentahydrate (2 mg, 0.02 mmol). The mixture was then heated for 7 min. at 80° C. under microwave irradiation, using an irradiation power of 300 W. After this time the solvents were partially removed, the residue was stirred with NH₄Cl ss (10 mL), and NH₄OH (0.5 mL) for 15 min, then extracted with EtOAc. The residue was finally purified on silica gel, to give final products (PE/EtOAc 98:2). Yield 76% ¹HNMR (400 MHz, CDCl₃-d): δ 8.31-8.29 (d, J=8.4 Hz, 2H), 7.97-7.95

Example 17

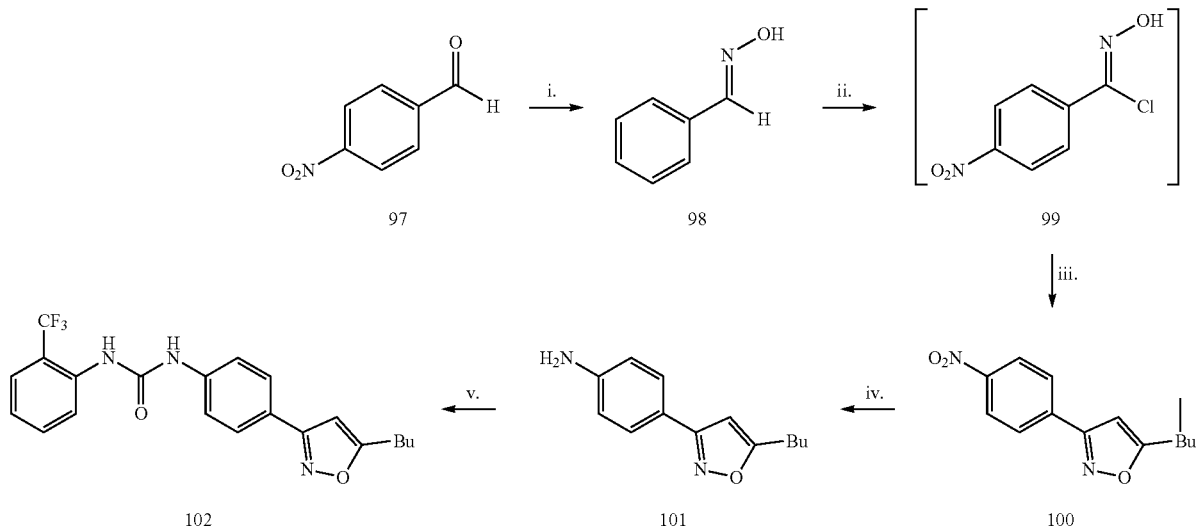

Reagents and conditions: i. NH₂OH.HCl/NaOH, EtOH/H₂O, rt., 1 h; ii. N-chlorosuccinimide, DMF dry, rt., 3 h; iii. 1-hexyne, CuSO₄.5 H₂O, sodium ascorbate, H₂O tBuOH (1:1), KHCO₃, MW 80° C., 15 min; iv. Zinc, DCM, CH₃COOH, rt., 7 min; v. 2-(trifluoromethyl)-phenyl-isocyanate, CH₂Cl₂ dry, rt., 12 h.

(d, J=8.4 Hz, 2H), 6.35 (s, 1H), 2.84-2.80 (t, J=7.2 Hz, 2H), 1.77-1.70 (m, 2H), 1.46-1.41 (q, J=7.2 Hz, 2H), 0.98-0.94 (t, J=7.2 Hz, 3H) ppm.

4-(5-butylisoxazol-3-yl)aniline (101): 99 (100 mg, 0.40 mmol) was dissolved in DCM and cooled to 0° C. Zinc dust (392 mg, 6 mmol) and AcOH (366 μL) were added and the reaction mixture was stirred at rt for 30 min. After this time the mixture was filtered off on a celite pad. The pH was adjusted to 7 by addition of NaHCO$_3$ (ss), and the mixture was extracted several times. The organic layers were collected, washed with Brine and dried over anhydrous Na$_2$SO$_4$ Yield 70%. $^1$HNMR (400 MHz, CDCl$_3$-d): δ 7.59-7.57 (m, 2H), 6.72-6.71 (d, J=7.2 Hz, 2H), 6.18 (s, 1H), 3.84 (s, 2H), 2.77-2.73 (t, J=7.6 Hz, 3H), 1.74-1.67 (m, 2H), 1.46-1.37 (m, 2H), 0.96-0.93 (t, J=7.6 Hz, 3H) ppm. MS (ESI) m/z 216.9 [M+H]$^+$ 1-(4-(5-butylisoxazol-3-yl)phenyl)-3-(2-(trifluoromethyl)phenyl)urea (102): 100 (100 mg, 0.46 mmol) was added to a solution of the 1-(Trifluoromethyl)phenyl isocyanate 24 (85 µL, 0.65 mmol) in anhydrous CH$_2$Cl$_2$ (10 mL) in one portion. The solution was stirred for 4 hours at r.t. under a nitrogen atmosphere. The solvent was removed, at reduced pressure and the residue purified by flash chromatography (PE/EtOAc 95:5) Yield 73% $^1$HNMR (400 MHz, CDCl$_3$-d): δ 7.99-7.97 (d, J=7.6 Hz, 2H), 7.71-7.69 (d, J=7.6 Hz, 2H), 7.58-7.56 (d, J=7.2 Hz, 2H), 7.51-7.18 (m, 2H), 7.03 (s, 2H), 2.78-2.77 (d, J=6.8 Hz, 2H), 1.71-1.61 (m, 2H), 1.42-1.40 (d, J=6.4 Hz, 2H), 0.96-0.87 (t, J=6.8 Hz, 3H) ppm $^{13}$C-NMR (100 MHz, CDCl$_3$-d): δ 174.66, 163.30, 152.83, 139.94, 136.25, 134.15, 133.10, 128.10, 126.20, 125.37, 124.86, 124.63, 124.22, 120.74, 98.30, 29.99, 26.83, 22.62, 13.94 ppm. MS (ESI) m/z 402.2 [M−H]$^-$ washed with brine and dried. Yield 88.3% $^1$HNMR (400 MHz, CDCl$_3$-d): δ 8.26-8.24 (d, J=8.4 Hz, 2H), 7.82-7.80 (d, J=8.2 Hz, 2H), 4.89 (s, 2H), 1.57 (s, 1H) ppm. MS (ESI) m/z 181.9 [M+H]$^+$MS (ESI) m/z 182.1 [M+H]$^+$ 5-butyl-3-(4-nitrophenyl)-1,2,4-oxadiazole (104): EDC HCl (1587 mg, 8.28 mmol), HOBt (373 mg, 2.76 mmol) and DIPEA (1.44 mL), were dissolved in a 10:1 mixture of DCM and DMF (22 mL) at 0° C. Valeric acid (300 µL, 8.28 mmol) was added, and the mixture was stirred under nitrogen atmosphere for 1 h at rt. After this time 103 (4.1 mmol) was added and the mixture was stirred at rt for 1 h, then at 110° C. for 12 h. After this time the solvent was removed at reduced pressure, and extracted with EtOAc. The organic phase was washed with 5% LiCl (aq) solution, and dried over Na$_2$SO$_4$. The residue was purified by flash chromatography on silica gel. (PE/EtOAc 9:1). Yield 73% $^1$HNMR (400 MHz, CDCl$_3$-d): δ 8.20-8.18 (d, J=8.4 Hz, 2H), 8.13-8.11 (d, J=8.8 Hz, 2H), 2.91-2.87 (t, J=7.6 Hz, 2H), 1.82-1.74 (m, 2H), 1.44-1.34 (m, 2H), 0.91-0.88 (t, J=7.6 Hz, 3H) ppm.

4-(5-butyl-1,2,4-oxadiazol-3-yl)aniline (105): 104 (95 mg, 0.38 mmol) was solubilized in a mixture of EtOH (30 mL) and water 2.5 mL. To this Iron powder (107.2 mg, 1.92 mmol) and NH$_4$Cl (11 mg, 0.19 mmol) were added. The reaction mixture was heated at 80° C. and stirred for 30 min. After this time the reaction was warmed to rt and filtered on a celite pad. The mixture was concentrated and water (15 mL) was added, followed by extraction with EtOAc. The Example 18

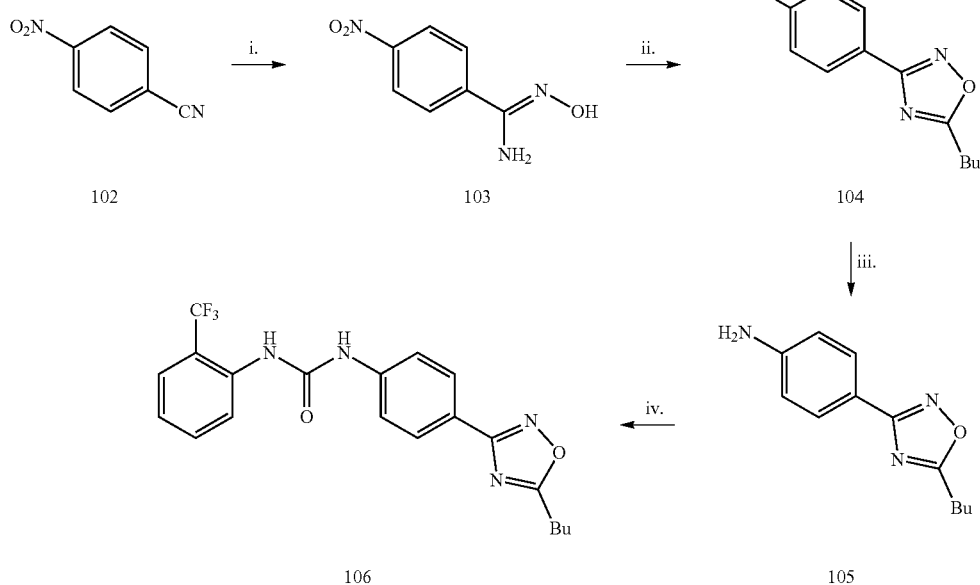

Reagents and conditions: i. NH$_2$OH.HCl/NaOH, EtOH/H$_2$O, r.t., 12 h; ii. valeric acid, EDC.HCl, HOBT, DMAP, CH$_2$Cl$_2$ dry, DMF dry, it, 12 h; iii. Fe$^0$, NH$_4$Cl, EtOH, H$_2$O, 80° C., 30 min; iv. 2-(trifluoromethyl)-phenylisocyanate, CH$_2$Cl$_2$ dry, it, 12 h.

N'-hydroxy-4-nitrobenzimidamide (103): hdroxylamine hydrochloride (469 mg, 6.75 mmol) was dissolved in water and neutralized with NaOH 2N. A solution of 102 (500 mg, 3.37 mmol) in ethanol was added with continuous stirring. The reaction mixture was stirred at rt for 12 hrs, then was extracted with DCM. The combined organic phase was organic layers were washed with Brine and dried over Na$_2$SO$_4$. Yield 95% $^1$HNMR (400 MHz, CDCl$_3$-d): δ 7.84-7.83 (d, J=7.2 Hz, 2H), 6.70-6.68 (d, J=7.2 Hz, 2H), 3.82 (s, 2H), 2.90-2.86 (t, J=6.8 Hz, 2H), 1.82-1.79 (t, J=6.8 Hz, 2H), 1.43-1.41 (d, J=7.2 Hz, 2H), 0.95-0.92 (t, J=6.4 Hz, 3H) ppm.

1-(4-(5-butyl-1,2,4-oxadiazol-3-yl)phenyl)-3-(2-(trifluoromethyl)phenyl)urea (106): 105 (0.46 mmol) was added to a solution of the 1-(Trifluoromethyl)phenyl isocyanate 24 (85 µL, 0.65 mmol) in anhydrous CH$_2$Cl$_2$ (10 mL) in one portion. The solution was stirred for 4 hours at r.t. under a nitrogen atmosphere. The solvent was removed, at reduced pressure and the residue purified by flash chromatography (PE/EtOAc 9:1) Yield 76% ¹HNMR (400 MHz, CDCl₃-d): δ 7.58-7.56 (d, J=7.6 Hz, 2H), 7.44-7.41 (m, 3H), 7.25 (s, 1H), 7.18 (s, 1H), 7.08 (s, 1H), 1.86-1.82 (t, J=7.2 Hz, 2H), 1.48-1.42 (m, 2H), 0.96-0.94 (t, J=7.6 Hz, 3H) ppm ¹³C-NMR (100 MHz, ACETONE-d₆): δ 180.10, 152.51, 142.51, 136.56, 132.78, 127.87, 125.98, 125.32, 123.81, 120.98, 118.33, 25.69, 21.82, 13.03 ppm.

K₂CO₃ (228.04 mg, 1.65 mmol) and I2 (155.63 mg, 0.66 mmol) were added. The reaction mixture was stirred at 100° C. for 12 h. After completion of the reaction the mixture was cooled and treated with Na₂S₂O₃, then extracted with EtOAc (3×25 mL), washed with Brine and dried over Na₂SO₄. The residue purified by flash chromatography. (PE/EtOAc 9:1). Yield: 70%: ¹HNMR (400 MHz, CDCl₃-d): δ 8.35-8.33 (d, J=8.4 Hz, 2H), 8.22-8.20 (d, J=8.4 Hz, 2H), 2.97-2.93 (t, J=7.6 Hz, 2H), 1.86-1.82 (t, J=7.2 Hz, 2H), 1.49-1.44 (m, 2H), 0.99-0.95 (t, J=6.8 Hz, 3H) ppm.

4-(5-butyl-1,3,4-oxadiazol-2-yl)aniline (111): Compound 110 (0.40 mmol) was solubilized in 30 mL of MeOH, and Example 19

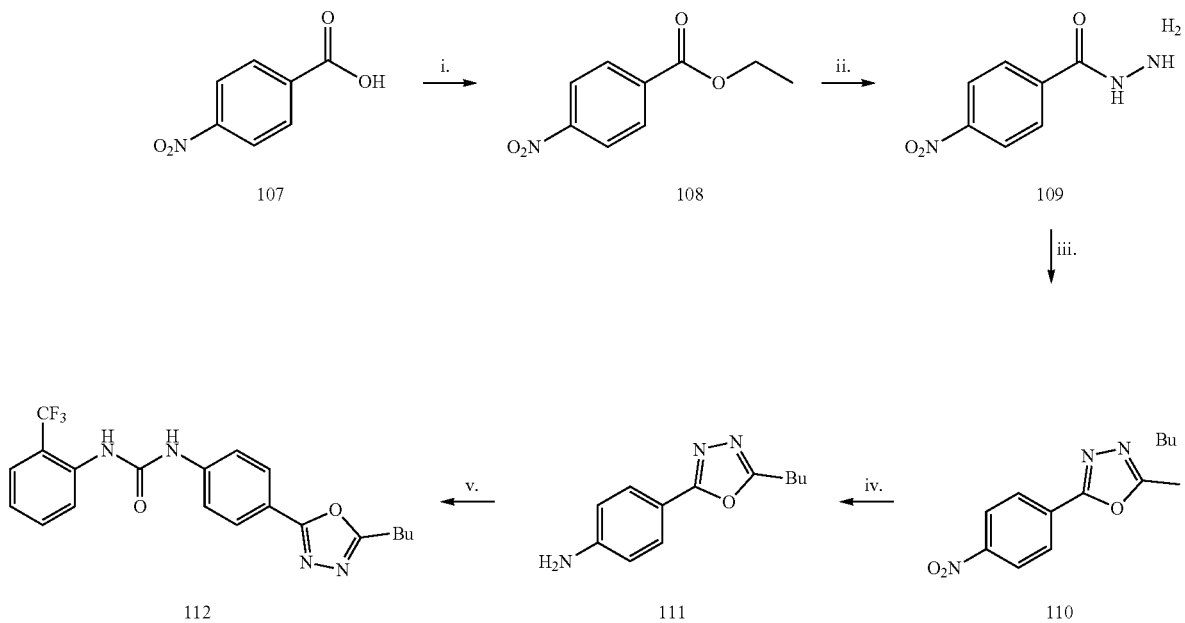

Reagents and conditions: i. H₂SO₄/EtOH, 100° C., 3 h; ii. N₂H₄·H₂O, EtOH, 100° C., 48 h; iii. a) Valeraldehyde, EtOH, 100° C., 12 h; b). I₂, K₂CO₃, DMSO, 100° C., 12 h; iv. H₂, Pd/C (10%), CH₃OH, 4 h; v. 2-(trifluoromethyl)-phenylisocyanate, CH₂Cl₂ dry, rt., 12 h.

ethyl 4-nitrobenzoate (108): 107 (200 mg, 1.19 mmol), was solubilized in a mixture of H₂SO₄ (4 mL) and EtOH (10 mL). The mixture was stirred at 100° C. for 1 h. After this time the solvent was partially evaporated at reduced pressure and the pH adjusted to 6 with NaHCO₃. The reaction was extracted with EtOAc, washed with Brine and dried over Na₂SO₄. Yield: 90%
¹HNMR (400 MHz, CDCl₃-d): δ 8.26-8.24 (d, J=8.8, 2H), 8.19-8.17 (d, J=8.8, 2H), 4.43-4.38 (m, 2H), 1.41-1.38 (t, J=7.2, 3H) ppm.

4-nitrobenzohydrazide (109): To a solution of 108 (180 mg, 0.92 mmol) in EtOH (20 mL), N₂H₄·H₂O (236 μL) was added. The resulting solution was heated to reflux for 48 h. After this time the mixture was warmed at rt, and the volatiles were removed in vacuo. The residue was crystallized in ACN. Yield 85% ¹HNMR (400 MHz, MeOD-d): δ 8.31-8.29 (d, J=8.8, 2H), 7.99-7.97 (d, J=8.8, 2H) ppm.

2-butyl-5-(4-nitrophenyl)-1,3,4-oxadiazole (110): A solution of valeraldehyde (58.7 μL, 0.55 mmol) and 109 (100 mg, 0.55 mmol) in EtOH, was heated at reflux for 12 h. After this time, the solvent was removed at reduced pressure. The resulting residue was redissolved in DMSO (3 mL) and 10% Palladium on charcoal (5 mg) was added. The reaction mixture was stirred under Hydrogen atmosphere for 1 h, then the mixture was filtered off on a celite pad and the solvent was evaporated at reduced pressure. Yield 99% Eluent. DCM/MeOH 98:2, Yield: 72%, ¹HNMR (400 MHz, CDCl₃-d): δ 7.80-7.78 (d, J=8.4 Hz, 2H), 6.71-6.69 (d, J=8.8 Hz, 2H), 4.07 (s, 2H), 2.88-2.84 (t, J=7.6 Hz, 2H), 1.82-1.75 (m, 2H), 1.48-1.39 (m, 2H), 0.96-0.93 (t, J=7.6 Hz, 3H) ppm.

1-(4-(5-butyl-1,3,4-oxadiazol-2-yl)phenyl)-3-(2-(trifluoromethyl)phenyl)urea (112): Aniline 111 (31 mg, 0.14 mmol) was added to a solution of 2-(Trifluoromethyl)phenyl isocyanate (22 μL, 0.15 mmol) in anhydrous CH₂Cl₂ (15 mL) in one portion. The solution was stirred for 9 hours at r.t. under a nitrogen atmosphere. The solvent was removed at reduced pressure and the residue purified on silica to furnish the final product as white solid. (Purification eluent: PE/EtOAc 7:3). Yield 71%, white solid. ¹HNMR (400 MHz, MeOD-d): δ 7.95-7.93 (d, J=8.4, 2H), 7.67-7.65 (d, J=8.8, 2H), 7.63-7.59 (m, 2H), 7.31-7.27 (m, 2H), 2.96-2.92 (d, J=7.6, 2H), 1.86-1.78 (m, 2H), 1.51-1.42 (m, 2H), 1.00-0.97 (t, J=7.2, 3H) ppm.

¹³C-NMR (100 MHz, ACETONE-d₆): δ 166.35, 164.11, 152.03, 142.81, 136.48, 132.79, 127.35, 125.90, 125.55, 123.65, 118.51, 29.30, 29.11, 28.92, 28.73, 28.54, 24.56, 21.82, 12.95 ppm.

Example 20

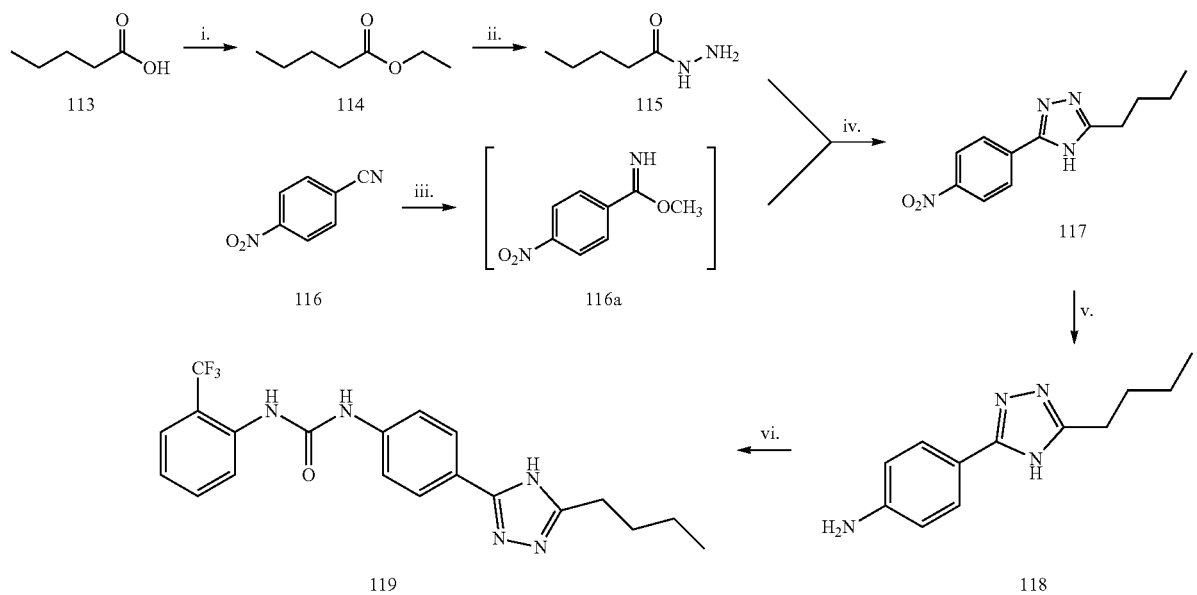

Reagents and conditions: i. EtOH/H$_2$SO$_4$, 100° C., 3 h; ii. N$_2$H$_4$.H$_2$O, EtOH, 100° C., 12 h.; iii. CH$_3$ONa, dry CH$_3$OH, rt., 1 h; iv., CH$_3$COOH, 0° C., 2 h; V. H$_2$, Pd/C (10%), CH$_3$OH, 3 h; vi. 2-(trifluoromethyl)-phenylisocyanate, CH$_2$Cl$_2$ dry, rt., 12 h.

4-nitrobenzohydrazide (109): To a solution of 108 (180 mg, 0.92 mmol) in EtOH (20 mL), N$_2$H$_4$.H$_2$O (236 μL) was added. The resulting solution was heated to reflux for 48 h. After this time the mixture was warmed at rt, and the volatiles were removed in vacuo. The residue was crystallized in ACN. Yield 85% $^1$HNMR (400 MHz, MeOD-d): δ 8.31-8.29 (d, J=8.8, 2H), 7.99-7.97 (d, J=8.8, 2H) ppm.

ethyl pentanoate (114): 113 (1000 mg, 9.79 mmol), was solubilized in a mixture of H$_2$SO$_4$ (4 mL) and EtOH (10 mL). The mixture was stirred at 100° C. for 3 h. After this time the solvent was partially evaporated at reduced pressure and the pH adjusted to 6 with NaHCO$_3$. The reaction was extracted with EtOAc, washed with Brine and dried over Na$_2$SO$_4$. Yield 99%.
$^1$HNMR (400 MHz, CDCl$_3$-d): δ 4.12-4.07 (q, J=7.2, 2H), 2.29-2.25 (t, J=8.0 Hz, 2H), 1.62-1.54 (m, 2H), 1.37-1.30 (q, J=8.0 Hz, 2H), 1.28-1.18 (t, J=8.0 Hz, 3H) ppm.

pentanehydrazide (115): To a solution of 114 (420 mg, 3.22 mmol) in EtOH (20 mL), N$_2$H$_4$.H$_2$O (783 μL) was added. The resulting solution was heated to reflux for 12 h. After this time the mixture was warmed at rt, and the volatiles were removed in vacuo. 115 was used for further reactions without additional purification. Yield: 99% $^1$HNMR (400 MHz, CDCl$_3$ d): δ 7.25 (s, 1H), 2.15-2.119 (d, J=7.6, 2H), 1.64-1.57 (m, 2H), 1.37-1.28 (m, 2H), 0.92-0.88 (t, J=7, 2, 3H) ppm.

3-butyl-5-(4-nitrophenyl)-4H-1,2,4-triazole (117): A 30% solution of MeONa (2.36 mmol) in anhydrous Methanol, was added dropwise to a solution of 116 (3.98 mmol) in CH$_3$OH. The reaction mixture was stirred at rt for 1 h. The pH was adjusted to 6 with CH$_3$COOH at 0° C., then 115 (4.3 mmol) was added. The rxn was stirred at rt for 2 h, then the solvent was removed at reduced pressure. Toluene (10 mL) was added and the reaction was heated at reflux with a Dean-Stark trap for 12 h. After this time the reaction was cooled and water and EtOAc were added. The mixture was stirred at rt for 30 min, then extracted, washed with Brine and dried over Na$_2$SO$_4$. The solvent was removed at reduced pressure and the residue was purified by flash chromatography. (PE/EtOAc 6:4). Yield 60%, $^1$HNMR (400 MHz, CDCl$_3$-d: δ 8.37-8.35 (d, J=8.4, 2H), 8.29-8.24 (d, J=7.6, 2H), 1.84-1-76 (m, 2H), 1.46-1.39 (m, 2H), 0.98-0.946 (t, J=7.2 Hz, 3H) ppm. $^{13}$C-NMR (100 MHz, ACETONE-d$_6$): δ 160.05, 159.25, 148.07, 136.95, 127.13, 124.00, 77.39, 77.08, 76.76, 29.98, 26.36, 22.29, 13.58 ppm.

4-(5-butyl-4H-1,2,4-triazol-3-yl)aniline (118): 117 (0.40 mmol) was solubilized in 30 mL of MeOH, and 10% Palladium on charcoal (5 mg) was added. The reaction mixture was stirred under Hydrogen atmosphere for 1 h, then the mixture was filtered off on a celite pad and the solvent was evaporated at reduced pressure. The residue was purified by flash chromatography (PE/EtOAc/TEA 6:4:0.5). Yield 70% $^1$HNMR (400 MHz, CDCl$_3$-d): δ 7.77-7.75 (d, J=6.8 Hz, 2H), 6.68-6.66 (d, J=6.8 Hz, 2H), 4.13 (s, 1H), 2.77-2.75 (d, J=7.6 Hz, 2H), 1.72-1.71 (d, J=7.2 Hz, 2H), 1.38-1.34 (d, J=8.0 Hz, 2H), 0.91-0.88 (m, 3H) ppm.

1-(4-(5-butyl-4H-1,2,4-triazol-3-yl)phenyl)-3-(2-(trifluoromethyl)phenyl)urea (119): Aniline 118 (25 mg, 0.11 mmol) was added to a solution of 2-(Trifluoromethyl)phenyl isocyanate (18 μL, 0.11 mmol) in anhydrous CH$_2$Cl$_2$ (15 mL) in one portion. The solution was stirred for 12 hours at r.t. under a nitrogen atmosphere. The solvent was removed at reduced pressure and the residue purified on silica to furnish the final product as white solid. (Purification eluent: PE/EtOAc 7:3). Yield 70%, white solid. $^1$HNMR (400 MHz, MeOD-d): δ 7.95-7.89 (m, 4H), 7.66-7.56 (m, 4H), 7.29-7.25 (m), 2.81-2.77 (d, J=7.6 Hz, 2H), 1.79-1.72 (m, 2H), 1.45-1.36 (m, 2H), 0.98-0.94 (t, J=7.6 Hz, 3H)ppm. $^{13}$C-NMR (100 MHz, MeOD-d$_6$): δ 153.58, 146.64, 140.81, 135.86, 132.40, 126.77, 126.01, 125.67, 124.01, 121.78, 121.44, 118.53, 30.00, 29.31, 25.76, 21.88, 12.61 ppm.

Example 21

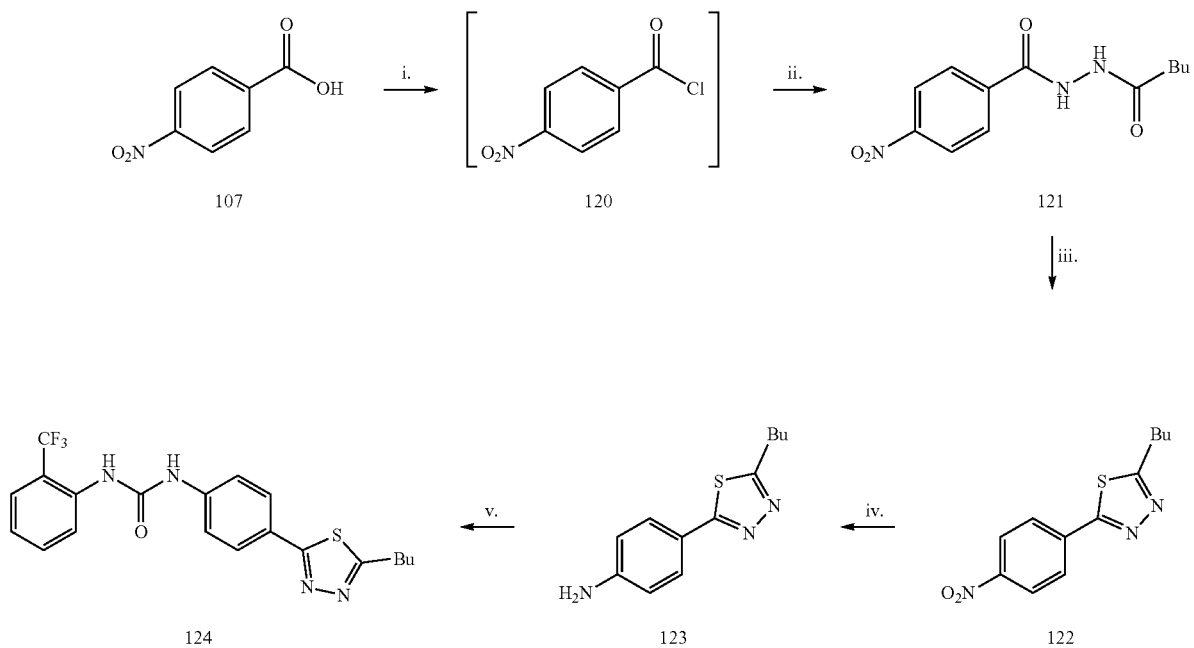

Reagents and conditions: i. SOCl$_2$, 100° C., 1 h; ii. 115, DMAP, CH$_2$Cl$_2$, 0° C., 12 h; iii. Lawesson's reagent, dioxane, 80° C., 12 h. iv. Fe$^0$, NH$_4$Cl, EtOH, H$_2$O, 80° C., 1 h; v. 2-(trifluoromethyl)-phenylisocyanate, CH$_2$Cl$_2$ dry, rt., 12 h.

4-nitrobenzoyl chloride (120): 107 (719.8 mg, 4.30 mmol), was stirred with 1 mL of anhydrous SOCl$_2$, at 100° C., for 1 h. The excess of SOCl$_2$ was removed by distillation. 120 was used for further reactions without additional purification.

4-nitro-N'-pentanoylbenzohydrazide (121): A solution of 120 (500 mg, 4.30 mmol) and DMAP (525 mg, 4.30 mmol) in dry DCM (5 mL) was added dropwise to a solution of 120 in anhydrous DCM. The resulting mixture was stirred at rt on. The solvent was removed at reduced pressure and the residue purified by flash chromatography (DCM/MeOH/TEA 98:2:0.5), Yield: 67%, $^1$HNMR (400 MHz, MeOD-d): δ 8.34-8.31 (d, J=8.8, 2H), 8.08-8.06 (d, J=8.8, 2H), 2.34-2.30 (q, J=7.2, 2H), 1.71-1.57 (q, 2H), 1.47-1.35 (t, J=7.7 Hz, 3H) ppm.

2-butyl-5-(4-nitrophenyl)-1,3,4-thiadiazole (122): Lawesson's reagent (458 mg, 1.31 mmol) was added to a stirring solution of 121 in anhydrous dioxane (20 mL). The reaction mixture was stirred at 80° C. for 24 h. Dioxane was removed under reduced pressure, and the residue obtained was dissolved in water. The pH was basified to 9 by adding of NaHCO$_{3(aq)}$ and the organic phases were washed with brine and dried over Na$_2$SO$_4$. The residue was purified by flash chromatography (PE/EtOAc 8:2), Yield 60% $^1$HNMR (400 MHz, CD$_3$OD): δ 8.39-8.37 (d, J=8.8 Hz, 2H), 8.26-8.24 (d, J=8.8 Hz, 2H), 3.22-3.18 (t, J=7.6 Hz, 2H), 1.87-1.79 (m, 2H), 1.51-1.42 (m, 2H), 0.98-0.94 (t, J=7.2 Hz, 3H) ppm.

4-(5-butyl-1,3,4-thiadiazol-2-yl)aniline (123): 122 (58 mg, 0.22 mmol) was solubilized in a mixture of EtOH (30 mL) and water 2.5 mL. To this Iron powder (62 mg, 1.1 mmol) and NH$_4$Cl (6 mg, 0.11 mmol) were added. The reaction mixture was heated at 80° C. and stirred for 30 min. After this time the reaction was warmed to rt and filtered on a celite pad. The mixture was concentrated and water (15 mL) was added, followed by extraction with EtOAc. The organic layers were washed with Brine and dried over Na$_2$SO$_4$. Yield 75% $^1$HNMR (400 MHz, CDCl$_3$-d): δ 7.72-7.70 (d, J=8.0, 2H), 6.70-6.68 (d, J=8.0, 2H), 3.96 (s, 2H), 3.10-3.06 (t, J=8.0, 2H), 1.82-1.75 (q, J=7.6 Hz, 2H), 1.49-1.40 (q, J=7.6 Hz, 2H), 0.97-0.93 (t, J=8.0 Hz, 3H) ppm. MS (ESI) m/z 234.1 [M+H]$^+$ 1-(4-(5-butyl-1,3,4-thiadiazol-2-yl)phenyl)-3-(2-(trifluoromethyl)phenyl)urea (124): Aniline 123 (25 mg, 0.11 mmol) was added to a solution of 2-(Trifluoromethyl)phenyl isocyanate (17 μL, 0.11 mmol) in anhydrous CH$_2$Cl$_2$ (15 mL) in one portion. The solution was stirred for 12 hours at r.t. under a nitrogen atmosphere. The solvent was removed at reduced pressure and the residue purified on silica to furnish the final product as white solid. (Purification eluent: PE/EtOAc 7:3). Yield 68%, white solid. $^1$H NMR (400 MHz, CDCl$_3$-d) δ 7.57 (m, 5H), 7.31-7.22 (m, 2H), 7.18 (dd, J=7.5, 1.6 Hz, 1H), 6.97 (td, J=7.5, 1.6 Hz, 1H), 4.18 (s, 1H), 2.75 (t, J=5.5 Hz, 2H), 1.65 (dq, J=7.7, 5.6 Hz, 2H), 1.46-1.32 (m, 2H), 1.32-1.07 (m, 3H) ppm.

Example 22

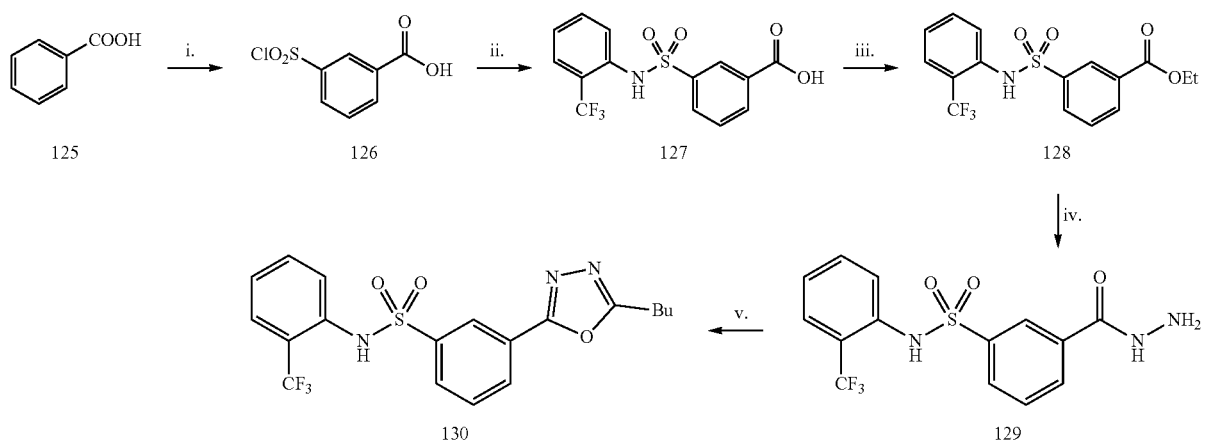

Reagents and conditions: i. HSO$_3$Cl, 2 h, 120° C. (82%); ii. Pyr, 5 h, rt; iii. H$_2$SO$_4$/EtOH, 100° C., 3 h; iv. N$_2$H$_4$.H$_2$O, EtOH, 100° C., 48 h; v. a) EtOH, 100° C., 12 oh; b). I$_2$, K$_2$CO$_3$, DMSO, 100° C., 12 h.

3-(Chlorosulfonyl)benzoic acid, (126): Chlorosulfonic acid (2 mL, 300.4 mmol) was added to 125, (500 mg, 40.9 mmol) and the mixture was stirred at 120° C. for 2 h. After this time the mixture was added dropwise to a mixture of EtOAc (200 mL) and crushed ice. The resulting precipitate was collected, dissolved in ethyl acetate, washed with water (3×25 mL) and Brine, dried over Na$_2$SO$_4$, and the solvent was removed under reduced pressure. $^1$H-NMR (400 MHz, DMSO-d$_6$): δ=8.80 (t, J=1.4 Hz, 1H), 8.40 (m 1H), 8.19 (m, 1H), 7.69 (t, J=7.5 Hz, 1H). ppm.

3-(N-(2-(trifluoromethyl)phenyl)sulfamoyl)benzoic acid (127): To a stirred solution of 2-trifluoromethyl-phenylaniline (1 eq.) in 5 mL of anhydrous pyridine, was added sulphonyl chloride 126 (1.1 eq) at 0° C. The corresponding solution was stirred at r.t. under nitrogen atmosphere, for 5 h. After completion of the reaction the mixture was acidified with 1N HCl, the aqueous phase was extracted with several times and the combined organic phases were dried (Na$_2$SO$_4$) and concentrated. (PE-AcOEt 95:5). Yield 75%, white solid. $^1$H NMR (400 MHz, CDCl$_3$-d): δ 9.44 (s, 1H), 8.72 (s, 1H), 8.39 (s, 1H), 8.23 (s, 1H), 7.71 (s, 1H), 7.35 (s, 1H), 7.20 (s, 1H), 6.82 (s, 1H), 6.71 (s, 1H), 6.08 (s, 1H). ppm. MS (ESI): m/z 344 [M–H]$^-$.

ethyl 3-(N-(2-(trifluoromethyl)phenyl)sulfamoyl)benzoate (128): 127 (200 mg, 1.19 mmol), was solubilized in a mixture of H$_2$SO$_4$ (4 mL) and EtOH (10 mL). The mixture was stirred at 100° C. for 1 h. After this time the solvent was partially evaporated at reduced pressure and the pH adjusted to 6 with NaHCO$_3$. The reaction was extracted with EtOAc, washed with Brine and dried over Na$_2$SO$_4$. Yield: 87% $^1$HNMR (400 MHz, CDCl$_3$-d): δ 8.41 (s, 1H), 8.20 (d, J=7.8 Hz, 1H), 7.91 (d, J=7.9 Hz, 1H), 7.83 (d, J=8.3 Hz, 1H), 7.60-7.44 (m, 2H), 7.25 (t, J=7.7 Hz, 1H), 6.74 (t, J=7.9 Hz, 1H), 4.36 (q, J=7.6 Hz, 2H), 1.38 (t, J=7.5 Hz, 3H). ppm.

3-(hydrazinecarbonyl)-N-(2-(trifluoromethyl)phenyl) benzenesulfonamide (129): To a solution of 128 (90 mg, 0.24 mmol) in EtOH (20 mL), N$_2$H$_4$.H$_2$O (58 μL) was added. The resulting solution was heated to reflux for 48 h. After this time the mixture was warmed at rt, and the volatiles were removed in vacuo. The residue was crystallized in ACN. Yield 85%

$^1$HNMR (400 MHz, Acetone-d$_6$): δ 7.39 (dd, J=7.5, 1.4 Hz, 1H), 7.18 (dd, J=19.2, 12.6, 1.0 Hz, 2H), 6.84 (td, J=7.5, 1.4 Hz, 1H), 6.71 (dd, J=7.5, 1.5 Hz, 1H), 6.07-6.01 (m, 2H), 5.79 (d, J=2.0 Hz, 1H), 5.64 (s, 1H), 2.05 (s, 1H), 2.00 (d, J=0.8 Hz, 3H), 1.66 (s, 1H). ppm.

2-butyl-5-(4-nitrophenyl)-1,3,4-oxadiazole (130): A solution of valeraldehyde (15 μL, 0.14 mmol) and 129 (50 mg, 0.14 mmol) in EtOH, was heated at reflux for 12 h. After this time, the solvent was removed at reduced pressure. The resulting residue was redissolved in DMSO (3 mL) and K$_2$CO$_3$ (58 mg, 0.42 mmol) and I$_2$ (43 mg, 0.16 mmol) were added. The reaction mixture was stirred at 100° C. for 12 h. After completion of the reaction the mixture was cooled and treated with Na$_2$S$_2$O$_3$, then extracted with EtOAc (3×25 mL), washed with Brine and dried over Na$_2$SO$_4$. The residue purified by flash chromatography. (PE/EtOAc 8:2). Yield: 73%

$^1$HNMR (400 MHz, CDCl$_3$-d): δ 8.21 (s, 2H), 8.04 (s, 2H), 7.86 (s, 2H), 7.65 (s, 2H), 7.33 (s, 2H), 7.17 (s, 2H), 6.81 (s, 2H), 6.69 (s, 2H), 6.19 (s, 2H), 2.73-2.68 (m, 4H), 1.67-1.62 (m, 3H), 1.40-1.35 (m, 3H), 1.01-0.96 (m, 6H). ppm. $^{13}$C NMR (100 MHz, CDCl$_3$-d) δ 166.44, 162.20, 144.51, 139.07, 135.27, 133.84, 132.13, 131.76, 128.46, 128.22, 127.97, 127.75, 123.87, 27.52, 26.97, 22.18, 14.02 ppm.

Example 23

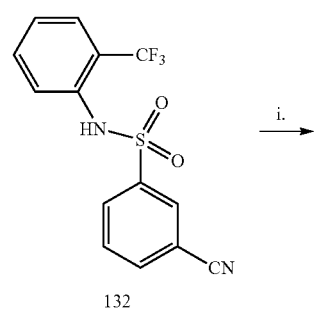

-continued

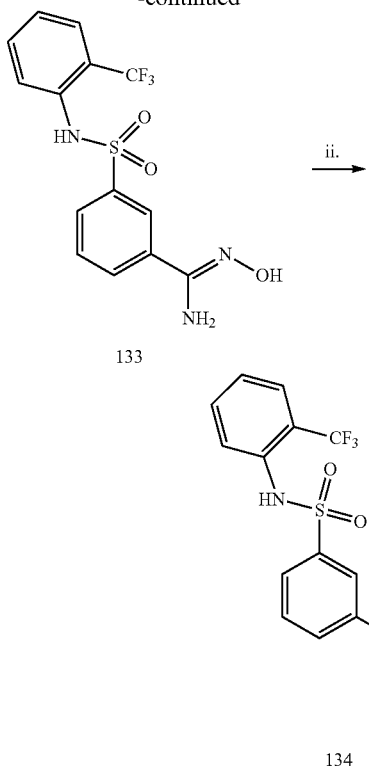

Reagents and conditions: i. NH$_2$OH.HCl/NaOH, EtOH/H$_2$O, r.t., 12 h; ii. valeric acid, EDC.HCl, HOBt, DMAP, CH$_2$Cl$_2$ dry, DMF dry, rt, 12 h.

hydroxy-3-(N-(2-(trifluoromethyl)phenyl)sulfamoyl)benzimidamide (133): hydroxylamine hydrochloride (469 mg, 6.75 mmol) was dissolved in water and neutralized with NaOH 2N. A solution of 132 (3.37 mmol) in ethanol was added with continuous stirring. The reaction mixture was stirred at rt for 12 hrs, then was extracted with DCM. The combined organic phase was washed with brine and dried. Yield 99% $^1$HNMR (400 MHz, Acetone): δ 8.23 (s, 1H), 7.98 (d, J=7.7 Hz, 1H), 7.83 (d, J=7.8 Hz, 1H), 7.66 (d, J=8.2 Hz, 1H), 7.58 (d, J=7.3 Hz, 2H), 7.47 (d, J=8.1 Hz, 1H), 7.39 (t, J=7.2 Hz, 1H). MS (ESI) m/z 362.1 [M+H]$^+$ 3-(5-butyl-1,2,4-oxadiazol-3-yl)-N-(2-(trifluoromethyl)phenyl)benzenesulfonamide (134): EDC HCl (1587 mg, 8.28 mmol), HOBt (373 mg, 2.76 mmol) and DIPEA (1.44 mL), were dissolved in a 10:1 mixture of DCM and DMF (22 mL) at 0° C. Valeric acid (300 μL, 8.28 mmol) was added, and the mixture was stirred under nitrogen atmosphere for 1 h at rt. After this time 133 (4.1 mmol) was added and the mixture was stirred at rt for 1 h, then at 110° C. for 12 h. After this time the solvent was removed at reduced pressure, and extracted with EtOAc. The organic phase was washed with 5% LiCl (aq) solution, and dried over Na$_2$SO$_4$. The residue was purified by flash chromatography on silica gel. (PE/EtOAc 7:3). Yield 73% $^1$H NMR (400 MHz, Acetone) δ 8.29 (s, 1H), 8.07 (d, J=7.8 Hz, 1H), 7.92 (d, J=7.8 Hz, 1H), 7.70-7.53 (m, 2H), 7.43 (dd, J=15.2, 7.8 Hz, 2H), 6.47 (s, 2H), 2.47 (t, J=7.4 Hz, 2H), 1.63 (dd, J=15.1, 7.5 Hz, 2H), 1.38 (dd, J=14.9, 7.5 Hz, 2H), 0.92 (t, J=7.4 Hz, 3H). ppm. $^{13}$C NMR (101 MHz, Acetone) δ 169.93, 154.59, 141.46, 134.45, 133.19, 130.93, 129.43, 128.77, 127.07, 126.88, 126.64, 125.30, 32.17, 26.90, 22.02, 13.12. MS (ESI) m/z 426.3 [M+H]$^+$ Example 24

In Vitro ADME Studies

ADME properties of compounds are of primary importance. Poor solubility and poor permeability are among the main causes of failure during drug-development. In general, it is important to try to find a good balance between lipid bilayer permeability, that affects gastrointestinal absorption by passive diffusion after oral dosing, and solubility. For these reasons, physicochemical properties of our compounds were predicted, starting from the first phases, using QikProp (QP) prediction program (QikProp, version 3.3, Schrödinger, LLC, New York, N.Y., 2010).

A few in vitro experiments were conducted to quickly establish the absorption/stability of drug candidates in the early phase: aqueous solubility, parallel artificial membrane permeability (PAMPA) assay and human liver microsome (HLM) stability determination.

Materials and Methods

Chemicals. All solvents, reagents, were from Sigma-Aldrich Srl (Milan, Italy). Dodecane was purchased from Fluka (Milan, Italy). Pooled Male Donors 20 mg mL$^{-1}$ HLM were from BD Gentest-Biosciences (San Jose, Calif.). Milli-Q quality water (Millipore, Milford, Mass., USA) was used. Hydrophobic filter plates (MultiScreen-IP, Clear Plates, 0.45 μm diameter pore size), 96-well microplates, and 96-well UV-transparent microplates were obtained from Millipore (Bedford, Mass., USA).

Parallel Artificial Membrane Permeability Assay (PAMPA). Donor solution (0.5 mM) was prepared by diluting 1 mM dimethylsulfoxide (DMSO) compound stock solution using phosphate buffer (pH 7.4, 0.025 M). Filters were coated with 5 μL of a 1% (w/v) dodecane solution of phosphatidylcholine prepared from CHCl$_3$ solution 10% w/v, for intestinal permeability. Donor solution (150 μL) was added to each well of the filter plate. To each well of the acceptor plate were added 300 μL of solution (50% DMSO in phosphate buffer). All compounds were tested in three different plates on different days. The sandwich was incubated for 5 h at room temperature under gentle shaking. After the incubation time, the plates were separated, and samples were taken from both receiver and donor sides and analyzed using LC with UV detection at 280 nm.

LC analysis were performed with a Varian Prostar HPLC system (Varian Analytical Instruments, USA) equipped with a binary pump with a manual injection valve and model Prostar 325 UV-VIS Detector. Chromatographic separations were conducted using a Polaris C18-A column (150-4.6 mm, 5 μm particle size) at a flow rate of 0.8 mL min$^{-1}$ with a mobile phase composed of 60% ACN/40% H$_2$O.

Permeability (Papp) for PAMPA was calculated according to the following equation, obtained from Wohnsland and Faller and Sugano et al. equation with some modification in order to obtain permeability values in cm s$^{-1}$, $$P_{app} = \frac{V_D V_A}{(V_D + V_A) A t} - \ln(1 - r)$$

where $V_A$ is the volume in the acceptor well, $V_D$ is the volume in the donor well (cm$^3$), A is the "effective area" of the membrane (cm$^2$), t is the incubation time (s) and r the ratio between drug concentration in the acceptor and equilibrium concentration of the drug in the total volume ($V_D + V_A$). Drug concentration is estimated by using the peak area integration.

Membrane retentions (%) were calculated according to the following equation:

$$\% \, MR = \frac{[r - (D + A)]100}{Eq}$$

where r is the ratio between drug concentration in the acceptor and equilibrium concentration, D, A, and Eq represented drug concentration in the donor, acceptor and equilibrium solution, respectively.

Water Solubility Assay. Each solid compound (1 mg) was added to 1 mL of water. The samples were shaken in a shaker bath at room temperature for 24-36 h. The suspensions were filtered through a 0.45 μm nylon filter (Acrodisc), and the solubilized compound determined by LC-MS-MS assay. For each compound the determination was performed in triplicate.

For the quantification was used an LC-MS system consisted of a Varian apparatus (Varian Inc) including a vacuum solvent degassing unit, two pumps (212-LC), a Triple Quadrupole MSD (Mod. 320-LC) mass spectrometer with ES interface and Varian MS Workstation System Control Vers. 6.9 software. Chromatographic separation was obtained using a Pursuit C18 column (50×2.0 mm) (Varian) with 3 μm particle size and gradient elution: eluent A being ACN and eluent B consisting of water. The analysis started with 0% of eluent A, which was linearly increased up to 70% in 10 min, then slowly increased up to 98% up to 15 min. The flow rate was 0.2 mL min$^{-1}$ and injection volume was 5 μL. The instrument operated in positive mode and parameters were: detector 1850 V, drying gas pressure 25.0 psi, desolvation temperature 300.0° C., nebulizing gas 40.0 psi, needle 5000 V and shield 600 V. Nitrogen was used as nebulizer gas and drying gas. Collision induced dissociation was performed using Argon as the collision gas at a pressure of 1.8 mTorr in the collision cell. Microsomal Stability Assay. Each compound in DMSO solution was incubated at 37° C. for 60 min in 125 mM phosphate buffer (pH 7.4), 5 μL of human liver microsomal protein (0.2 mg mL$^{-1}$), in the presence of a NADPH-generating system at a final volume of 0.5 mL (compound final concentration, 50 ∞M); DMSO did not exceed 2% (final solution). The reaction was stopped by cooling on ice and adding 1.0 mL of acetonitrile. The reaction mixtures were then centrifuged, and the parent drug and metabolites were subsequently determined by LC-UV-MS. Chromatographic analysis was performed with an Agilent 1100 LC/MSD VL system (G1946C) (Agilent Technologies, Palo Alto, Calif.) constituted by a vacuum solvent degassing unit, a binary high-pressure gradient pump, an 1100 series UV detector, and an 1100 MSD model VL benchtop mass spectrometer.

Chromatographic separation was obtained using a Varian Polaris C18-A column (150-4.6 mm, 5 μm particle size) and gradient elution: eluent A being ACN and eluent B consisting of water. The analysis started with 2% of eluent A, which was rapidly increased up to 70% in 12 min, then slowly increased up to 98% in 20 min. The flow rate was 0.8 mL min$^{-1}$ and injection volume was 20 μL.

The Agilent 1100 series mass spectra detection (MSD) single-quadrupole instrument was equipped with the orthogonal spray API-ES (Agilent Technologies, Palo Alto, Calif.). Nitrogen was used as nebulizing and drying gas. The pressure of the nebulizing gas, the flow of the drying gas, the capillary voltage, the fragmentor voltage, and the vaporization temperature were set at 40 psi, 9 L/min, 3000 V, 70 V, and 350° C., respectively. UV detection was monitored at 280 nm. The LC-ESI-MS determination was performed by operating the MSD in the positive ion mode. Spectra were acquired over the scan range m/z 100-1500 using a step size of 0.1 u. The percentage of not metabolized compound was calculated by comparison with reference solutions.

TABLE 3

ADME properties of selected compounds

| Cmpd ID | Structure | PAMPA Papp *10$^{-6}$ (cm/s) GI (RM %) | Aq. Solub. (μg/mL) | LogS | QP Pred. LogS |
|---|---|---|---|---|---|
| 20a | 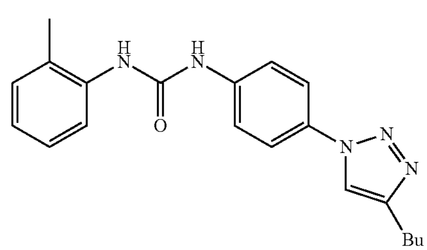 | 2.86 (19.1) | 0.135 | −7.05 | −6.4 |

TABLE 3-continued

ADME properties of selected compounds

| Cmpd ID | Structure | PAMPA Papp *10⁻⁶ (cm/s) GI (RM %) | Aq. Solub. (µg/mL) | LogS | QP Pred. LogS |
|---|---|---|---|---|---|
| 20b | 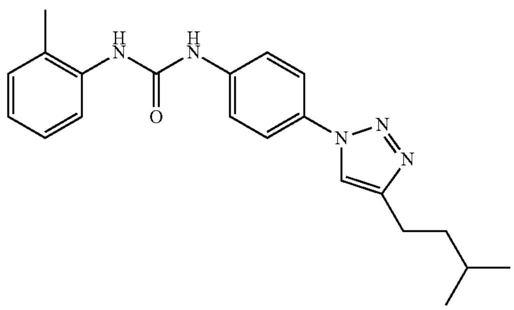 [SMILES: Cc1ccccc1NC(=O)Nc1ccc(-n2cc(CCC(C)C)nn2)cc1] | 1.93 (26.7) | <0.001 | <−8.6 | <−6.7 |
| 21b | 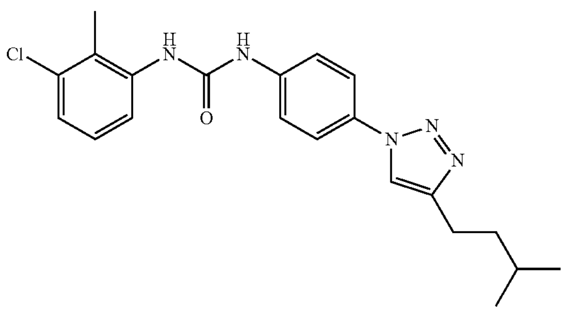 [SMILES: Cc1c(Cl)cccc1NC(=O)Nc1ccc(-n2cc(CCC(C)C)nn2)cc1] | 2.51 (59.1) | <0.001 | <−8.6 | −7.3 |
| 81 | 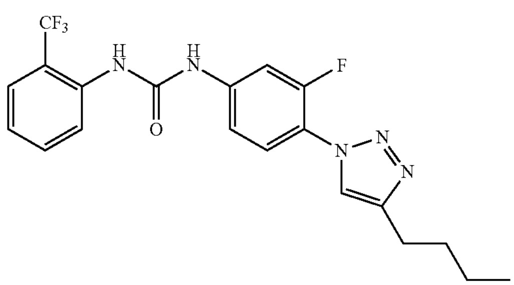 [SMILES: CCCCc1cn(-c2ccc(NC(=O)Nc3ccccc3C(F)(F)F)cc2F)nn1] | 7.22 (30.4) | 80.11 | −6.4 | −7.3 |
| 22a | 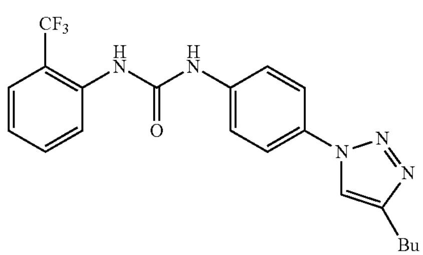 | 7.47 (23.9) | 0.107 | −7.43 | −7.1 |

TABLE 3-continued

ADME properties of selected compounds

| Cmpd ID | Structure | PAMPA Papp *10⁻⁶ (cm/s) GI (RM %) | Aq. Solub. (μg/mL) | LogS | QP Pred. LogS |
|---|---|---|---|---|---|
| 22b | [structure: 2-CF₃-phenyl urea linked to phenyl-triazole with isobutyl chain] | 7.41 (24.8) | 0.002 | <−8.6 | −7.5 |
| 49 | [structure: 2-methylphenyl urea linked to phenyl-tetrazole with N-Bu] | 7.57 (24.8) | <0.001 | <−8.5 | −5.74 |
| 20f | [structure: 2-methylphenyl urea linked to phenyl-triazole with CH₂CH₂OMe] | 0.69 (7.4) | 26.27 | −4.3 | −5.12 |
| 64e | [structure: butyl-triazolyl-phenyl sulfonamide of isoquinolin-5-yl] | 0.68 (0) | 1.37 | −5.57 | −5.47 |
| 68e | [structure: (ethoxymethyl)-triazolyl-phenyl sulfonamide of isoquinolin-5-yl] | 0.44 (0) | 45.35 | −4.26 | −4.7 |

TABLE 4

Metabolic stability of selected compounds

| Cmpd ID | Structure | Sability % |
|---|---|---|
| 20a | 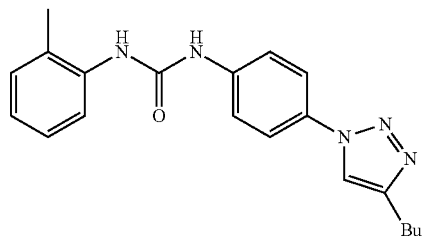 | 99 |
| 81 | 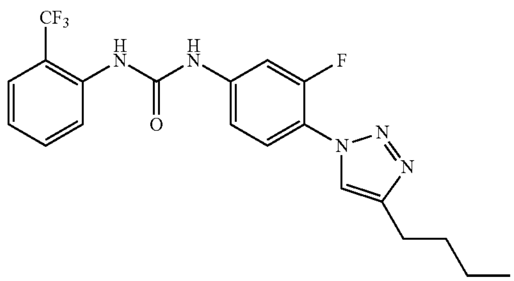 [SMILES: CCCCc1cn(-c2ccc(NC(=O)Nc3ccccc3C(F)(F)F)cc2F)nn1] | 94 |
| 49 | 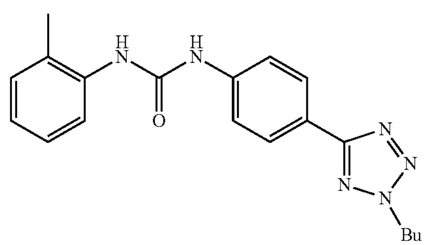 | 95.6 |
| 64d | 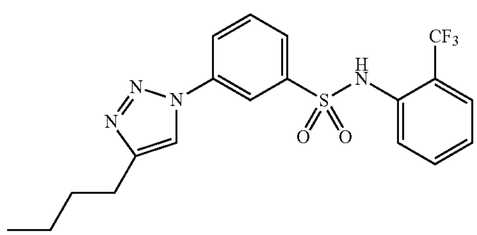 [SMILES: CCCCc1cn(-c2cccc(S(=O)(=O)Nc3ccccc3C(F)(F)F)c2)nn1] | 99 |
| 64e | 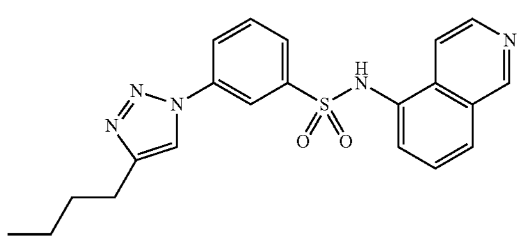 [SMILES: CCCCc1cn(-c2cccc(S(=O)(=O)Nc3cccc4cnccc34)c2)nn1] | 98 |
| 68e | 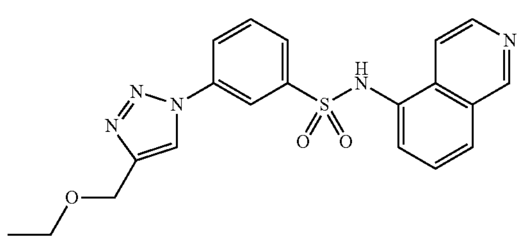 [SMILES: CCOCc1cn(-c2cccc(S(=O)(=O)Nc3cccc4cnccc34)c2)nn1] | 95.7 |

Example 25

Helicase Assays

The helicase activity of DDX3 wt was monitored by measuring the conversion of a double stranded (ds) RNA (labelled at the 5'-end of one strand with a 6-FAM fluorescent) into single stranded (ss) nucleic acid. A final concentration of 25 nM RNA substrate was used in the experiments, unless otherwise stated. Reactions were performed in 50 mM TrisHCl pH 7.5, 1 mM DTT, 0.2 mg/ml BSA, 5% glycerol and 100 µM ATP, 10 mM $MgCl_2$ at 37° C. degrees for 10' and stopped by adding EDTA 50 mM pH 8. Products were separated through non-denaturating 8% PAGE at 5 W for 4 hours in TBE buffer at 4° C. Substrates and products were quantified by laser scanning densitometry (Thyphoon-TRIO, GE Healthcare).

Proteins

Human recombinant DDX3 was cloned, expressed and purified as described (Franca et al. *Proteins* 2007, 67, 1128-37).

Cell Cultures and Reagents

Cells were purchased from American Type Culture Collection (ATCC, Manassas, Va., USA). The LNCaP (ATCC® CRL-1740™), A549 (ATCC® CCL-185™), MDA-MB-231 (ATCC® CRM-HTB-26™), 22Rv1 (ATCC® CRL-2505™), HCT-116 (ATCC® CCL-247™) and PC3 (ATCC® CRL-1435™) cells were maintained in Roswell Park Memorial Institute 1640 medium (RPMI; Euroclone, ECB9006L) supplemented with 10% fetal bovine serum (Euroclone; ECS0180L), 2 mM L-glutamine, 100 units/mL penicillin and 100 mg/mL streptomycin at 37° C. in an atmosphere of 5% $CO_2$/air. DU145 (ATCC® HTB-81™), and DAOY (ATCC® HTB-186™) cells were maintained in Eagle's minimal essential medium (EMEM; Euro-clone, ECM0445L) supplemented with 10% fetal bovine serum (Euroclone; ECS0180L), 2 mM L-glutamine, 100 units/ml penicillin and 100 mg/mL streptomycin at 37° C. in an atmosphere of 5% $CO_2$/air. SH-SY5Y (ATCC® CRL-2266™), DBRTG (ATCC® CRL-2020™), HeLa (ATCC® CCL-2™), HN6 cells (kindly provided by Dr Silvio Gutkind, UCSD Medical Center, Moores Cancer Center USA, Chen J. J et al, Oncotarget 2013, 4, 206-217)), U2OS (ATCC® HTB-96™), RD18 cells (kindly provided by Dr P. Boccuni Memorial Sloan-Kettering Cancer Center, New York, USA Vella S. et al. Clin Epigenetics. 2015 6; 7-82), cells were maintained in Dulbecco's modified Eagle's medium (DMEM; Euroclone, ECB7501L) supplemented with 10% fetal bovine serum (Euroclone; ECS0180L), 2 mM L-glutamine, 100 units/ml penicillin and 100 mg/mL streptomycin at 37° C. in an atmosphere of 5% $CO_2$/air.

Cytotoxicity Test

Cell lines were seeded at appropriate densities in 2 mL growth medium in 6-wells culture plates 24 hours before the treatment with the inhibitor compounds. After 24 h the culture medium was removed and fresh medium containing increasing concentrations of chemical compounds was added to cells. The fixed final concentrations were: 0.1 µM, 1 µM, 10 µM, 100 µM. DMSO was the vehicle used for dilution of the compounds and its final concentration on cells was less than 0.2%. Medium-only containing wells were included as controls. Cells were incubated 48 hours with drugs and, then, cell viability was evaluated.

Inhibition Growth Curve Calculation

Cells were detached from each well of the 6-wells plates with 300 µL of Trypsin and suspended in culture medium to a final volume of 1 mL. Cell viability was then assessed through cell counting. Cells were diluted in 1:50 ratio of an isotonic buffered diluent, Isoton (Backman Coulter), following the manufacturer's instructions, and counted using an automated cell counter (Z2 series Coulter Counter, Beckman Coulter). Each cell count was performed in three replicates. The values corresponding to the relative survival of cells in presence of each chemical compound at single concentrations were normalized to the untreated controls. Then, the half maximal inhibitory concentration ($IC_{50}$) value, which represent the drug concentration that is required to induce a 50% growth inhibition in vitro, was calculated with Graph-Pad Prism 6.0 software using the best fitting sigmoid curve.

Anti-Enzymatic Activity

The anti-enzymatic activity of representative compounds against the DDX3 helicase is reported in Table 5.

TABLE 5

Activity of representative compounds of the invention against DDX3 RNase.

| Compound ID | Structure | $ID_{50}$ (µM)$^a$ |
|---|---|---|
| EI01D published reference compound[b] | | 1 |
| 8a | 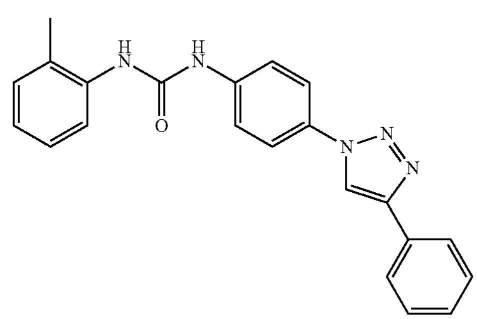 [SMILES: Cc1ccccc1NC(=O)Nc1ccc(-n2cc(-c3ccccc3)nn2)cc1] | nd |

TABLE 5-continued

Activity of representative compounds of the invention against DDX3 RNase.

| Compound ID | Structure | ID$_{50}$ (μM)[a] |
|---|---|---|
| 20a | 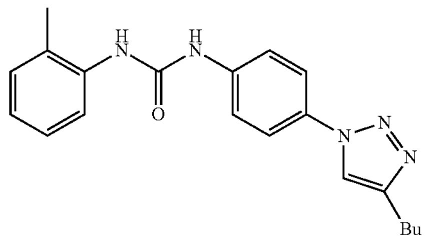 | 0.3 |
| 8b | 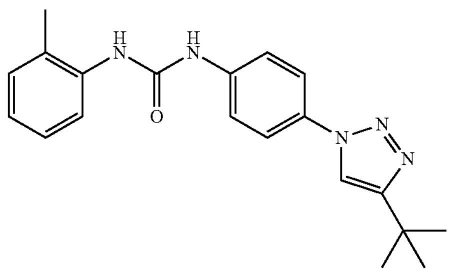 [SMILES: Cc1ccccc1NC(=O)Nc1ccc(-n2cc(C(C)(C)C)nn2)cc1] | 3.36 |
| 8c | 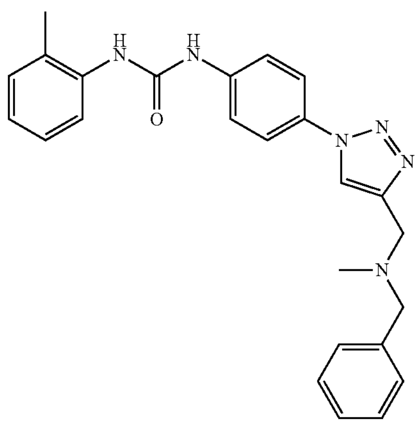 [SMILES: Cc1ccccc1NC(=O)Nc1ccc(-n2cc(CN(C)Cc3ccccc3)nn2)cc1] | 22.8 |
| 8f | 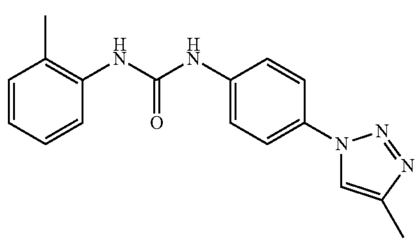 [SMILES: Cc1cn(-c2ccc(NC(=O)Nc3ccccc3C)cc2)nn1] | n.a |
| 8g | 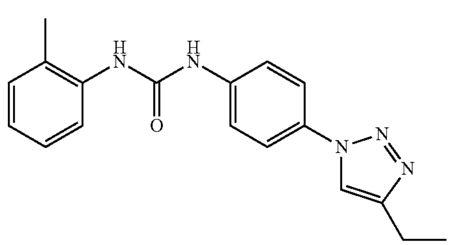 [SMILES: CCc1cn(-c2ccc(NC(=O)Nc3ccccc3C)cc2)nn1] | 0.98 |

TABLE 5-continued

Activity of representative compounds of the invention against DDX3 RNase.

| Compound ID | Structure | ID$_{50}$ (μM)$^a$ |
|---|---|---|
| 20b | 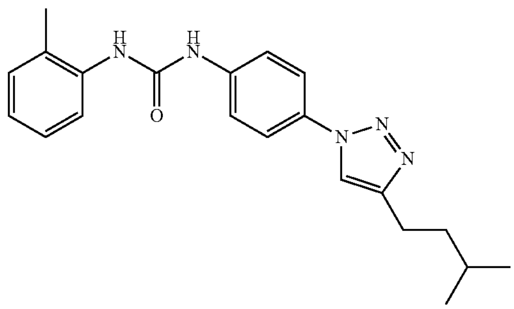 [SMILES: Cc1ccccc1NC(=O)Nc1ccc(-n2cc(CCC(C)C)nn2)cc1] | 0.5 |
| 20e | 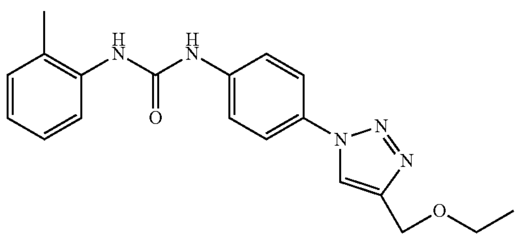 [SMILES: CCOCc1cn(-c2ccc(NC(=O)Nc3ccccc3C)cc2)nn1] | 0.94 |
| 20f | 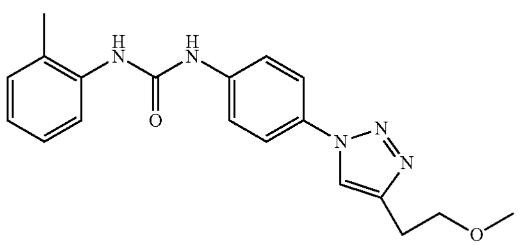 [SMILES: COCCc1cn(-c2ccc(NC(=O)Nc3ccccc3C)cc2)nn1] | 1 |
| 22a | 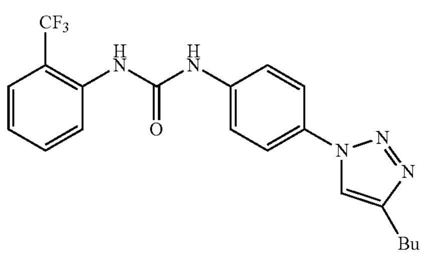 | 0.3 |
| 22b | 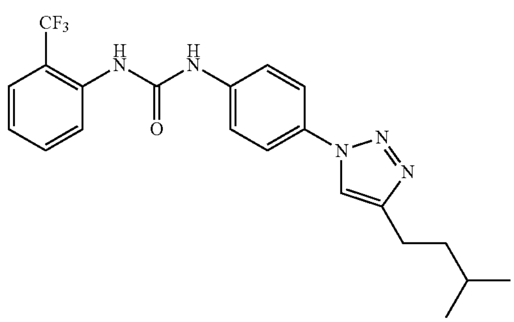 [SMILES: CC(C)CCc1cn(-c2ccc(NC(=O)Nc3ccccc3C(F)(F)F)cc2)nn1] | 0.17 |

TABLE 5-continued
Activity of representative compounds of the invention against DDX3 RNase.
| Compound ID | Structure | ID$_{50}$ (μM)[a] |
|---|---|---|
| 20d | 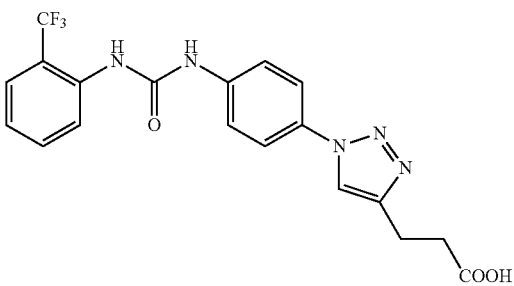 [SMILES: O=C(O)CCc1cn(-c2ccc(NC(=O)Nc3ccccc3C(F)(F)F)cc2)nn1] | n.a |
| 22g | 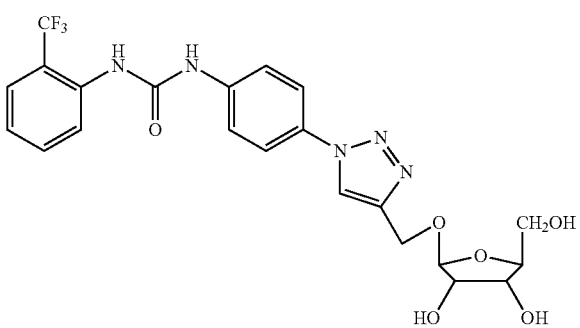 [SMILES: O=C(Nc1ccc(-n2cc(COC3OC(CO)C(O)C3O)nn2)cc1)Nc1ccccc1C(F)(F)F] | n.a |
| 35a | 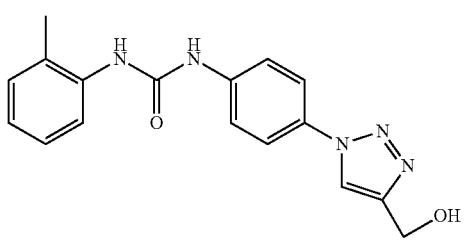 [SMILES: Cc1ccccc1NC(=O)Nc1ccc(-n2cc(CO)nn2)cc1] | 17.5 |
| 35b | 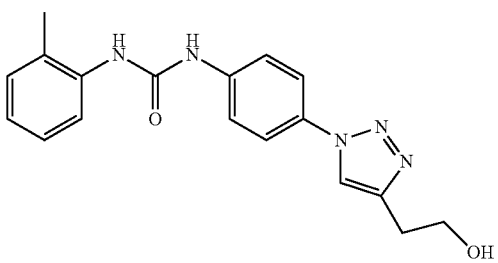 [SMILES: Cc1ccccc1NC(=O)Nc1ccc(-n2cc(CCO)nn2)cc1] | 20 |
| 35e | 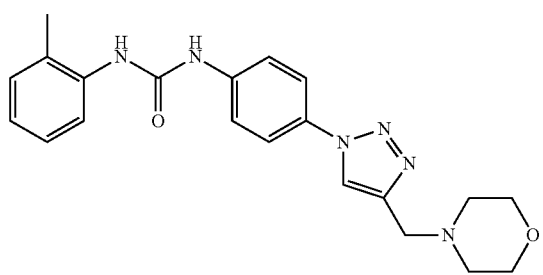 [SMILES: Cc1ccccc1NC(=O)Nc1ccc(-n2cc(CN3CCOCC3)nn2)cc1] | n.a |

TABLE 5-continued
Activity of representative compounds of the invention against DDX3 RNase.
| Compound ID | Structure | ID$_{50}$ (μM)$^a$ |
|---|---|---|
| 35h | 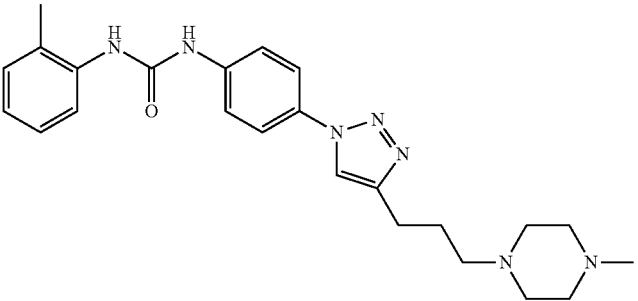 [SMILES: Cc1ccccc1NC(=O)Nc1ccc(-n2cc(CCCN3CCN(C)CC3)nn2)cc1] | 40 |
| 35i | 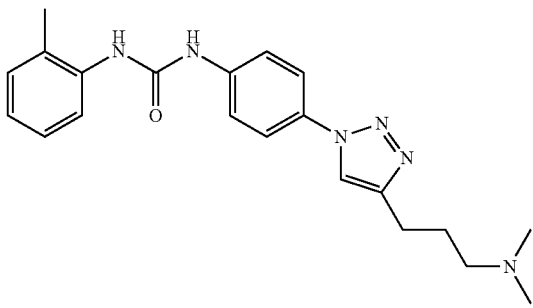 [SMILES: Cc1ccccc1NC(=O)Nc1ccc(-n2cc(CCCN(C)C)nn2)cc1] | 2.9 |
| 36 | 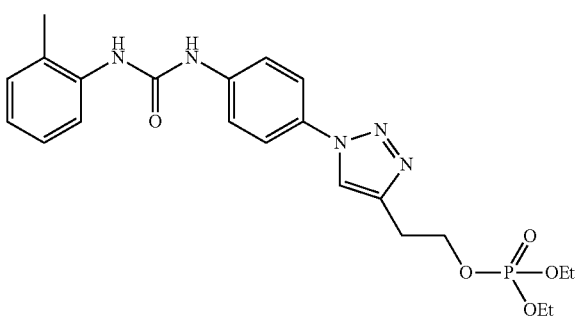 [SMILES: CCOP(=O)(OCC)OCCc1cn(-c2ccc(NC(=O)Nc3ccccc3C)cc2)nn1] | 0.9 |
| 37 | 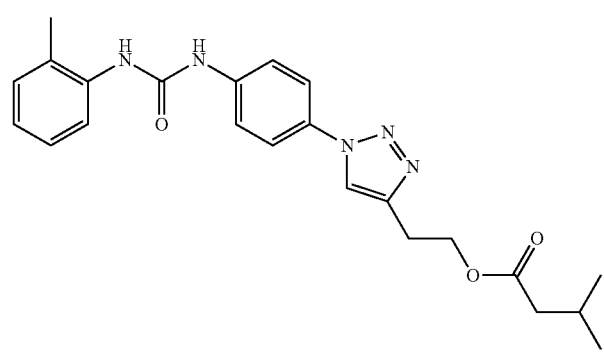 [SMILES: Cc1ccccc1NC(=O)Nc1ccc(-n2cc(CCOC(=O)CC(C)C)nn2)cc1] | 1.3 |

TABLE 5-continued

Activity of representative compounds of the invention against DDX3 RNase.

| Compound ID | Structure | ID$_{50}$ (μM)$^a$ |
|---|---|---|
| 38 | 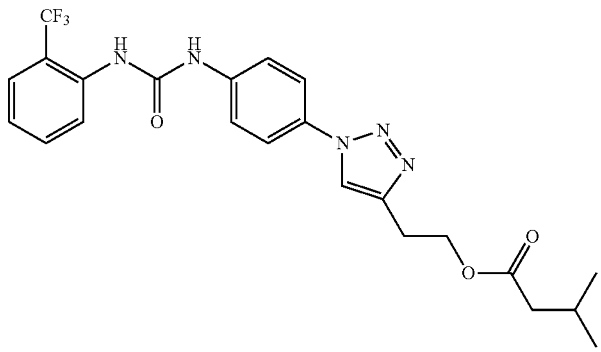 [SMILES: CC(C)CC(=O)OCCc1cn(-c2ccc(NC(=O)Nc3ccccc3C(F)(F)F)cc2)nn1] | 0.4 |
| 39 | 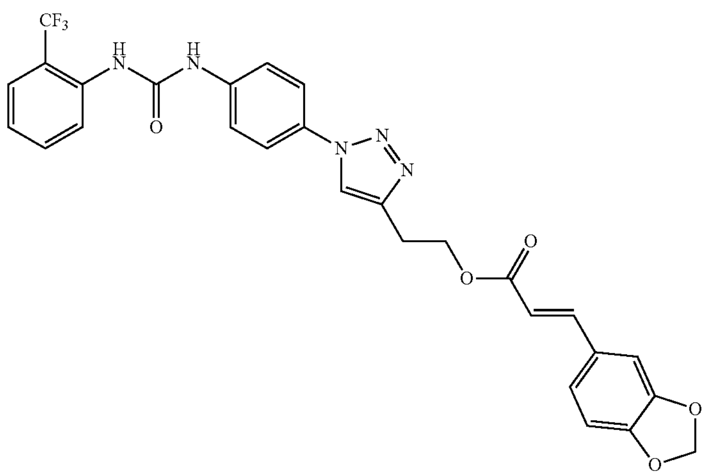 [SMILES: O=C(Nc1ccc(-n2cc(CCOC(=O)/C=C/c3ccc4c(c3)OCO4)nn2)cc1)Nc1ccccc1C(F)(F)F] | 5.1 |
| 42c | 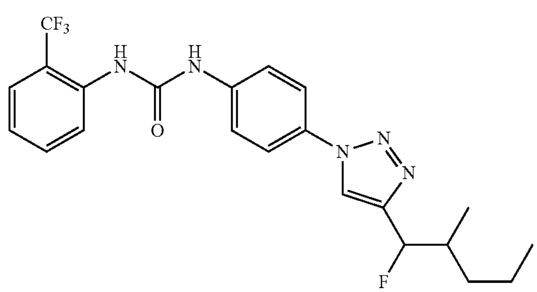 [SMILES: CCCC(C)C(F)c1cn(-c2ccc(NC(=O)Nc3ccccc3C(F)(F)F)cc2)nn1] | 0.3 |
| 20c | 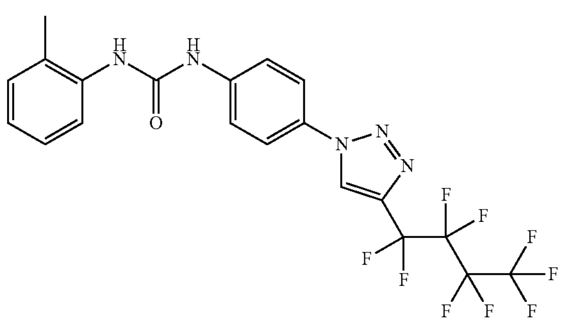 [SMILES: Cc1ccccc1NC(=O)Nc1ccc(-n2cc(C(F)(F)C(F)(F)C(F)(F)C(F)(F)F)nn2)cc1] | 6 |

TABLE 5-continued

Activity of representative compounds of the invention against DDX3 RNase.

| Compound ID | Structure | ID$_{50}$ (μM)[a] |
|---|---|---|
| 81 | 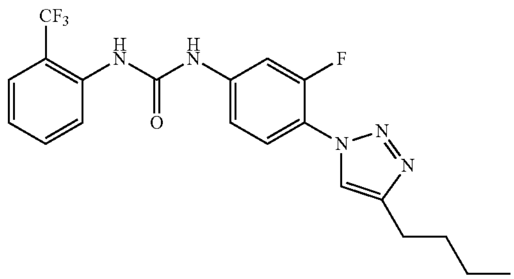 [SMILES: CCCCc1cn(-c2ccc(NC(=O)Nc3ccccc3C(F)(F)F)cc2F)nn1] | 1 |
| 49 | 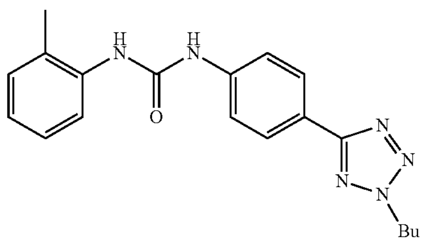 | 4.9 |
| 50 | 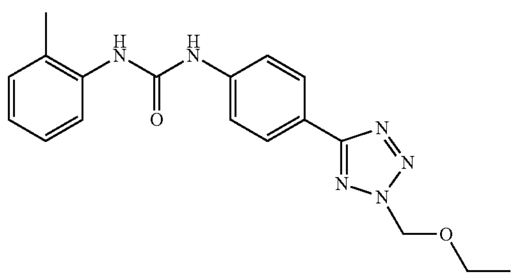 [SMILES: CCOCn1nnc(-c2ccc(NC(=O)Nc3ccccc3C)cc2)n1] | 14 |
| 51 | 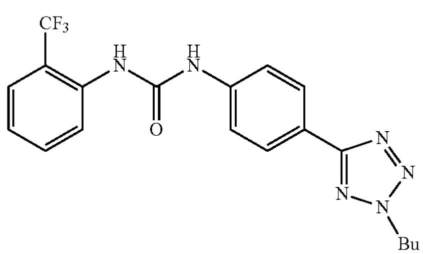 | 0.8 |
| 52 | 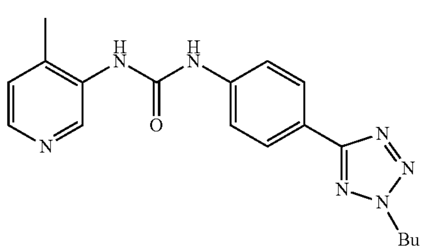 | 2.49 |

TABLE 5-continued

Activity of representative compounds of the invention against DDX3 RNase.

| Compound ID | Structure | ID$_{50}$ (μM)$^a$ |
|---|---|---|
| 55a | 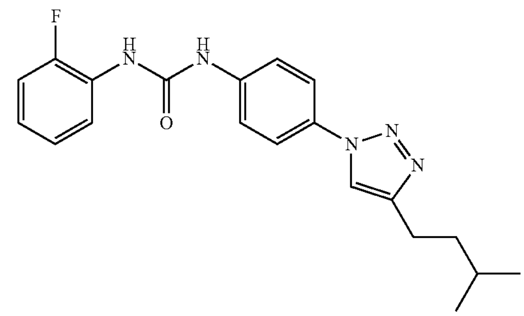 [SMILES: CC(C)CCc1cn(-c2ccc(NC(=O)Nc3ccccc3F)cc2)nn1] | 0.12 |
| 55b | 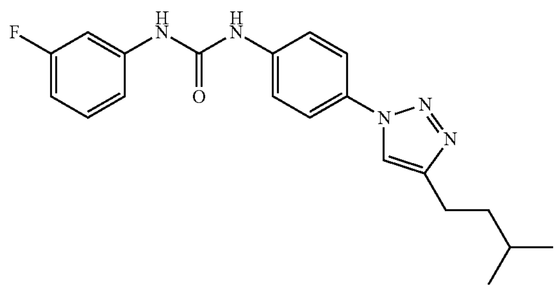 [SMILES: CC(C)CCc1cn(-c2ccc(NC(=O)Nc3cccc(F)c3)cc2)nn1] | 0.2 |
| 55e | 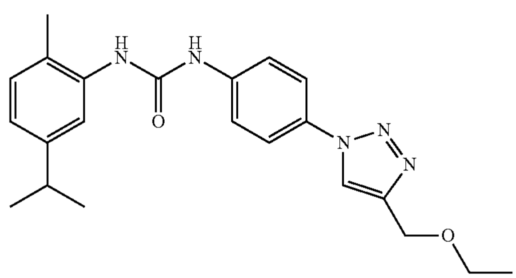 [SMILES: CCOCc1cn(-c2ccc(NC(=O)Nc3cc(C(C)C)ccc3C)cc2)nn1] | 0.9 |
| 55f | 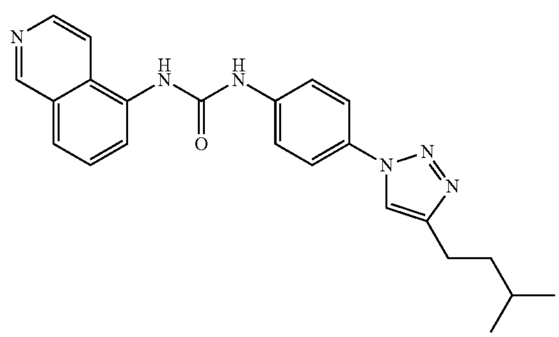 [SMILES: CC(C)CCc1cn(-c2ccc(NC(=O)Nc3cccc4cnccc34)cc2)nn1] | 0.5 |
| 55g | 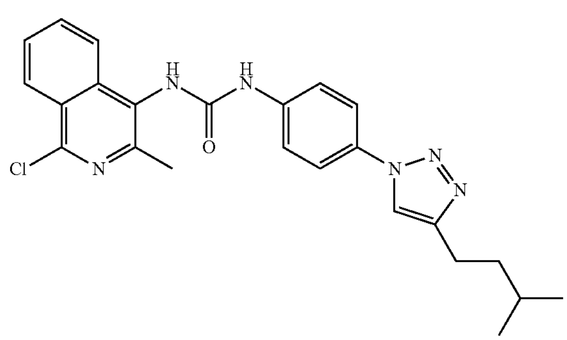 [SMILES: Cc1nc(Cl)c2ccccc2c1NC(=O)Nc1ccc(-n2cc(CCC(C)C)nn2)cc1] | 10 |

TABLE 5-continued

Activity of representative compounds of the invention against DDX3 RNase.

| Compound ID | Structure | ID$_{50}$ (μM)$^a$ |
|---|---|---|
| 15a | 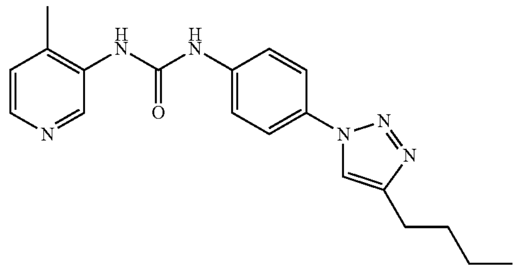 [SMILES: CCCCc1cn(-c2ccc(NC(=O)Nc3cnccc3C)cc2)nn1] | 1.47 |
| 15b | 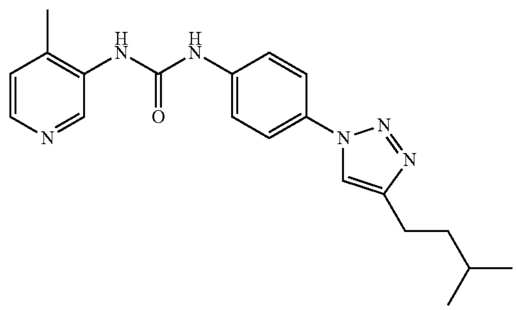 | 2.0 |
| 58a | 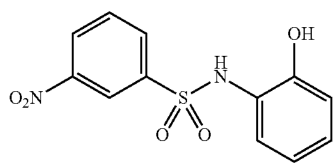 [SMILES: O=[N+]([O-])c1cccc(S(=O)(=O)Nc2ccccc2O)c1] | 0.37 |
| 64a | 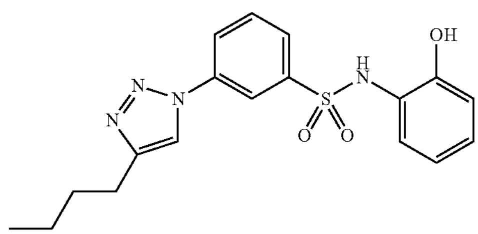 [SMILES: CCCCc1cn(-c2cccc(S(=O)(=O)Nc3ccccc3O)c2)nn1] | n.d* |
| 64b | 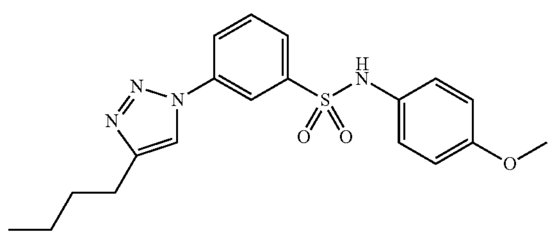 [SMILES: CCCCc1cn(-c2cccc(S(=O)(=O)Nc3ccc(OC)cc3)c2)nn1] | 52.2 |
| 64d | 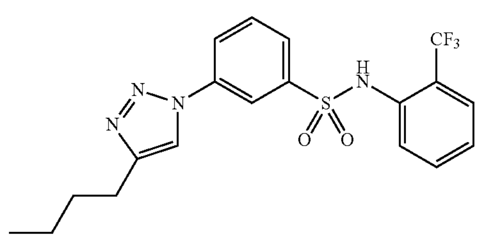 [SMILES: CCCCc1cn(-c2cccc(S(=O)(=O)Nc3ccccc3C(F)(F)F)c2)nn1] | 0.4 |

TABLE 5-continued

Activity of representative compounds of the invention against DDX3 RNase.

| Compound ID | Structure | ID$_{50}$ (μM)$^a$ |
|---|---|---|
| 66d | 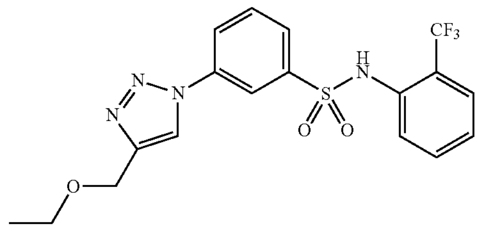 [SMILES: CCOCc1cn(-c2cccc(S(=O)(=O)Nc3ccccc3C(F)(F)F)c2)nn1] | 0.4 |
| 67d | 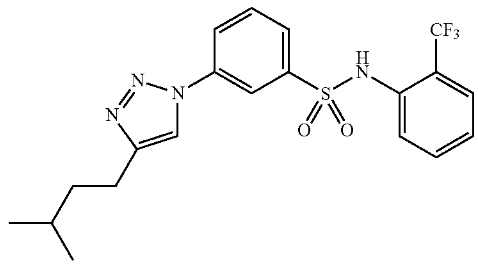 [SMILES: CC(C)CCc1cn(-c2cccc(S(=O)(=O)Nc3ccccc3C(F)(F)F)c2)nn1] | n.a |
| 64e | 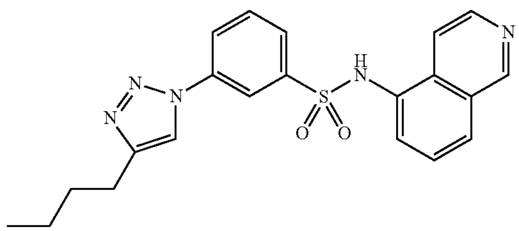 [SMILES: CCCCc1cn(-c2cccc(S(=O)(=O)Nc3cccc4cnccc34)c2)nn1] | 0.16 |
| 68e | 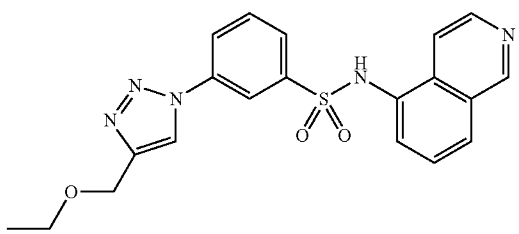 | n.d* |
| 65a | 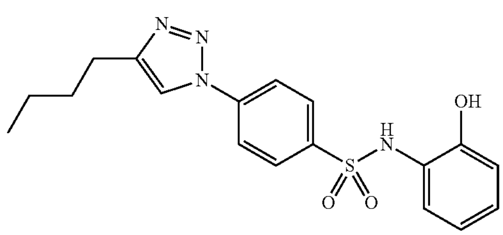 | 15.5 |
| 65c | 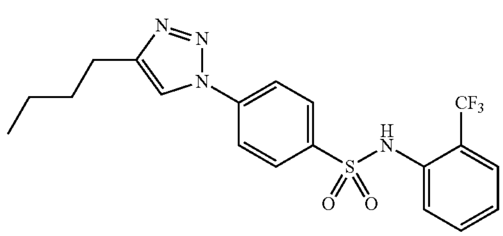 [SMILES: CCCCc1cn(-c2ccc(S(=O)(=O)Nc3ccccc3C(F)(F)F)cc2)nn1] | n.a |

TABLE 5-continued

Activity of representative compounds of the invention against DDX3 RNase.

| Compound ID | Structure | ID$_{50}$ (μM)$^a$ |
|---|---|---|
| 134 | 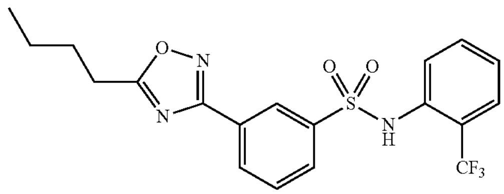 [SMILES: CCCCc1nc(-c2cccc(S(=O)(=O)Nc3ccccc3C(F)(F)F)c2)no1] | 1 |
| 112 | 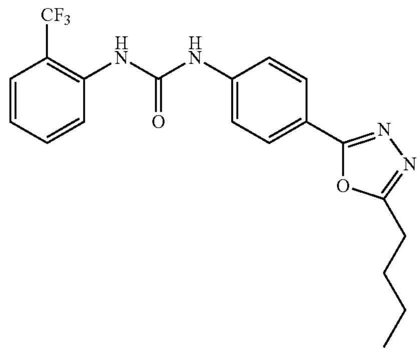 [SMILES: CCCCc1nnc(-c2ccc(NC(=O)Nc3ccccc3C(F)(F)F)cc2)o1] | 1 |
| 106 | 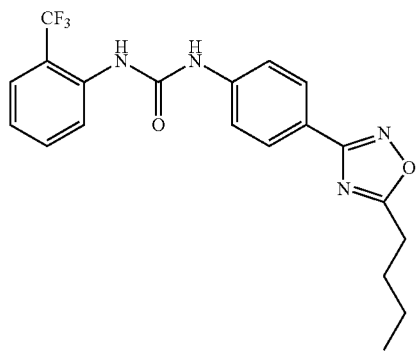 [SMILES: CCCCc1nc(-c2ccc(NC(=O)Nc3ccccc3C(F)(F)F)cc2)no1] | 0.1 |
| 8e | 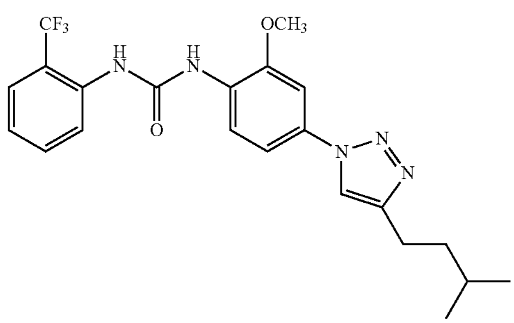 [SMILES: COc1cc(-n2cc(CCC(C)C)nn2)ccc1NC(=O)Nc1ccccc1C(F)(F)F] | 0.6 |
| 80 | 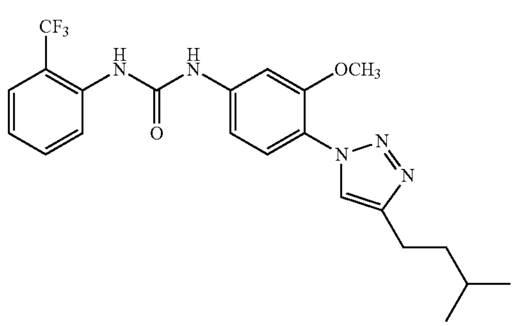 [SMILES: COc1cc(NC(=O)Nc2ccccc2C(F)(F)F)ccc1-n1cc(CCC(C)C)nn1] | 0.4 |

TABLE 5-continued

Activity of representative compounds of the invention against DDX3 RNase.

| Compound ID | Structure | ID$_{50}$ (μM)$^a$ | |
|---|---|---|---|
| 86 | 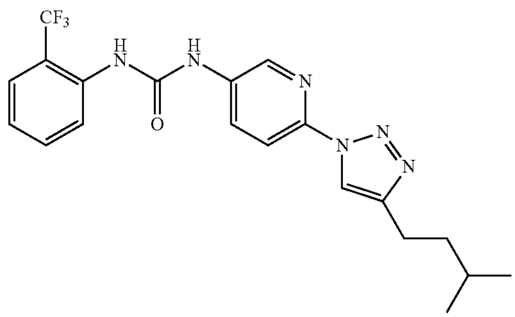 [SMILES: CC(C)CCc1cn(-c2ccc(NC(=O)Nc3ccccc3C(F)(F)F)cn2)nn1] | 51 | 1 |
| 55h | 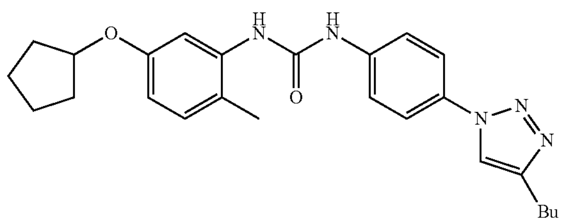 | 0.1 | |
| 124 | 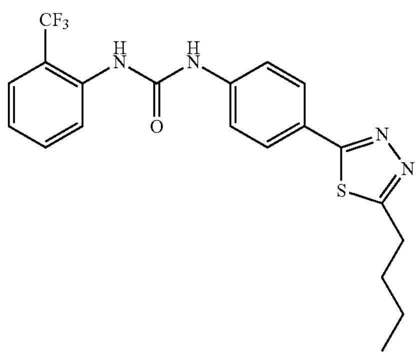 | nd* | |
| 119 | 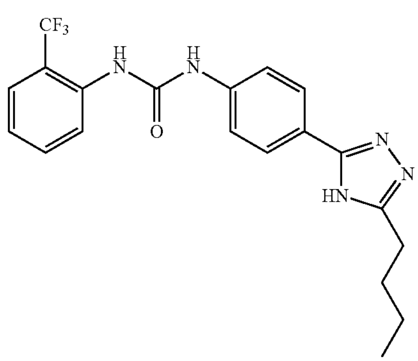 [SMILES: CCCCc1nnc(-c2ccc(NC(=O)Nc3ccccc3C(F)(F)F)cc2)[nH]1] | 1 | |

$^a$IC$_{50}$: inhibiting concentration 50 or needed dose to inhibit 50% of the enzyme, n.a Compound not active.
*not determined compound reprecipitate from medium Several DDX3 inhibitors of the invention showed submicromolar activity. In particular compounds 22b, 55a, 55b, 64e are approximately ten-fold more active than compound EI01D previously reported.

TABLE 6

Selectivity data on compound 20a

| ATPase DDX3 IC50, µM | DDX1 IC50, µM | NS3 (DENV) IC50, µM | NS3 (HCV) IC50, µM |
|---|---|---|---|
| >200 | >200 | >200 | 16.8 |

[a] The value >200 indicates that less than 20% of inhibition was observed at 200 µM, the highest concentration tested.

Anticancer Activity

Selected compounds from Table 5 were tested against the hyperproliferative disorders in which DDX3 is involved.

The anticancer potencies of representative compounds are summarized in the Tables 7-18 below. It is important to note that DDX3 inhibitors identified are able to inhibit the proliferation of different cancer cell-lines such as: Human Prostate Adenocarcinoma cell line -LNCaP, Human Prostate cell line derived from brain metastasis DU-145, Human Prostate carcinoma epithelial cell line 22Rv1, Human Prostate cancer cell line (PC3), Human Neuroblastoma cell line SH-SY5Y, Human breast adenocarcinoma cell line MDA-MB-231, Human cervical carcinoma cell line HeLa, Human Glioblastoma cell line U 87, Human adenocarcinomic alveolar basal epithelial cell line A549, Human colorectal carcinoma cell line HCT116, Human osteosarcoma cell line U205, Human head and neck squamous carcinoma cell line HN6, Human muscle rhabdomyosarcoma cell line RD18, Human brain glioblastoma cell line DBTRG, Human medulloblastoma cell line DAOY.

Example 26

TABLE 7

Anti-hyperproliferative activity against Human Prostate cell lines:

| Compound ID | $IC_{50}^{a}$ | $IC_{50}^{b}$ | $IC_{50}^{c}$ | $IC_{50}^{d}$ |
|---|---|---|---|---|
| 64d | 16.7 µM | 3.0 µM | 14 µM | nt* |
| 64e | nt* | 16 µM | 11 µM | nt* |
| 22a | nt | 0.1 µM | nt | 25.6 µM |
| 55f | nt | 0.6 µM | nt | 32.4 µM |
| 119 | nt | 12.9 µM | nt | 46.3 µM |

$^{a}IC_{50}$: Half maximal inhibitory concentration evaluated in Human Prostate Adenocarcinoma cell line (LNCaP),
$^{b}IC_{50}$: Half maximal inhibitory concentration evaluated in Human Prostate cell line derived from brain metastasis (DU-145),
$^{c}IC_{50}$: Half maximal inhibitory concentration evaluated in Human Prostate carcinoma epithelial cell line (22Rv1),
$^{d}IC_{50}$: Half maximal inhibitory concentration evaluated in Human Prostate cancer cell line (PC3),
nt* not tested.

Example 27

TABLE 8

Anti-hyperproliferative activity against Human Neuroblastoma cell line:

| Compound ID | $IC_{50}$ (µM)$^{a}$ |
|---|---|
| 20a | 149 |
| 64d | 18.8 |

$^{a}IC_{50}$: Half maximal inhibitory concentration evaluated in Human Neuroblastoma cell line (SH-SY5Y).

Example 28

TABLE 9

Anti-hyperproliferative activity against Human breast adenocarcinoma cell line:

| Compound ID | $IC_{50}$ (µM)$^{a}$ |
|---|---|
| 20a | 18.7 |
| 64d | 15.7 |
| 50 | 23.5 |
| 81 | 25.1 |
| 64e | 9.3 |
| 22b | 13.1 |
| 22a | 1.4 |
| 112 | 33.6 |
| 42c | 33.6 |

$^{a}IC_{50}$: Half maximal inhibitory concentration evaluated in Human breast adenocarcinoma cell line (MDA-MB-231).

Example 29

TABLE 10

Anti-hyperproliferative activity against Human cervical carcinoma cell line:

| Compound ID | $IC_{50}^{a}$ |
|---|---|
| 20a | 54 mM |
| 64d | 51.7 µM |
| 22a | 6.29 µM |

$^{a}IC_{50}$: Half maximal inhibitory concentration evaluated in Human cervical carcinoma cell line (HeLa).

Example 30

TABLE 11

Anti-hyperproliferative activity against Human Glioblastoma cell line:

| Compound ID | $IC_{50}^{a}$ |
|---|---|
| 20a | 37 mM |
| 64d | 87 µM |

$^{a}IC_{50}$: Half maximal inhibitory concentration evaluated in Human Glioblastoma cell line (U87).

Example 31

TABLE 12

Anti-hyperproliferative activity against human adenocarcinomic alveolar cells:

| Compound ID | $IC_{50}$ (µM)$^{a}$ |
|---|---|
| 22a | 1.4 |
| 64d | 21.3 |
| 112 | 57.1 |
| 106 | 32.6 |
| 42c | 57.2 |
| 119 | 14.0 |
| 64e | 28.5 |

$^{a}IC_{50}$: Half maximal inhibitory concentration evaluated in Human adenocarcinomic alveolar basal epithelial cell line (A549).

Example 32

TABLE 13

Anti-hyperproliferative activity against human colorectal carcinoma cells:

| Compound ID | IC$_{50}$ (μM)$^a$ |
|---|---|
| 22a | 3.9 |
| 112 | 38.2 |
| 106 | 36.8 |

$^a$IC$_{50}$: Half maximal inhibitory concentration evaluated in Human colorectal carcinoma cell line (HCT116).

Example 33

TABLE 14

Anti-hyperproliferative activity against human osteosarcoma cells:

| Compound ID | IC$_{50}$ (μM)$^a$ |
|---|---|
| 22a | 4.2 |
| 51 | 51.5 |
| 106 | 35.35 |
| 124 | 60.1 |
| 42c | 22.5 |

$^a$IC$_{50}$: Half maximal inhibitory concentration evaluated in Human osteosarcoma cell line (U2OS).

Example 34

TABLE 15

Anti-hyperproliferative activity against human head and neck squamous carcinoma cells:

| Compound ID | IC$_{50}$ (μM)$^a$ |
|---|---|
| 22a | 0.8 |
| 55f | 6.1 |
| 51 | 16.4 |
| 112 | 75.7 |
| 106 | 18.2 |
| 42c | 6.32 |

$^a$IC$_{50}$: Half maximal inhibitory concentration evaluated in Human head and neck squamous carcinoma cell line (HN6).

Example 35

TABLE 16

Anti-hyperproliferative activity against human muscle rhabdomyosarcoma cells:

| Compound ID | IC$_{50}$ (μM)$^a$ |
|---|---|
| 22a | 3.2 |

$^a$IC$_{50}$: Half maximal inhibitory concentration evaluated in Human muscle rhabdomyosarcoma cell line (RD18).

Example 36

TABLE 17

Anti-hyperproliferative activity against human brain glioblastoma cells:

| Compound ID | IC$_{50}$$^a$ |
|---|---|
| 22a | 5.8 μM |

$^a$IC$_{50}$: Half maximal inhibitory concentration evaluated in Human brain glioblastoma cell line (DBTRG).

Example 37

TABLE 18

Anti-hyperproliferative activity against human medulloblastoma cells:

| Compound ID | IC$_{50}$$^a$ |
|---|---|
| 22a | 3.3 μM |

$^a$IC$_{50}$: Half maximal inhibitory concentration evaluated in Human medulloblastoma cell line (DAOY).

The results demonstrate that compounds showed broad spectrum anticancer activity against different cancer cell lines (Human Prostate Adenocarcinoma cell line -LNCaP, Human Prostate cell line derived from brain metastasis DU-145, Human Prostate carcinoma epithelial cell line 22Rv1, Human Prostate cancer cell line (PC3), Human Neuroblastoma cell line SH-SY5Y, Human breast adenocarcinoma cell line MDA-MB-231, Human cervical carcinoma cell line HeLa, Human Glioblastoma cell line U 87, Human adenocarcinomic alveolar basal epithelial cell line A549, Human colorectal carcinoma cell line HCT116, Human osteosarcoma cell line U205, Human head and neck squamous carcinoma cell line HN6, Human muscle rhabdomyosarcoma cell line RD18, Human brain glioblastoma cell line DBTRG, Human medulloblastoma cell line DAOY.

The results obtained and reported in the Examples show that the compounds of the invention were able to:
1) Inhibit helicase activity of human DDX3 protein by interacting with the RNA binding site and interfering with the subsequent catalytic steps;
2) Suppress cellular proliferation in Human Prostate Adenocarcinoma cell line -LNCaP, Human Prostate cell line derived from brain metastasis DU-145, Human Prostate carcinoma epithelial cell line 22Rv1, Human Prostate cancer cell line (PC3), Human Neuroblastoma cell line SH-SY5Y, Human breast adenocarcinoma cell line MDA-MB-231, Human cervical carcinoma cell line HeLa, Human Glioblastoma cell line U 87, Human adenocarcinomic alveolar basal epithelial cell line A549, Human colorectal carcinoma cell line HCT116, Human osteosarcoma cell line U205, Human head and neck squamous carcinoma cell line HN6, Human muscle rhabdomyosarcoma cell line RD18, Human brain glioblastoma cell line DBTRG, Human medulloblastoma cell line DAOY.

REFERENCES

1. Paul Ahlquist, et al., *J. Virol.* 2003, 15, 8181-8186.
2. Andrew Prussia, et al., *Int. J. Mol. Sci.* 2011, 12, 4027-4052.

3. Brian M. Friedrich, et al., *Virus Research* 2011, 161, 101-114.
4. Rupp D, et al., *Semin Liver Dis.* 2014, 34, 9-21.
5. Garbelli, A., et al., *Curr Med Chem.;* 2011, 18, 3015-3027.
6. Chen H H, et al., *Oncogene.* 2015 21:2790-800.
7. Sun M, et al., *Biochim Biophys Acta.* 2011 3, 438-47.
8. Radi, M.; et al., *Med. Chem. Lett.* 2012, 22, 2094-2098.
9. Samal S K, et al., *Sci Rep* (2015) 5, 9982.
10. Bol G M, et al., *EMBO Mol Med* (2015) 7(5):648-669.
11. Yedavalli V S, et al., *Cell* 2004; 119, 381-92.
12. Yang Q, et al., *Nat Struct Mol Biol* 2006; 13, 981-6.
13. Rocak S, et al., *Nat Rev Mol Cell Biol* 2004, 5, 232-41.
14. Kohler A et al., *Nat Rev Mol Cell Biol,* 2007, 8, 761-73.
15. Mardsen S, et al., *J Mol Biol* 2006, 361, 327-35.
16. Shih J W, et al., *Oncogene* 2008, 27, 700-14.
17. Cruciat C M, et al., *Science.* 2013, 339, 1436-41.
18. Botlagunta M, et al., *Oncogene* 2008, 11, 3912-22
19. Kwong A D, et al., *Nat Rev Drug Discov* 2005, 4, 845-53.
20. Wu D W, et al., *Oncogene.* 2014 Mar. 20; 33(12): 1515-26.
21. Soulat D, et al., *EMBO J* 2008, 26, 26.
22. Chang P C, et al., *Oncogene* 2006, 25, 1991-2003.
23. Chao C H, et al., *Cancer Res* 2006, 66, 6579-88.
24. Huang J S, et al., *Biochem Biophys Res Commun* 2004, 315, 950-8.
25. Soto-Rifo R, et al., *EMBO J.,* 2012, 31, 3745-56.
26. Skinner D E, et al., *Trends Parasitol.* 2014, 3, 123-9.
27. Usha Kant Misra; Overview: Japanese encephalitis. *Prog Neurobiol.* 2010, 2, 108-20.
28. Berge S. M. et al., *J. Pharm. Sci.* 1977, 66, 1-19;
29. Gould P. L. *Int. J. Pharm* 1986, 33, 201-217; and Bighley et al. Encyclopedia of Pharmaceutical Technology, Marcel Dekker Inc, New York 1996, Volume 13, page 453-497.
30. Remington "The Science and Practice of Pharmacy", Lippincott Williams & Wilkins, 2000.
31. Paolucci S, et al., *Antimicrob Agents Chemother.* 2004, 48, 4611-7.
32. Wohnsland, F et al., *J. Med. Chem.* 2001 44, 923-930.
33. Sugano, K et al., *J. Biomol. Screen.* 2001, 6, 189-196.
34. Chen J. J et al, *Oncotarget* 2013, 4, 206-217
35. Vella S. et al. *Clin Epigenetics.* 2015 6, 7-82.

The invention claimed is:
1. A method for the treatment of a cancer modulated by DDX3, the method comprising administering to a subject in need thereof an effective amount of a compound of formula:

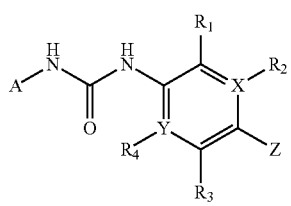

wherein
X and Y are each independently C or N;
A is phenyl substituted by one or more groups independently selected from methyl, isopropyl, $CF_3$, F, Cl, OH, or OMe or unsubstituted or substituted heteroaryl, wherein the one or more substituents on the heteroaryl are independently selected from unsubstituted or substituted $C_1$-$C_6$ alkyl, unsubstituted or substituted $C_2$-$C_6$ alkenyl, unsubstituted or substituted $C_2$-$C_6$ alkynyl, haloalkyl, halogen, $OR_A$, $SR_A$, $S(=O)(=O)—R_A$, $SO_2NHR_A$, $COOR_B$, $OC(O)R_B$, $C(O)R_B$, $NR_AR_B$, $OP(O)(OR_A)_2$, $NHC(O)R_A$, $COONR_AR_B$, OS or

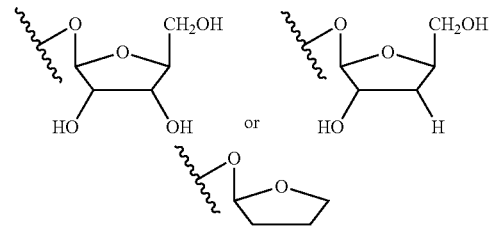

wherein the one or more substituents on the $C_1$-$C_6$ alkyl or on the $C_2$-$C_6$ alkenyl or on the $C_2$-$C_6$ alkynyl are independently selected from $OR_A$, $COOR_B$, $OC(O)R_B$, $C(O)R_B$, $NR_AR_B$, $OP(O)(OR_A)_2$, $NHC(O)R_A$, $NHC(O)OR_A$, $COONR_AR_B$, $SR_A$, $S(=O)(=O)—R_A$, $SO_2NHR_A$;
$R_1$, $R_2$, $R_3$, and $R_4$, are each independently selected from H, halogen, alkoxy, $C_1$-$C_6$ alkyl, haloalkyl, $OR_A$, $SR_A$, $S(=O)(=O)—R_A$, $SO_2NHR_A$, $COOR_B$, $OC(O)R_B$, $NR_AR_B$, $OP(O)(OR_A)_2$, $NHC(O)R_A$, $COONR_AR_B$, $NO_2$, CN;
Z is a heteroaryl group selected from:

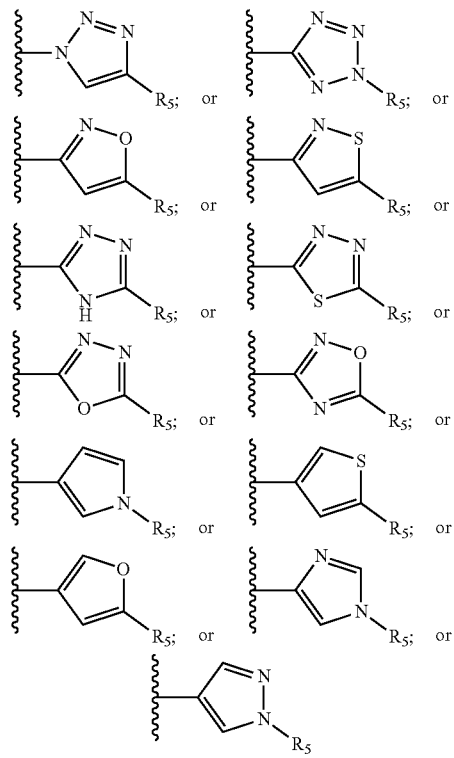

wherein
$R_5$ is H, unsubstituted or substituted $C_1$-$C_{10}$ alkyl, unsubstituted or substituted phenyl, wherein the one or more substituents on the $C_1$-$C_{10}$ alkyl are independently selected from halogen, $OR_A$, $COOR_B$, $OC(O)R_B$, $NR_AR_B$, $OP(O)(OR_A)_2$, $OC(O)NR_AR_B$, $C(O)R_B$, $NHC(O)OR_A$, $NHC(O)R_A$, $COONR_AR_B$, $OC(O)CHCHR_C$,

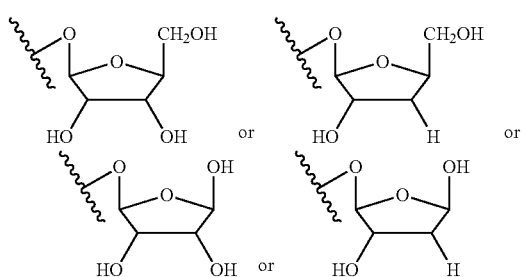

$R_A$ and $R_B$ are each independently selected from H, substituted or unsubstituted $C_1$-$C_6$ alkyl, $C_1$-$C_6$ cycloalkyl, unsubstituted or substituted aralkyl, haloalkyl, or $R_A$ and $R_B$ together with the nitrogen to which they are attached, form a 4-7 membered saturated or partially unsaturated ring optionally containing one or more additional heteroatoms independently selected from N, S and O the ring being optionally substituted by one, two or more groups independently selected from halogen, $C_1$-$C_6$ alkyl, haloalkyl, OH, alkoxy;

$R_C$ is substituted or unsubstituted phenyl or 1,3 benzodioxolyl, wherein the one or more substituent(s) on the phenyl are independently selected from halogen, haloalkyl, alkoxy, $C_1$-$C_3$ alkyl, or OH;

or salt, solvate, stereoisomer thereof, provided that compounds:

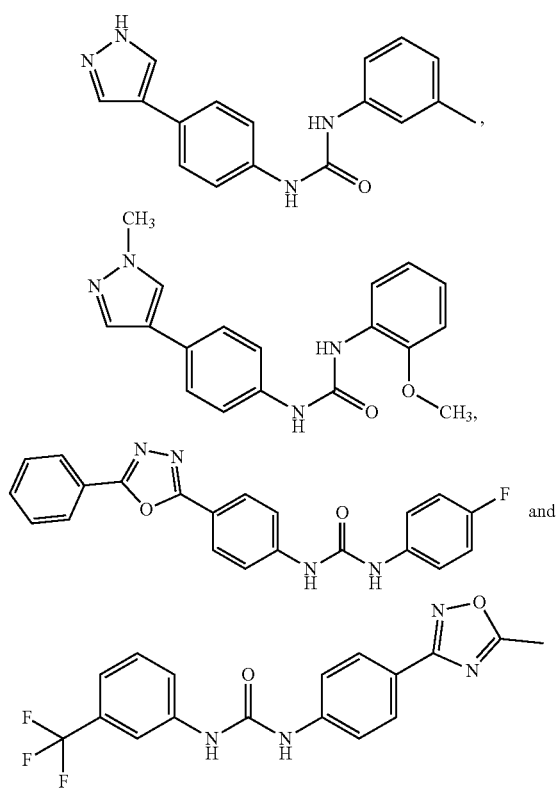

are excluded.

2. The method according to claim 1, wherein X and Y are C.

3. The method according to claim 1 wherein A is phenyl substituted by one or more groups independently selected from methyl, isopropyl, $CF_3$, F, Cl, OH, or OMe.

4. The method according to claim 1, wherein A is unsubstituted or substituted heteroaryl.

5. The method according to claim 4, wherein the substituted heteroaryl is pyridinyl or isoquinolinyl.

6. The method according to claim 1, wherein X and Y are C and A is unsubstituted or substituted heteroaryl.

7. The method according to claim 1, wherein $R_A$ and $R_B$ together with the nitrogen to which they are attached, form a 6 membered saturated ring containing one or more additional heteroatoms independently selected from N and O the ring being selected from morpholinyl or piperazinyl optionally substituted by one, two or more groups independently selected from $C_1$-$C_6$ alkyl, haloalkyl, OH, alkoxy.

8. The method according to claim 1, wherein Z is selected from:

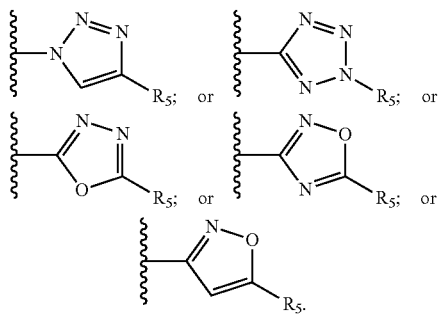

9. A method for the treatment of a cancer modulated by DDX3, the method comprising administering to a subject in need thereof an effective amount of a compound selected from:

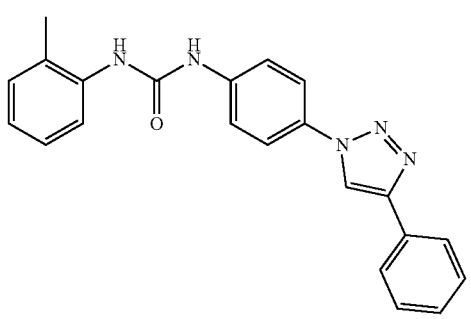

8a

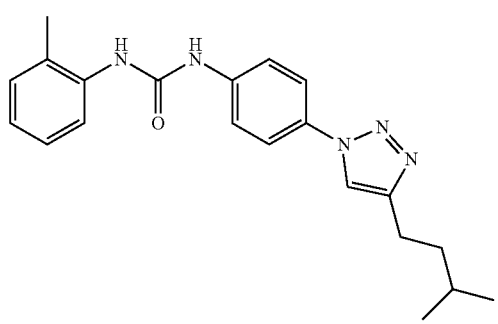

20b

-continued
22b
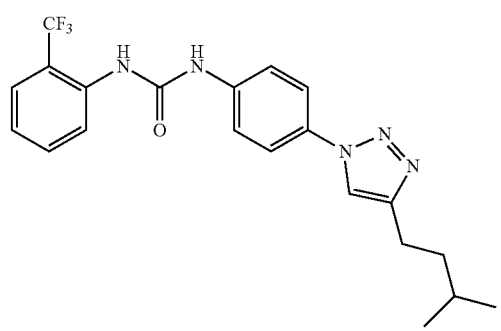
8f
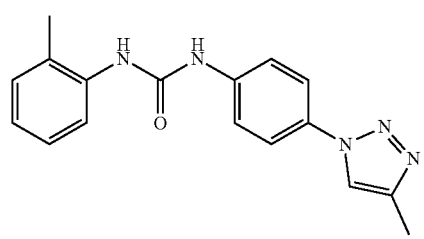
8g
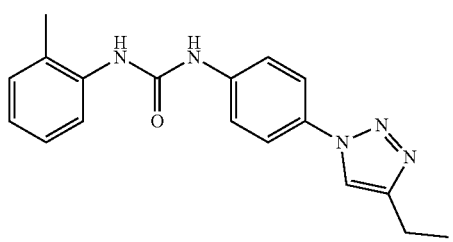
8b
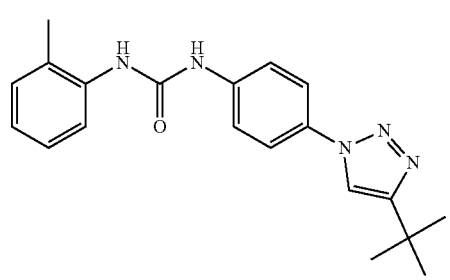
22a
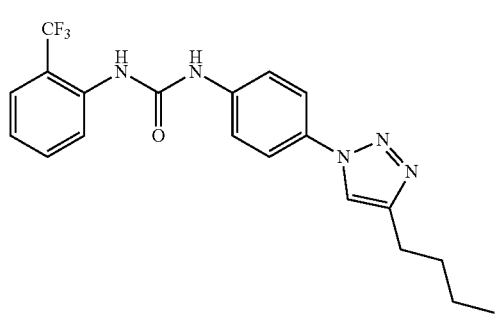
-continued
20a
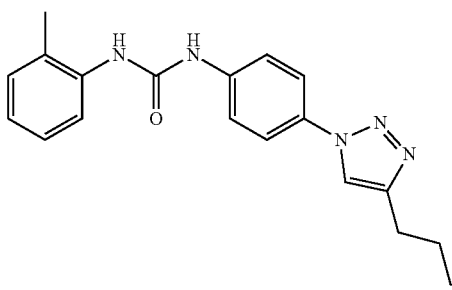
15a
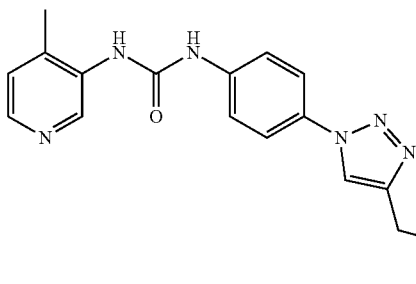
35g
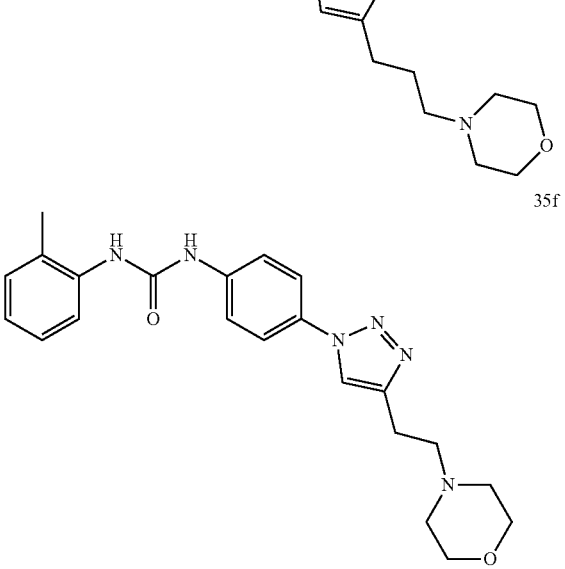
35f
35e
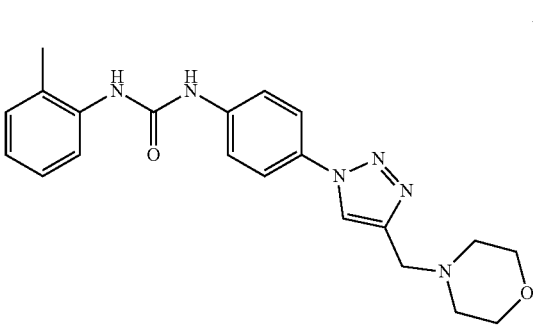

167
-continued
35i
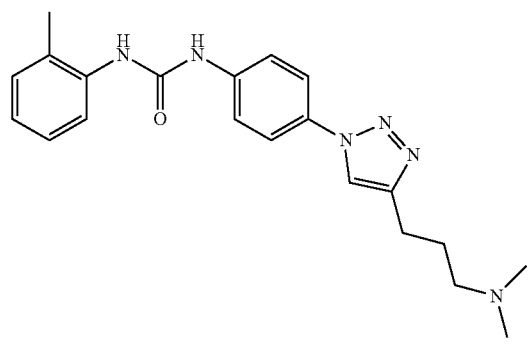
8c
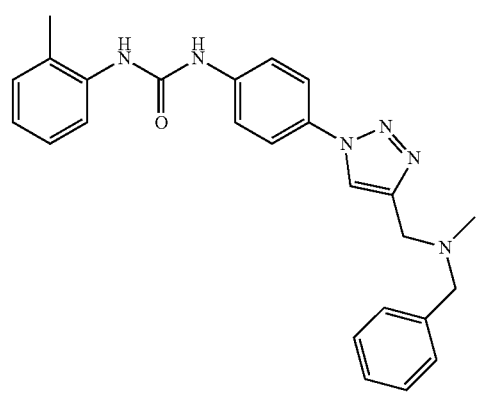
35h
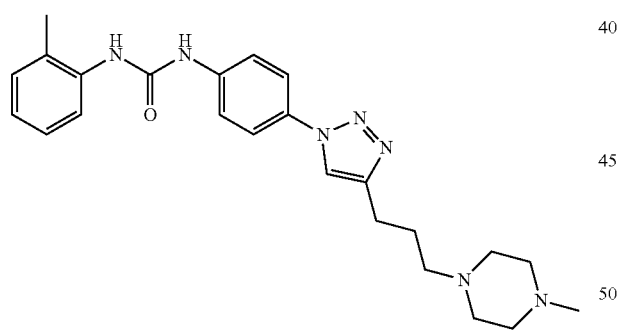
20e
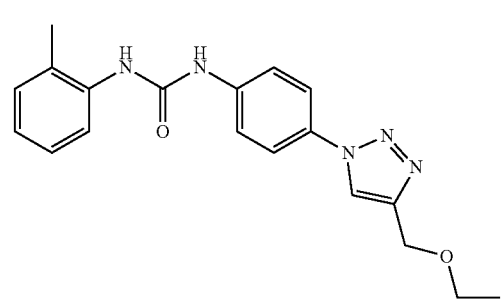
168
-continued
20f
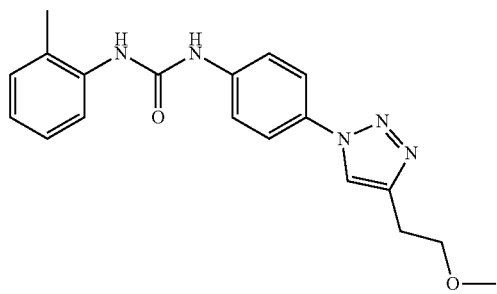
35b
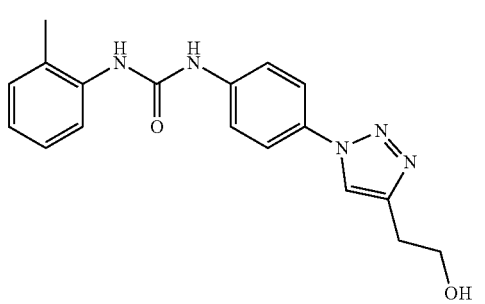
35a
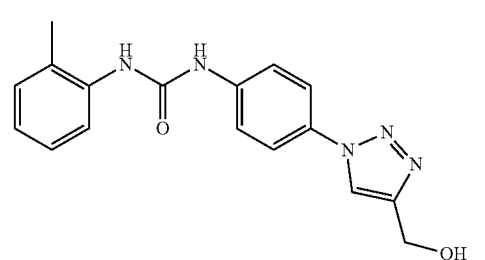
49
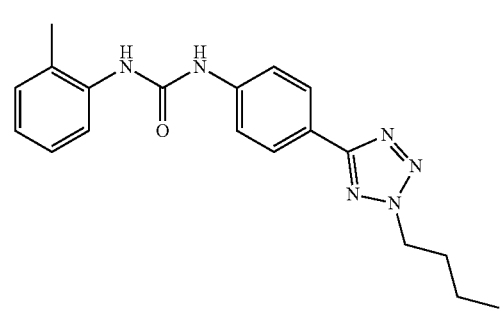
50
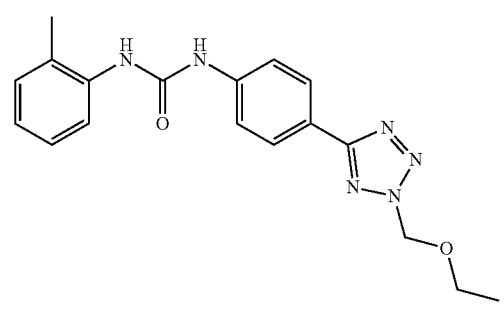

20c
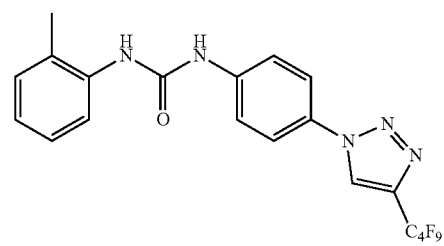
42b
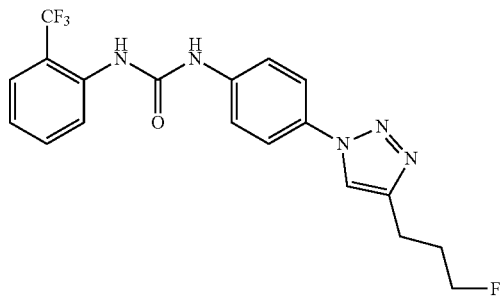
51
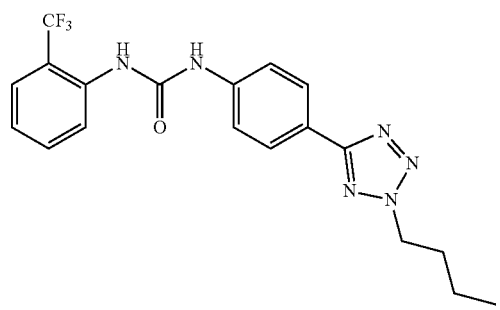
81
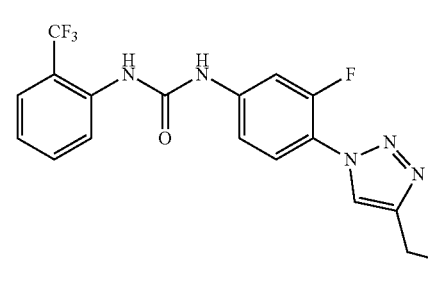
55f
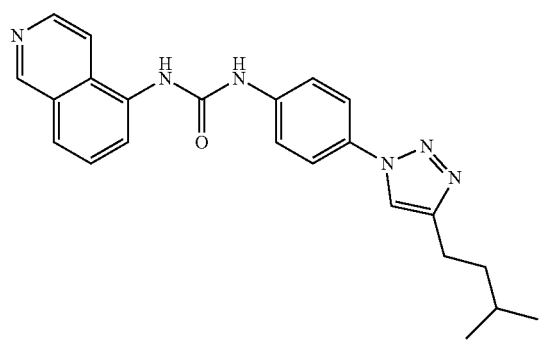
55e
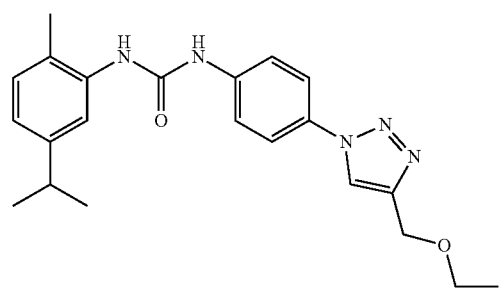
8d
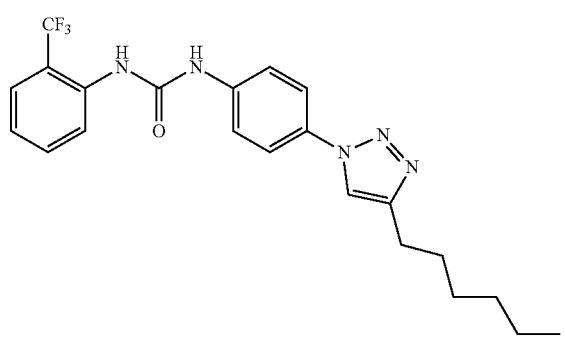
21b
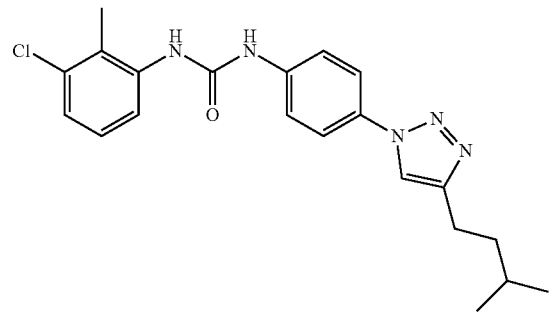
86
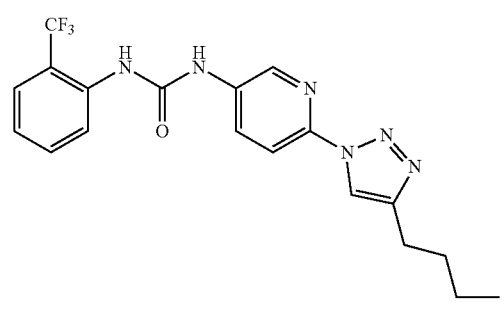
15b
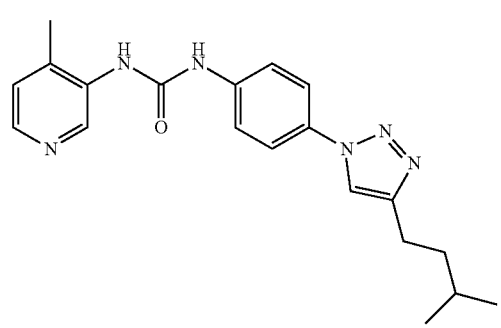

20d
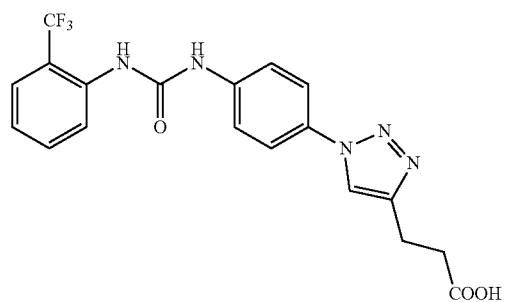
55a
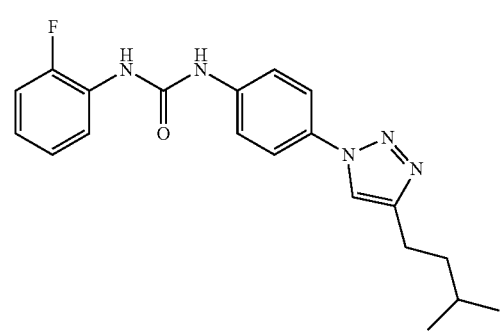
37
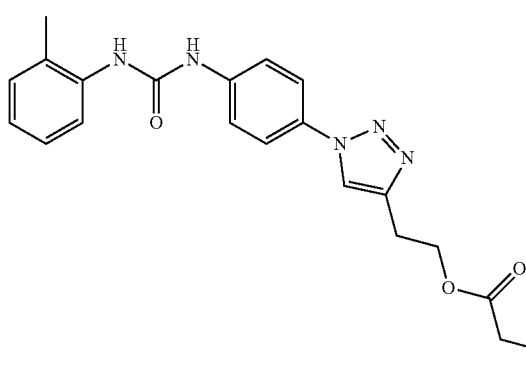
39
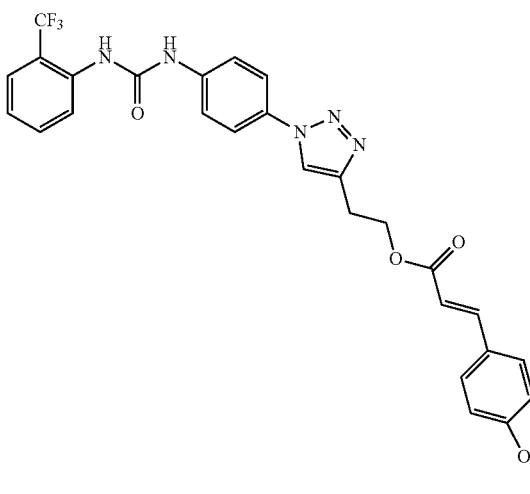
55b
36
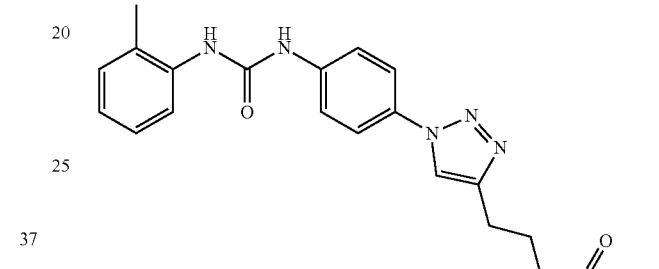
38
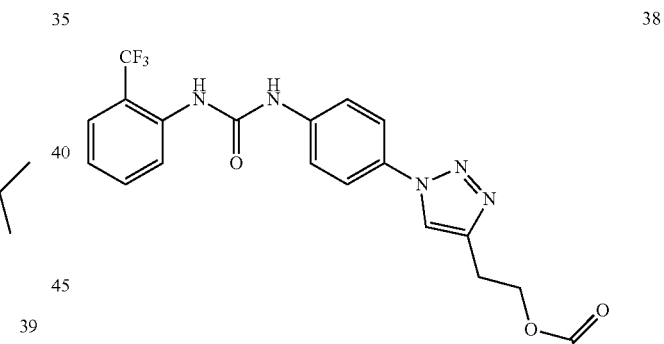
55c
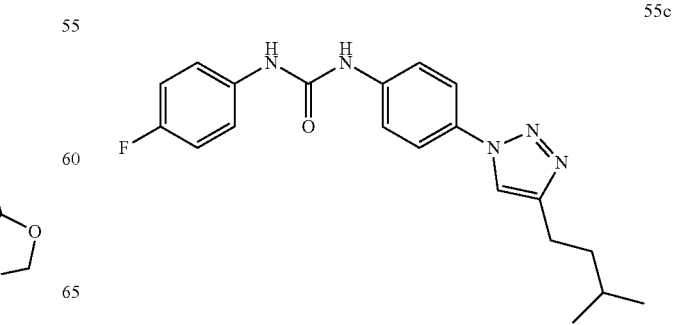

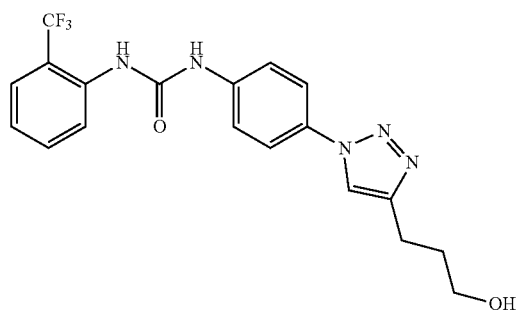 35e
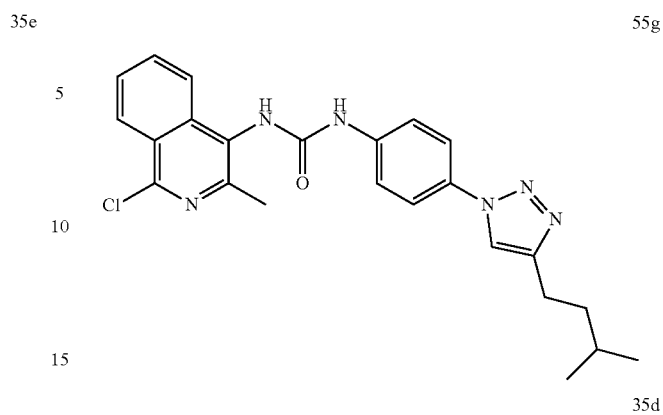 55g
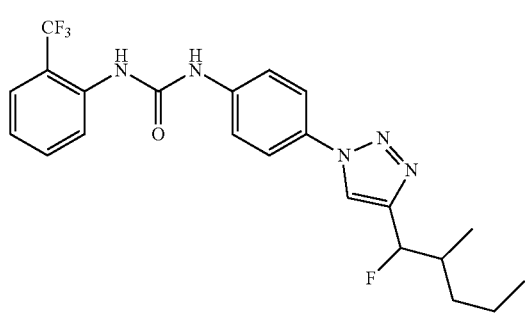 42c
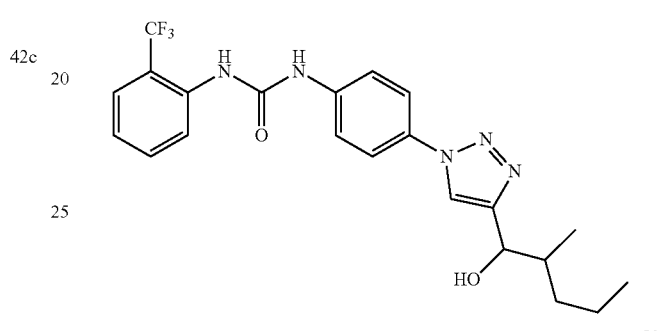 35d
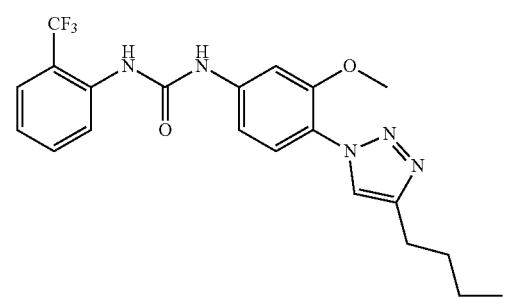 78
 52
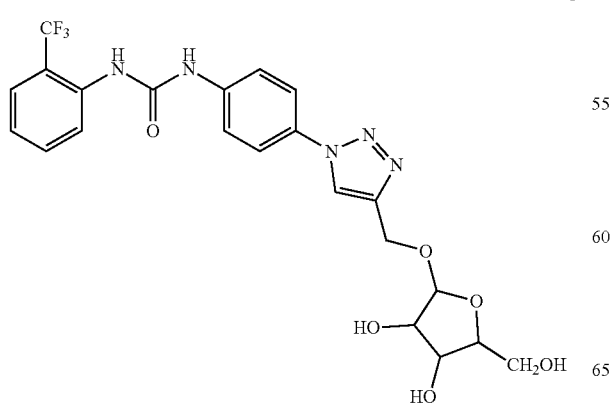 22g
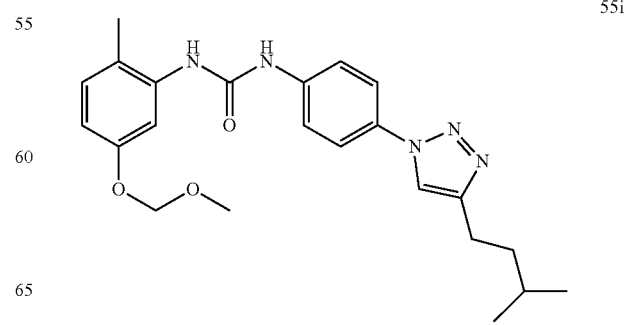 55l
55i

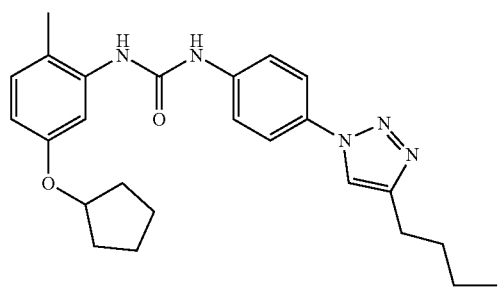
55h
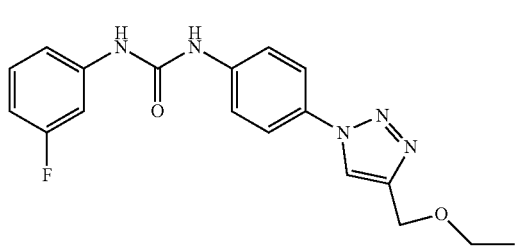
55o
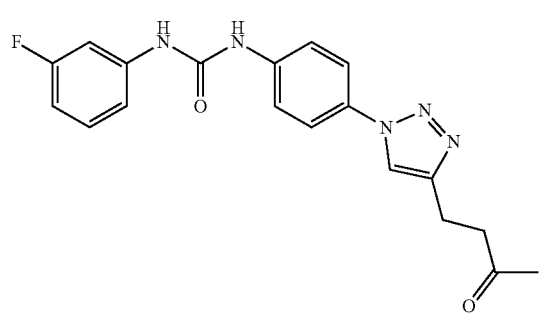
55n
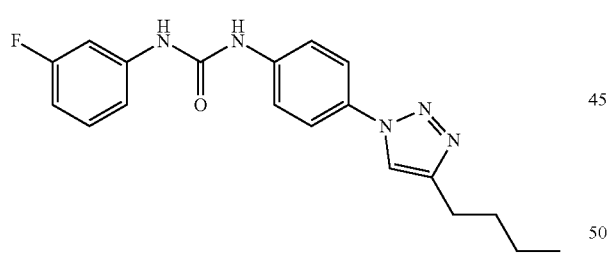
55m
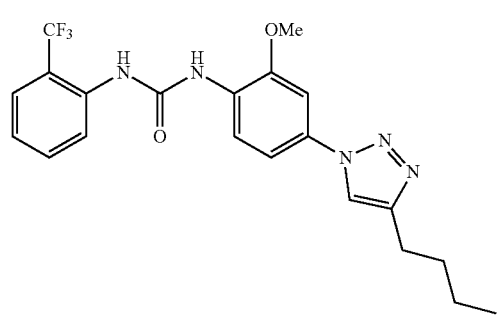
8e
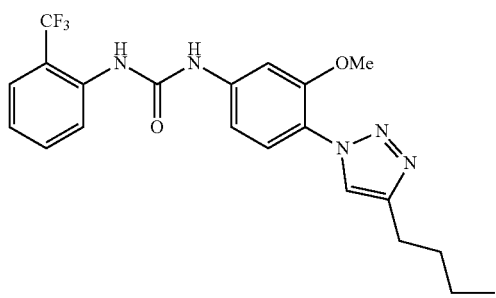
81
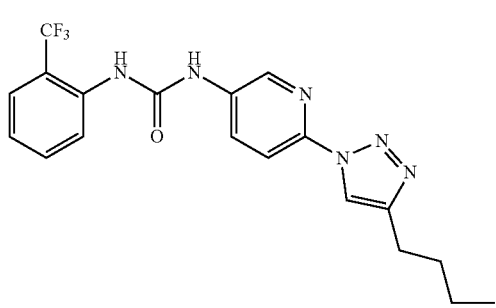
51
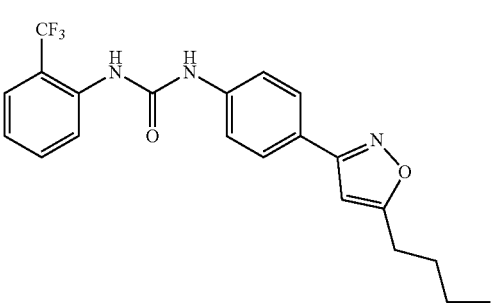
102
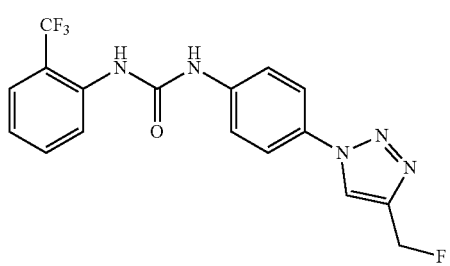
42a
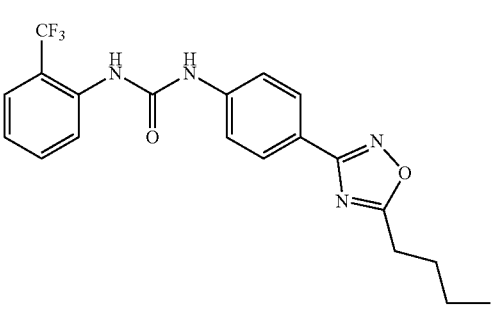
106

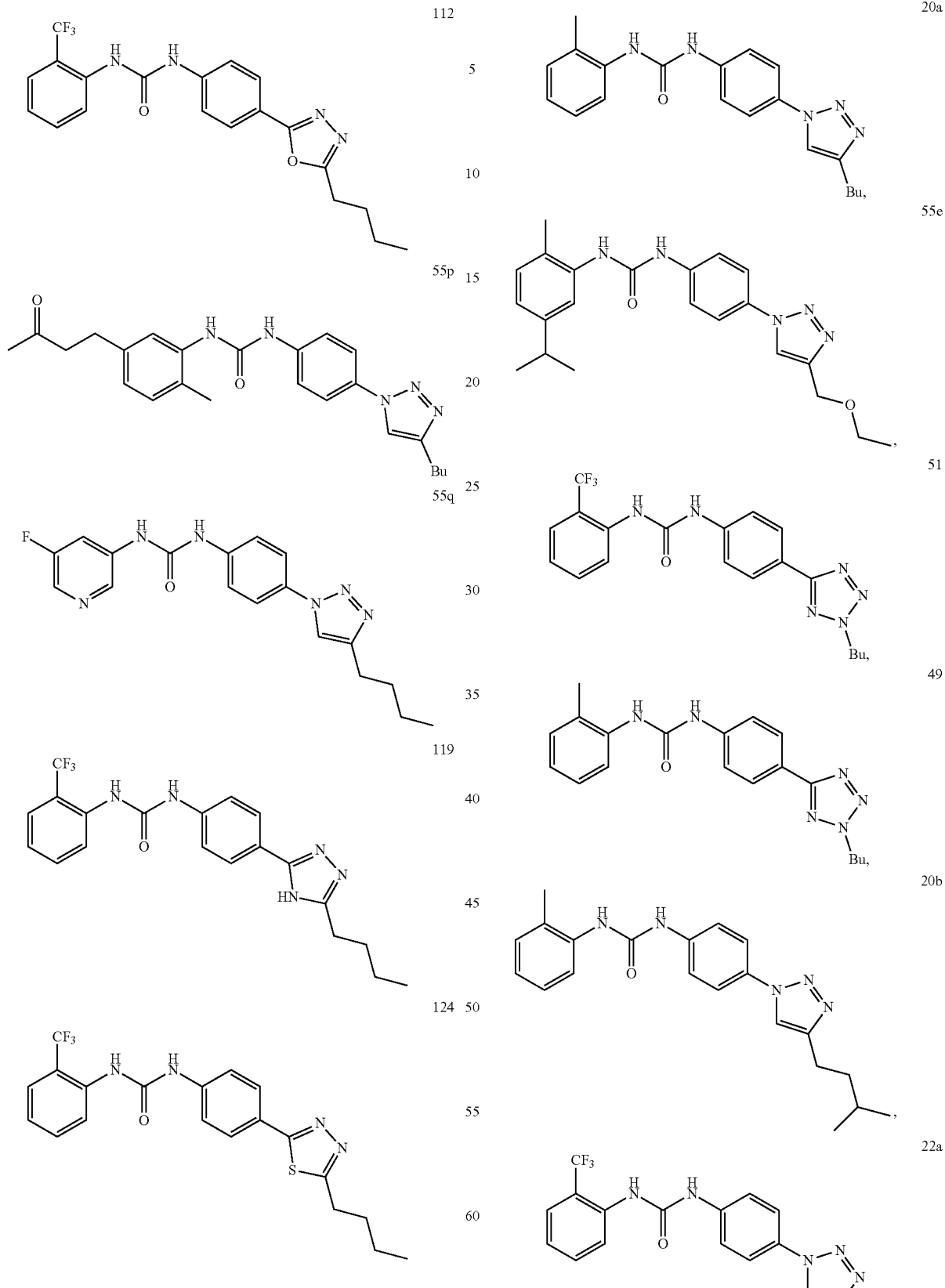
or salt, solvate, stereoisomer thereof.
10. The method according claim 9, wherein the compound is selected from:

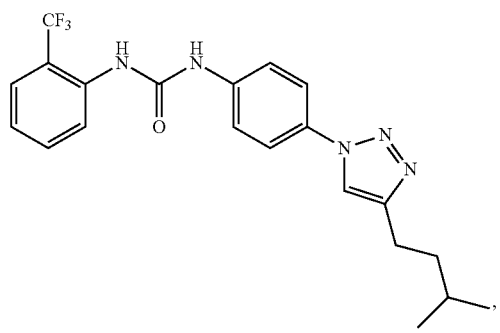

22b

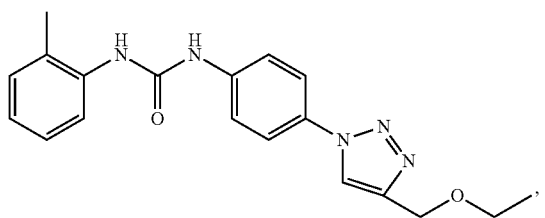

20e

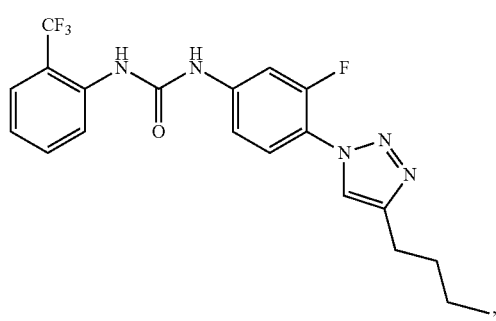

81

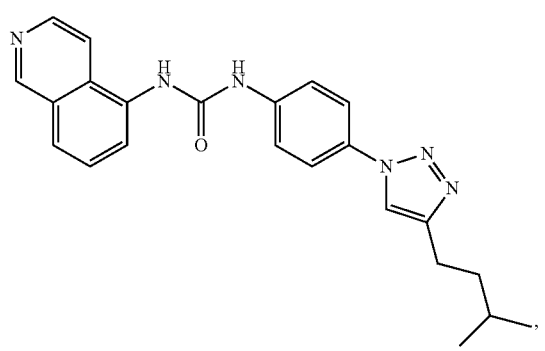

55f

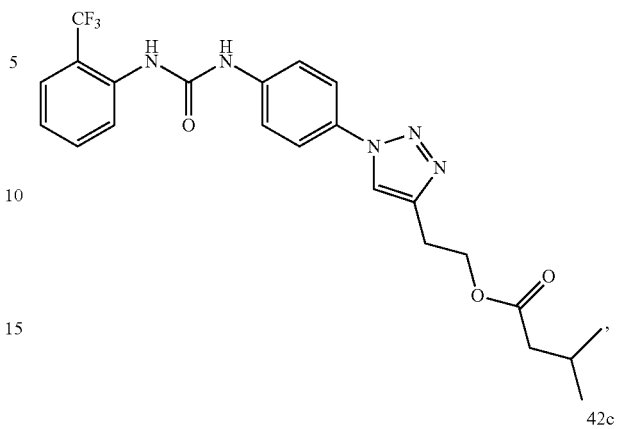

38

42c

55a

55b or salt, solvate, stereoisomer thereof.

11. The method according to claim 1, wherein the cancer is selected from the group consisting of: breast cancer, prostate cancer, lung cancer, glioblastoma, glioblastoma multiforme, kidney cancer, oral cancer, colorectal cancer, neuroblastoma, medulloblastoma, head and neck squamous carcinoma, cervical carcinoma, pontine tumours, hepatocarcinoma, retinoblastoma, hepatoblastoma, gallbladder cancer, melanoma, sarcomas and leukemia.

12. The method according to claim 11, wherein the cancer is a sarcoma and the sarcoma is muscle rhabdomyosarcoma, osteosarcoma, or Ewing sarcoma.

13. The method according to claim 1, wherein the cancer is a primary cancer.

14. The method according to claim 1, wherein the compound of formula I or II is administered together with a further anti-hyperproliferative treatment and/or therapeutic agent.

15. The method according to claim 14, wherein the further anti-hyperproliferative treatment is selected from the group consisting of: radiotherapy and chemotherapy.

16. The method according to claim 15, wherein the chemotherapy is selected from the group consisting of: a pro-apoptotic agent, a monoclonal antibody, an interleukin or interferon.

17. The method according to claim 14, wherein the further therapeutic agent is an: anti-pain agent or an anti-emetic agent.

18. The method according to claim 17, wherein the anti-emetic agent is selected from the group consisting of aprepitant, fosaprepitant, Dolasetron, granisetron, ondansetron, palonosetron, tropisetron, or ramosetron, and Dexamethasone.

19. The method according to claim 1, wherein the cancer is a metastasis.

20. The method according to claim 5, wherein the pyridinyl or isoquinolinyl are substituted by one or more groups independently selected from methyl, isopropyl, CF3, F, Cl, OH, OMe.

* * * * *